(12) United States Patent
Thurieau et al.

(10) Patent No.: US 7,238,695 B2
(45) Date of Patent: *Jul. 3, 2007

(54) IMIDAZOLYL DERIVATIVES

(75) Inventors: Christophe Alain Thurieau, Paris (FR); Lydie Francine Poitout, Paris (FR); Marie-Odile Galcera, Bondoufle (FR); Christophe Philippe Moinet, Chatenay Malabry (FR); Thomas D. Gordon, Medway, MA (US); Barry A. Morgan, Franklin, MA (US)

(73) Assignee: Societe de Conseils de Recherches et d'Applications Scientifiques, SAS, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/771,725

(22) Filed: Feb. 4, 2004

(65) Prior Publication Data

US 2004/0176379 A1  Sep. 9, 2004

Related U.S. Application Data

(60) Division of application No. 09/719,457, filed as application No. PCT/US99/12760 on Jun. 8, 1999, now Pat. No. 6,852,725, which is a continuation of application No. 09/096,431, filed on Jun. 12, 1998, now abandoned.

(60) Provisional application No. 60/089,087, filed on Jun. 12, 1998.

(51) Int. Cl.
| | |
|---|---|
| A01N 43/50 | (2006.01) |
| A61K 31/415 | (2006.01) |
| C07D 233/00 | (2006.01) |
| C07D 413/00 | (2006.01) |
| C07D 403/00 | (2006.01) |

(52) U.S. Cl. .................. 514/254.05; 514/235.8; 514/256; 514/400; 544/139; 544/333; 544/370; 548/338.1

(58) Field of Classification Search ........... 544/370; 548/338.1
See application file for complete search history.

(56) References Cited

U.S. PATENT DOCUMENTS

| 5,128,355 | A | | 7/1992 | Carini et al. ............. 514/381 |
|---|---|---|---|---|
| 5,733,882 | A | * | 3/1998 | Carr et al. .............. 514/19 |
| 6,852,725 | B1 | * | 2/2005 | Thurieau et al. ....... 514/254.08 |
| 7,026,289 | B2 | * | 4/2006 | Cawthorne et al. ........ 514/11 |
| 2004/0072734 | A1 | * | 4/2004 | Cawthorne et al. ......... 514/9 |

FOREIGN PATENT DOCUMENTS

| EP | 0 253 310 B1 | | 10/1994 |
|---|---|---|---|
| FR | 2.132.632 | * | 11/1972 |
| HU | 218 460 B | | 9/1987 |
| WO | 94/04494 | | 3/1994 |
| WO | WO 95/08550 | * | 3/1995 |
| WO | 96/11927 | | 4/1996 |
| WO | 97/24119 | | 7/1997 |
| WO | 97/30053 | | 8/1997 |
| WO | 97/43278 | | 11/1997 |
| WO | 97/45425 | | 12/1997 |
| WO | 98/27108 | | 6/1998 |
| WO | 99/64401 | | 12/1999 |
| WO | 99/65942 | | 12/1999 |
| WO | 00/00477 | | 1/2000 |

OTHER PUBLICATIONS von Geldern et al, "Azole Endothelin Antagonists. 1. A Receptor Model Explains an Unusual Structure-Activity Profile" Journal Medicinal Chemistry, vol. 39(4), pp. 957-967 (1996).*
Al-Dabbagh and Smith, "Species differences in oxidative drug metabolism: some basic considerations." Archives of toxicology. Supplement. Archiv fur Toxikologie. supplement, vol. 7, pp. 219-231 (1984).*
Hans Bundgaard, Design of Prodrugs, p. 1. © 1985 Elsevier Science Publishers.*
Richard B. Silverman, The Organic Chemistry of Drug Design and Drug Action, pp. 352-400. © 1992 Academic Press, Inc.*
Emery et al, "Anti-Secretory properties of non-peptide somatostatin receptor agonists in isolated rat colon: luminal activity and possible interaction with p-glycoprotein" British Journal of Pharmacology, vol. 135, pp. 1443-1448 (2002).*
Gordon et al, "Synthetic Approaches to the "Azole" Peptide Mimetics" Tetrahedron Letters, vol. 34(12), pp. 1901-1904 (1993).*
Robbins, R.J., J. Clin. Endocr. Metab., 82:15-17 (1997).*
Flogstad A.K., et al., J. Clin. Endocr. Metab. 82:23-28 (1997).*
Caron P., et al., J. Clin. Endocr. Metab. 82:18-22 (1997).*
Grant, M.B., et al., Circulation, 89:1511-1517 (1994).*
Fedorak, R.N., et al., Can. J. Gastroenterology, 3, No. 2, 53-57 (1989).*
Soudah, H., et al., Gastroenterology, 98, No. 5, Part 2, Suppl., A129 (1990).*
Hartley, J.E., et al., J. Roy. Soc. Med., 85, pp. 107-108 (1992).*
Koberstein, B., et al., Z. Gastroenterology, 28, 295-301 (1990).*
Christensen, C., Acta Chir. Scand. 155, 541-543 (1989).*

(Continued)

*Primary Examiner*—Zachary C Tucker
(74) *Attorney, Agent, or Firm*—Fish & Richardson; Alan F. Feeney; Tony K. Uhm

(57) ABSTRACT

The present invention is directed to imidazolyl derivatives or pharmaceutically acceptable salts thereof which are useful as agonists or antagonists of somatostatin receptors, having the following formula (I),

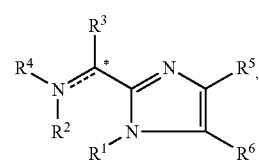

wherein the substituents are defined in the specification.

5 Claims, No Drawings

OTHER PUBLICATIONS

Laron, Z., Israel J. Med. Sci., 26, No. 1, 1-2 (1990).*
Wilson, D.C., Irish J. Med. Sci., 158, No. 1, 31-32 (1989).*
Micic, D., et al., Digestion, 16, Suppl. 1.70. Abs. 193 (1990).*
Bauer, W., Europ. J. Pharmacol., 183, 55 (1990).*
Mozell, E., et al., Surg. Gynec. Obstet., 170, 476-484 (1990).*
Cello, J.P., et al., Gastroenterology, 98, No. 5, Part 2, Suppl., A163 (1990).*
Petrelli, N., et al., Proc. Amer. Soc. Clin. Oncol., vol. 10, P 138, Abstr. No. 417 (1991).*
Soudah, H., et al., Clin. Res., vol. 39, p. 303A (1991).*
O'Donnell, L.J.D., et al., Aliment. Pharmacol. Therap., vol. 4., 177-181 (1990).*
Tulassay, Z., et al., Gastroenterology, 98, No. 5, Part 2, Suppl., A238 (1990).*
Nott, D.M., et al., Brit. J. Surg., vol. 77, p. A691 (1990).*
Branch, M.S., et al., Gastroenterology, vol. 100, No. 5, Part 2 Suppl., p. A425 (1991).*
Hasler, W., et al., Gastroenterology, vol. 100, No. 5, Part 2, Suppl., p. A448 (1991).*
Clark, R.V., et al., Clin. Res. 38, p. 943A (1990).*
Ambrosi B., et al., Acta Endocr. (Copenh.) 122, 569-576 (1990).*
Miller, D., et al., Canad. Med. Ass. J., vol. 145, pp. 227-228 (1991).*
Chang, T.C., et al., Brit. Med. J., 304, p. 158 (1992).*
Chan, A.W., et al., Horm. Res., 36:86-87 (1991).*
Palmieri, G.M.A., et al., J. of Bone and Mineral Research, 7, (Suppl. 1), p. S240 (Abs. 591) (1992).*
Prelevic, G.M., et al., Metabolism Clinical and Experimental, 41, Suppl. 2, pp. 76-79 (1992).*
Weckbecker, G., et al., Pharmac. Ther., 60:245-264 (1993).*
Bartlett, D.L., et al., Surg. Forum., 42, pp. 14-16 (1991).*
Hoeldtke, R.D., et al., Arch. Phys. Med. Rehabil., 69, 895-898 (1988).*
Kooner, J.S., et al., Brit. J. Clin. Pharmacol., 28, 735P-736P (1989).*
Hoeldtke, R.D., et al., Am. J. Med., 81:83-87 (1986).*
Abelson, J.L., et al., Clin. Psychopharmacol., 10, 128-132 (1990).*
Malarkey, W.B., et al., Neuroendocrinology, 49:267-274 (1989).*
Dimitriadis, G., et al., Metabolism, 32:987-992 (1983).*
Orskov, L., et al., Metabolism, 45:211-217 (1996).*
McCombe, M., et al., Eye, 5:569-575 (1991).*
Campbell, P.J., et al., Metabolism, 37:34-37 (1988).*
Flyvbjerg, A., et al., Kidney Int., 41:805-812 (1992).*
Kayasseh L, Lancet, 1:844-846 (1980).*
Nubiola, P., et al., Ann. Surg., 210:56-58 (1989): Erratum in Ann. Surg., 211:246, (1990).*
Anand, B.S., et al., Am. J. Gastroenterol., 89:267-270 (1994).*
Hopman, W.P., et al., Ann. Surg., 207:155-159 (1988).*
Eriksson, B., et al., Scand. J. Gastroenterol., 23:508-512 (1988).*
Buchler, M.W., et al., Gut, 35:S15-S19 (1994).*
Souquet, J.C., et al., Cancer, 59:1654-1660 (1987).*
Danesi, R., et al., Clin. Cancer Res., 3:265-72 (1997).*
Mantyh, P.W., et al., Peptides, 10:627-645 (1989).*
Hayry, P., et al., FASEB J. 7:1055-1060 (1993.*
Yumi, K., et al., Lab. Invest., 76:329-338 (1997).*
Rossini, F.P., et al., Am. J. Gastroenterol., 88:1424-1427 (1993).*
Ladas, S.D., et al., Hepatogastroenterology, 45:761-4 (1998.*
Albert, Rainer, et al.; "Direct Synthesis of [DOTA-Dphe$^1$]-Octreotide (SMT487) : . . . "; Bioorganic & Medicinal Chemistry Letters, 1998,vol. 8; pp. 1207-1210; XP002124712.
Gramberg, Dieter et al; "Synthesis of a Type Vibeta-Turn Peptide . . . ";Helvetica Chimica Acta; 1995, vol. 78, pp. 1588-1606; XP000612160.
Hirschmann, Ralph et al.; "De Novo Design and Synthesis of Somatostatin . . . "; Journal of the American Chemical Society; 1996, vol. 115, No. 26; pp. 12550-12568; XP002124710.
Hirschmann, Ralph et al.; "Nonpeptidal Peptidomimetics with a beta-D-glucose Scaffolding"; Journal of the American Chemical Society; 1992, vol. 114, No. 23; XP002124711.
Papageorgiou, Christos et al.; "A Non-peptide ligand for the Somatostatin Receptor having a Benzodiazepinone Structure"; Bioorganic & Medicinal Chemistry Letters; 1996, vol. 6, No. 3; pp. 267-272; XP004135075.
Ellinger and Goldberg; J. Chem. Soc.; 1949; 263, 266; Beilstein Registry No. 1965.
Ellinger and Goldberg; J. Chem. Soc.; 1949; 263, 266; Beilstein Registry No. 3689018.
Ellinger and Goldberg; J. Chem. Soc.; 1949; 263, 266; Beilstein Registry No. 3798855.
Bornowski, Heinz et al.; Chem. Abstract 1973, 78:136289.
Gordon, Thomas D. et al.; Chem. Abstract 1997, 127:248417.
Stocker, Fred B. et al.; Chem. Abstract, 1970, 72:121434.
Towliati, Hossein; Chem. Abstract, 1971, 74:53642.
Von Geldern, Thomas W. et al.; Chem Abstract, 1996, 124:193276.
Von Geldern, Thomas W. et al.; Chem. Abstract, 1996, 124:127005.
Von Geldern, Thomas W. et al.; Chem. Abstract, 1996, 124:164291.

* cited by examiner

IMIDAZOLYL DERIVATIVES

CROSS-REFERENCE TO RELATED APPLICATIONS

This application is a divisional of U.S. application Ser. No. 09/719,457, filed on Jun. 13, 2001 now U.S. Pat. No. 6,852,725, which is the National Stage of International Application Serial No. PCT/US99/12760 filed on Jun. 8, 1999, which is a continuation of U.S. application Ser. No. 09/096,431, filed on Jun. 12, 1998 (Now Abandoned) and claims the benefit of U.S. Provisional Application Ser. No. 60/,089,087, filed on Jun. 12, 1998. The contents of these four applications are incorporated herein by reference in their entireties.

BACKGROUND OF THE INVENTION

The present invention is directed to compounds and compositions containing said compounds which bind selectively to somatostatin receptor subtypes and the use of said compounds for treating medical disorders which are mediated by somatostatin receptor subtypes. Somatostatin (somatotropin release inhibiting factor, SRIF), a tetradecapeptide hormone, originally isolated from bovine hypothalami (Brazeau, P. et al., Science 179, 77-79, 1973) has been shown to have a wide range of regulatory effects on the release of a variety of hormones such as growth hormone, prolactin, glucagon, insulin, gastrin (Bloom, S. R. and Poldack, J. M., Brit. Med. J. 295, 288-289, 1987). In addition, antiproliferative properties (Reichlin, S., N. Engl. J . Med. 309, 1495-1501, 1983) have been obtained with somatostatin analogs in metastatic prostatic cancer (Parmar, H. et al, Clin. Exp. Metastasis, 10, 3-11, 1992) and in several other neuroendocrine neoplasms in man (Anthony, L. et al, Acta Oncol., 32, 217-223, 1993). Metabolism of somatostatin by aminopeptidases and carboxypeptidases leads to a short duration of action.

The actions of somatostatin are mediated via membrane bound receptors. The heterogeneity of its biological functions has led to studies to identify structure-activity relationships of peptides analogs at the somatostatin receptors which resulted in the discovery of five receptor subtypes (Yamada, et al, Proc. Natl. Acad. Sci. U.S.A, 89, 251-255, 1992; Raynor, K. et al, Mol. Pharmacol., 44, 385-392, 1993). The functional roles of these receptors are under extensive investigation. Binding to the different types of somatostatin subtypes have been associated with the treatment of the following conditions and/or diseases. Activation of types 2 and 5 have been associated with growth hormone suppression and more particularly GH secreting adenomas (Acromegaly) and TSH secreting adenomas. Activation of type 2 but not type 5 has been associated with treating prolactin secreting adenomas. Other indications associated with activation of the somatostatin subtypes are restenosis, inhibition of insulin and/or glucagon and more particularly diabetes mellitus, hyperlipidemia, insulin insensitivity, Syndrome X, angiopathy, proliferative retinopathy, dawn phenomenon and Nephropathy; inhibition of gastric acid secretion and more particularly peptic ulcers, enterocutaneous and pancreaticocutaneous fistula, irritable bowel syndrome, Dumping syndrome, watery diarrhea syndrome, AIDS related diarrhea, chemotherapy-induced diarrhea, acute or chronic pancreatitis and gastrointestinal hormone secreting tumors; treatment of cancer such as hepatoma; inhibition of angiogenesis, treatment of inflammatory disorders such as arthritis; chronic allograft rejection; angioplasty; preventing graft vessel and gastrointestinal bleeding. Somatostatin agonists can also be used for decreasing body weight in a patient.

In drug research, it is a key issue to minimize side effects by developing highly potent and selective drug molecules. Recent work on the development of nonpeptide structures (Hirschmann, R. et al, J. Am. Chem. Soc. 115, 12550-12568, 1993; Papageorgiou, C. and Borer, X., Bioorg. Med. Chem. Lett. 6, 267-272, 1996) have described compounds with low somatostatin receptor affinity.

The present invention is directed to a family of nonpeptide compounds, which are selective and potent somatostatin receptor ligands.

SUMMARY OF THE INVENTION

In one aspect the present invention is directed to a compound of the formula (I),

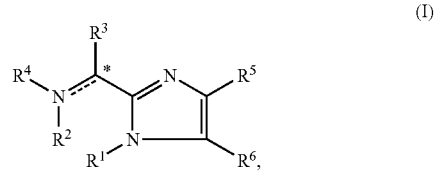

the racemic-diastereomeric mixtures and optical isomers of said compound of formula (I), the pharmaceutically-acceptable salts and prodrugs thereof or a pharmaceutically acceptable salt thereof, wherein — represents an optional bond;

$R^1$ is H, —$(CH_2)_m$—C(O)—$(CH_2)_m$—$Z^1$, —$(CH_2)_m$—$Z^1$, —$(CH_2)_m$—O—$Z^1$ or —$(C_0$-$C_6)$alkyl-C(O)—NH—$(CH_2)_m$—$Z^3$;

$Z^1$ is an optionally substituted moiety selected from the group consisting of $(C_1$-$C_{12})$alkyl, benzo[b]thiophene, phenyl, naphthyl, benzo[b]furanyl, thiophene, isoxazolyl, indolyl,

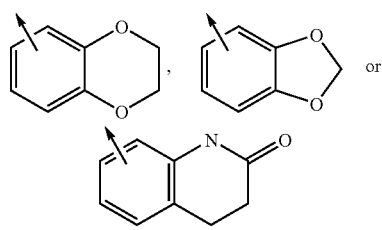

$R^2$ is H or $(C_1$-$C_6)$alkyl;

or $R^1$ and $R^2$ are taken together with the nitrogen atoms to which they are attached to form a compound of formula (Ia), (Ib) or (Ic),

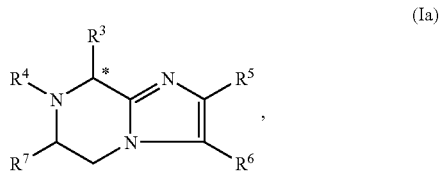

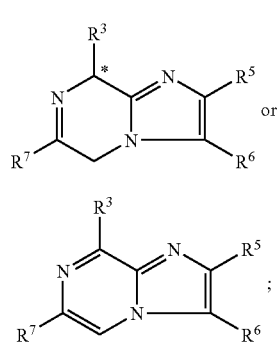

(Ib)

(Ic)

$R^3$ is —$(CH_2)_m$—E—$(CH_2)_m$—$Z^2$;

E is O, S, —C(O)—, —C(O)—O—, —NH—C(O)—O— or a bond;

$Z^2$ is H, $(C_1-C_{12})$alkyl, amino, $(C_1-C_{12})$alkylamino, N,N-di-$(C_1-C_{12})$alkylamino, $(C_1-C_{12})$alkylguanidino, or an optionally substituted moiety selected from the group consisting of phenyl, indolyl, imidazolyl, thiophene, benzothiophene, pyridinyl and naphthyl;

$R^4$ is H or —$(CH_2)_m$—$A^1$;

$A^1$ is —C(=Y)—N($X^1X^2$), —C(=Y)—$X^2$, —C(=NH)—$X^2$ or $X^2$;

Y is O or S;

$X^1$ is H, $(C_1-C_{12})$alkyl, —$(CH_2)_m$—NH—$(C_1-C_6)$alkyl, —$(CH_2)_m$—N-di-$(C_1-C_6)$alkyl or —$(CH_2)_m$-aryl;

$X^2$ is —$(CH_2)_m$—$Y^1$—$X^3$ or optionally substituted $(C_1-C_{12})$alkyl;

$Y^1$ is O, S, NH, C=O, $(C_2-C_{12})$alkenyl having one or more double bonds, —NH—CO—, —CO—NH—, —NH—CO—O—$(CH_2)_m$—, —C≡C—, $SO_2$ or a bond;

$X^3$ is H, an optionally substituted moiety selected from the group consisting of $(C_1-C_{12})$alkyl, $(C_3-C_8)$cycloalkyl, $(C_1-C_{12})$alkoxy, aryloxy, $(C_1-C_{12})$alkylamino, N,N-di-$(C_1-C_{12})$alkylamino, —CH-di-$(C_1-C_{12})$alkoxy, pyrrolidinyl, pyridinyl, thiophene, imidazolyl, piperidinyl, piperazinyl, benzothiazolyl, furanyl, indolyl, morpholino, benzo[b]furanyl, quinolinyl, isoquinolinyl, —$(CH_2)_m$-phenyl, naphthyl, fluorenyl, phthalamidyl, pyrimidinyl,

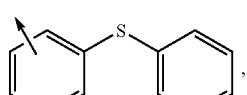

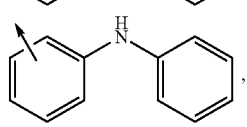

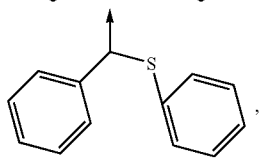

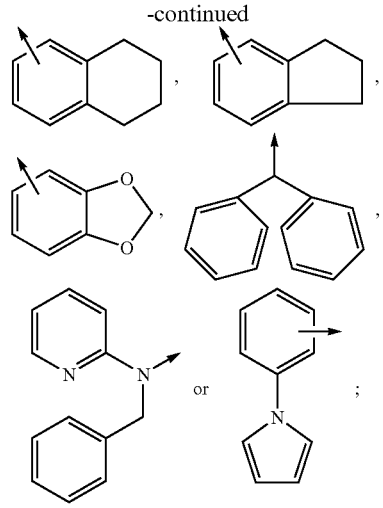

or $X^1$ and $x^2$ are taken together with the nitrogen to which they are attached to form an optionally substituted moiety selected from the group consisting of thiazolyl

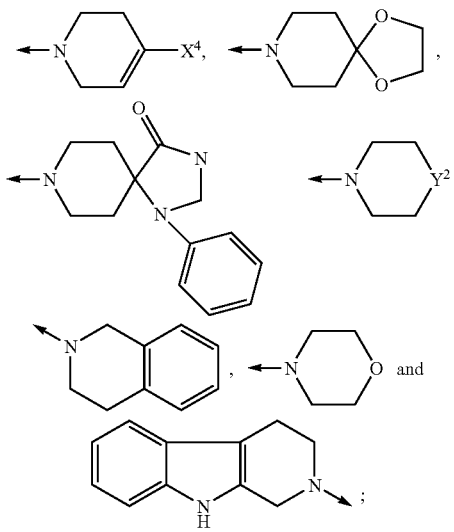

$Y^2$ is CH—$X^4$, N—$X^4$, —C($X^4X^4$), O or S;

$X_4$ for each occurrence is independently —$(CH_2)_m$—$Y^3$—$X^5$;

$Y^3$ is —C(O)—, —C(O)O— or a bond;

$X^5$ is hydroxy, $(C_1-C_{12})$alkyl, amino, $(C_1-C_{12})$alkylamino, N,N-di-$(C_1-C_{12})$alkylamino, or an optionally substituted moiety selected from the group consisting of aryl, aryl$(C_1-C_4)$alkyl, furanyl, pyridinyl, indolyl, —CH(phenyl)$_2$,

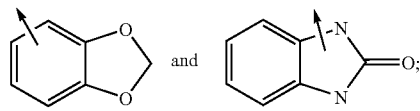

$R^5$ is $(C_1-C_{12})$alkyl, $(C_0-C_6)$alkyl-C(O)—O-$Z^5$, $(C^0-C_6)$ alkyl-C(O)—NH—$(CH_2)_m$—$Z^3$ or optionally substituted aryl;

$Z^3$ for each occurrence is independently amino, $(C_1-C_{12})$ alkylamino, N,N-di-$(C_1-C_{12})$alkylamino, —NH—C(O)—O—$(CH_2)_m$-phenyl —NH—C(O)—O—$(CH_2)_m$—$(C_1-C_6)$alkyl or an optionally substituted moiety selected from the group consisting of imidazolyl, pyridinyl, morpholino, piperidinyl, piperazinyl, pyrazolidinyl, furanyl and thiophene;

$R^6$ is H or $(C_1-C_6)$alkyl;

$R^7$ is $(C_1-C_{12})$alkyl or —$(CH_2)_m$—$Z^4$;

$Z^4$ is an optionally substituted moiety selected from the group consisting of phenyl, naphthyl, indolyl, thiophene, benzo[b]furan, benzo[b]thiophene, isoxazolyl,

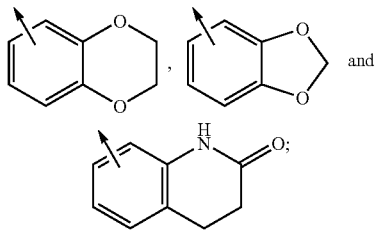

$Z^5$ is H, $(C_1-C_{12})$alkyl, $(CH_2)_m$-aryl;

wherein an optionally substituted moiety is optionally substituted by one or more substituents, each independently selected from the group consisting of Cl, F, Br, I, $CF_3$, CN, $N_3$, $NO_2$, OH, $SO_2NH_2$, —$OCF_3$, $(C_1-C_{12})$alkoxy, —$(CH_2)_m$-phenyl-$(X^6)_n$, —S-phenyl-$(X^6)_n$, —S—$(C_1-C_{12})$alkyl, —O—$(CH_2)_m$-phenyl-$(X^6)_n$, —$(CH_2)_m$—C(O)—O—$(C_1-C_6)$alkyl, $(CH_2)_m$—C(O)—$(C_1-C_6)$alkyl, —O—$(CH_2)_m$—$NH_2$, —O—$(CH_2)_m$—NH—$(C_1-C_6)$alkyl, —O—$(CH_2)_m$—N-di-$((C_1-C_6)$alkyl) and —$(C_0-C_{12})$alkyl-$(X^6)_n$;

$X^6$ for each occurrence is independently selected from the group consisting of hydrogen, Cl, F, Br, I, $NO_2$, $N_3$, CN, OH, —$CF_3$, —$OCF_3$, $(C_1-C_{12})$alkyl, $(C_1-C_{12})$ alkoxy, —$(CH_2)_m$—$NH_2$, —$(CH_2)_m$—NH—$(C_1-C_6)$alkyl, —$(CH_2)_m$—N-di-$((C_1-C_6)$alkyl) and —$(CH_2)_m$-phenyl;

m for each occurrence is independently O or an integer from 1 to 6; and n for each occurrence is independently an integer from 1 to 5;

provided that:

(a) when $R^5$ is $(C_1-C_{12})$alkyl, or —C(O)—O-$Z^5$ and $Z^5$ is $(C_1-C_{12})$alkyl or optionally substituted aryl; $R^6$ is H or $(C_1-C_6)$alkyl; $R^7$ is $(C_1-C_{12})$alkyl or $Z^4$ and $Z^4$ is thiophene or optionally substituted phenyl, then $R^3$ is not —C(O)—O—$(CH_2)_m$—Z where m is 0 and Z is H or $(C_1-C_{12})$alkyl or where m is 1 to 6 and Z is H;

(b) when $R^5$ is $(C_1-C_{12})$alkyl or optionally substituted phenyl; $R^6$ is H or $(C_1-C_6)$alkyl; $R^7$ is $(C_1-C_{12})$alkyl and $R^3$ is —O—$(CH_2)$-$Z^2$, then $Z^2$ is not an optionally substituted moiety selected from the group consisting of phenyl, indolyl, imidazolyl, thiophene, benzothiophene, pyridinyl, and naphthyl; and (c) when $R^5$ is H or $(C_1-C_{12})$alkyl; $R^6$ is $(C_1-C_6)$alkyl; $R^7$ is $(C_1-C_{12})$alkyl; and $R^3$ is —O-$Z^2$ or —S-$Z^2$, then $Z^2$ is not an optionally substituted moiety selected from the group consisting of phenyl, naphthyl, thiophene, benzothienyl and indolyl.

A preferred compound of formula I is where $R^1$ is H; $R^2$ is H; $R^3$ is —$CH_2$-phenyl; $R^4$ is —$(CH_2)_m$—$A^1$ where m in the definition of $R^4$ is 0; $R^5$ is phenyl; $R^6$ is H;

where $A^1$ is —C(=Y)—N($X^1X^2$);

Y is O; $X^1$ is H or methyl;

$X^2$ is —$(CH_2)_m$—$Y^1$—$X^3$;

m in the definition of $X^2$ is 0, 1, 2 or 3; $Y^1$ is a bond or O; and $X^3$ is N-methylpyrrolidin-2-yl, diethylamino, pyridinyl, thiophene, imidazolyl, diethoxymethyl, 1-benzyl-piperidin-4-yl, optionally substituted phenyl or

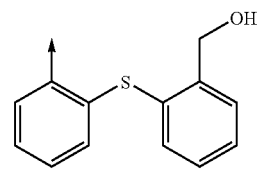

Another preferred compound of formula (I) is where $R^1$ is H; $R^2$ is H; $R^3$ is —$CH_2$-phenyl; $R^4$ is —$(CH_2)_m$—$A^1$ where m in the definition of $R^4$ is 0; $R^5$ is phenyl; $R^6$ is H;

where $A^1$ is —C(=Y)—N($X^1X^2$);

Y is O;

$X^1$ is benzyl and $X^2$ is 2-hydroxyethyl;

or $X^1$ and $X^2$ are taken together with the nitrogen atom to which they are attached to form

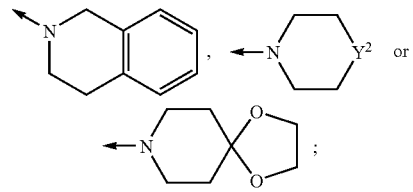

where $Y^2$ is C—$X^4$ or N—$X^4$;

$X^4$ is —$(CH_2)_m$—$Y^3$—$X^5$ where m in the definition of $X^4$ is 0 or 1; and $X^5$ is selected from the group consisting of furanyl, benzyl, phenyl, amino,

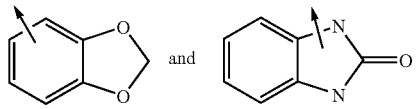

Another preferred compound of formula (I) is where $R^1$ is H; $R^2$ is H; $R^3$ is —$CH_2$-phenyl; $R^4$ is —$(CH_2)_m$—$A^1$ where m in the definition of $R^4$ is 0; $R^5$ is phenyl; $R^6$ is H;

where $A^1$ is —C(=Y)—$X^2$;

Y is O; $X^2$ is —$(CH_2)_m$—$Y^1$—$X^3$;

where m in the definition of $X^2$ is 0, 1 or 2;

$Y^1$ is O, —NH—CO—, —CO—NH—, —NH—CO—O—$CH_2$—, $SO_2$ or a bond; and $X^3$ is methyl, furanyl, pentyl, phenyl, indolyl, p-$NO_2$-phenyl, naphthyl, fluorenyl, —CH(phenyl)$_2$, benzothiazolyl, phthalamidyl, N,N-dimethylamino,

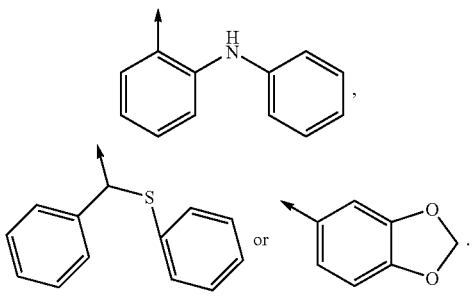

or

Another preferred compound of formula (I) is where $R^1$ is H; $R^2$ is H; $R^3$ is —$CH_2$-indol-3-yl; $R^4$ is —$(CH_2)_m$—$A^1$ where m in the definition of $R^4$ is 0; $R^5$ is phenyl or t-Bu; $R^6$ is H;

$A^1$ is —C(=Y)—N($X^1X^2$);

Y is O or S; $X^1$ is H; $x^2$ is —$(CH_2)_m$—$Y^1$—$X^3$;

m in the definition of $X^2$ is 0, 1 or 2;

$Y^1$ is a bond; and $X^3$ is phenyl, o-Cl-phenyl, m-Cl-phenyl, p-phenyloxy-phenyl, 2,6-di-isopropylphenyl, m-$CF_3$-phenyl, p-ethoxycarbonyl-phenyl, 2,4-difluorophenyl, m-$NO_2$-phenyl, p-benzyloxyphenyl, o-isopropylphenyl, n-hexyl, 4-morpholino, naphthyl or

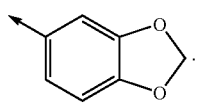

Another compound of formula (I) is where $R^1$ is H; $R^2$ is H; $R^3$ is —$CH_2$-indol-3-yl;

$R^4$ is —$(CH_2)_m$—$A^1$ where m in the definition of $R^4$ is 0; $R^5$ is phenyl or t-Bu; $R^6$ is H;

where $A^1$ is —C(=Y)—$X^2$;

Y is O; $X^2$ is —$(CH_2)_m$—$Y^1$—$X^3$;

where m in the definition of $x^2$ is 0, 1 or 2;

$Y^1$ is O, —CO—NH—, —NH—CO—O—$CH_2$— or a bond; and $X^3$ is methyl, 3-pentyl, phenyl, p-$NO_2$-phenyl, phthalamidyl, N,N-dimethylamino, p-aminophenyl, fluorenyl or

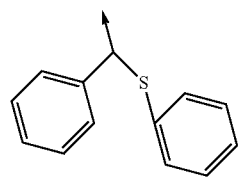

Another preferred compound of formula (I) is where $R^1$ is H; $R^2$ is H; $R^3$ is —$CH_2$-indol-3-yl; $R^4$ is —$(CH_2)_m$-$A^1$ where m in the definition of $R^4$ is 0; $R^5$ is phenyl or t-Bu; $R^6$ is H;

where $A^1$ is —C(=Y)—N($X^1X^2$);

Y is O; $X^1$ is hydrogen; $X^2$ is —$(CH_2)_m$—$Y^1$—$X^3$;

where m in the definition of $X^2$ is 0, 1, 2 or 3;

$Y^1$ is O, or a bond; and $X^3$ is cyclopentyl, 4-OH-butyl, N,N-diethylamino, N-methyl-pyrrolidin-3-yl, —CH(ethoxy)$_2$, phenyl, p-$SO_2NH_2$-phenyl p-OH-phenyl, o-$CF_3$-phenyl, p-Cl-phenyl, —CH(phenyl)$_2$,

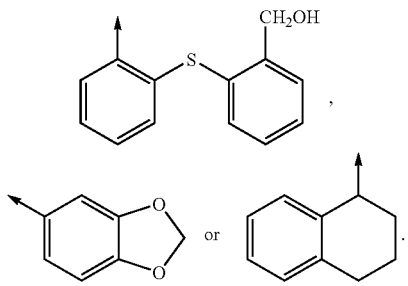

or

Another preferred compound of formula (I) is where $R^1$ is H; $R^2$ is H; $R^3$ is —$CH_2$-indol-3-yl; $R^4$ is $(CH_2)_m$—$A^1$ where m in the definition of $R^4$ is 0; $R^5$ is phenyl or t-Bu; $R^6$ is H;

where $A^1$ is —C(=Y)—$X^2$;

Y is O; $X^2$ is —$(CH_2)_m$—$Y^1$—$X^3$;

where m in the definition of $X^2$ is 0, 1, 2 or 3;

$Y^1$ is —NH—CO, —C=C—, —C≡C— or a bond; and $X^3$ is t-butyl, 1-methylcarbonyl-piperidin-4-yl, phenyl, p-Cl-phenyl, m-$CF_3$-phenyl, 4-nitro-naphthyl, p-methoxy-phenyl, m-(phenylethyl)-phenyl, indol-3-yl or p-aminophenyl.

Another preferred compound of formula (I) is where $R^1$ is H; $R^2$ is H; $R^3$ is —$CH_2$-indol-3-yl, —$(CH_2)_4$—NH—CO—O-t-Bu or —$(CH_2)_4$—$NH_2$; $R^4$ is —$(CH_2)_m$—$A^1$ where m in the definition of $R^4$ is 0; $R^5$ is phenyl, o-methoxyphenyl, p-Br-phenyl, p-nitro-phenyl or p-N,N-diethylamino-phenyl; $R^6$ is H;

where $A^1$ is —C(=Y)—N($X^1X^2$);

Y is O; $X^1$ is H; $X^2$ is —$(CH_2)_m$—$Y^1$—$X^3$;

where m in the definition of $X^2$ is 0;

$Y^1$ is a bond; and $X^3$ is o-Br-phenyl, m-Br-phenyl, p-Br-phenyl, o-Cl-phenyl, m-Cl-phenyl, p-Cl-phenyl, o-nitro-phenyl, m-nitro-phenyl, p-nitro-phenyl, o-$CF_3$-phenyl, m-$CF_3$-phenyl, p-$CF_3$-phenyl, p-F-phenyl, 2,4-di-F-phenyl, 2,5-di-F-phenyl, 2,5-di-methoxy-phenyl, m-OMe-phenyl, p-OMe-phenyl, 2-$CF_3$-4-Cl-phenyl or 3-nitro-4-F-phenyl.

Of the immediately above compounds it is preferred that when $R^5$ is phenyl and $R^3$ is —$(CH_2)$-indol-3-yl that the stereochemistry at the carbon to which $R^3$ is attached is in the R-configuration.

Another preferred compound of formula (I) is where $R^1$ is H; $R^2$ is H; $R^3$ is —$CH_2$-indol-3-yl, —$(CH_2)_4$—NH—CO—O-t-Bu or —$(CH_2)_4$—$NH_2$; $R^4$ is —$(CH_2)_m$—$A^1$ where m in the definition of $R^4$ is 0; $R^5$ is phenyl, o-methoxyphenyl, p-methoxyphenyl, p-Br-phenyl, p-nitro-phenyl or p-N,N-diethylamino-phenyl; $R^6$ is H;

where $A^1$ is —C(=Y)—$X^2$;

Y is O; $X^2$ is —$(CH_2)_m$—$Y^1$—$X^3$;

where m in the definition of $X^2$ is 1;

$Y^1$ is a bond; and $X^3$ is phenyl, o-Br-phenyl, m-Br-phenyl, p-Br-phenyl, o-Cl-phenyl, m-Cl-phenyl, p-Cl-phenyl, o-nitrophenyl, m-nitro-phenyl, p-nitro-phenyl, O-$CF_3$-phenyl, m-$CF_3$-phenyl, p-$CF_3$-phenyl, o-F-phenyl, m-F-phenyl, p-F-phenyl, N,N-di-methylamino-phenyl, o-OMe-phenyl, m-OMe-phenyl, p-OMe-phenyl, 3,4-di-Cl-phenyl, 3,4,5-tri-OMe-phenyl, p-Me-phenyl, p-OH-phenyl or 2,4-di-F-phenyl.

Of the immediately foregoing compounds when $R^5$ is phenyl or o-OMe-phenyl and $R^3$ is —(CH$_2$)-indol-3-yl; it is preferred that the compounds are the separated enantiomers (R or S configuration) according to the carbon to which $R^3$ is attached.

Another preferred compound of formula (I) is where $R^1$ is H; $R^2$ is H; $R^3$ is —(CH$_2$)$_4$—NH—CO—O-t-Bu or —(CH$_2$)$_4$—NH$_2$; $R^4$ is —(CH$_2$)$_m$—A$^1$ where m in the definition of $R^4$ is 0; $R^5$ is phenyl; $R^6$ is H;
 where A$^1$ is —C(=Y)—X$^2$;
  Y is O; X$^2$ is —(CH$_2$)$_m$—Y$^1$—X$^3$;
   where m in the definition of X$^2$ is 0, 1 or 2;
   Y$^1$ is S, SO$_2$ or a bond; and X$^3$ is phenyl, 3,4-di-Cl-phenyl, 3,4,5-tri-OMe-phenyl, p-Me-phenyl, p-OH-phenyl, 2,4-di-F-phenyl, 2-furanyl, 2-pyridinyl, 3-pyridinyl, naphthyl, 2-quinolinyl, 3-quinolinyl, 4-quinolinyl, 8-quinolinyl, 1-isoquinolinyl, 2-thiophene or 2-pyrimidinyl.

Another preferred compound of formula (I) is where $R^1$ is H; $R^2$ is H; $R^3$ is —(CH$_2$)$_4$—NH—CO—O-t-Bu or —(CH$_2$)$_4$—NH$_2$; $R^4$ is —(CH$_2$)$_m$—A$^1$ where m in the definition of $R^4$ is 0; $R^5$ is phenyl; $R^6$ is H;
 where A$^1$ is —C(=Y)—X$^2$;
  Y is O; X$^2$ is —(CH$_2$)$_m$—Y$^1$—X$^3$;
   where m in the definition of X$^2$ is 0, 1, 2 or 3;
   Y$^1$ is a bond; and X$^3$ is 5-indolyl, 3-indolyl, 4-indolyl, 2-indolyl, 5-OMe-indol-3-yl, 5-OMe-indol-2-yl, 5-OH-indol-2-yl, 5-OH-indol-3-yl, 5-Br-indol-3-yl, 2-Me-indol-3-yl, 2-benzothiophene, 3-benzothiophene or 2-benzofuran.

Another preferred compound of formula (I) is where $R^1$ is H; $R^2$ is H; $R^3$ is —(CH$_2$)$_m$-indol-3-yl, —(CH$_2$)$_4$—NH—CO—O-t-Bu or —(CH$_2$)$_4$—NH$_2$; $R^4$ is —(CH$_2$)$_m$—A$^1$ where m in the definition of $R^4$ is 0; $R^5$ is phenyl, o-OMe-phenyl or p-OMe-phenyl; $R^6$ is H;
 where A$^1$ is X$^2$;
  X$^2$ is —(CH$_2$)$_m$—Y$^1$—X$^3$;
   where m in the definition of X$^2$ is 1, 2 or 3;
   Y$^1$ is S, O or a bond; and X$^3$ is phenyl, o-OH-phenyl, p-OH-phenyl, o-F-phenyl, m-F-phenyl, p-F-phenyl, o-CF$_3$-phenyl, o-OMe-phenyl, m-OMe-phenyl, o-nitro-phenyl, p-nitro-phenyl, 3,4-di-Cl-phenyl, 2-nitro-3-OMe-phenyl, o-Br-phenyl, m-Br-phenyl, p-Br-phenyl, 2-thiophene, 3,4,5-tri-OMe-phenyl, p-N,N-dimethylamino-phenyl, p-OCF$_3$-phenyl, p(3-(N,N-dimethylamino)propoxy) phenyl, 3-F-4-OMe-phenyl, 2-pyridinyl, 3-pyridinyl, 4-pyridinyl, 2-Cl-quinolin-3-yl, 2-quinolinly, methyl, n-butyl, n-pentyl, n-hexyl, 3,3-dimethyl-butyl, benzyl, cyclohexyl or p-t-Bu-phenyl.

Another preferred compound of formula (I) is where $R^1$ is H; $R^2$ is H; $R^3$ is —(CH$_2$)$_4$—NH—CO—O-t-Bu or —(CH$_2$)$_4$—NH$_2$; $R^4$ is —(CH$_2$)$_m$—A$^1$ where m in the definition of $R^4$ is 0; $R^5$ is phenyl; $R^6$ is H;
 where A$^1$ is X$^2$;
  X$^2$ is —(CH$_2$)$_m$—Y$^1$—X$^3$;
   where m in the definition of X$^2$ is 1, 2 or 3;
   Y$^1$ is O or a bond; and X$^3$ is phenyl, o-OH-phenyl, p-OH-phenyl, o-F-phenyl, m-F-phenyl, p-F-phenyl, o-CF$_3$-phenyl, o-OMe-phenyl, m-OMe-phenyl, p-OMe-phenyl, o-nitro-phenyl, p-nitro-phenyl, 3,4-di-Cl-phenyl, 2-nitro-3-OMe-phenyl, o-Br-phenyl, m-Br-phenyl, p-Br-phenyl, p-phenyl-phenyl, 2-thiophene, 3,4,5-tri-OMe-phenyl, p-N,N-dimethylamino-phenyl, p-benzyloxy-phenyl, p-OCF$_3$-phenyl, p-(3-(N,N-dimethylamino) propoxy)phenyl, 3-F-4-OMe-phenyl, 2-pyridinyl, 3-pyridinyl, 4-pyridinyl, 2-Cl-quinolin-3-yl, 2-quinolinly, 3-indolyl, 6-methoxycarbonyl-indol-3-yl, 1-methyl-indol-3-yl, 2-methyl-indol-3-yl, methyl, n-butyl, n-pentyl, n-hexyl, 3,3-dimethyl-butyl, benzyl, cyclohexyl or p-t-Bu-phenyl.

Another preferred compound of formula (I) is where $R^1$ is —(CH$_2$)—CO-Z$^1$; $R^2$ is H;
$R^3$ is —(CH$_2$)$_4$—NH—CO—O-t-Bu, —(CH$_2$)$_4$—NH—CO—O-benzyl, —(CH$_2$)-phenyl or —(CH$_2$)-indol-3-yl; $R^4$ is —(CH$_2$)$_m$—A$^1$ where m in the definition of $R^4$ is 0; $R^5$ is phenyl; $R^6$ is H;
 where Z$^1$ is ethyl, phenyl, p-OMe-phenyl, p-phenyl-phenyl, p-C$_1$-phenyl, p-Br-phenyl, p-N$_3$-phenyl, p-F-phenyl, m-nitro-phenyl, p-nitro-phenyl, p-CN-phenyl, 2,5-di-OMe-phenyl, 3,4-di-Cl-phenyl, N,N-dimethylamino-phenyl, 3-methyl-4-Cl-phenyl or naphthyl;
 A$^1$ is —C(=Y)—X$^2$;
  Y is O; X$^2$ is —(CH$_2$)$_m$—Y$^1$—X$^3$;
   where m in the definition of X$^2$ is 0;
   Y$^1$ is O; and X$^3$ is t-Bu.

Another preferred compound of formula (I) is where $R^1$ is —(CH$_2$)—CO—(CH$_2$)$_m$-Z$^1$ where m in the definition of $R^1$ is 0, 1 or 2; $R^2$ is H; $R^3$ is —(CH$_2$)-indol-3-yl or —(CH$_2$)$_4$—NH—CO—O-t-Bu; $R^4$ is H or —(CH$_2$)$_m$-A$^1$ where m in the definition of $R^4$ is 0; $R^5$ is phenyl, o-OMe-phenyl, p-nitro-phenyl, p-Br-phenyl, t-Bu, —CH(CH$_3$)$_2$—CO—NH—(CH$_2$)$_2$—CO—O-t-Bu, —CH(CH$_3$)$_2$—CO—NH—(CH$_2$)$_3$-imidazol-1-yl, —CH(CH$_3$)$_2$—CO—NH—(CH$_2$)$_2$-pyridin-2-yl, —CH(CH$_3$)$_2$—CO—NH—(CH$_2$)$_3$-4-morpholino, —CH(CH$_3$)$_2$—CO—NH—(CH$_2$)-pyridin-4-yl or —CH(CH$_3$)$_2$—CO—NH—(CH$_2$)$_2$-N,N-diethylamino; $R^6$ is H;
 where Z$^1$ is ethyl, propyl, phenyl, p-OMe-phenyl, p-Cl-phenyl, p-Br-phenyl, p-F-phenyl, p-nitro-phenyl, m-nitro-phenyl, p-CN-phenyl, p-N$_3$-phenyl, p-phenyl-phenyl, 3-Me-4-Cl-phenyl, p-N,N-diethylamino-phenyl, 2,5-di-OMe-phenyl, 3,4-di-Cl-phenyl, 3,4-di-F-phenyl, p-OCF$_3$-phenyl, p-benzyloxy-phenyl, p-pentyl-phenyl, 3,4,-tri-OMe-phenyl, 3-nitro-4-Cl-phenyl, 3-Cl-nitro-phenyl, 3-methyl-5-chloro-benzothiophen-2-yl, 2-benzofuranyl, 3-benzothiophene, 3-phenyl-isoxazol-5-yl, 3-(2,4-di-Cl-phenyl)-isoxazol-5-yl, 3-indolyl, 5-Br-thiophen-2-yl, naphthyl, A$^1$ is —C(=Y)—X$^2$;
 Y is O; X$^2$ is —(CH$_2$)$_m$—Y$^1$—X$^3$;
  where m in the definition of X$^2$ is 0;
  Y$^1$ is O; and X$^3$ is t-Bu.

Another preferred compound of formula (I) is where $R^1$ and $R^2$ are taken together to form a compound of formula (Ib) or (Ic);
$R^3$ is —(CH$_2$)-indol-3-yl, —(CH$_2$)-phenyl, —(CH$_2$)$_4$—NH—CO—O-benzyl or —(CH$_2$)$_4$—NH$_2$;

$R^5$ is phenyl, o-OMe-phenyl, p-OMe-phenyl, p-Br-phenyl, p-nitro-phenyl, t-Bu or —CH(CH$_3$)$_2$—CO—NH—(CH$_2$)$_2$—NH$_2$; $R^6$ is H;

$R^7$ is ethyl, propyl, phenyl, p-OMe-phenyl, p-Cl-phenyl, p-Br-phenyl, p-F-phenyl, p-nitro-phenyl, m-nitro-phenyl, p-CN-phenyl, p-N$_3$-phenyl, p-phenyl-phenyl, 3-Me-4-Cl-phenyl, p-N,N-diethylamino-phenyl, 2,5-di-OMe-phenyl, 3,4-di-Cl-phenyl, 3,4-di-F-phenyl, p-OCF$_3$-phenyl, p-benzyloxy-phenyl, p-pentyl-phenyl, 3,4,5-tri-OMe-phenyl, 3-nitro-4-Cl-phenyl, 3-Cl-4-nitro-phenyl, 3-methyl-5-chloro-benzothiophen-2-yl, 2-bezofuranyl, 3-benzothiophene, 3-phenyl-isoxazol-5-yl, 3-(2,4di-Cl-phenyl)-isoxazol-5-yl, 3-indolyl, 5-Br-thiophen-2-yl, naphthyl,

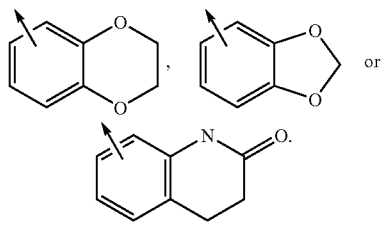

In another aspect, the present invention is directed to a compound of the formula (II),

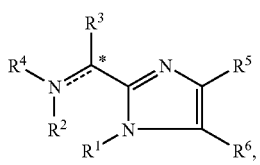

(II)

the racemic-diastereomeric mixtures and optical isomers of said compound of formula (II), the pharmaceutically-acceptable salts or prodrugs thereof or a pharmaceutically acceptable salt of said prodrug, wherein — represents an optional bond;

$R^1$ is H, —(CH$_2$)$_m$—C(O)—(CH$_2$)$_m$—Z$^1$, —(CH$_2$)$_m$—Z$^1$, —(CH$^2$)$_m$—O—Z$^1$ or —(C$_0$-C$_6$)alkyl-C(O)—NH—(CH$_2$)$_m$—Z$^3$;

$Z^1$ is an optionally substituted moiety selected from the group consisting of (C$_1$-C$_{12}$)alkyl, benzo[b]thiophene, phenyl, naphthyl, benzo[b]furanyl, thiophene, isoxazolyl, indolyl,

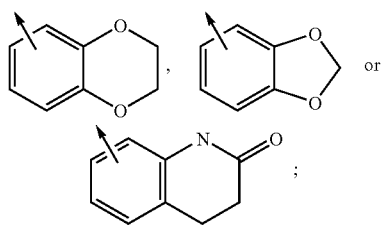

$R^2$ is H or (C$_1$-C$_6$)alkyl;

or $R^1$ and $R^2$ are taken together with the nitrogen atoms to which they are attached to form a compound of formula (IIa), (IIb) or (IIc),

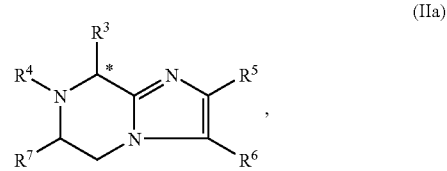
(IIa)

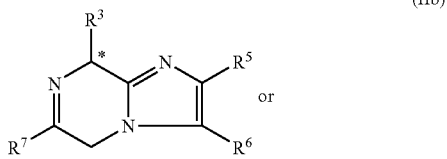
(IIb)

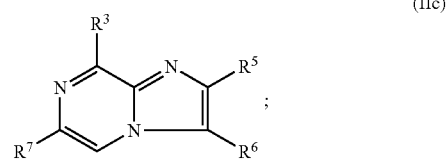
(IIc)

$R^3$ is —(CH$_2$)$_m$—E—(CH$_2$)$_m$—Z$^2$;

E is O, S, —C(O)—, —C(O)—O—, —NH—C(O)—O—, —N(C$_1$-C$_6$)alkyl-C(O)—O— or a bond;

$Z^2$ is H, (C$_1$-C$_{12}$)alkyl, amino, (C$_1$-C$_{12}$)alkylamino, N,N-di-(C$_1$-C$_{12}$)alkylamino, (C$_1$-C$_{12}$)alkylguanidino, or an optionally substituted moiety selected from the group consisting of phenyl, indolyl, imidazolyl, thiophene, benzothiophene, pyridinyl and naphthyl;

$R^4$ is H or —(CH$_2$)$_m$—A$^1$;

$A^1$ is —C(=Y)—N(X$^1$X$^2$), —C(=Y)—X$^2$, —C(=NH)—X$^2$ or X$^2$;

Y is O or S;

$X^1$ is H, (C$_1$-C$_{12}$)alkyl, —(CH$_2$)$_m$—NH—(C$_1$-C$_6$)alkyl, —(CH$_2$)$_m$-N-di-(C$_1$-C$_6$)alkyl or —(CH$_2$)$_m$-aryl;

$X^2$ is —(CH$_2$)$_m$—Y$^1$—X$^3$ or optionally substituted (C$_1$-C$_{12}$)alkyl;

$Y^1$ is O, S, NH, C=O, (C$_2$-C$_{12}$)alkenyl having one or more double bonds, —NH—CO—, —CO—NH—, —NH—CO—O—(CH$_2$)$_m$—, —C≡C—, SO$_2$ or a bond;

$X_3$ is H, an optionally substituted moiety selected from the group consisting of (C$_1$-C$_{12}$)alkyl, (C$_3$-C$_8$)cycloalkyl, (C$_1$-C$_{12}$)alkoxy, aryloxy, (C$_1$-C$_{12}$)alkylamino, N,N-di-(C$_1$-C$_{12}$)alkylamino, —CH-di-(C$_1$-C$_{12}$)alkoxy, pyrrolidinyl, pyridinyl, thiophene, imidazolyl, piperidinyl, piperazinyl, benzothiazolyl, furanyl, indolyl, morpholino, benzo[b]furanyl, quinolinyl, isoquinolinyl, —(CH$_2$)$_m$-phenyl, naphthyl, fluorenyl, phthalamidyl, pyrimidinyl,

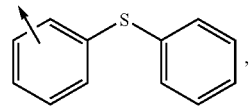

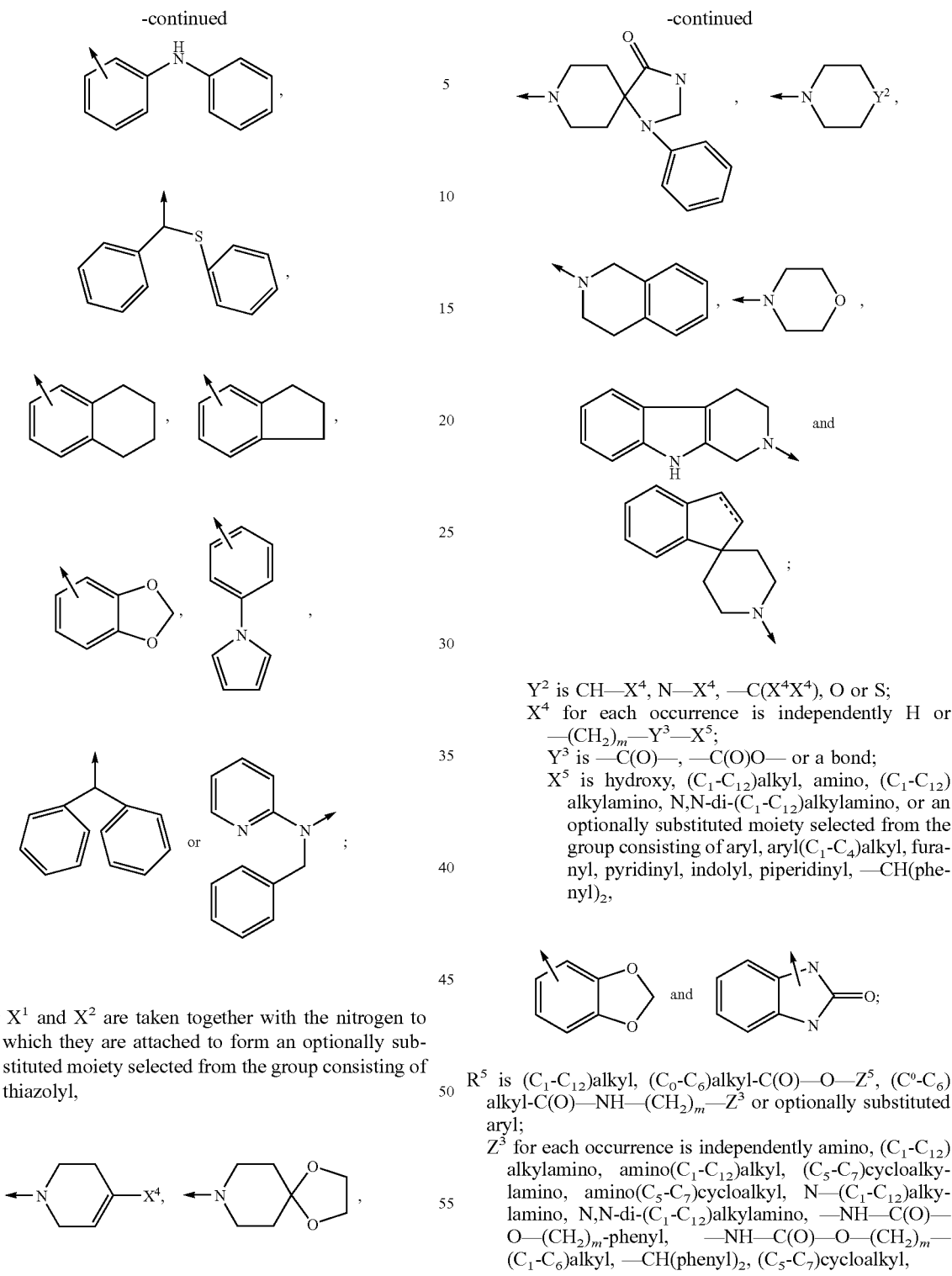

or an optionally substituted moiety selected from the group consisting of imidazolyl, pyridinyl, morpholino, piperidinyl, piperazinyl, pyrazolidinyl, furanyl, phenyl, indolyl and thiophene, provided that when m is 0 in the formula for $R^5$ then $Z^3$ is not —NH—C(O)—O—$(CH_2)_m$-phenyl or —NH—C(O)—O—$(CH_2)_m$—$(C_1$-$C_6)$alkyl;

$R^6$ is H or $(C_1$-$C_6)$alkyl;

$R^7$ is $(C_1$-$C_{12})$alkyl or —$(CH_2)_m$—$Z^4$;

$Z^4$ is an optionally substituted moiety selected from the group consisting of phenyl, naphthyl, indolyl, thiophene, benzo[b]furan, benzo[b]thiophene, isoxazolyl,

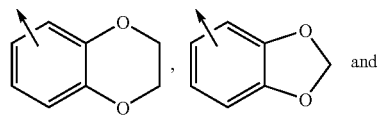, and

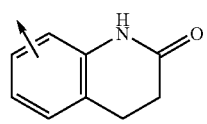

$Z^5$ is H, $(C_1$-$C_{12})$alkyl, or —$(CH_2)_m$-aryl;

wherein an optionally substituted moiety is optionally substituted by one or more substituents, each independently selected from the group consisting of Cl, F, Br, I, $CF_3$, CN, $N_3$, $NO_2$, OH, $SO_2NH_2$, —$OCF_3$, $(C_1$-$C_{12})$alkoxy, —$(CH_2)_m$-phenyl-$(X^6)_n$, —S-phenyl-$(X^6)_n$, —S—$(C_1$-$C_{12})$alkyl, —O—$(CH_2)_m$-phenyl-$(X^6)_n$, —$(CH_2)_m$—C(O)—O—$(C_1$-$C_6)$alkyl, —$(CH_2)_m$—C(O)—$(C_1$-$C_6)$alkyl, —O—$(CH_2)_m$—$NH_2$, —O—$(CH_2)_m$—NH—$(C_1$-$C_6)$alkyl, —O—$(CH_2)_m$—N-di-$((C_1$-$C_1)$alkyl), —$(C_0$-$C_{12})$alkyl-$(X^6)_n$ and —$(CH_2)_m$-phenyl-$X^7$;

$X^6$ for each occurrence is independently selected from the group consisting of hydrogen, Cl, F, Br, I, $NO_2$, $N_3$, CN, OH, —$CF_3$, —$OCF_3$, $(C_1$-$C_{12})$alkyl, $(C_1$-$C_{12})$alkoxy, —$(CH_2)_m$—$NH_2$, —$(CH_2)_m$—NH—$(C_1$-$C_6)$alkyl, —$(CH_2)_m$—N-di-$((C_1$-$C_8)$alkyl) and —$(CH_2)_m$-phenyl;

$X^7$ is —NH—C(=NH.HI)—$X^8$, wherein $X^8$ is thiophene, $(C_1$-$C_6)$alkyl or phenyl;

m for each occurrence is independently 0 or an integer from 1 to 6; and n for each occurrence is independently an integer from 1 to 5;

provided that:

(a) when $R^5$ is $(C_1$-$C_{12})$alkyl, or —C(O)—O—$Z^5$ and $Z^5$ is $(C_1$-$C_{12})$alkyl or optionally substituted aryl; $R^6$ is H or $(C_1$-$C_6)$alkyl; $R^7$ is $(C_1$-$C_{12})$alkyl or $Z^4$ and $Z^4$ is thiophene or optionally substituted phenyl, then $R^3$ is not —C(O)—O—$(CH_2)_m$—Z where m is 0 and Z is H or $(C_1$-$C_{12})$alkyl or where m is 1 to 6 and Z is H;

(b) when $R^5$ is $(C_1$-$C_{12})$alkyl or optionally substituted phenyl; $R^6$ is H or $(C_1$-$C_6)$alkyl; $R^7$ is $(C_1$-$C_{12})$alkyl and $R^3$ is —O—$(CH_2)$—$Z^2$, then $Z^2$ is not an optionally substituted moiety selected from the group consisting of phenyl, indolyl, imidazolyl, thiophene, benzothiophene, pyridinyl, and naphthyl; and (c) when $R^5$ is H or $(C_1$-$C_{12})$alkyl; $R^6$ is $(C_1$-$C_6)$alkyl; $R^7$ is $(C_1$-$C_{12})$alkyl; and $R^3$ is —O-$Z^2$ or —S-$Z^2$, then $Z^2$ is not an optionally substituted moiety selected from the group consisting of phenyl, naphthyl, thiophene, benzothienyl and indolyl.

A preferred group of compounds of formula (II) have the following formula:

(R configuration)

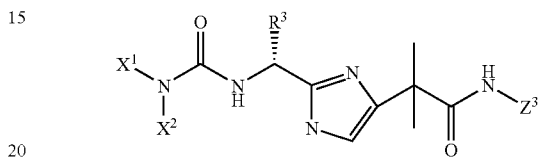

wherein $Z^3$ is —$CH_2$—$NH_2$, —$(CH_2)_2$—$NH_2$, —$(CH_2)_3$—$NH_2$ or ; and

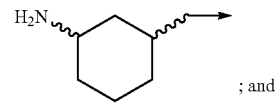

; and $X^1$ is —$(CH_2)_2$—$N(CH_3)_2$ and $X^2$ is benzyl; or $X^1$ and $X^2$ are taken together with the nitrogen atom to which they are attached, to form

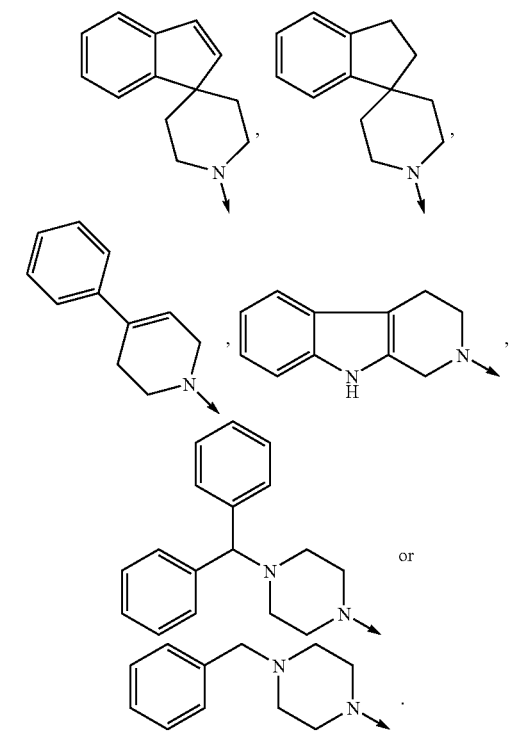

Another preferred group of compounds of formula (II) have the following formula:

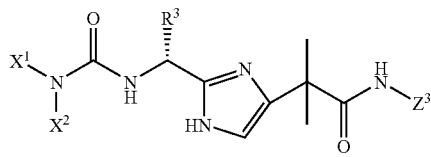

(R configuration)

wherein
$Z^3$ is

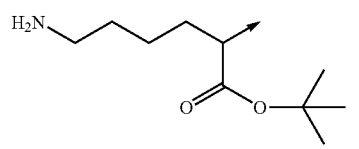

or

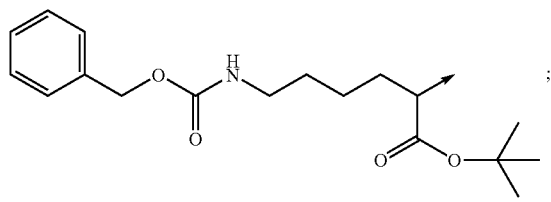

and $X^1$ is —$(CH_2)_2$—$N(CH_3)_2$ and $X^2$ is benzyl; or
$X^1$ and $X^2$ are taken together with the nitrogen atom to which they are attached, to form

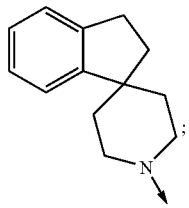

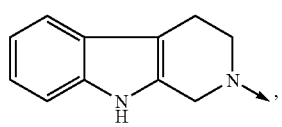

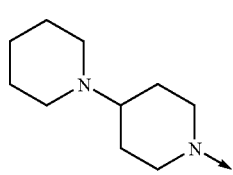

Yet another preferred group of compounds of formula (II) have the following formula:

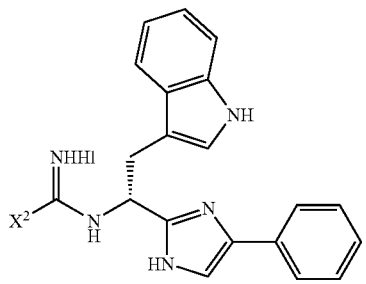

wherein $X^2$ is p-chloro-phenyl, p-methoxy-phenyl, 2,4difluoro-phenyl or thienyl.

Still another preferred group of compounds of formula (II) have the following formula:

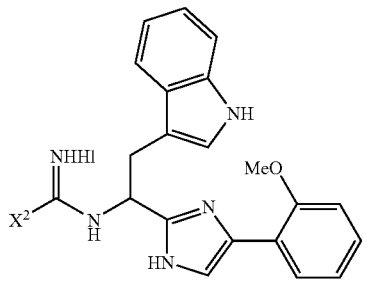

wherein $X^2$ is p-chloro-phenyl, p-methoxy-phenyl, phenyl or thienyl.

Further still a preferred compound of formula (II) has the following formula:

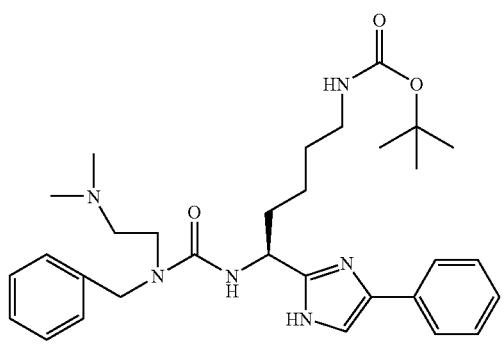

Further still another preferred compound of formula (II) has the following formula:

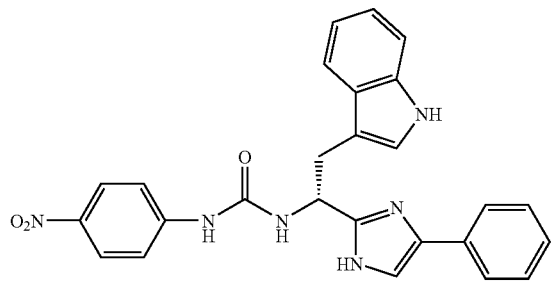

Further still another preferred group of compounds of formula (II) have the following formula:

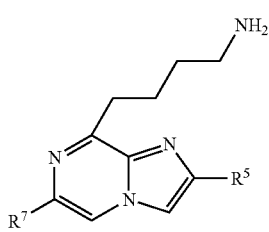

wherein
R⁵ is

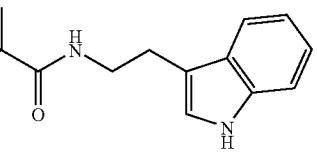

and R⁷ is m-nitro-phenyl or 2-phenyl-ethyl; or
R⁵ is

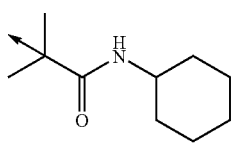

and R⁷ is

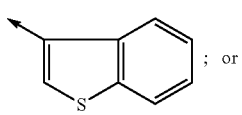

; or

R⁵ is

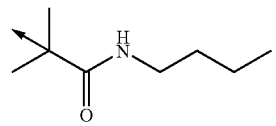

and R⁷ is 3,4-dichlorophenyl or

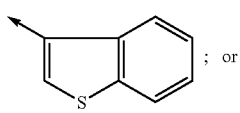

; or

R⁵ is

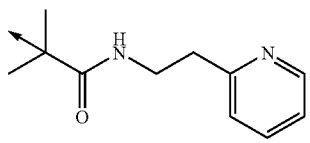

and R⁷ is 3,4-dichlorophenyl.

In another aspect, this invention is directed to a pharmaceutical composition comprising one or more of a compound of formula (I) or formula (II), as defined hereinabove, and a pharmaceutically acceptable carrier.

In another aspect, the present invention is directed to a method of eliciting an agonist effect from one or more of a somatostatin subtype receptor in a subject in need thereof, which comprises administering a compound of formula (I) or formula (II) or a pharmaceutically acceptable salt thereof to said subject.

In another aspect, the present invention is directed to a method of eliciting an antagonist effect from one or more of a somatostatin subtype receptor in a subject in need thereof, which comprises administering a compound of formula (I) or formula (II) or a pharmaceutically acceptable salt thereof to said subject.

In another aspect, the present invention is directed to a method of binding one or more of a somatostatin subtype receptor in a subject in need thereof, which comprises administering a compound of formula (I) or formula (II) or a pharmaceutically acceptable salt thereof to said subject.

In another aspect, the present invention is directed to a method of treating acromegaly, restenosis, Crohn's disease, systemic sclerosis, external and internal pancreatic pseudocysts and ascites, VIPoma, nesidoblastosis, hyperinsulinism, gastrinoma, Zollinger-Ellison syndrome, diarrhea, AIDS related diarrhea, chemotherapy related diarrhea, scleroderma, Irritable Bowel Syndrome, pancreatitis, small bowel obstruction, gastroesophageal reflux, duodenogastric reflux, Cushing's Syndrome, gonadotropinoma, hyperparathyroidism, Graves' Disease, diabetic neuropathy, Paget's disease, polycystic ovary disease, cancer, cancer cachexia, hypotension, postprandial hypotension, panic attacks, GH secreting adenomas or TSH secreting adenomas, in a subject in need thereof, which comprises administering a compound of formula (I) or formula (II) or a pharmaceutically acceptable salt thereof to said subject.

In another aspect, the present invention is directed to a method of treating diabetes mellitus, hyperlipidemia, insulin insensitivity, Syndrome X, angiopathy, proliferative retinopathy, dawn phenomenon, Nephropathy, peptic ulcers, enterocutaneous and pancreaticocutaneous fistula, Dumping syndrome, watery diarrhea syndrome, acute or chronic pancreatitis, gastrointestinal hormone secreting tumors, angiogenesis, inflammatory disorders, chronic allograft rejection, angioplasty, graft vessel bleeding or gastrointestinal bleeding in a subject in need thereof, which comprises administering a compound of formula (I) or formula (II) or a pharmaceutically acceptable salt thereof to said subject.

In another aspect, the present invention is directed to a method of inhibiting the proliferation of helicobacter pylori in a subject in need thereof, which comprises administering a compound of formula (I) or formula (II) or a pharmaceutically acceptable salt thereof, to said subject.

DETAILED DESCRIPTION OF THE INVENTION

One of ordinary skill will recognize that certain substituents listed in this invention may have reduced chemical stability when combined with one another or with heteroatoms in the compounds. Such compounds with reduced chemical stability are not preferred.

In general, the compounds of Formula I or II can be made by processes which include processes known in the chemical arts for the production of compounds. Certain processes for the manufacture of Formula I or II compounds are provided as further features of the invention and are illustrated by the following reaction schemes and examples.

In the above structural formulae and throughout the instant application, the following terms have the indicated meanings unless expressly stated otherwise:

The alkyl groups are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl and the like.

When the definition "$C_0$-alkyl" occurs in the definition, it means a single covalent bond.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term halogen or halo is intended to include the halogen atoms fluorine, chlorine, bromine and iodine.

The term cycloalkyl is intended to include a mono-cycloalkyl group or a bi-cycloalkyl group of the indicated carbon number known to those of skill in the art.

The term aryl is intended to include aromatic rings known in the art, which can be mono-cyclic, bi-cyclic or tri-cyclic, such as phenyl, naphthyl and anthracene.

The term heterocycle includes mono-cyclic, bi-cyclic and tri-cyclic systems having one or more heteroatoms, such as oxygen, nitrogen and/or sulfur. The ring systems may be aromatic, for example pyridine, indole, quinoline, pyrimidine, thiophene (also known as thienyl), furan, benzothiophene, tetrazole, dihydroindole, indazole, N-formylindole, benzimidazole, thiazole, and thiadiazole. The ring systems may be non-aromatic, for example pyrrolidine, piperidine, morpholine and the like.

The chemist of ordinary skill will recognize that certain combinations of heteroatom-containing substituents listed in this invention define compounds which will be less stable under physiological conditions. Accordingly, such compounds are less preferred.

When a chemical structure as used herein has an arrow emanating from it, the arrow indicates the point of attachment. For example, the structure

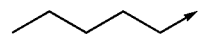

is a pentyl group. When an arrow is drawn through a cyclic moiety, the arrow indicates that the cyclic moiety can be attached at any of the available bonding points, for example

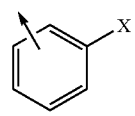

means that the phenyl can be bonded ortho, meta or para to the X group. When an arrow is drawn through a bi-cyclic or a tri-cyclic moiety, the arrow indicates that the bi-cyclic or tri-cyclic ring can be attached at any of the available bonding points in any of the rings, for example

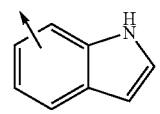

means that the indole is bonded either through the phenyl portion of the ring or the nitrogen containing ring portion.

The compounds of the instant invention have at least one asymmetric center as noted by the asterisk in the structural formula (I), (Ia) and (Ib), above. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the scope of the instant invention.

The instant compounds can be generally isolated in the form of their pharmaceutically acceptable acid addition salts, such as the salts derived from using inorganic and organic acids. Examples of such acids are hydrochloric, nitric, sulfuric, phosphoric, acetic, propionic, maleic, succinic, D-tartaric, L-tartaric, malonic, methane sulfonic and the like. In addition, certain compounds containing an acidic function such as a carboxy can be isolated in the form of their inorganic salt in which the counter-ion can be selected from sodium, potassium, lithium, calcium, magnesium and the like, as well as from organic bases.

The pharmaceutically acceptable salts are formed by taking about 1 equivalent of a compound of formula (I) or (II) and contacting it with about 1 equivalent of the appropriate corresponding acid of the salt which is desired. Work-up and isolation of the resulting salt is well-known to those of ordinary skill in the art.

As is known in the art, agonists and antagonists of somatostatin are useful for treating a variety of medical conditions and diseases, such as inhibition of *H. pylori* proliferation, acromegaly, restenosis, Crohn's disease, systemic sclerosis, external and internal pancreatic pseudocysts and ascites, VIPoma, nesidoblastosis, hyperinsulinism, gastrinoma, Zollinger-Ellison Syndrome, diarrhea, AIDS related diarrhea, chemotherapy related diarrhea, scleroderma, Irritable Bowel Syndrome, pancreatitis, small bowel obstruction, gastroesophageal reflux, duodenogastric reflux and in treating endocrinological diseases and/or conditions, such as Cushing's Syndrome, gonadotropinoma, hyperparathyroidism, Graves' Disease, diabetic neuropathy, Paget's disease, and polycystic ovary disease; in treating various types of cancer such as thyroid cancer, hepatome, leukemia, meningioma and conditions associated with cancer such as cancer cachexia; in the treatment of such conditions as hypotension such as orthostatic hypotension and postprandial hypotension and panic attacks; GH secreting adenomas (Acromegaly) and TSH secreting adenomas. Activation of type 2 but not type 5 subtype receptor has been associated with treating prolactin secreting adenomas. Other indications associated with activation of the somatostatin subtypes are inhibition of insulin and/or glucagon and more particularly diabetes mellitus, hyperlipidemia, insulin insensitivity, Syndrome X, angiopathy, proliferative retinopathy, dawn phenomenon and Nephropathy; inhibition of gastric acid secretion and more particularly peptic ulcers, enterocutaneous and pancreaticocutaneous fistula, Dumping syndrome, watery diarrhea syndrome, acute or chronic pancreatitis and gastrointestinal hormone secreting tumors; inhibition of angiogenesis, treatment of inflammatory disorders such as arthritis; chronic allograft rejection; angioplasty; preventing graft vessel and gastrointestinal bleeding. Somatostatin agonists can also be used for decreasing body weight in a patient. Accordingly, the compounds of the instant invention are useful for the foregoing methods.

Accordingly, the present invention includes within its scope pharmaceutical compositions comprising, as an active ingredient, at least one of the compounds of Formula (I) or (II) in association with a pharmaceutically acceptable carrier.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention can be administered in a sustained release composition such as those described in the following patents. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. application Ser. No. 08/929,363 filed Sep. 9, 1997, teaches polymeric sustained release compositions comprising a bioactive agent and chitosan. U.S. application Ser. No. 08/740,778 filed Nov. 1, 1996, teaches sustained release compositions comprising a bioactive agent and cyclodextrin. U.S. application Ser. No. 09/015,394 filed Jan. 29, 1998, teaches absorbable sustained release compositions of a bioactive agent. The teachings of the foregoing patents and applications are incorporated herein by reference.

In general, an effective dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment, all of which are within the realm of knowledge of one of ordinary skill in the art. Generally, dosage levels of between 0.0001 to 100 mg/kg of body weight daily are administered to humans and other animals, e.g., mammals.

A preferred dosage range is 0.01 to 10.0 mg/kg of body weight daily, which can be administered as a single dose or divided into multiple doses.

Compounds of the instant invention can be and were assessed for its ability to bind to a somatostatin subtype receptor according to the following assays. Human somatostatin subtype receptor binding studies:

The affinity of a compound for human somatostatin subtype receptors 1 to 5 ($sst_1$, $sst_2$, $sst_3$, sst4 and $sst_5$, respectively) is determined by measuring the inhibition of [$^{125}$I-Tyr$^{11}$]SRIF-14 binding to CHO—K1 transfected cells.

The human $sst_1$ receptor gene was cloned as a genomic fragment. A 1.5 Kb Pstl-Xmnl segment containing 100 bp of the 5'-untranslated region, 1.17 Kb of the entire coding region, and 230 bp of the 3'-untranslated region was modified by the Bg1ll linker addition. The resulting DNA fragment was subcloned into the BamHl site of a pCMV-81 to produce the mammalian expression plasmid (provided by Dr. Graeme Bell, Univ. Chicago). A clonal cell line stably expressing the sst, receptor was obtained by transfection into CHO—K1 cells (ATCC) using the calcium phosphate co-precipitation method (1). The plasmid pRSV-neo (ATCC) was included as a selectable marker. Clonal cell lines were selected in RPMI 1640 media containing 0.5 mg/ml of G418 (Gibco), ring cloned, and expanded into culture.

The human $sst_2$ somatostatin receptor gene, isolated as a 1.7 Kb BamHI-HindIII genomic DNA fragment and subcloned into the plasmid vector pGEM3Z (Promega), was kindly provided by Dr. G. Bell (Univ. of Chicago). The mammalian cell expression vector is constructed by inserting the 1.7 Kb BamH1-HindII fragment into compatible restriction endonuclease sites in the plasmid pCMV5. A clonal cell line is obtained by transfection into CHO—K1 cells using the calcium phosphate co-precipitation method. The plasmid pRSV-neo is included as a selectable marker.

The human $sst_3$ was isolated at genomic fragment, and the complete coding sequence was contained within a 2.4 Kb BamHI/HindIII fragment. The mammalian expression plasmid, pCMV-h3 was constructed by inserting the a 2.0 Kb NcoI-HindIII fragment into the EcoR1 site of the pCMV vector after modification of the ends and addition of EcoR1 linkers. A clonal cell line stably expressing the $sst_3$ receptor was obtained by transfection into CHO-K1 cells (ATCC) using the calcium phosphate co-precipitation method. The plasmid pRSV-neo (ATCC) was included as a selectable marker. Clonal cell lines were selected in RPMI 1640 media containing 0.5 mg/ml of G418 (Gibco), ring cloned, and expanded into culture.

The human $sst_4$ receptor expression plasmid, pCMV-HX was provided by Dr. Graeme Bell (Univ. Chicago). The vector contains the 1.4 Kb Nhel-Nhel genomic fragment encoding the human $sst_4$, 456 bp of the 5'-untranslated region and 200 bp of the 3'-untranslated region, clone into the Xbal/EcoR1 sites of PCMV-HX. A clonal cell line stably expressing the $sst_4$ receptor was obtained by transfection into CHO-K1 cells (ATCC) using the calcium phosphate co-precipitation method. The plasmid pRSV-neo (ATCC) was included as a selectable marker. Clonal cell lines were selected in RPMI 1640 media containing 0.5 mg/ml of G418 (Gibco), ring cloned, and expanded into culture.

The human $sst_5$ gene was obtained by PCR using a λ genomic clone as a template, and kindly provided by Dr. Graeme Bell (Univ. Chicago). The resulting 1.2 Kb PCR fragment contained 21 base pairs of the 5'-untranslated region, the full coding region, and 55 bp of the 3'-untranslated region. The clone was inserted into EcoR1 site of the plasmid pBSSK(+). The insert was recovered as a 1.2 Kb HindIII-XbaI fragment for subcloning into pCVM5 mammalian expression vector. A clonal cell line stably expressing the $SST_5$ receptor was obtained by transfection into CHO—K1 cells (ATCC) using the calcium phosphate co-precipitation method. The plasmid pRSV-neo (ATCC) was included as a selectable marker. Clonal cell lines were selected in RPMI 1640 media containing 0.5 mg/ml of G418 (Gibco), ring cloned, and expanded into culture. CHO-K1 cells stablie expressing one of the human sst receptor are grown in RPMI 1640 containing 10% fetal calf serum and 0.4 mg/ml geneticin. Cells are collected with 0.5 mM EDTA, and centrifuged at 500 g for about 5 min. at about 4° C. The pellet is resuspended in 50 mM Tris, pH 7.4 and centrifuged twice at 500 g for about 5 min. at about 4° C. The cells are lysed by sonication and centrifuged at 39000 g for about 10 min. at about 4° C. The pellet is resuspended in the same buffer and centrifuged at 50000 g for about 10 min. at about 4° C. and membranes in resulting pellet are stored at −80° C.

Competitive inhibition experiments of [$^{125}$I-Tyr$^{11}$]SRIF-14 binding are run in duplicate in polypropylene 96 w II plates. Cell membranes (10 μg protein/well) are incubated with [$^{125}$I-Tyr$^{11}$]SRIF-14 (0.05 nM) for about 60 min. at about 37° C. in 50 mM HEPES (pH 7.4), 0.2% BSA, 5 mM $MgCl_2$, 200 KIU/ml Trasylol, 0.02 mg/ml bacitracin and 0.02 mg/ml phenylmethylsulphonylfluoride.

Bound from free [$^{125}$I-Tyr$^{11}$]SRIF-14 is separated by immediate filtration through GF/C glass fiber filter plate (Unifilter, Packard) presoaked with 0.1% polyethylenimine (P.E.I.), using Filtermate 196 (Packard) cell harvester. Filters are washed with 50 mM HEPES at about 0-4° C. for about 4 sec. and assayed for radioactivity using Packard Top Count.

Specific binding is obtained by subtracting nonspecific binding (determined in the presence of 0.1 μM SRIF-14) from total binding. Binding data are analyzed by computer-assisted nonlinear regression analysis (MDL) and inhibition constant (Ki) values are determined.

The determination of whether a compound of the instant invention is an agonist or an antagonist is determined by the following assay.

Functional assay: Inhibition of CAMP intracellular production:

CHO-K1 Cells expressing human somatostatin (SRIF-14) subtype receptors are seeded in 24-well tissue culture multidishes in RPMI 1640 media with 10% FCS and 0.4 mg/ml geneticin. The medium is changed the day before the experiment.

Cells at $10^5$ cells/well are washed 2 times by 0.5 ml and fresh RPMI with 0.2% BSA supplemented with 0.5 mM (1) 3isobutyl-1-methylxanthine (IBMX) and incubated for about 5 min at about 37° C.

Cyclic AMP production is stimulated by the addition of 1 mM forskolin (FSK) for about 15-30 minutes at about 37° C.

The agonist effect of a compound is measured by the simultaneous addition of FSK (1 μM), SRIF-14 ($10^{-12}$ M to $10^{-6}$ M) and a test compound ($10^{-10}$ M to $10^{-5}$ M).

The antagonist effect of a compound is measured by the simultaneous addition of FSK (1 μM), SRIF-14 (1 to 10 nM) and a test compound ($10^{-10}$ M to $10^{-5}$ M).

The reaction medium is removed and 200 ml 0.1 N HCl is added. cAMP is measured using radioimmunoassay method (Kit FlashPlate SMP001A, New England Nuclear).

The compounds of the instant invention are synthesized according to the following procedures and examples.

SYNTHESIS OF BROMOKETONES

General Procedure: Two different methods can be applied: starting either from a carboxylic acid or an arylketone.

First method: Starting from a carboxylic acid (Macholan, L.; Skursky, L., *Chemlisty* 1955, 49, 1385-1388. Bestman, H. J., Seng, F., *Chem. Ber.,* 1963, 96, 465-469).

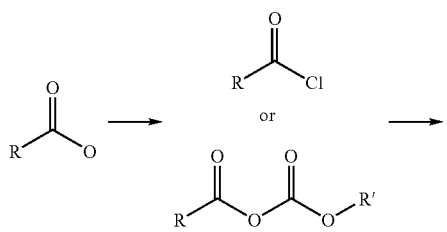

-continued

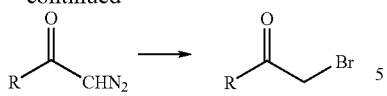

A carboxylic acid is first converted into an acyl chloride using oxalyl chloride or thionyl chloride or activated as a mixed anhydride with an alkylchloroformate (isobutylchloroformate (Krantz, A., Copp, L. J., *Biochemistry*, 1991, 30, 4678-4687) or ethylchloroformate (Podlech, J., Seebach, D., *Liebigs Ann.*, 1995, 1217-1228)) in the presence of a base (triethylamine or N-methyl morpholine).

The activated carboxyl group is then transformed into a diazoketone using ethereal diazomethane or trimethylsilyldiazomethane (Aoyama, T., Shiori, T., *Chem. Pharm. Bull.*, 1981, 29, 3249-3255) in an aprotic solvent such as diethyl ether, tetrahydrofuran or acetonitrile.

The bromination is then carried out using a brominating agent such as HBr in acetic acid, hydrobromic acid in water or in diethyl ether.

Preparation 1

1-Bromo-3-(4-chloro-phenoxy)-3-methyl-butan-2-one

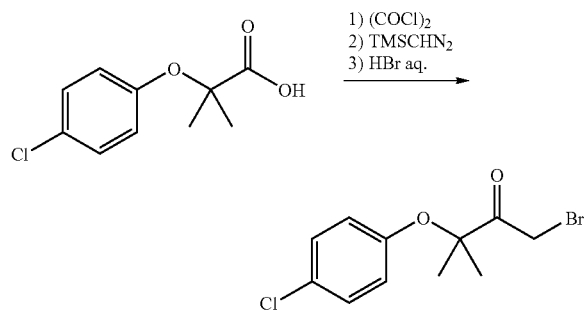

To a solution of chloro-4-phenoxy-2-isobutyric acid (2.15 g, 10 mmol) in 10 ml of anhydrous dichloromethane at about 0° C. were added oxalyl chloride (5.5 ml, 11 mmol of a 2M solution in dichloromethane) and DMF (2 drops, catalytic amount) via a septum under nitrogen atmosphere. The solution was stirred and allowed to warm up to room temperature over about 3 hrs. Concentration under reduced pressure afforded the crude acid chloride which was used directly without further purification.

The acylchloride was added dropwise at about 0° C. to a solution of TMSCHN$_2$ (11 ml, 22 mmol) in THF-acetonitrile (1:1, 10 ml). The mixture was stirred at about 25° C. for about 1 hour and then evaporated in vacuo.

A solution of the diazoketone in dichloromethane (10 ml) was added dropwise during about 10 minutes to a vigorously stirred mixture of concentrated hydrobromic acid (5 ml) in dichloromethane (20 ml). Nitrogen was evolved and a slight temperature rise occurred. After stirring for about a further 10 min., the mixture was diluted and the organic layer was washed with water (3 times 20 ml), dried over magnesium sulfate and evaporated. Flash chromatography of the residue eluting with AcOEt/Heptane (1:4) afforded the desired product with a yield of 79% (2.3 g).

$^1$H-NMR in CDCl$_3$ (100 MHz) δ: 7.05 (m, 4H, arom. H), 4.41 (s, 2H, CH$_2$), 1.53 (s, 6H, 2 CH$_3$).

Preparations 2-6

The following compounds were prepared analogously to the procedure described for Preparation 1:

| Prep. # | R | Yield |
|---|---|---|
| 2 | benzyl * | 78% |
| 3 | phenethyl * | 60% |
| 4 | tert-butyl * | 10% |
| 5 | 2-(4-chlorophenoxy)-2-methylpropyl * | 79% |
| 6 | (1H-indol-3-yl)methyl | 41% |

*Compounds already described in literature.

Second Method: Starting from a Methyl Ketone

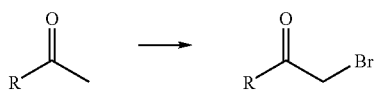

A methyl ketone is converted to a bromoketone by using different brominating agents:

CuBr$_2$ (King, L. C., Ostrum, G. K., *J. Org. Chem.*, 1964, 29, 3459-3461) heated in AcOEt or dioxane.

N-bromosuccinimide in CCl$_4$.

Bromine in glacial acetic acid or sulfuric acid.

Phenyltrimethylammonium tribromide (Sanchez, J. P., Parcell, R. P., *J. Heterocyclic Chem.*, 1988, 25, 469-474) at 20-80° C. in an aprotic solvent such as THF.

Use of a polymer supported brominating agent such as perbromide on Amberlyst A-26, poly(vinylpyridinium hydrobromide perbromide) resin (Frechet, J. M. J., Farrall, M. J., *J. Macromol. Sci. Chem.*, 1977, 507-514) in a protic solvent such as methanol at about 20-35° C. for about 2-100 h.

Preparation 7

1-Bromo-2-(3,4,5-trimethoxy-phenyl)-ethanone

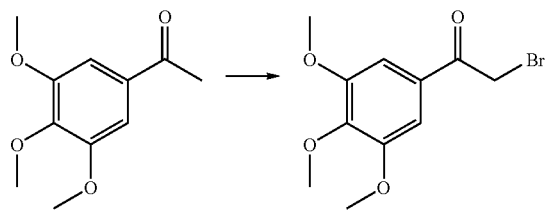

To a solution of 3,4,5-trimethoxyacetophenone (2.1 g, 10 mmol) in methanol (30 ml) was added pyridine hydrobromide perbromide polymer (1.4 eq). The resulting mixture was shaken at room temperature for about 2 hours and the reaction was stopped by filtration. The polymer was washed with methanol and the filtrate was evaporated in vacuo. The product was then purified by flash chromatography (AcOEt/Heptane, 1:4) affording 1.5 g (53%) of a white solid.

$^1$H-NMR in CDCl$_3$ (100 MHz) δ: 7.2 (s, 2H, H arom.), 4.4 (s, 2H, CH$_2$), 3.9 (m, 9H, 3 OCH$_3$).

Preparations 8-17

The following compounds were prepared analogously to the procedure described for Preparation 7:

| Prep. # | R | Reaction time (h) | Yield |
|---|---|---|---|
| 8 | benzothiophen-3-yl* | 8 | 78 |
| 9 | benzofuran-2-yl* | 7 | 72 |
| 10 | 2-chloro-5-nitrophenyl* | 85 | 62 |
| 11 | 4-butylphenyl* | 2 | 62 |
| 12 | 5-bromothiophen-2-yl* | 10 | 56 |
| 13 | 3,4,5-trimethoxyphenyl* | 2 | 53 |
| 14 | 3,4-difluorophenyl* | 8.5 | 27 |
| 15 | indol-3-yl | 3 | 43 |
| 16 | 2-(methoxycarbonyl)propan-2-yl | 3 | 77 |
| 17 | 4-benzyloxyphenyl* | 3 | 95 |

*Compound already described in literature.

Synthesis of Imidazoyl Compounds

General Procedure: An amino acid is transformed to its cesium salt using cesium carbonate in a polar solvent such as DMF/H$_2$O (1:1) or EtOH/H$_2$O (1:1). An ester is then obtained using an appropriate bromoketone in a polar aprotic solvent such as dry DMF. The cesium bromide formed is filtered off and ammonium acetate is added in an aprotic solvent having a high boiling point such as xylene or toluene or in a protic acidic solvent such as acetic acid. The mixture is refluxed using a Dean-Stark trap for about 0.5-10 hours. In the scheme immediately below, PG is a protecting group, preferably a carbamate, such as t-Boc or benzyl carbamate.

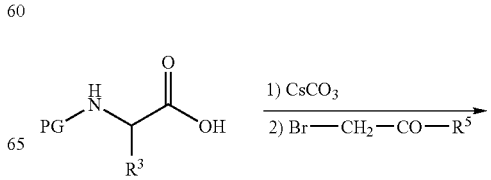

-continued

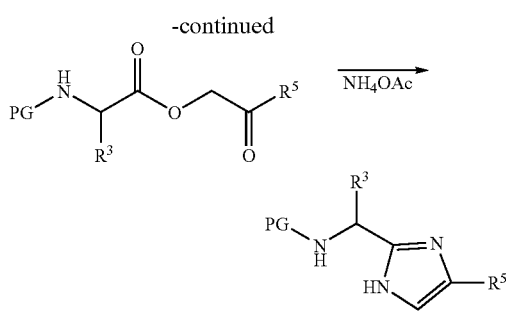

EXAMPLE 1

2-{(1S)-1-[tertbutoxycarbonylamino]-2-[(1H)-indol-3-yl]ethyl}-4-(2-methoxyphenyl)-1H-imidazole

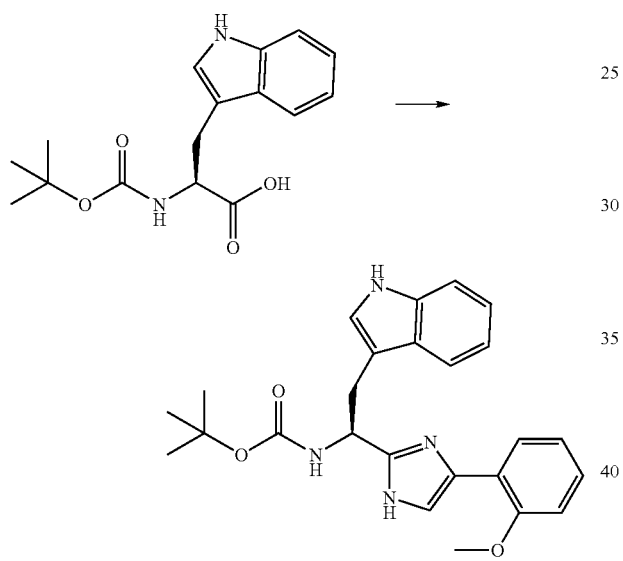

A solution of Boc-(D,L)-Trp-OH (10 g, 32.8 mmol) and cesium carbonate (0.5 eq., 5.34 g) in EtOH/H$_2$O (1:1, 70 ml) was shaken for about 30 minutes at room temperature, and then concentrated in vacuo at about 40° C.

To the resulting salt in 40 mL of dry DMF was added 40 ml of a solution of 2-bromo-2'-methoxyacetophenone (7.66 g, 1 eq.) in dry DMF. The mixture was stirred for about 1 hr at room temperature under argon and then concentrated under reduced pressure. Ethyl acetate was added (100 ml), the mixture filtered, and the CsBr washed with ethyl acetate. The filtrate was then concentrated under reduced pressure.

A solution of the foregoing filtrate and ammonium acetate (50.5 9, 20 eq.) in xylene (240 ml) was refluxed for about 3 hours at about 150° C. Excess NH$_4$OAc and H$_2$O were removed using a Dean-Stark trap. The progress of the reaction was monitored by t.l.c. (eluent: CH$_2$Cl$_2$:MeOH, 95:5). The mixture was then concentrated under reduced pressure. The resulting residue was dissolved in ethyl acetate (100 ml) and washed with saturated aqueous NaHCO$_3$ solution until basic pH, and with brine until neutral pH. The organic layer was then dried over MgSO$_4$, and concentrated under reduced pressure.

Purification of the resulting residue by flash chromatography (eluent: CH$_2$Cl$_2$:MeOH, 95:5) afforded the desired compound (8.7 g, yield: 61%).

$^1$H-NMR (CDCl$_3$, 100 MHz) δ: 8.00 (s, 1H, NH), 7.80 (m, 2H, arom. H), 7.20 (m, 9H, arom. H, NH), 5.40 (m, 1H, NH), 5.10 (m, 1H, CH), 3.80 (s, 3H, OCH$_3$), 3.50 (m, 2H, CH$_2$), 1.50 (s, 9H, 6 CH$_3$). LC/MS: m/z=433.3 (M+H).

EXAMPLE 2

N-[2-tertbutoxycarbonylamino ethyl]-2-{2-[(1S)-1-(tertbutoxycarbonylamino)-2-(1H)-indol-3-yl)ethyl]-1H-imidazol-4-yl}-isobutyramide

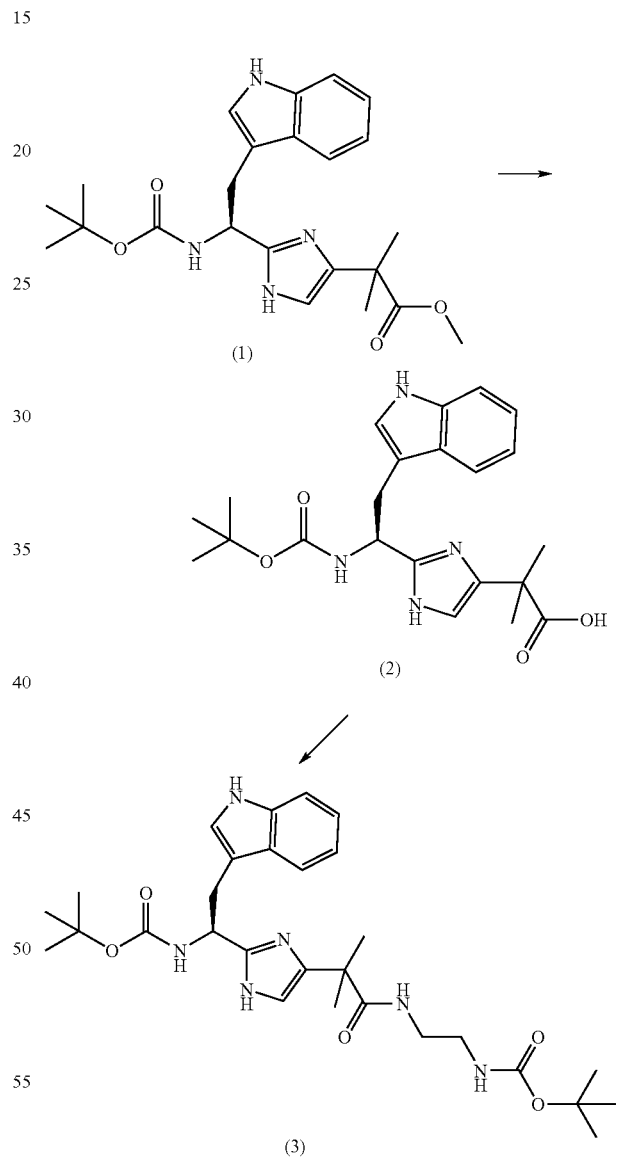

A solution of the 2-{2-[(1S)-1-(tertbutoxycarbonylamino)-2-(indol-3-yl)ethyl]-1H-imidazol-4-yl}-2-methylpropionic acid-methyl ester 1 (2.6 g, 6 mmol), (prepared according to the procedure described in Example 1) and LiOH.H$_2$O (1.7 g, 6.6 eq.) in THF (50 ml) were stirred at about 80° C. for about 3 hours. The progress of the reaction was monitored by t.l.c. (CH$_2$Cl$_2$:MeOH, 95:5). The resulting mixture was then concentrated in vacuo. About 50 ml of water was added to the residue which was then acidified with glacial acetic acid until about pH 5. The product of the reaction was then extracted with ethyl acetate (3×50 ml) and washed with brine until neutral pH. The organic layer was dried with MgSO₄, and concentrated under reduced pressure. The resulting intermediate 2 was obtained after crystallization in diethyl ether with a yield of 80% (2 g). ¹H-NMR (400 MHz, DMSO) δ: 10.9 (s, 1H, NH), 7.1 (m, 7H, arom. H, NH), 5.00 (m, 1H, CH), 3.3 (m, 2H, CH₂), 1.3 (m, 15H, 5 CH₃). LC/MS: m/z=525.1 (M+TFA), m/z=413.2 (M+H).

The 2-{2-[(1S)-1-(tertbutoxycarbonylamino)-2-[(1H)-indol-3-yl]ethyl]-1H-imidazol-4-yl}-2-methyl-propionic acid 2 can be activated preferentially by carbonyldiimidazole in an aprotic solvent such as THF or DMF at about 20-100° C. for about 1-4 hours.

A solution of the acid 2 (1 g, 2.4 mmol) and carbonyldiimidazole (0.39 g, 2.4 mmol) in dry THF (20 ml) was shaken for about 1 hour at room temperature (25° C.).

N-Boc-ethylene-diamine (0.43 g, 2.7 mmol) was added and the mixture was shaken for about 1 hour at about 25° C.

The mixture was diluted in ethyl acetate (100 ml) and washed with saturated aqueous NaHCO₃ solution (2×50 ml) and brine until neutral pH. The organic layer was then dried over MgSO₄, and concentrated in vacuo.

Purification of the resulting residue by flash-chromatography (in CH₂Cl₂:MeOH, 95:5) afforded the desired product 3 with a yield of 77% (1 g).

¹H-NMR (400 MHz, DMSO) δ: 11.6 (s, 1H, NH), 10.7 (s, 1H, NH), 7.00 (m, 9H, arom. H, NH), 4.8 (m, 1H, CH), 3.00 (m, 6H, 3 CH₂), 1.3 (m, 24H, 8 CH₃). LC/MS: m/z=667.3 (M+TFA), 555.3 (M+H).

EXAMPLES 3-1178

The following compounds were prepared analogously to the procedure described for Example 1 or 2 using the appropriate starting materials, which can be obtained from commercial sources or synthesized according to methods known to those skilled in the art or as enabled by the teachings herein. Each combination of R³, R⁵ shown below, were or can be synthesized, therefore, the number of Examples are calculated by multiplying (PG(2 substituents) R³ (12 substituents)(R⁵ (49 substituents))=1176.

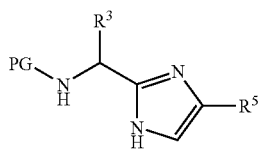

PG can also be hydrogen in the foregoing formula, R³:

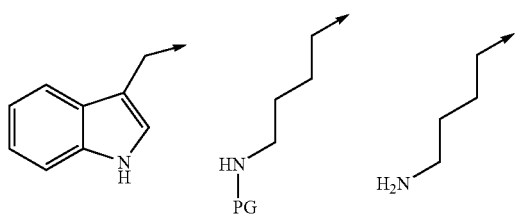

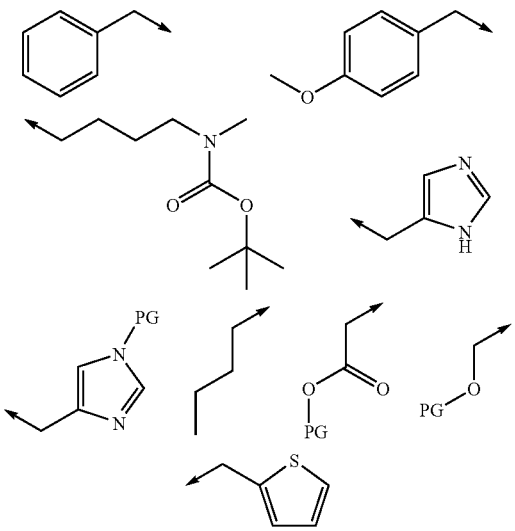

R⁵:

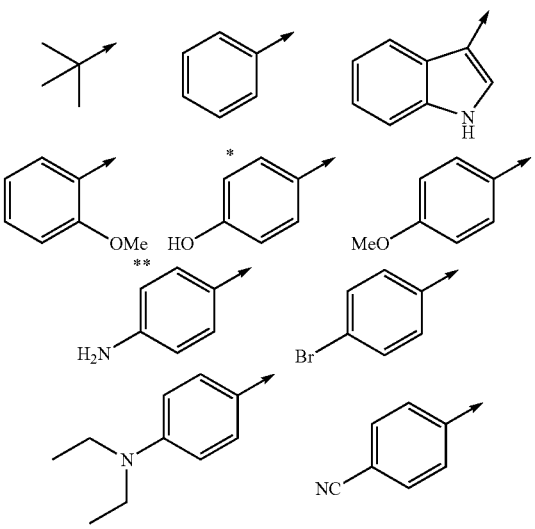

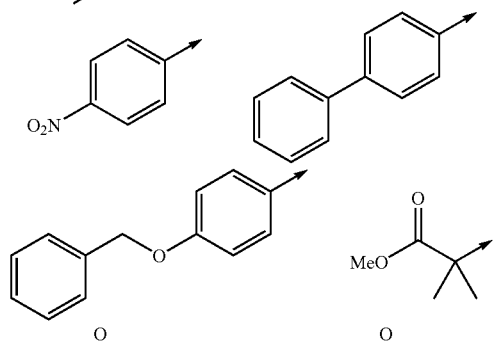

\* for this substituent, the corresponding imidazole derivative was obtained after deprotection via catalytic hydrogenation of the benzyloxyphenyl substituent
\*\* for the substituent, the corresponding imidazole derivative was obtained after deprotection via catalytic hydrogenation of the nitrophenyl substituent $Z^3$:

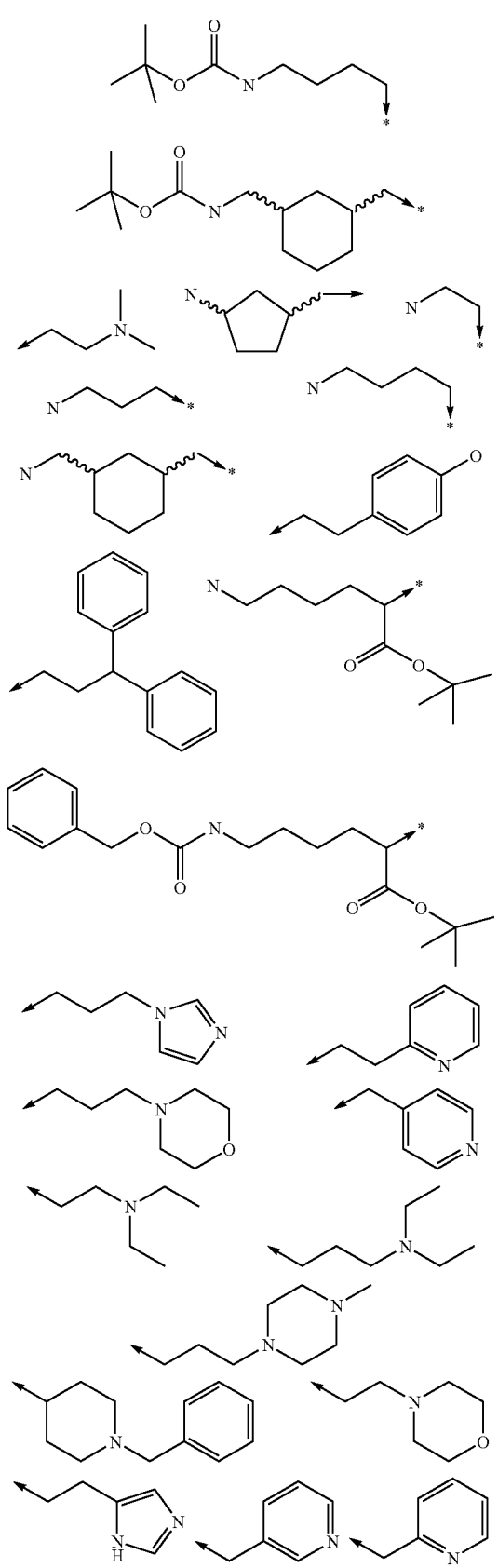
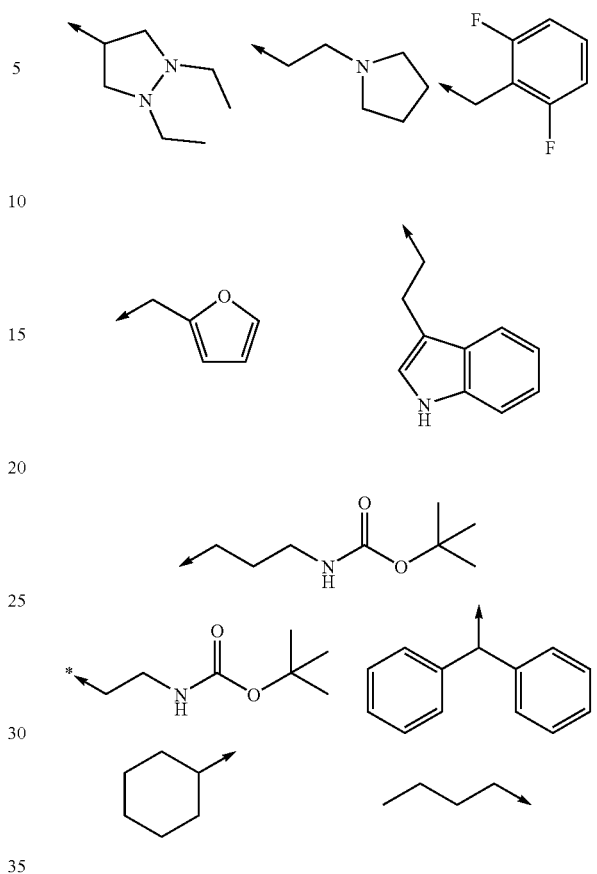

Synthesis of Amides from Imidazoyl Intermediates

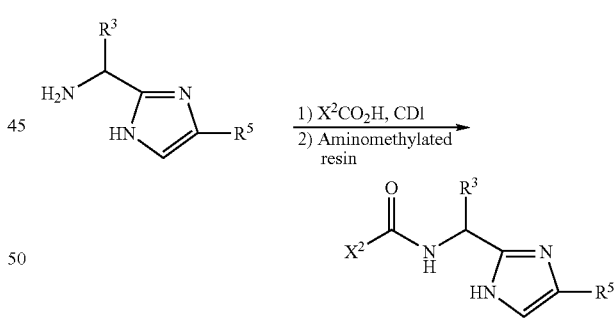

General procedure: Carboxylic acids are activated overnight at room temperature with carbonyldiimidazole in an aprotic solvent such as chloroform, THF or THF/DMF before addition of an amino starting material as shown above followed by a further 12-15 hours of stirring. The excess acylating agent is quenched with aminomethylated resin for about 12-15 hours and then purified on silica gel pad with dichloromethane or ethyl acetate as eluent.

For protected basic derivatives ($R^3$=(CH$_2$)$_4$NHBoc and/or $X^2$ containing NHBoc group), the corresponding deprotected compounds were obtained after treatment under acidic condition (DCM/TFA 10%) to remove the Boc group.

EXAMPLE 1179

2-{(1S)-1-[(2-Furanyl)carbonylamino]-2-[indol-3-yl]ethyl}-4phenyl-1H-imidazole (C$_{24}$H$_{20}$N$_4$O$_2$, MW=396.45)

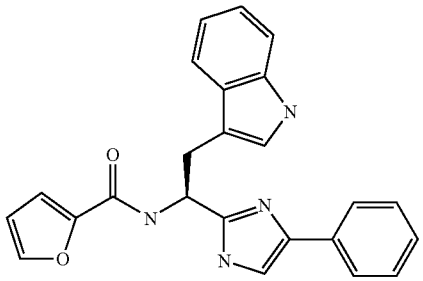

2-Furancarboxylic acid (12.6 mg, 0.11 mmol) was activated overnight at about 22° C. with carbonyldiimidazole (0.11 mmol, 0.2M in chloroform). 2-{(1S)-1-Amino-2-[indol-3-yl]ethyl}-4-phenyl-1H-imidazole (0.1 mmol, 0.5M in chloroform) was added to the media and the mixture was stirred for about 12 hours at about 22° C. Aminomethylated resin was then added (50-60 mg, 1.2 mmol/g, Novabiochem) in order to quench the excess of acylating agent for about 12 hours. Purification on silica gel pad (200 mg, Alltech) with ethyl acetate as eluent gave the expected product (37.2 mg, 94%). $^1$H-NMR (CDCl$_3$, 100 MHz) δ: 8.36 (br s, 1H); 7.67-6.4 (m, 16H); 5.48 (qd, J=7.1 Hz, 1H); 3.6 (ABX system, 2H). LC/MS: m/z=397 (M+H).

EXAMPLES 1180-3615

The following compounds were prepared analogously to the procedure described for Example 1179 using the appropriate starting materials, which can be obtained from commercial sources or synthesized according to methods known to those skilled in the art or as enabled by the teachings herein. Each combination of R$^3$, R$^5$ and X$^2$, shown below, were or can be synthesized, therefore, the number of Examples are calculated by multiplying (R$^3$ (4 substituents))(R$^5$ (7 substituents))(X$^2$ (87 substituents))=2436.

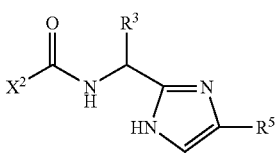

R$^3$:

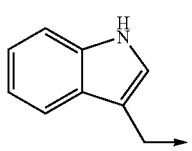

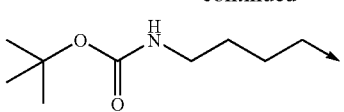

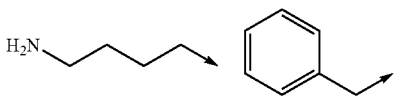

R$^5$:

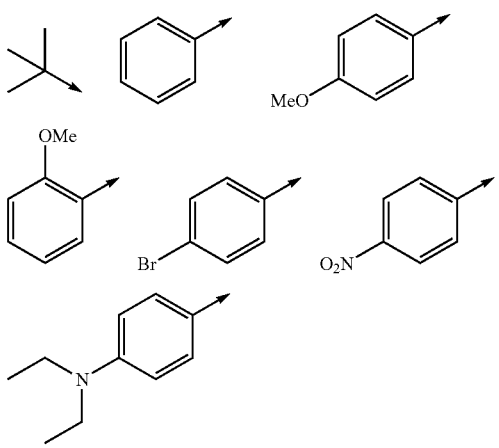

X$^2$:

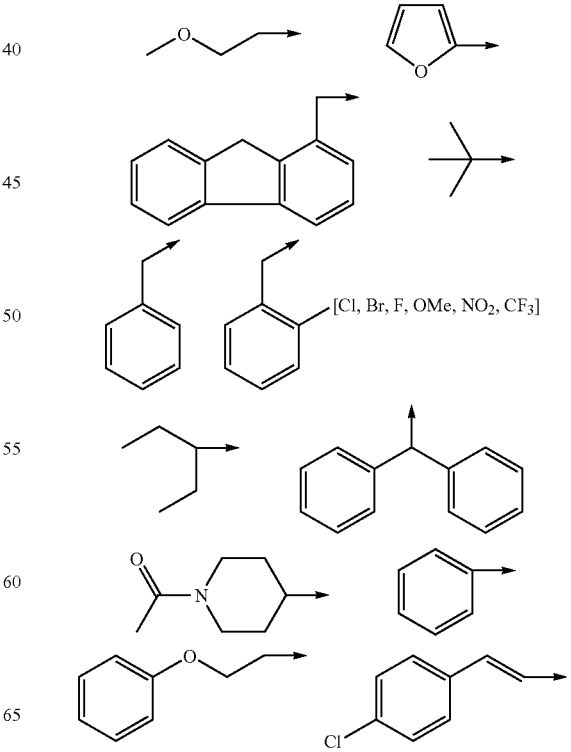

-continued
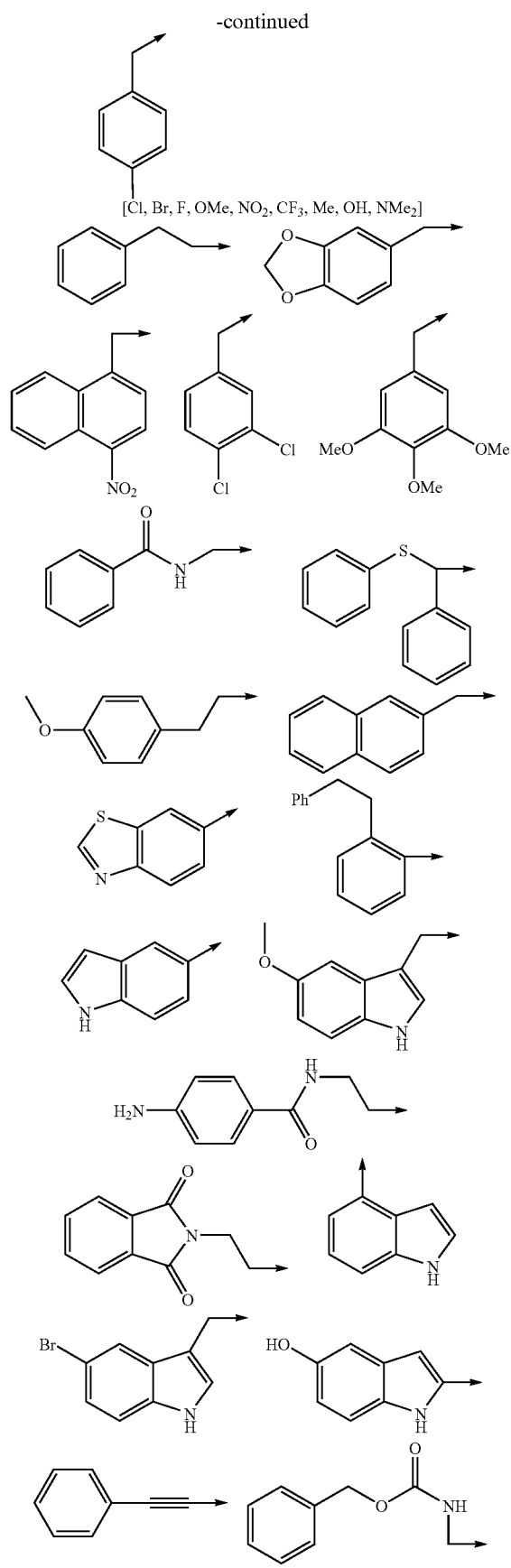
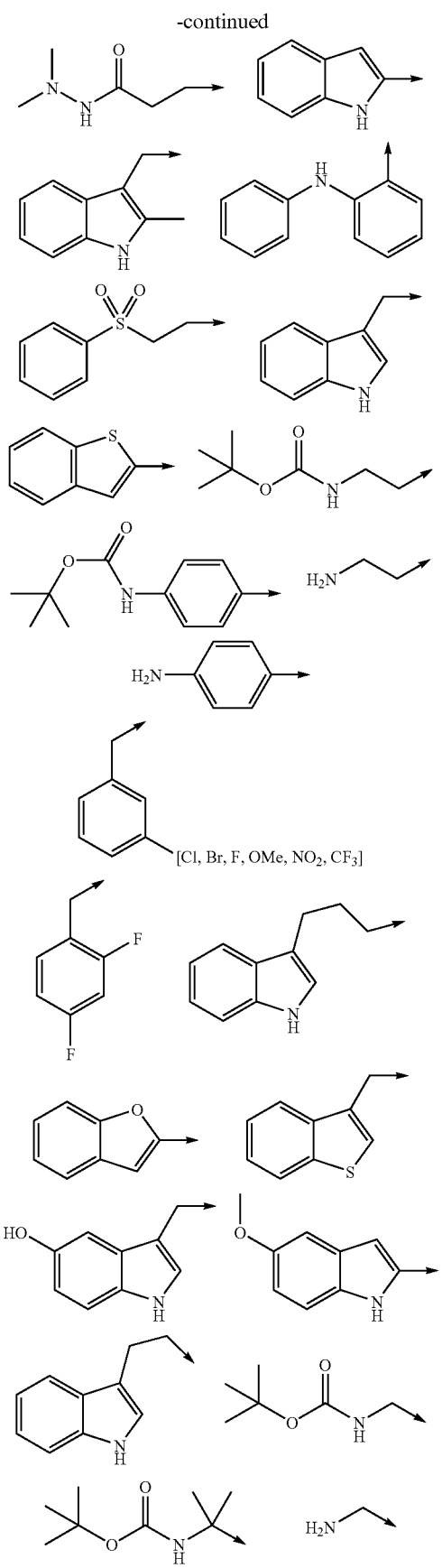

-continued

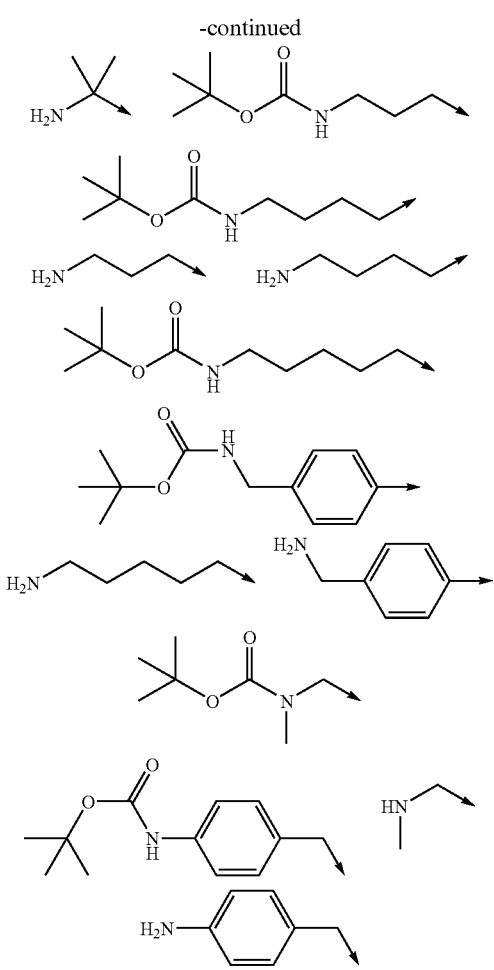

Synthesis of Ureas and Thioureas from Imidazoyl Intermediates

From Isocyanates and Isothiocyanates:

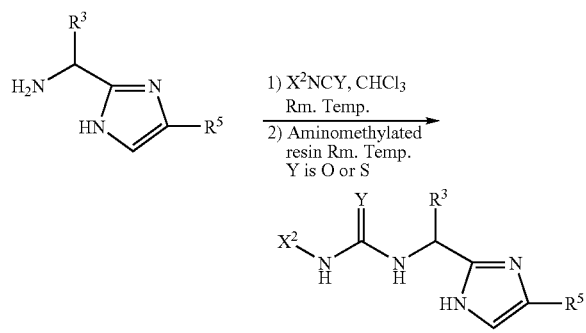

General procedure: Isocyanates or isothiocyanates are shaken overnight at room temperature with an imidazoyl intermediate in an aprotic solvent like dichloromethane, chloroform or chloroform/DMF. The reaction is quenched by addition of aminomethylated resin for about 12-15 hours and purified on silica gel pad with ethyl acetate as eluent.

For protected basic derivatives ($R^3$=(CH$_2$)$_4$NHBoc), the corresponding deprotected compounds were obtained after treatment under acidic condition (DCM/TFA 10%) to remove the Boc group.

EXAMPLE 3616

2-{(1R)-1-[(2, 4-Difluorophenyl)aminocarbonylamino]-2-[indol-3-yl]ethyl}-4-phenyl-1H-imidazole ($C_{26}H_{21}F_2N_5O$, MW=457.49)

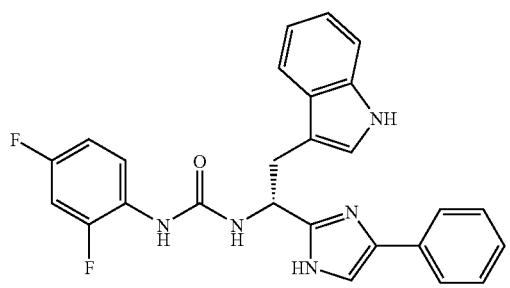

2,6-Difluorophenylisocyanate (36 µL, 0.3 mmol) and 2-{(1R)-1-amino-2-[indol-3-yl]ethyl}-4-phenyl-1H-imidazole (60.4 mg, 0.2 mmol) were stirred overnight in 2 mL of anhydrous dichloromethane. Filtration and purification by flash chromatography on silica gel (ethyl acetate/heptane 1:1 as eluent) afforded the expected product as a white powder (27 mg, 30%). $^1$H-NMR (DMSO D$_6$, 400 MHz) δ: 12.03 (s, 1H); 10.77 (s, 1H); 8.47 (s, 1H); 8.1 (dd, 1H); 7.8-6.92 (m, 14H); 5.11 (dd, J=7 and 14 Hz, 1H); 3.3 (m, 2H). LC/MS. m/z=458 (M+H).

EXAMPLES 3617-4435

The following compounds were prepared analogously to the procedure described for Example 3616, using the appropriate starting materials, which can be obtained from commercial sources or synthesized according to methods known to those skilled in the art or as enabled by the teachings herein. Each combination of $R^3$, $R^5$, and $X^2$ with Y is O or $X^2$ with Y is S, shown below, were or can be synthesized, therefore, the number of Examples are calculated by multiplying ($R^3$ (3 substituents))($R^5$ (7 substituents))($X^2$ (39 substituents))=819.

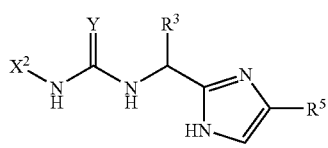

$R^3$:

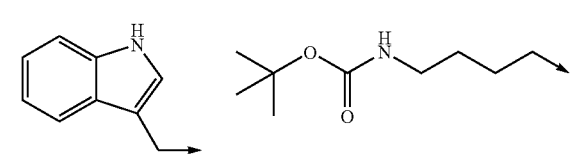

R⁵:
X² when Y is O:
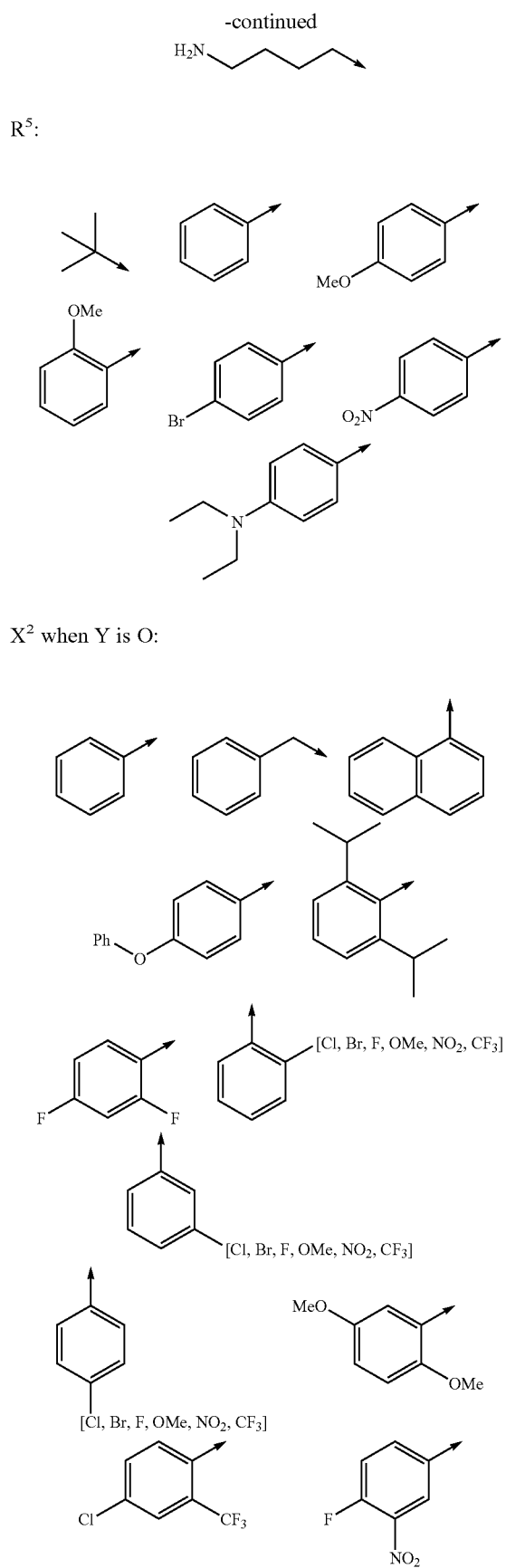
X² when Y is S:
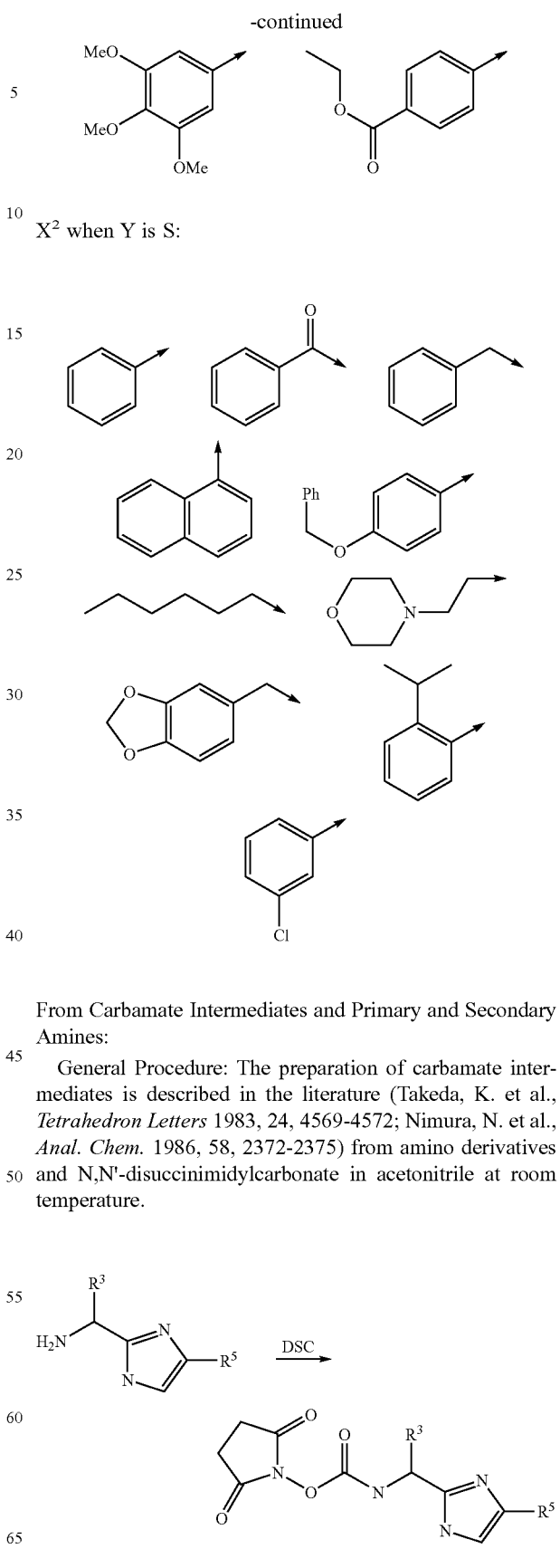
From Carbamate Intermediates and Primary and Secondary Amines:
General Procedure: The preparation of carbamate intermediates is described in the literature (Takeda, K. et al., *Tetrahedron Letters* 1983, 24, 4569-4572; Nimura, N. et al., *Anal. Chem.* 1986, 58, 2372-2375) from amino derivatives and N,N'-disuccinimidylcarbonate in acetonitrile at room temperature.

EXAMPLE 4436

2-{(1R)-1-[(2,5-Dioxo-1-pyrrrolidinyloxy)carbonylamino]-2-[indol-3-yl]ethyl}-4-phenyl-1H-imidazole ($C_{24}H_{21}N_5O_4$, MW=443.46):

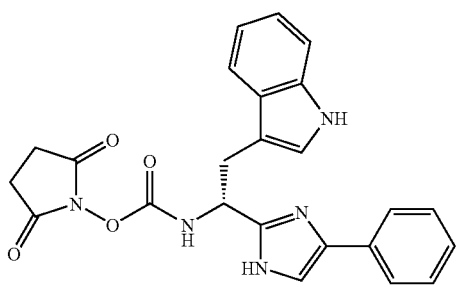

302.4 mg (1 mmol) of 2-{(1R)-1-amino-2-[indol-3-yl]ethyl}-4-phenyl-1H-imidazole previously dissolved in 20 mL of anhydrous acetonitrile was added dropwise to a solution of N,N'-disuccinimidylcarbonate (528 mg, 2 mmol, DSC) in 20 mL of anhydrous acetonitrile during 1.5 hour. After a further 4 hours of stirring at room temperature, the solvent was evaporated in vacuo and the residue redissolved in 30 mL of chloroform. Excess DSC was then discarded and the organic layer washed with water (4×30 mL), dried over $MgSO_4$ and concentrated to obtain a brown solid (215 mg 49%). $^1$H-NMR ($CDCl_3$, 100 MHz) δ: 8.22 (br s, 1 H); 8.1-7.08 (m, 12H); 5.9 (br s, 1H); 4.97 (dd, J=3.6 and 9.3 Hz, 1H); 3.75 (dd, J=3.6 and 14.8 Hz, 1H); 3.06 (dd, J=9.7 and 14.6 Hz, 1H); 2.96 (s, 2H); 2.89 (s, 2H). LC/MS: m/z=329 ((M+H)-SuOH).

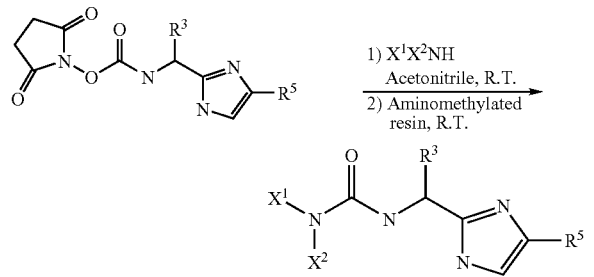

General procedure: A primary or secondary amine is stirred for about 2-15 hours at room temperature with a carbamate intermediate in an aprotic solvent like acetonitrile. Tetrahydrofuran and aminomethylated resin are then added and the reaction is then stirred for about 12-15 hours. Ureas are isolated after filtration, rinsed with ethyl acetate and evaporated in vacuo.

For protected basic derivatives ($R^3$=(CH$_2$)$_4$NHBoc), the corresponding deprotected compounds were obtained after treatment under acidic condition (DCM/TFA 10%) to remove the Boc group.

EXAMPLE 4437

2-{(1R)-1-[(Benzylamino)carbonylamino]-2-[indol-3-yl]ethyl}-4-phenyl-1H-imidazole ($C_{27}H_{25}N_5O$, MW=435.53)

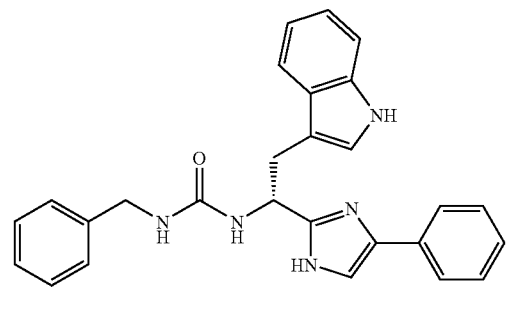

Benzylamine (5 μL, 50 mmol) and 2-{(1R)-1-amino-2-[indol-3-yl]ethyl}-phenyl-1H-imidazole (24 mg, 54 mmol) were stirred for about 2 hours at room temperature in anhydrous acetonitrile. Aminomethylated resin (50 mg, 0.75 mmol/g, Novabiochem) was then added and after further stirring overnight, the title product was obtained by filtration on silica gel pad (200 mg) and evaporated in vacuo as a brown powder (20 mg, 92%). $^1$H-NMR (DMSO $D_6$, 100 MHz) δ: 10.8 (br s, 1H); 7.9-6.88 (m, 17H); 6.53 (m, 2H); 5.12 (dd, J=6 and 14.6 Hz, 1H); 4.28 (m, 2H); 3.25 (m, 2H). LC/MS: m/z=436 (M+H).

EXAMPLES 4438-8469

The following compounds were prepared analogously to the procedure described for Example 4437, using the appropriate starting materials, which can be obtained from commercial sources or synthesized according to methods known to those skilled in the art or as enabled by the teachings herein. Each combination of $R^3$, $R^5$ and $NX^1X^2$, shown below, were or can be synthesized, therefore, the number of Examples are calculated by multiplying ($R^3$ (3 substituents)) ($R^5$ (12 substituents))($NX^1X^2$ (112 substituents))=4032.

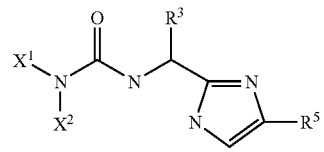

$R^3$:

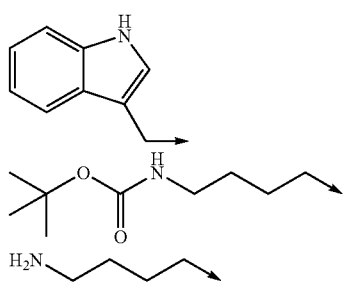

R⁵:
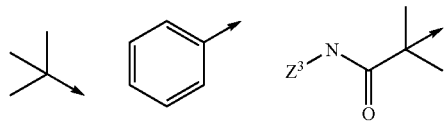
Z³:
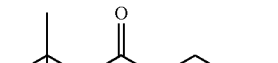
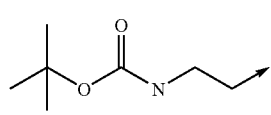
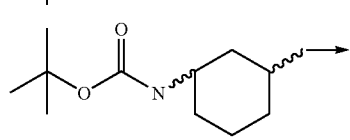
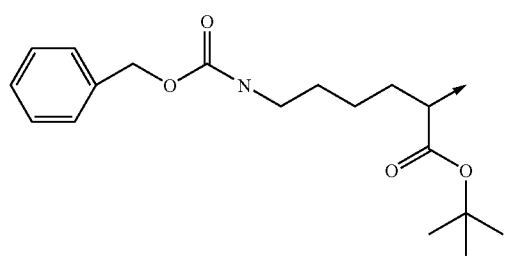
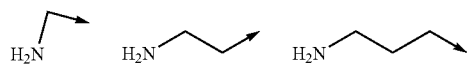
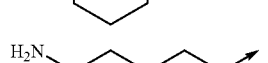
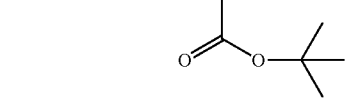
X¹X²N:
  Primary Amines
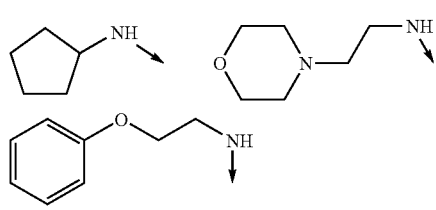
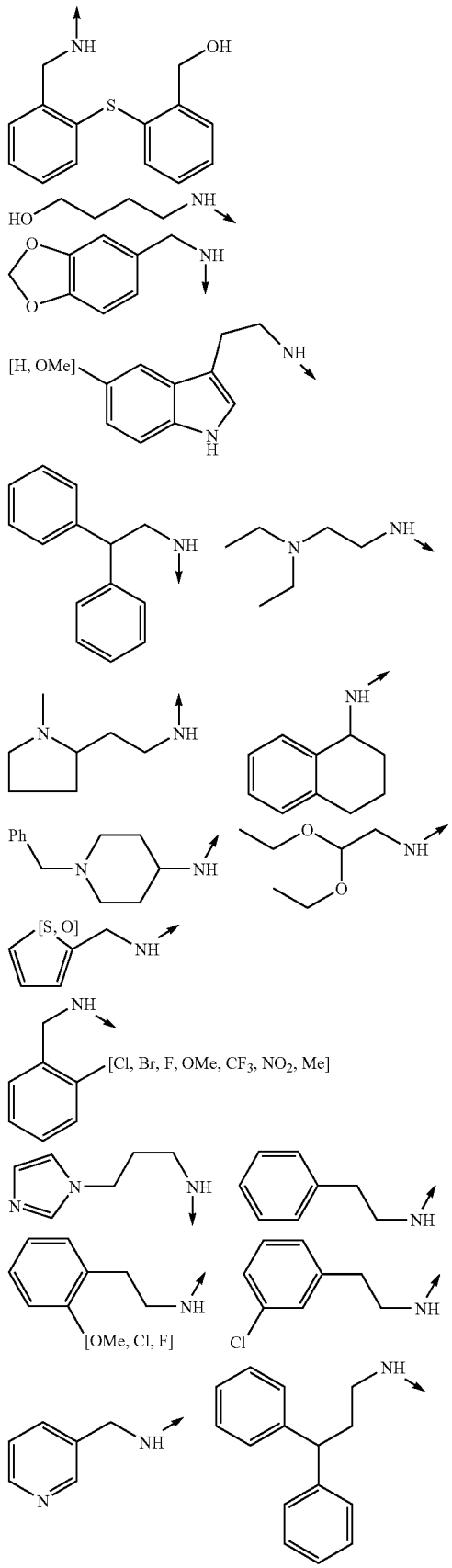

Secondary Amines
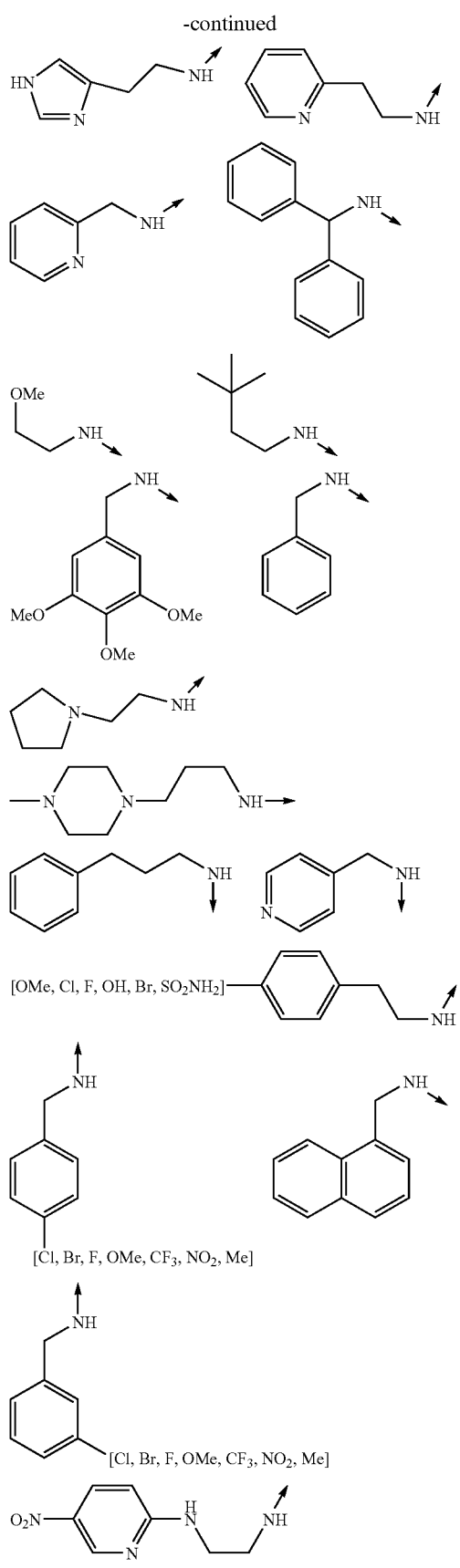
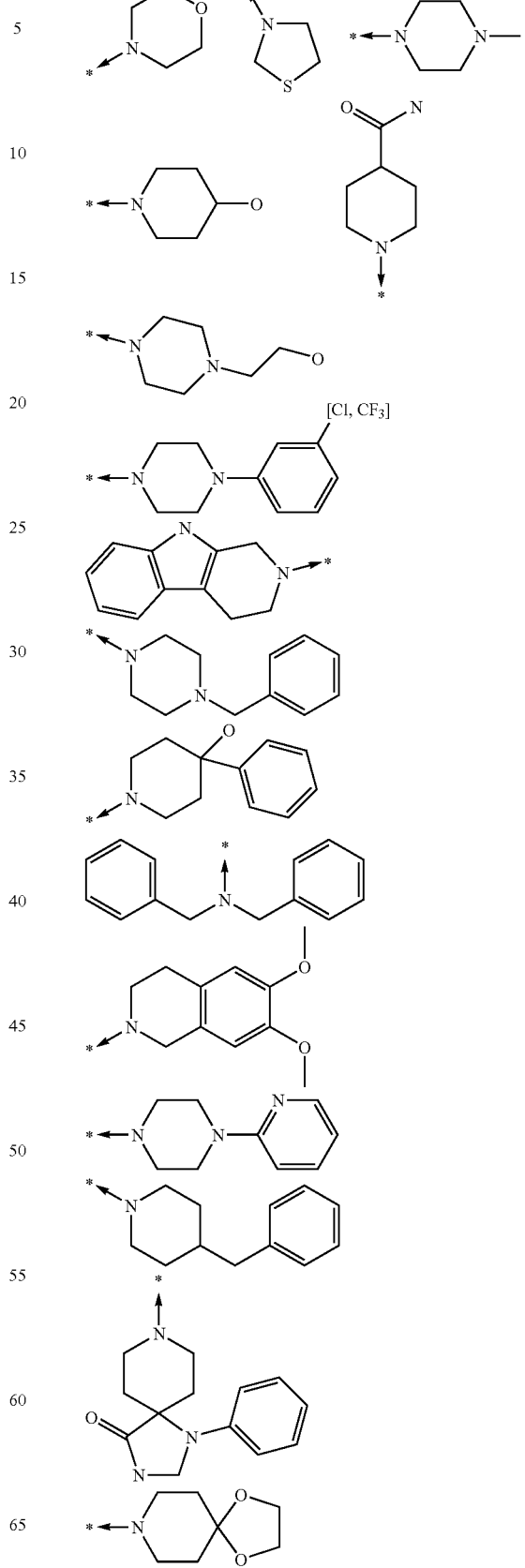

-continued
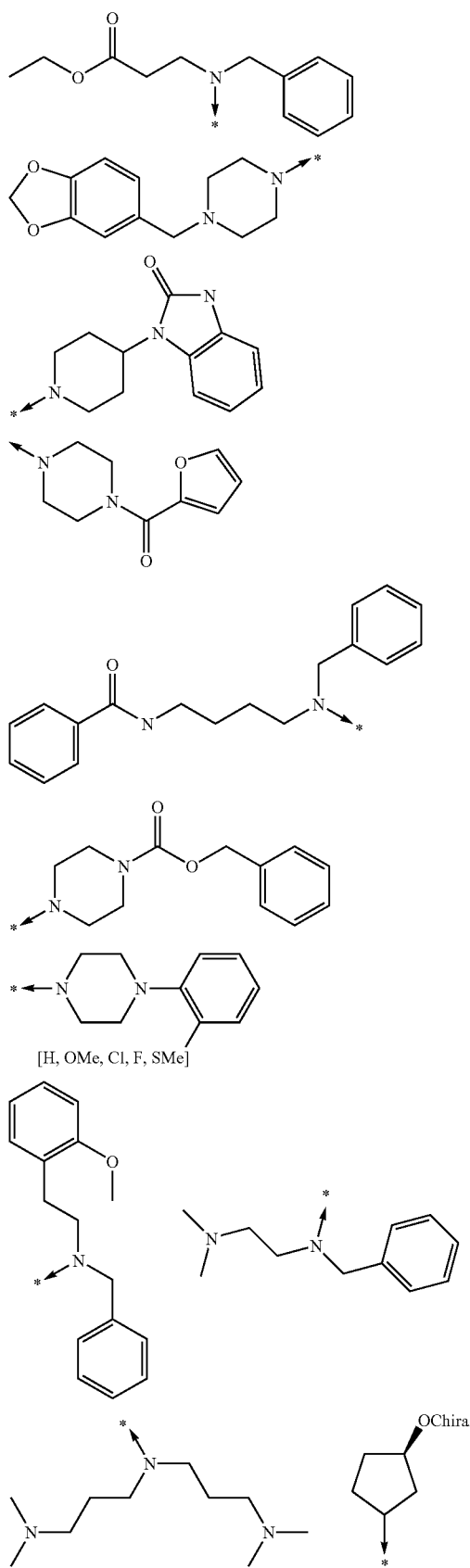
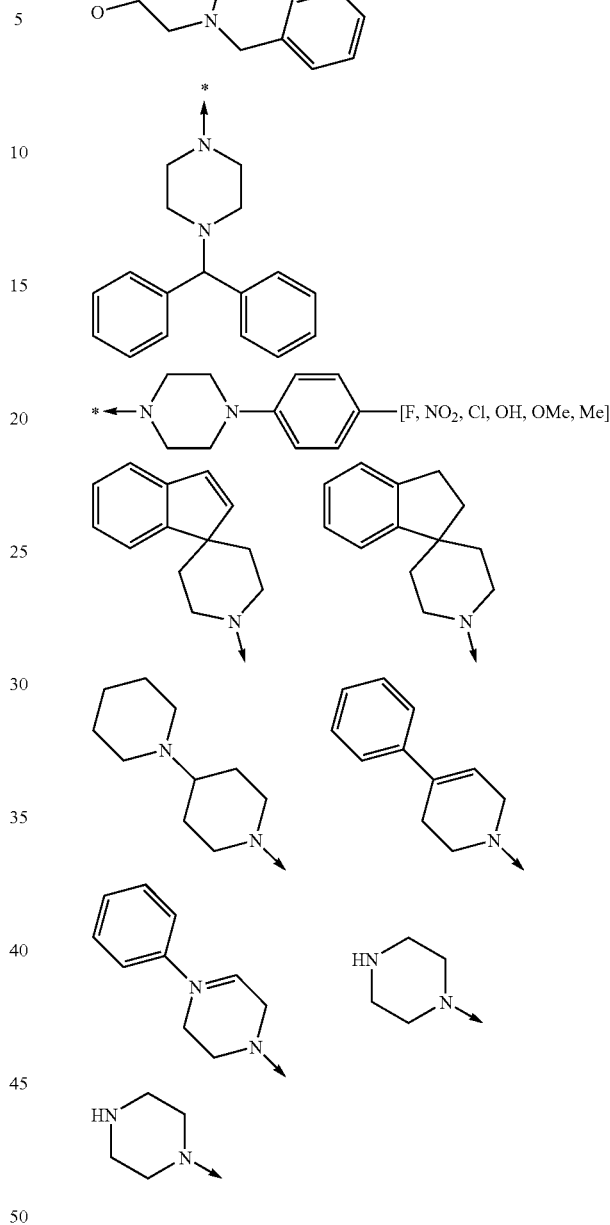
Synthesis of Secondary Amines by Reductive Aminations of Imidazolyl Intermediates
(Kaldor, S. W. Siegel; M. G.; Fritz, J. E.; Dressman, B. A.; Hahn, P. J. *Tetrahedron Letters* 1996, 37, 7193-7196)
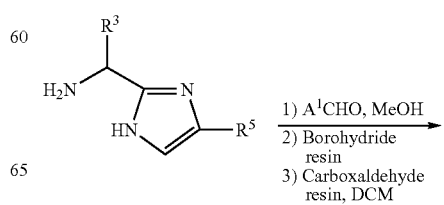

-continued

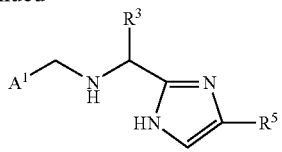

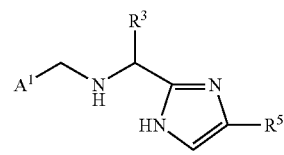

General procedure: Condensation of aldehydes with an imidazolyl intermediate in a protic solvent like methanol yields imines which are reduced in presence of AMBER-LITE® IRA-400 borohydride. The slurry is then shaken overnight and the excess amino intermediate is quenched by addition of dichloromethane and aldehyde Wang resin. After further overnight stirring, the mixture is filtered, evaporated and purified on silica gel pad with ethyl acetate as eluent.

For protected basic derivatives ($R^3$=$(CH_2)_4$NHBoc), the corresponding deprotected compounds were obtained after treatment under acidic condition (DCM/TFA 10%) to remove the Boc group.

EXAMPLE 8470

2-{(1R)-1-[(4-Methoxybenzyl)amino]-2-[indol-3-yl]ethyl}-4-phenyl-1H-imidazole ($C_{27}H_{26}N_4O$, MW=422.54)

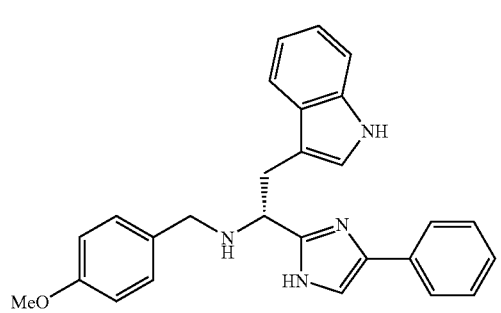

2-{(1R)-1-Amino-2-[indol-3-yl]ethyl}-4-phenyl-1H-imidazole (36.3 mg, 0.12 mmol) and p-anisaldehyde (12 μL, 0.1 mmol) in 1 mL of methanol were shaken for about 2 hours at about 22° C. Borohydride resin (76 mg, 2.5 mmol/g, AMBERLITE® IRA-400) was then added and the slury was stirred overnight before addition of dichloromethane (1 mL) and aldehyde Wang resin (31 mg, 3.22 mmol/g, Novabiochem). After about 8 hours of stirring, the slurry was then filtered and evaporated in vacuo to give a yellow solid (32.2 mg, 76%). $^1$H-NMR (CDCl$_3$, 100 MHz) δ: 8.86 (br s, 1H); 7.73-6.68 (m, 15H); 4.62 (s, 1H); 4.33 (dd, J=4.7 and 8.5 Hz, 1H); 3.81 (s, 2H); 3.74 (s, 3H); 3.27 (ABX system, 2H) 2.26 (s, 1H). LC/MS: m/z=423 (M+H).

EXAMPLES 8471-9331

The following compounds were prepared analogously to the procedure described for Example 8470, using the appropriate starting materials, which can be obtained from commercial sources or synthesized according to methods known to those skilled in the art or as enabled by the teachings herein. Each combination of $R^3$, $R^5$ and $A^1$, shown below, were or can be synthesized, therefore, the number of Examples are calculated by multiplying ($R^3$ (3 substituents))(Rs (7 substituents))($X^2$ (41 substituents))=861.

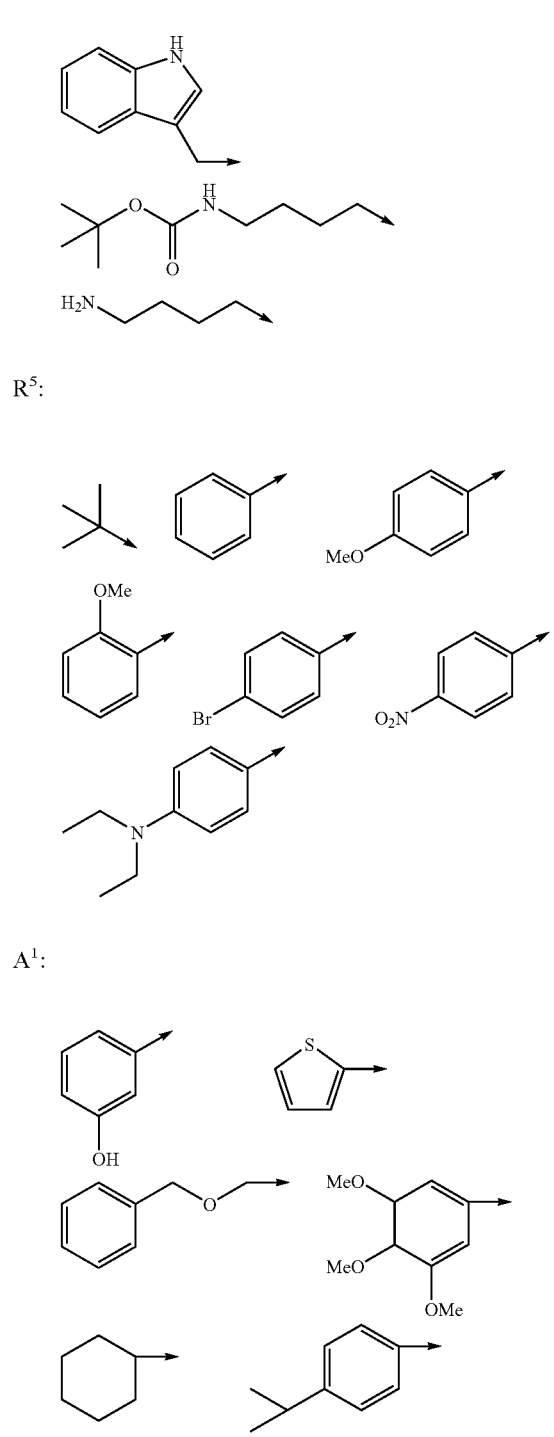

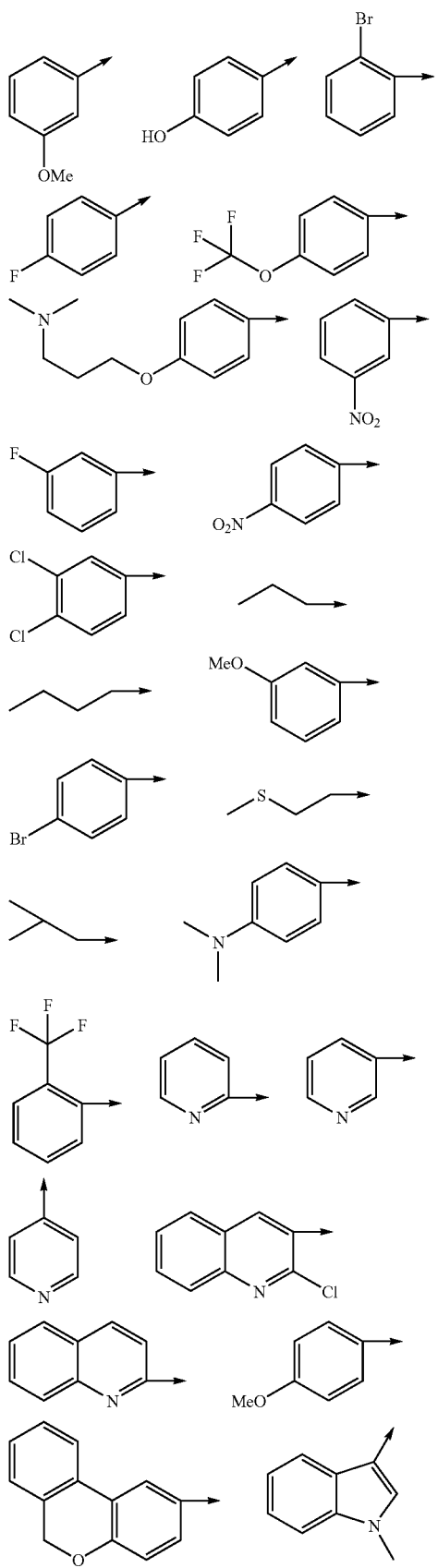
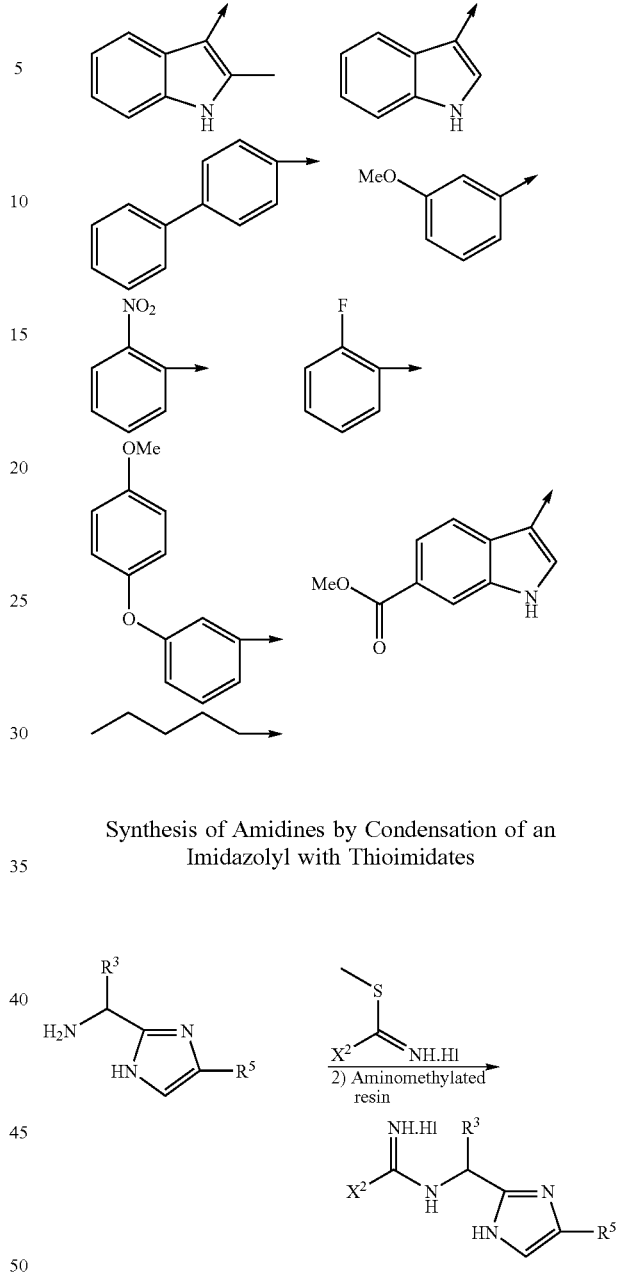

Synthesis of Amidines by Condensation of an Imidazolyl with Thioimidates

A series of thioimidates were previously synthesized by condensation of thioamides and iodomethane in acetone at room temperature. The precipitate was collected and then rinsed with acetone. Thioimidates so formed were used without further purification.

General procedure: Thioimidates are stirred overnight at room temperature with an amino intermediate in 2-propanol or 2-propanol/DMF before addition of tetrahydrofuran and aminomethylated resin. Further stirring overnight followed by filtration and washing with ethyl acetate yields an iodohydrate amidine after evaporation in vacuo.

For protected basic derivatives ($R^3$=(CH$_2$)$_4$NHBoc), the corresponding deprotected compounds were obtained after treatment under acidic condition (DCM/TFA 10%) to remove the Boc group.

EXAMPLE 9332

2-{(1R)-1-[(2-Thienyl(imino)methyl)amino]-2-[indol-3-yl]ethyl}-4-phenyl-1H-imidazole hydroiodide ($C_{24}H_{21}N_5S \cdot HI$, MW=539.43)

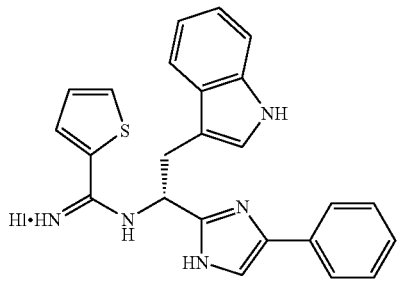

2-{(1R)-1-Amino-2-[indol-3-yl]ethyl}-4-phenyl-1H-imidazole (15.1 mg, 0.05 mmol) and S-methyl-2-thiophenethiocarboximide hydroiodide (13 mg, 0.06 mmol) were shaken in 1 mL of 2-propanol for about 16 hours. Aminomethylated resin (50 mg, 1.31 mmol/g, Novabiochem) was then added and after further stirring overnight, a brown solid (19.8 mg, 84%) was isolated by filtration and evaporation in vacuo. $^1$H-NMR (MeOD, 100 MHz) δ: 8.15 (m, 1H); 7.84-6.96 (m, 13H); 5.3 (m, 1H); 3.61 (m, 2H). LC/MS :m/z=412 (M+H).

EXAMPLES 9333-9920

The following compounds were prepared analogously to the procedure described for Example 9332, using the appropriate starting materials, which can be obtained from commercial sources or synthesized according to methods known to those skilled in the art or as enabled by the teachings herein. Each combination of $R^3$, $R^5$ and $X^2$, shown below, were or can be synthesized, therefore, the number of Examples are calculated by multiplying ($R^3$ (7 substituents)) ($R^5$ (7 substituents))($X^2$ (12 substituents))=588.

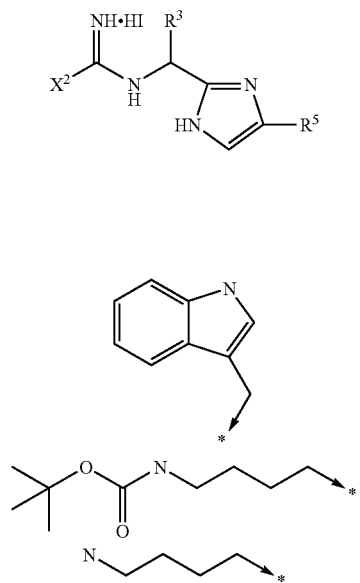

$R^3$:

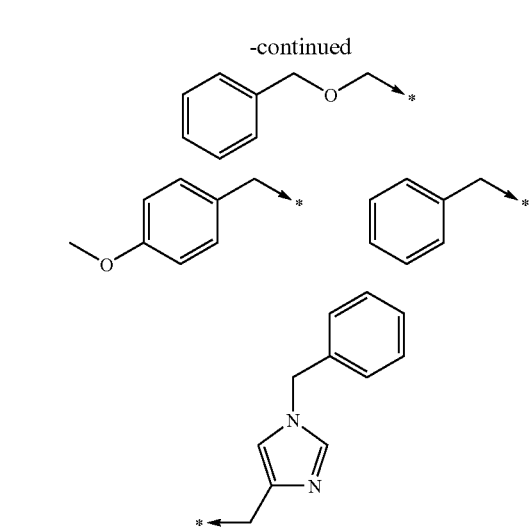

$R^5$:

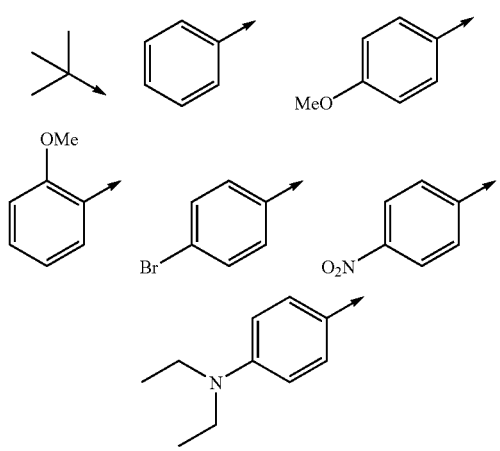

$X^2$:

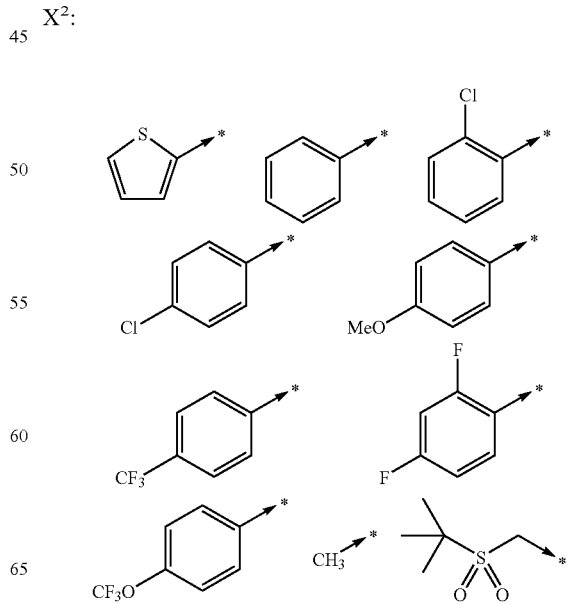

-continued

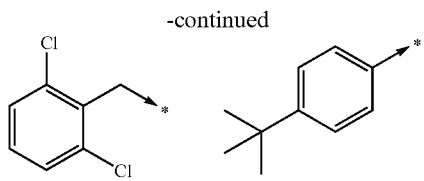

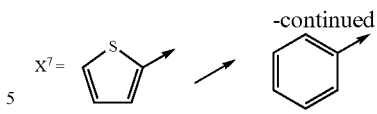

Imidazole Derivatives N-Alkylation

Synthesis of Amidines by Condensation of an Aniline with Thioimidates

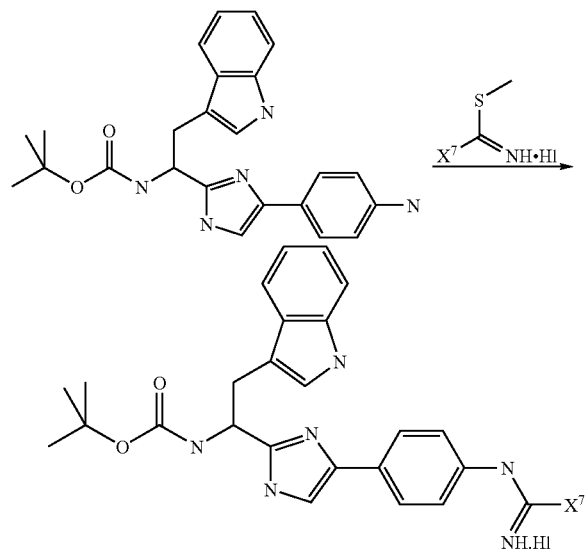

General procedure: A solution of an imidazole intermediate, an alkylating agent such as an α-bromoketone, an α-bromoester, an aryl or alkyl bromide or a sulfonyl chloride, in the presence of an organic or non-organic base which can be or not be supported on a resin such as polystyrene resin, in an aprotic solvent like THF, CH$_3$CN, DMF is heated at 20-80° C. for 2-48 hours. The resulting N-alkylated compound can be isolated either by aqueous work-up followed by flash chromatography on silica gel, or by addition to the reaction mixture of a nucleophile supported on polymer (to trap the excess of electrophile) such as aminomethyl or thiomethyl polystyrene resin followed by filtration and then rapid purification of the resulting residue on a silica gel pad (using Alltech silica cartridge and Alltech manifold).

EXAMPLES 9921-9926

The following compounds were prepared analogously to the procedure described for Example 9332, using the appropriate starting materials, which can be obtained from commercial sources or synthesized according to methods known to those skilled in the art or as enabled by the teachings herein. Each combination of R$^4$ and X$^7$, shown below, were or can be synthesized, therefore, the number of Examples are calculated by multiplying (R$^4$ (2 substituents))(X$^7$ (3 substituents))=6.

EXAMPLE 9927

2-[1(S)-{1,1-Dimethylethoxy)carbonylamino}-2-phenylethyl]-1-(2-oxo-butyl)-4-phenyl-1H-imidazole

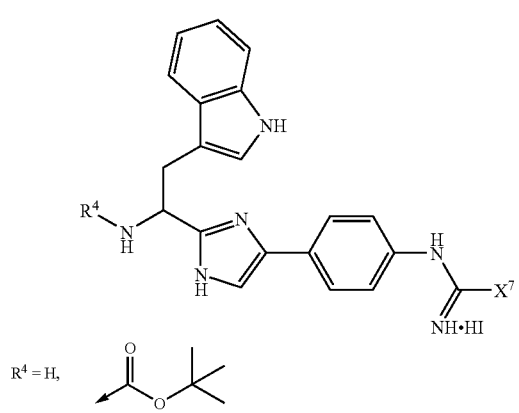

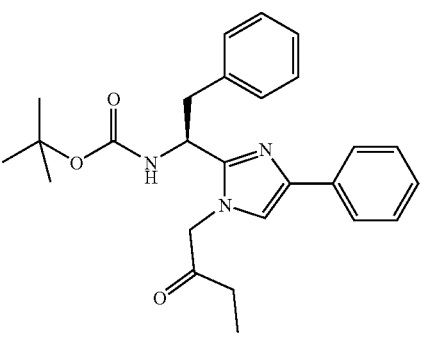

To a solution of 2-[1(S)-{(1,1-dimethylethoxy)carbonylamino}-2-phenylethyl]-4-phenyl-1H-imidazole (100 mg, 1 eq) in DMF (2 mL) were successively added morpholinomethyl polystyrene resin (Novabiochem, loading: 3.51 mmol/g, 159 mg, 2 eq) and 1-bromo-2-butanone (28 mL, 2 eq). After about 18 hours of stirring at about 20° C., 2 mL DMF were added to the reaction mixture followed by aminomethylpolystyrene resin (Novabiochem, loading: 1.73 mmol/g, 319 mg). The mixture was stirred overnight at 20° C. and filtered. The filtrate was concentrated under reduced pressure and then purified by a rapid filtration on a silica gel pad (Alltech silica cartridges) with ethylacetate as eluent to yield 107 mg (90% yield) of the title compound. NMR ($^1$H, 400 MHz, CDCl$_3$) δ: 7.80-6.98 (m, 11H, arom. H), 5.45 (d, 1H, NH), 4.80 (m, 1H, CH), 4.40 (AB, J=18 Hz, NCH$_2$CO), 3.33 (m, 2H, CH$_2$Ph), 2.25 (m, 2H, CH$_2$CH$_3$), 1.0 (t, 3H, CH$_3$). LC/MS: calculated MW=433.5, m/z=434.2 (M+H), m/z=432.2 (M−H).

EXAMPLES 9928-12307

The following compounds were prepared analogously to the procedure described for Example 9927, using the appropriate starting materials, which can be obtained from commercial sources or synthesized according to methods known to those skilled in the art or as enabled by the teachings herein. Each combination of R$^3$, R$^5$ and R$^1$, shown below, were or can be synthesized, therefore, the number of Examples are calculated by multiplying (R$^1$ (34 substituents {see definitions of Z$^1$}))(R$^3$ (5 substituents))(R$^5$ (14 substituents))=2380.

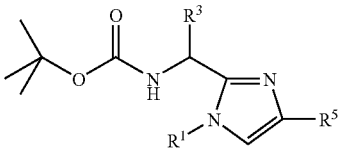

R$^1$:

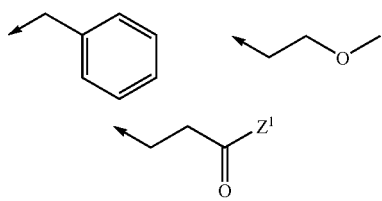

R$^3$:

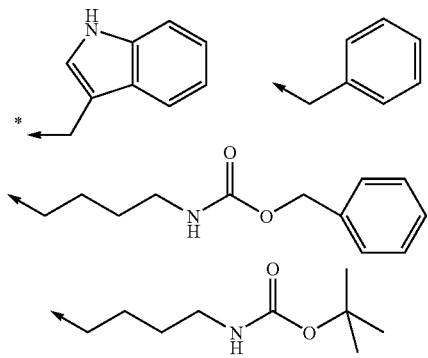

R$^5$:

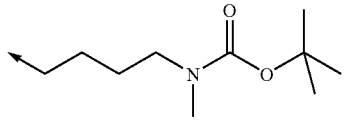

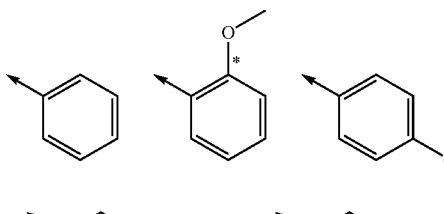

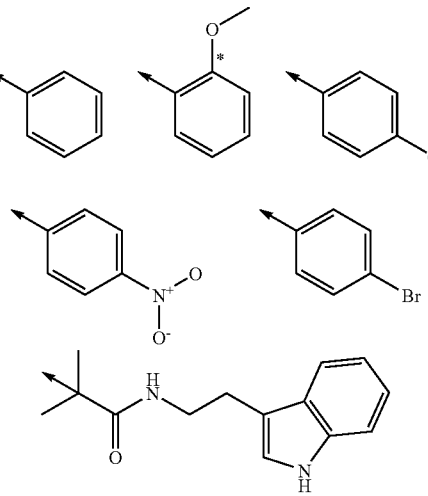

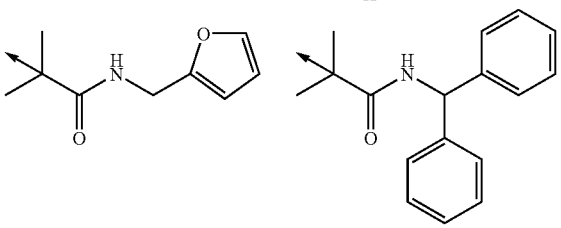

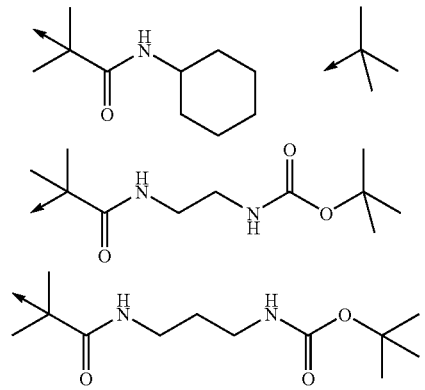

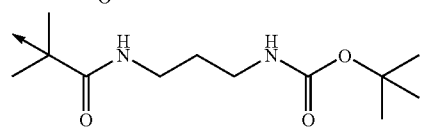

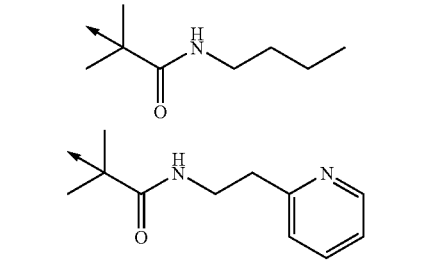

* In case of bromide derivatives, casium carbonate was used instead of morpholinomethylpolystyrene resin and thiomethyl resin was used instead of aminomethylresin $Z^1$:
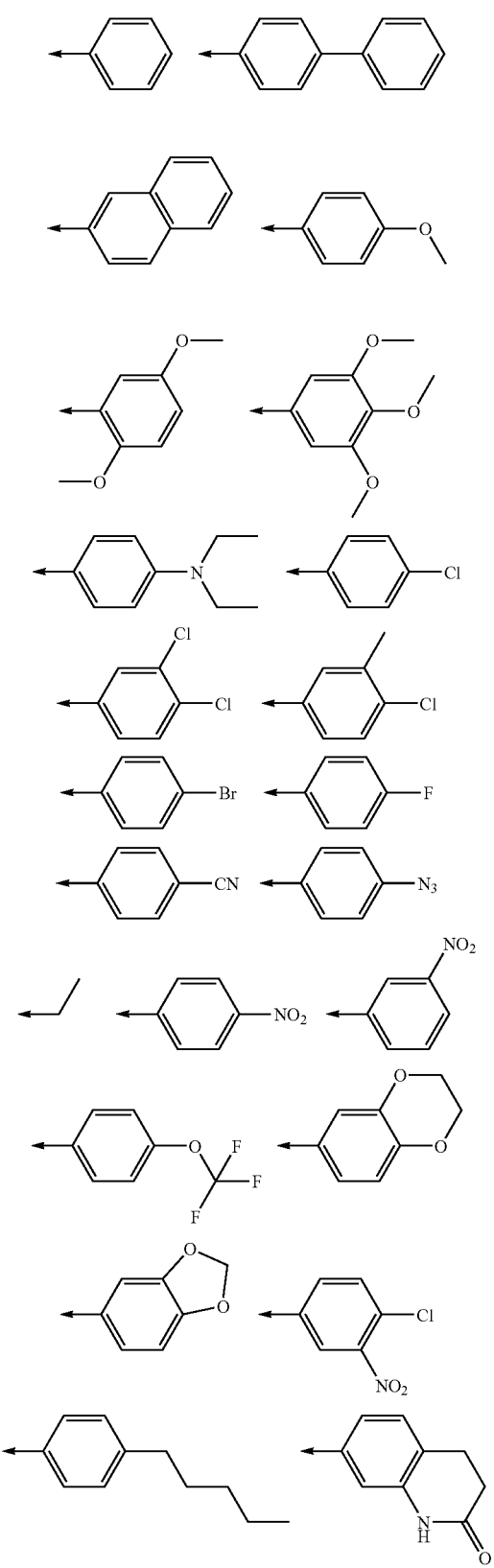
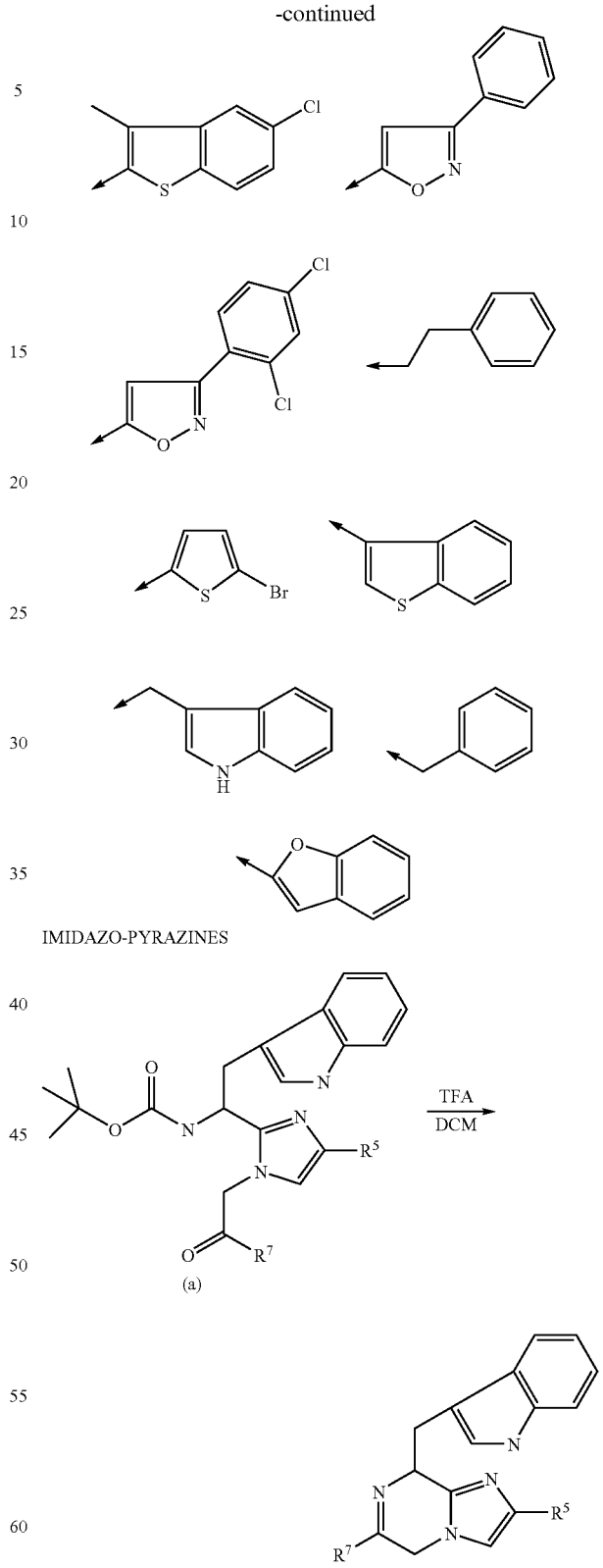
IMIDAZO-PYRAZINES
General procedure: Intermediate (a) is treated with an acidic solution preferably TFA in DCM at about 20-30° C. for about 1-4 hours. The mixture is then concentrated under reduced pressure to afford a dihydro-imidazo-pyrazine.

EXAMPLE 12308

5,8-Dihydro-8-(3-indolyl)methyl-2,6-diphenyl-imidazo[1,2-a]pyrazine

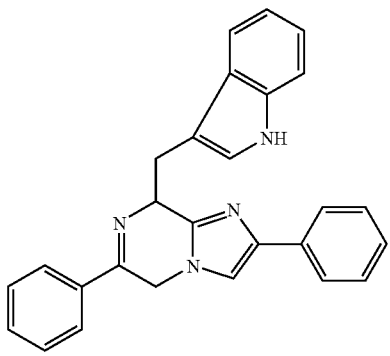

A solution of 2-[1(S)-{1,1-dimethylethoxy)carbonylamino}-2-(3-indolyl)ethyl]-1-(benzoylmethyl)-4-phenyl-1H-imidazole (prepared as described previously) (100 mg) in a mixture of 10% TFA in DCM (1.3 mL) was stirred for about 3 hours at about 20° C. and concentrated under reduced pressure to yield the expected dihydro-imidazopyrazine (yield=95%). LC/MS: calculated MW: 402.19, m/z=403.2 (M+H).

EXAMPLES 12309-12532

The following compounds were prepared analogously to the procedure described for Example 12308, using the appropriate starting materials, which can be obtained from commercial sources or synthesized according to methods known to those skilled in the art or as enabled by the teachings herein. Each combination of $R^5$ and $R^7$, shown below, were or can be synthesized, therefore, the number of Examples are calculated by multiplying ($R^5$ (7 substituents)) ($R^7$ (32 substituents))=224.

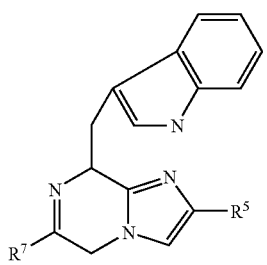

$R^5$:

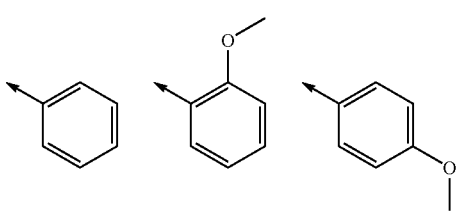

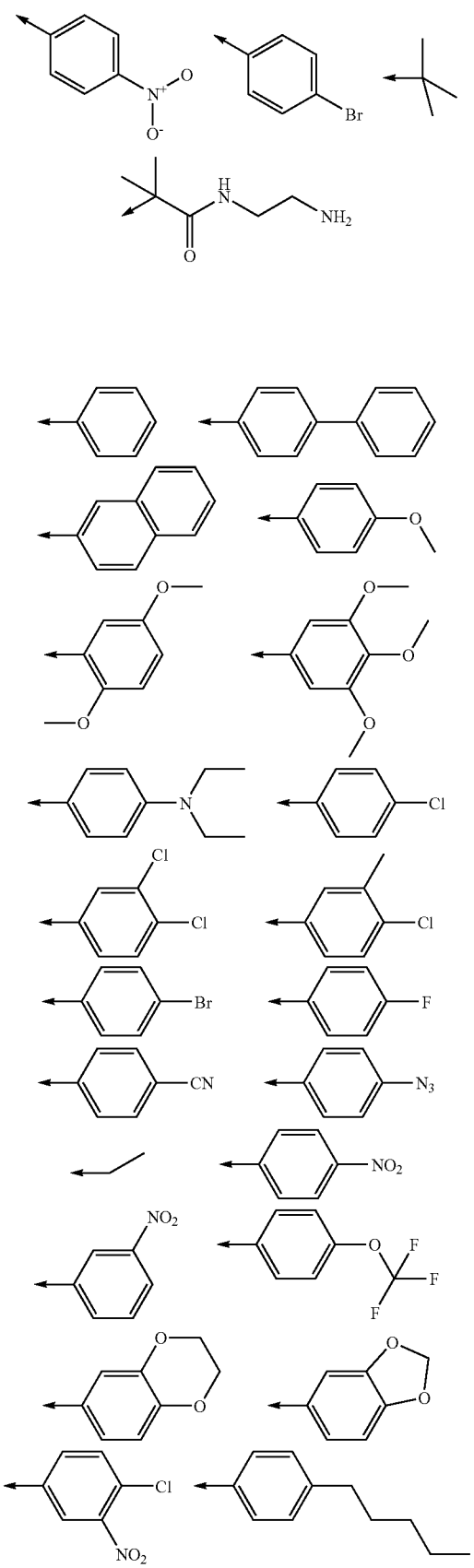

-continued

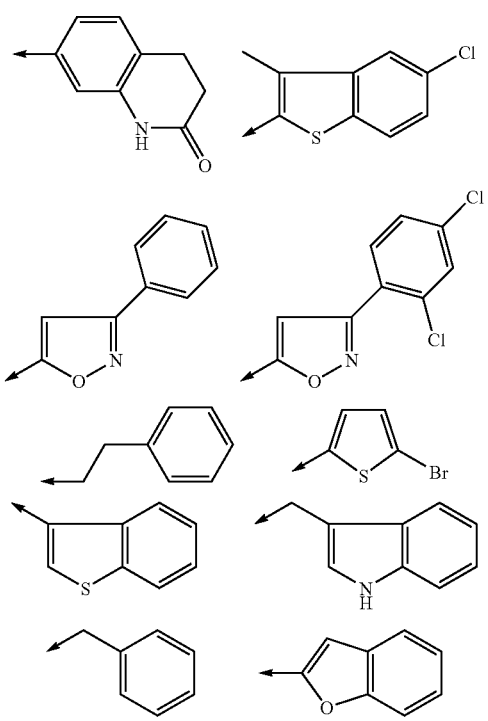

IMIDAZO-PYRAZINES

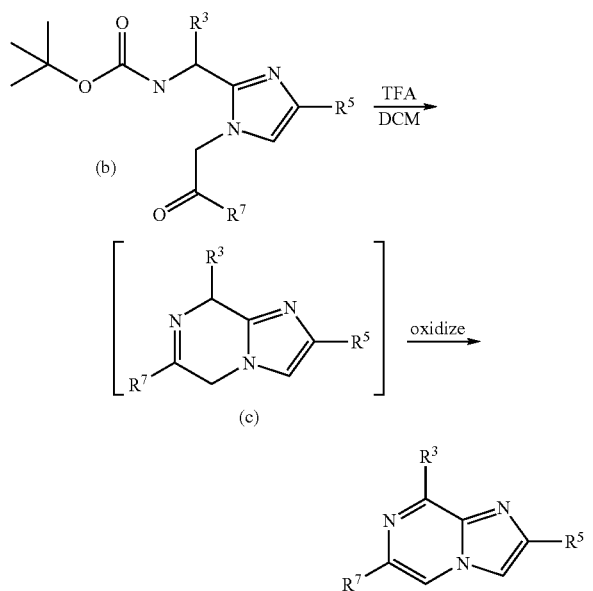

General procedure: Intermediate (b) is treated with an acidic solution preferably TFA in DCM at 20-30° C. for 1-4 hours. The mixture is then concentrated under reduced pressure to afford compound (c) which is oxidized to the corresponding fully aromatized imidazopyrazine either by keeping it in solution in methanol or DMSO for 5 hours-3 days at about 20° C. or by using an oxidative reagent such as manganese dioxide in a protic or aprotic solvent such as MeOH, toluene or chloroform at 20-70° C. for 2-10 hours or chromic acid supported or not on a resin in a protic solvent like methanol at 40-70° C. for 3-15 hours.

EXAMPLE 12533

2,6-Diphenyl-imidazo[1,2-a]pyrazine-8-butanamine

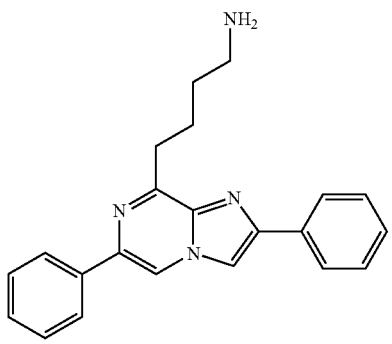

A solution of 2-[1,5-bis{(1,1-dimethylethoxy) carbonylamino}pentyl]-4-phenyl-1H-imidazole (50 mg) in a mixture of TFA/DCM 10% (700 mL) was stirred at about 20° C. for about 3 hours and then concentrated under reduced pressure to yield the intermediate dihydro-imidazo-pyrazine as its trifloroacetate salt. This salt was dissolved in MeOH (1 mL) and manganese dioxide (30 mg) was added. After about 3 hours of stirring at about 20° C., the mixture was filtered on a CELITE® pad and the filtrate concentrated under reduced pressure to afford the fully aromatized imidazo-pyrazine (78% yield). NMR ($^1$H, 400 MHz, $CD_3OD$): 8.75-7.34 (m, 12H, arom. H), 3.32 (m, 4H, $CH_2$), 2.10 (m, 2H, $CH_2$), 1.90 (m, 2H, $CH_2$). LC/MS: calculated MW=342.4, m/z=343.2 (M+H).

EXAMPLES 12534-13773

The following compounds were prepared analogously to the procedure described for Example 12533, using the appropriate starting materials, which can be obtained from commercial sources or synthesized according to methods known to those skilled in the art or as enabled by the teachings herein. Each combination of $R^3$ and $R^7$, shown below, were or can be synthesized, therefore, the number of Examples are calculated by multiplying ($R^3$ (5 substituents))($R^5$ (8 substituents))($R^7$ (31 substituents))=1240.

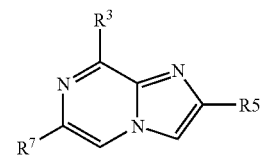

$R^3$:

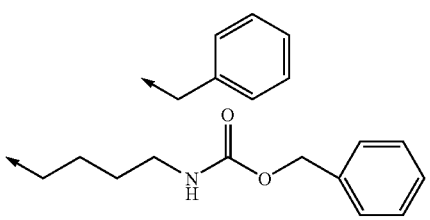

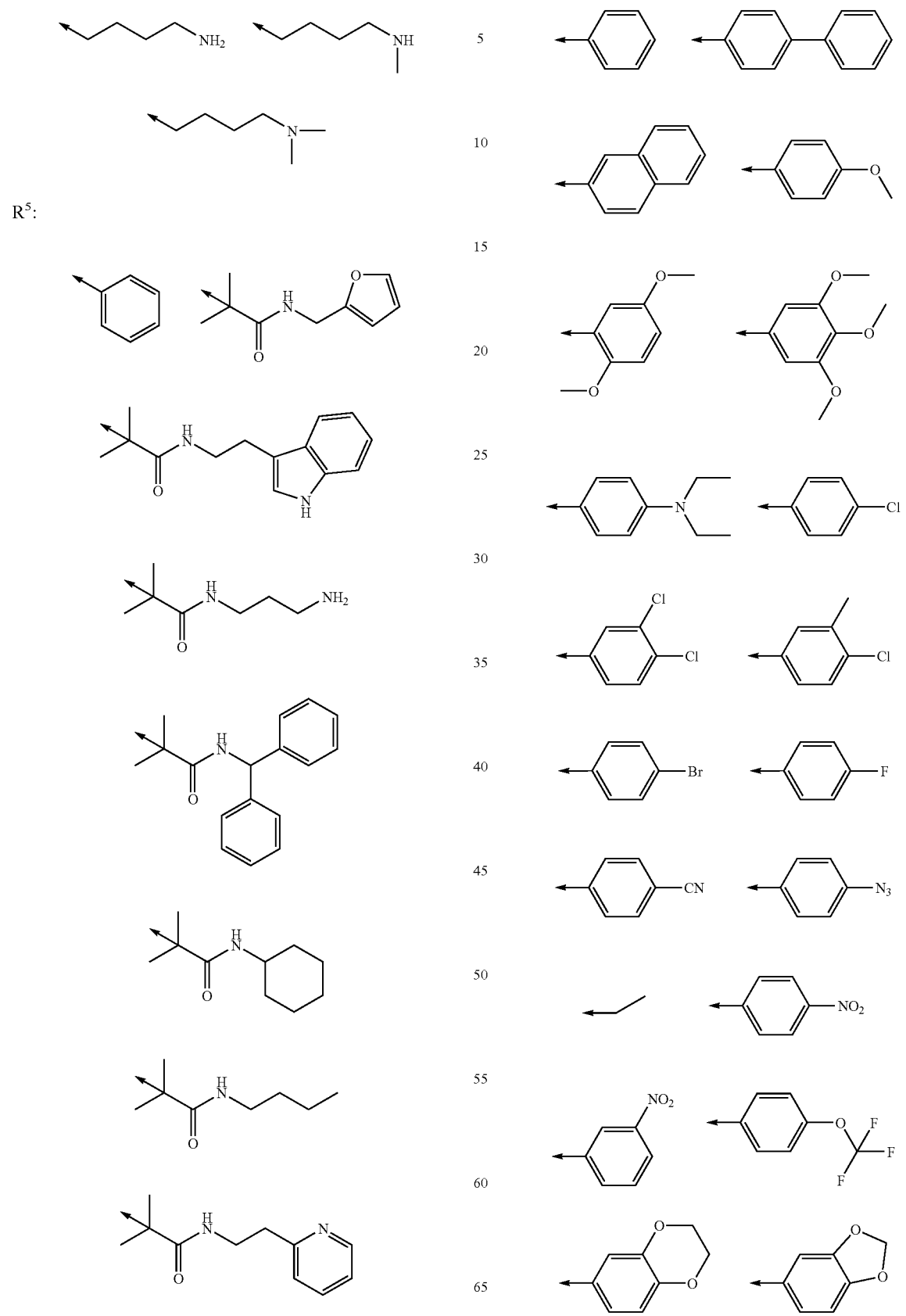

-continued

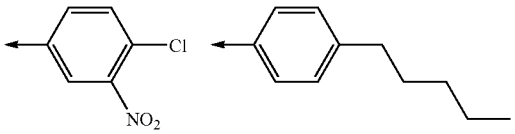

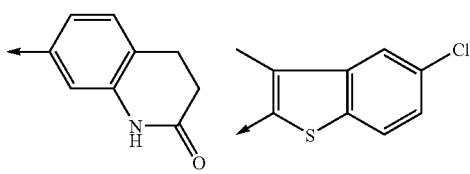

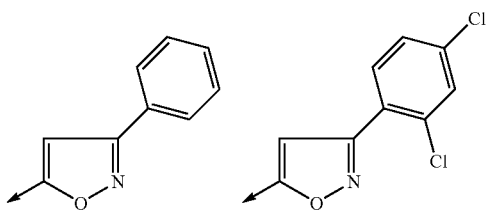

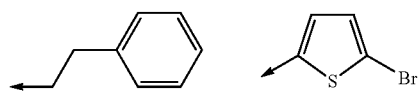

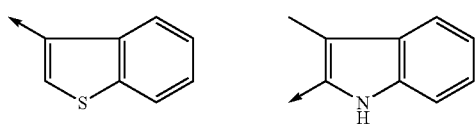

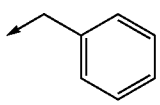

TETRAHYDRO-IMIDAZO-PYRAZINES

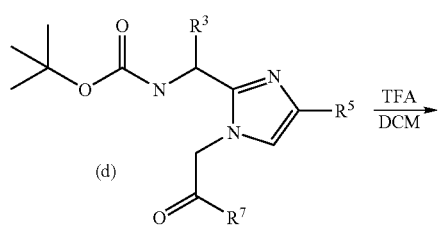

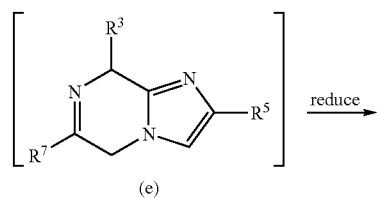

-continued

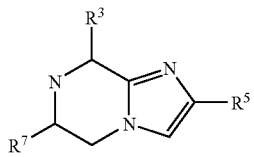

General procedure: Intermediate (d) is treated with an acidic solution preferably TFA in DCM at 20-30° C. for 1-4 hours. The mixture is then concentrated under reduced pressure to afford the intermediate dihydro-imidazopyrazine (e). Reduction of (e) to the corresponding tetrahydro-imidazopyrazine is achieved by catalytic hydrogenation or by using any reducing agent such as $NaBH_4$ (which can be supported on a resin), $NaBH(OAc)_3$, $NaBH_3CN$ in a protic solvent such as MeOH at pH maintained weakly acidic (around pH 5) by addition of acetic acid or TFA.

EXAMPLE 13774

6-Ethyl-5,6,7,8-tetrahydro-2-phenyl-8(S)-phenylmethyl-imidazo[1,2-a]pyrazine

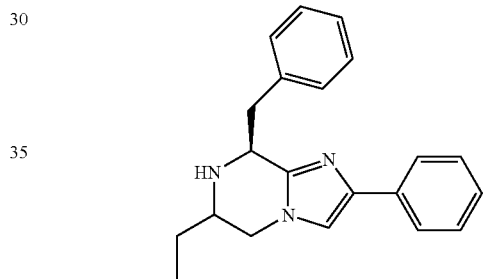

2-[1(S)-{1,1-Dimethylethoxy)carbonylamino}-2-phenylethyl]-1-(2-oxo-butyl)-4-phenyl-1H-imidazole (60 mg) in a mixture of 10% TFA in DCM was stirred at about 20° C. for about 3 hours and then concentrated under reduced pressure. The resulting intermediate dihydro-imidazo-pyrazine was dissolved in methanol and borohydride supported on resin (AMBERLITE® IRA 400, Aldrich, 2.5 mmol $BH_4^-$/g; 4 eq) was added. The pH was maintained at about 5 by addition of drops of TFA. After about 2 hours of stirring at about 20° C., the mixture was filtered and the filtrate concentrated under reduced pressure. The residue was purified by flash chromatography (ethyl acetate/Heptane 7:3; Rf=0.30). The tetrahydro-imidazo-pyrazine was obtained as a single diastereoisomer in 86% yield (38 mg). NMR ($^1$H, 400 MHz, $CDCl_3$) δ: 7.80-7.10 (m, 11H, arom. H), 4.28 (dd, 1H, $^3$J=10 Hz, $^3$J=3 Hz, H8), 3.95 (dd, 1H, $^2$J=11.5 Hz, $^3$J=3.6 Hz), 3.85 (dd, 1H, $^2$J=13.6 Hz, $^3$J=3.0 Hz), 3.60 (t, 1H, $^2$J=$^3$J=11.5 Hz), 3.85 (dd, 1H, $^2$J=13.6 Hz, $^3$J=10. Hz), 2.98 (m, 2H), 1.85 (s, 1H, NH), 1.55 (m, 2H, $CH_2$), 0.95 (t, 3H, $CH_3$). NMR ($^{13}$C, 100 MHz, $CDCl_3$): 146.3, 140.9, 138.0, 134.4, 129.4, 128.6, 128.5, 126.6, 126.5, 124.8, 113.8, 55.9, 54.4, 50.2, 40.0, 26.6, 10.0.

LC/MS: calculated MW=317.43, m/z=318.20 (M+H).

EXAMPLE 13775

The following compound was prepared analogously to the procedure described for Example 13774 using the appropriate starting materials, which can be obtained from commercial sources or synthesized according to methods known to those skilled in the art or as enabled by the teachings herein.

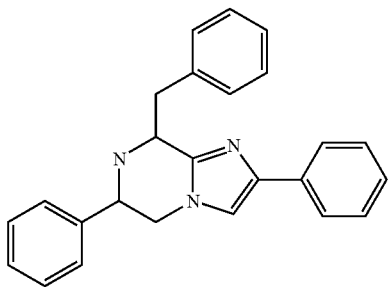

Example 13775

N-SUBSTITUTED TETRAHYDRO-IMIDAZO-PYRAZINES

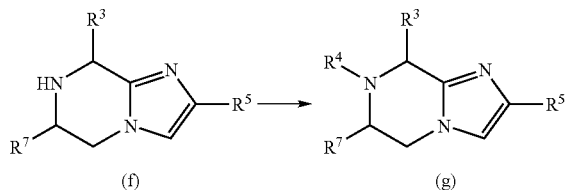

General procedure: A compound of formula (f) can react with isocyanates, isothiocyanates, N-succinimidyl carbamates, acyl chlorides or activated carboxylic acids in an aprotic solvent at 20-70° C. for 2-18 hours. The resulting derivative can be isolated by evaporation of the mixture followed by flash chromatography on silica gel or by addition to the mixture of a nucleophile supported on polymer such as aminomethyl or thiomethyl polystyrene resin followed by a filtration.

EXAMPLE 13776

5,6,7,8-Tetrahydro-7-(methoxymethylcarbonyl)-2,6-diphenyl-8(S)-phenylmethyl-imidazo[1,2-a]pyrazine

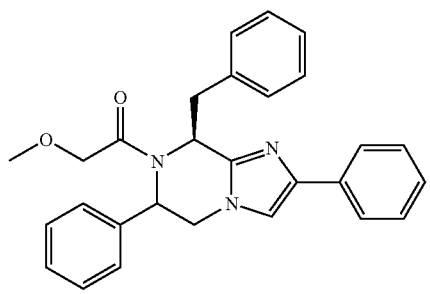

To a solution of 5,6,7,8-tetrahydro-2,6-diphenyl-8(S)-phenylmethyl-imidazo[1,2-a]pyrazine (29 mg) in chloroform were successively added morpholinom thylpolystyrene resin (Novabiochem, loading=3.51 mmol/g, 50 mg, 2eq) and methoxyacetylchloride (10 mL, 1.3 eq). After about 3 hours of stirring at about 20° C., chloroform was added to the mixture followed by aminomethylpolystyrene resin (Novabiochem, loading=1.2 mmol/g, 132 mg, 2 eq). The reaction mixture was stirred for another 2 hours and then filtered. The filtrate was concentrated under reduced pressure to afford 23 mg of the title compound (yield=68%). NMR ($^1$H, 100 MHz, CDCl$_3$): 7.9-7.0 (m, 16H, arom. H), 6.6 (m, 1H, H$_8$), 5.3 (m, 1H, H$_6$), 4.6 (dd, 1H, $^2$J=13 Hz, H5), 4.35 (dd, 1H, $^2$J=13 Hz, $^3$J=5 Hz, H5'), 3.7-2.9 (m, 5H, CH$_2$Ph, OCH$_3$).

The following tables of compounds illustrate some of the compounds of the present invention that were synthesized and provide the hplc retention time (denoted Rt or Tr) in minutes and mass spectra results of each compound.

Mass spectra were acquired on a single quadrupole electrospray mass spectrometer (Micromass, Platform model), 0.8 Da resolution. A monthly calibration, between 80 and 1000 Da, is performed with sodium and rubidium iodide solution isopropanol/water (1/1 Vol.).

HPLC retention times were acquired on an HPLC system: HP1100 (Hewlett-Packard) equipped with a photodiode array UV detector.

The HPLC conditions are as follows and the conditions used for each of the following tables of compounds are noted below, the wavlength of the UV detector is noted in parenthesis after the formula number.

| Condition A: Solvent: A: Water + 0.4% Formic acid B: Acetonitrile + 0.4% Formic acid | | |
|---|---|---|
| T(min) | A % | B % |
| 0 | 90 | 10 |
| 5 | 90 | 10 |
| 16 | 40 | 60 |
| 17 | 10 | 90 |
| 20 | 10 | 90 |

Flow rate: 1 ml/min
Injection volume volume: 20 μL
Column: Kromasil ODS 5 μm 150 * 4.6 mm i.d.
Temp.: 40° C.

| Condition A$_2$: Solvent: A: Water + 0.4% Formic acid B: Acetonitrile + 0.4% Formic acid | | |
|---|---|---|
| T(min) | A % | B % |
| 0 | 90 | 10 |
| 2 | 90 | 10 |
| 14 | 10 | 90 |
| 20 | 10 | 90 |

Flow rate: 1 ml/min
Injection volume: 20 μL
Column: Kromasil ODS 5 μm 150 * 4.6 mm i.d.
Temp.: 40° C.

Condition A₃:
Solvent:
A: Water + 0.4% Formic acid
B: Acetonitrile + 0.4% Formic acid

| T(min) | A % | B % |
|---|---|---|
| 0 | 90 | 10 |
| 5 | 90 | 10 |
| 16 | 46 | 54 |
| 17.5 | 10 | 90 |
| 22 | 10 | 90 |

Flow rate: 1 ml/min
Injection volume: 20 μL
Column: Kromasil ODS 5 μm 150 * 4.6 mm i.d.
Temp.: 40° C.

Condition A₄:
Solvent:
A: Water + 0.4% Formic acid
B: Acetonitrile + 0.4% Formic acid

| T(min) | A % | B % |
|---|---|---|
| 0 | 90 | 10 |
| 5 | 90 | 10 |
| 20 | 10 | 90 |
| 25 | 10 | 90 |

Flow rate: 1 ml/min
Injection volume: 20 μL
Column: Kromasil ODS 5 μm 150 * 4.6 mm i.d.
Temp.: 40° C.

Condition A₅:
Solvent:
A: Water + 0.4% Formic acid
B: Acetonitrile + 0.4% Formic acid

| T(min) | A % | B % |
|---|---|---|
| 0 | 90 | 10 |
| 5 | 90 | 10 |
| 25 | 10 | 90 |
| 30 | 10 | 90 |

Flow rate: 1 ml/min
Injection volume: 20 μL
Column: Kromasil ODS 5 μm 150 * 4.6 mm i.d.
Temp.: 40° C.

Condition B:
Solvent:
A: Water + 0.02% Trifluoroacetic acid
B: Acetonitrile

| T(min) | A % | B % |
|---|---|---|
| 0 | 100 | 0 |
| 1 | 100 | 0 |
| 8 | 30 | 70 |
| 10 | 30 | 70 |

Flow rate: 1.1 ml/min
Injection volume: 5 μL
Column: Uptisphere ODS 3 μm 33 * 4.6 mm i.d
Temp.: 40° C.

Condition C:
Solvent:
A: Water + 0.02% Trifluoroacetic acid
B: Acetonitrile

| T(min) | A % | B % |
|---|---|---|
| 0 | 100 | 0 |
| 1 | 100 | 0 |
| 10 | 85 | 25 |
| 12 | 85 | 25 |

Flow rate: 1.1 ml/min
Injection volume: 5 μL
Column: Uptisphere ODS 3 μm 33 * 4.6 mm i.d
Temp.: 40° C.

Condition D:
Solvent:
A: Water + 0.04% Trifluoroacetic acid
B: Acetonitrile

| T(min) | A % | B % |
|---|---|---|
| 0 | 100 | 0 |
| 1 | 100 | 0 |
| 8 | 30 | 70 |
| 10 | 30 | 70 |

Flow rate: 1.1 ml/min
Injection volume: 5 μL
Column: Uptisphere ODS 3 μm 33 * 4.6 mm i.d
Temp.: 40° C.

Condition E:
Solvent:
A: Water + 0.04% Trifluoroacetic acid
B: Acetonitrile

| T(min) | A % | B % |
|---|---|---|
| 0 | 90 | 10 |
| 1 | 90 | 10 |
| 8 | 0 | 100 |
| 10 | 0 | 100 |

Flow rate: 1.1 ml/min
Injection volume: 5 μL
Column: Uptisphere ODS 3 μm 33 * 4.6 mm i.d
Temp.: 40° C.

In the following description Formula numbers are noted in bold and the wavelength is in parenthesis.

Method A=Used for Tables of compounds of Formulas: 17 (250), 18 (250) and 57 (220).

Method A₄=Used for Tables of compounds of Formulas: 58 (210).

Method B=Used for Tables of compounds of Formulas: 7 (220), 8 (220), 9 (220), 10 (220), 11 (220), 12 (250), 19 (220), 20 (260), 21 (250), 25 (240), 26 (220), 27 (220), 28 (220), 29 (220), 37 (220), 38 (220), 39 (220), 40 (240), 44 (220), 45 (220), 46 (220), 47 (220), 48 (220), 49 (250), 55 (260), and 56 (220).

Method C=Used for Tables of compounds of Formulas: 1 (220), 2 (220), 3 (220), 4 (260), 5 (220), 6 (220), 13 (220), 14 (220), 16 (260), 23 (250), 24 (250), 30 (220), 31 (254), 32 (250), 33 (250), 34 (250), 35 (250), and 36 (254).

Method D=Used for Tables of compounds of Formulas: 15 (220), 51 (220), 52 (220), 53 (220), and 54 (220).

Method E=Used for Tables of compounds of Formulas: 22 (250), 41 (220), 42 (250), 43 (220), and 50 (250).

FORMULA 1
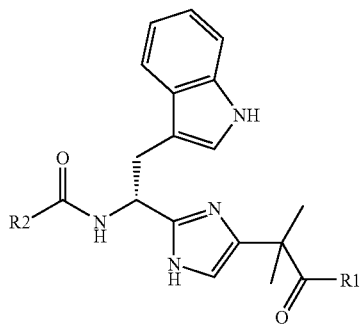
| | R1 | R2 | Analysis | |
|---|---|---|---|---|
| | | | Rt (min) | [M + H]+ |
| 1 | tert-butyl carbamate ethylamine | spiro[indene-piperidine] | 7.0 | 666.5 |
| 2 | tert-butyl carbamate ethylamine | spiro[indane-piperidine] | 7.1 | 668.5 |
| 3 | tert-butyl carbamate ethylamine | benzimidazolone-piperidine | 6.2 | 712.5 |
| 4 | tert-butyl carbamate ethylamine | 4-piperidinopiperidine | 6.1 | 698.5 |
| 5 | tert-butyl carbamate ethylamine | 4-piperidinopiperidine | 5.0 | 649.5 |

-continued

FORMULA 1

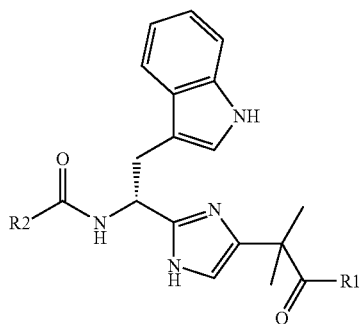

| | R1 | R2 | Analysis | |
|---|---|---|---|---|
| | | | Rt (min) | [M + H]+ |
| 6 | tert-butyl (2-aminoethyl)carbamate | 4-benzylpiperidine | 7.2 | 656.5 |
| 7 | tert-butyl (2-aminoethyl)carbamate | 4-hydroxy-4-phenylpiperidine | 6.2 | 658.5 |
| 8 | tert-butyl (2-aminoethyl)carbamate | 1-phenylpiperazine | 6.4 | 643.5 |
| 9 | tert-butyl (2-aminoethyl)carbamate | 1-(2-fluorophenyl)piperazine | 6.7 | 661.5 |
| 10 | tert-butyl (2-aminoethyl)carbamate | 1-(2-methylthiophenyl)piperazine | 7.0 | 689.5 |
| 11 | tert-butyl (2-aminoethyl)carbamate | 1-(2-furoyl)piperazine | 5.8 | 661.4 |
| 12 | tert-butyl (2-aminoethyl)carbamate | 1-benzylpiperazine | 5.3 | 657.5 |

-continued

FORMULA 1

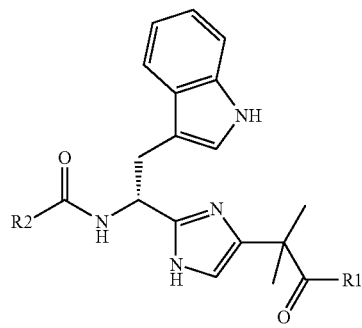

| | R1 | R2 | Rt (min) | [M + H]+ |
|---|---|---|---|---|
| 13 | tert-butyl (2-aminoethyl)carbamate | 1-(benzo[d][1,3]dioxol-5-ylmethyl)piperazine | 5.4 | 701.5 |
| 14 | tert-butyl (2-aminoethyl)carbamate | 1-benzhydrylpiperazine | 6.2 | 733.5 |
| 15 | tert-butyl (2-aminoethyl)carbamate | 2,3,4,9-tetrahydro-1H-pyrido[3,4-b]indole | 6.7 | 653.5 |
| 16 | tert-butyl (2-aminoethyl)carbamate | N-benzyl-N',N'-dimethylethane-1,2-diamine | 5.5 | 659.5 |
| 17 | tert-butyl (2-aminoethyl)carbamate | 2-(piperazin-1-yl)ethanol | 4.8 | 611.4 |
| 18 | tert-butyl (2-aminoethyl)carbamate | tert-butyl piperidin-4-ylcarbamate | 6.4 | 681.5 |
| 19 | tert-butyl (2-aminoethyl)carbamate | tert-butyl piperazine-1-carboxylate | 6.4 | 667.5 |

-continued
FORMULA 1
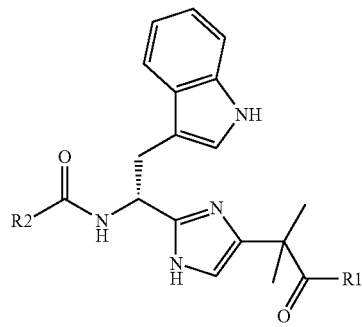
| | R1 | R2 | Analysis Rt (min) | [M + H]+ |
|---|---|---|---|---|
| 20 | tert-butyl N-(2-aminoethyl)carbamate-* | 1-benzylpiperidin-4-ylamino-* | 5.4 | 671.5 |
| 21 | tert-butyl N-(3-aminopropyl)carbamate-* | spiro[indene-1,4'-piperidine]-N-* | 7.2 | 680.5 |
| 22 | tert-butyl N-(3-aminopropyl)carbamate-* | spiro[indane-1,4'-piperidine]-N-* | 7.2 | 682.5 |
| 23 | tert-butyl N-(3-aminopropyl)carbamate-* | 1-phenyl-1,3,8-triazaspiro[4.5]decan-4-one-N-* | 6.4 | 726.5 |

-continued

FORMULA 1

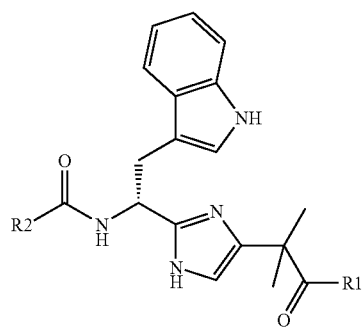

| | R1 | R2 | Analysis Rt (min) | [M + H]+ |
|---|---|---|---|---|
| 24 | tert-butyl N-(3-aminopropyl)carbamate | 1-(piperidin-4-yl)-1,3-dihydro-2H-benzimidazol-2-one | 6.2 | 712.5 |
| 25 | tert-butyl N-(3-aminopropyl)carbamate | 4-(piperidin-1-yl)piperidine | 5.1 | 663.5 |
| 26 | tert-butyl N-(3-aminopropyl)carbamate | 4-benzylpiperidine | 7.2 | 670.5 |
| 27 | tert-butyl N-(3-aminopropyl)carbamate | 4-hydroxy-4-phenylpiperidine | 6.3 | 672.5 |
| 28 | tert-butyl N-(3-aminopropyl)carbamate | 1-phenylpiperazine | 6.6 | 657.5 |
| 29 | tert-butyl N-(3-aminopropyl)carbamate | 1-(2-fluorophenyl)piperazine | 6.8 | 675.5 |

-continued
FORMULA 1
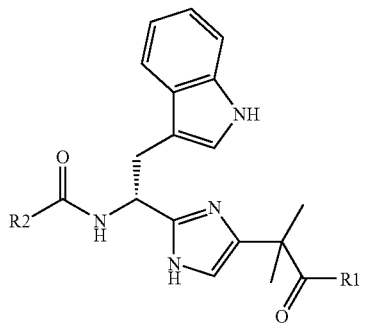
|    | R1 | R2 | Rt (min) | [M + H]+ |
|----|----|----|----------|----------|
| 30 | (Boc-NH-propyl-NH-*) | (2-methylthiophenyl-piperazine-*) | 7.1 | 703.5 |
| 31 | (Boc-NH-propyl-NH-*) | (furan-2-carbonyl-piperazine-*) | 5.9 | 675.4 |
| 32 | (Boc-NH-propyl-NH-*) | (benzyl-piperazine-*) | 5.4 | 671.5 |
| 33 | (Boc-NH-propyl-NH-*) | (piperonyl-piperazine-*) | 5.5 | 715.5 |
| 34 | (Boc-NH-propyl-NH-*) | (diphenylmethyl-piperazine-*) | 6.3 | 747.5 |
| 35 | (Boc-NH-propyl-NH-*) | (tetrahydro-β-carboline-*) | 6.8 | 667.5 |
| 36 | (Boc-NH-propyl-NH-*) | (N-benzyl-N',N'-dimethylethylenediamine-*) | 5.6 | 673.5 |

-continued

FORMULA 1

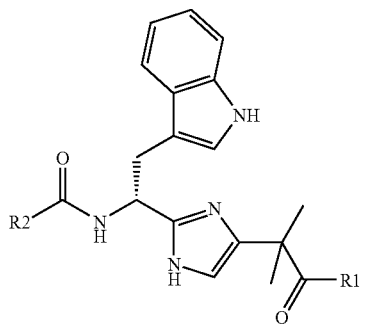

| | R1 | R2 | Analysis | |
|---|---|---|---|---|
| | | | Rt (min) | [M + H]+ |
| 37 | tert-butyl N-(3-aminopropyl)carbamate | 1-(2-hydroxyethyl)piperazine | 4.9 | 625.5 |
| 38 | tert-butyl N-(3-aminopropyl)carbamate | tert-butyl piperidin-4-ylcarbamate | 6.5 | 681.5 |
| 39 | tert-butyl N-(3-aminopropyl)carbamate | tert-butyl piperazine-1-carboxylate | 6.5 | 695.5 |
| 40 | tert-butyl N-(3-aminopropyl)carbamate | 1-benzylpiperidin-4-amine | 5.5 | 685.5 |
| 41 | tert-butyl N-(4-aminobutyl)carbamate | spiro[indene-1,4'-piperidine] | 7.2 | 694.5 |

FORMULA 1
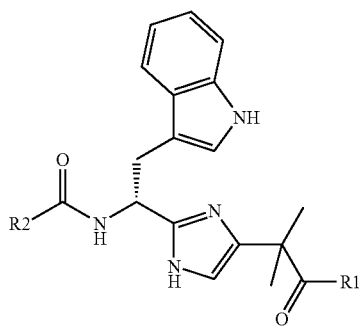
| | R1 | R2 | Analysis Rt (min) | [M + H]+ |
|---|---|---|---|---|
| 42 | | | 7.3 | 696.5 |
| 43 | | | 6.4 | 740.5 |
| 44 | | | 6.3 | 726.5 |
| 45 | | | 5.2 | 677.5 |
| 46 | | | 7.3 | 684.5 |

-continued

FORMULA 1

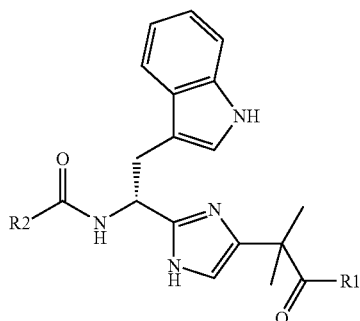

| | R1 | R2 | Analysis | |
|---|---|---|---|---|
| | | | Rt (min) | [M + H]+ |
| 47 | tert-butyl N-(4-aminobutyl)carbamate | 4-hydroxy-4-phenylpiperidine | 6.4 | 686.5 |
| 48 | tert-butyl N-(4-aminobutyl)carbamate | 4-phenylpiperazine | 6.6 | 671.5 |
| 49 | tert-butyl N-(4-aminobutyl)carbamate | 4-(2-fluorophenyl)piperazine | 6.8 | 689.5 |
| 50 | tert-butyl N-(4-aminobutyl)carbamate | 4-(2-methylthiophenyl)piperazine | 7.1 | 717.5 |
| 51 | tert-butyl N-(4-aminobutyl)carbamate | 4-(furan-2-carbonyl)piperazine | 6.0 | 689.5 |
| 52 | tert-butyl N-(4-aminobutyl)carbamate | 4-benzylpiperazine | 5.5 | 685.5 |
| 53 | tert-butyl N-(4-aminobutyl)carbamate | 4-(benzo[d][1,3]dioxol-5-ylmethyl)piperazine | 5.5 | 729.5 |

-continued

FORMULA 1

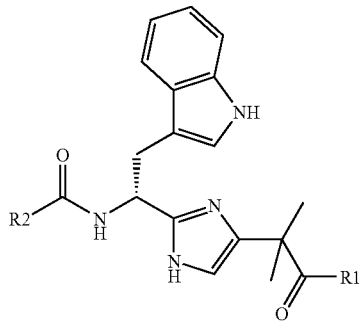

| | R1 | R2 | Analysis | |
|---|---|---|---|---|
| | | | Rt (min) | [M + H]+ |
| 54 | tert-butyl N-(4-aminobutyl)carbamate | 4-benzhydrylpiperazine | 6.4 | 761.5 |
| 55 | tert-butyl N-(4-aminobutyl)carbamate | 2,3,4,9-tetrahydro-1H-β-carboline | 6.9 | 681.4 |
| 56 | tert-butyl N-(4-aminobutyl)carbamate | N-benzyl-N',N'-dimethylethylenediamine | 5.6 | 687.5 |
| 57 | tert-butyl N-(4-aminobutyl)carbamate | 1-(2-hydroxyethyl)piperazine | 5.0 | 639.5 |
| 58 | tert-butyl N-(4-aminobutyl)carbamate | tert-butyl piperidin-4-ylcarbamate | 6.6 | 709.5 |
| 59 | tert-butyl N-(4-aminobutyl)carbamate | tert-butyl piperazine-1-carboxylate | 6.6 | 695.5 |

-continued
FORMULA 1
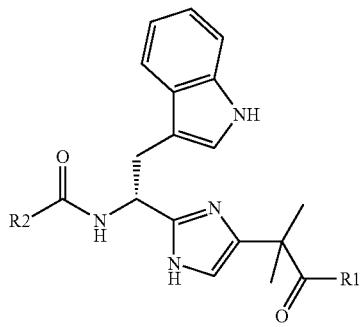
| | R1 | R2 | Analysis Rt (min) | [M + H]+ |
|---|---|---|---|---|
| 60 | | | 5.5 | 699.5 |
| 61 | | | 7.68 + 7.8 | 748.5 |
| 62 | | | 7.7 | 750.5 |
| 63 | | | 7.0 | 794.5 |

-continued

FORMULA 1

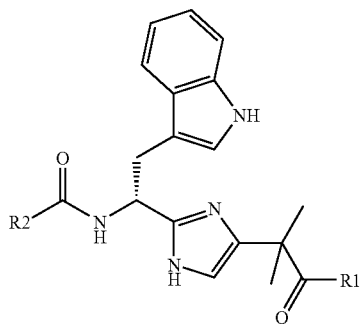

| | R1 | R2 | Rt (min) | [M + H]+ |
|---|---|---|---|---|
| 64 | tert-butyl carbamate-CH2-cyclohexyl-CH2-NH-* | benzimidazol-2-one-piperidinyl-* | 6.8 | 780.5 |
| 65 | tert-butyl carbamate-CH2-cyclohexyl-CH2-NH-* | 4-piperidinopiperidinyl-* | 5.8 | 731.6 |
| 66 | tert-butyl carbamate-CH2-cyclohexyl-CH2-NH-* | 4-benzylpiperidinyl-* | 7.8 | 738.5 |
| 67 | tert-butyl carbamate-CH2-cyclohexyl-CH2-NH-* | 4-hydroxy-4-phenylpiperidinyl-* | 6.9 | 743.5 |
| 68 | tert-butyl carbamate-CH2-cyclohexyl-CH2-NH-* | 4-phenylpiperazinyl-* | 7.2 | 725.5 |
| 69 | tert-butyl carbamate-CH2-cyclohexyl-CH2-NH-* | 4-(2-fluorophenyl)piperazinyl-* | 7.3 | 743.5 |

-continued

FORMULA 1

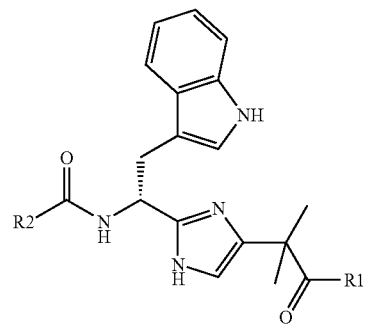

| | R1 | R2 | Analysis Rt (min) | [M + H]+ |
|---|---|---|---|---|
| 70 | tert-butyl carbamate-cyclohexyl-CH2-NH-* | 2-(methylthio)phenyl-piperazine-* | 7.6 | 771.5 |
| 71 | tert-butyl carbamate-cyclohexyl-CH2-NH-* | furan-2-carbonyl-piperazine-* | 6.5 | 743.5 |
| 72 | tert-butyl carbamate-cyclohexyl-CH2-NH-* | benzyl-piperazine-* | 6.0 | 739.5 |
| 73 | tert-butyl carbamate-cyclohexyl-CH2-NH-* | benzo[d][1,3]dioxol-5-ylmethyl-piperazine-* | 6.0 | 783.5 |
| 74 | tert-butyl carbamate-cyclohexyl-CH2-NH-* | diphenylmethyl-piperazine-* | 6.8 | 815.6 |
| 75 | tert-butyl carbamate-cyclohexyl-CH2-NH-* | tetrahydro-β-carboline-* | 7.4 | 735.5 |

-continued
FORMULA 1
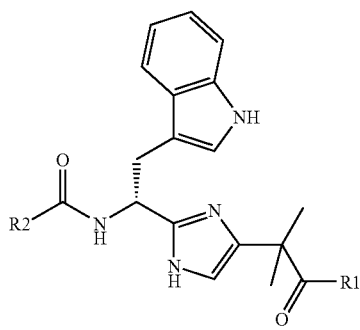
| | R1 | R2 | Rt (min) | [M + H]+ |
|---|---|---|---|---|
| 76 | | | 6.1 | 741.5 |
| 77 | | | 5.6 | 693.5 |
| 78 | | | 7.1 + 7.2 | 749.5 |
| 79 | | | 7.1 + 7.2 | 753.5 |
| 80 | | | 6.0 | 753.5 |

FORMULA 2
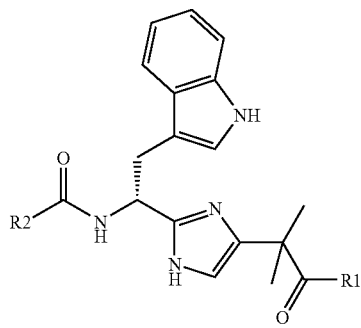
| | R1 | R3 | Rt (min.) | [M + H]+ |
|---|---|---|---|---|
| 1 | H₂N⌒NH—* | spiro[indene-1,4'-piperidine] | 5.5 | 566.3 |
| 2 | H₂N⌒NH—* | spiro[indane-1,4'-piperidine] | 5.6 | 568.3 |
| 3 | H₂N⌒NH—* | 1-phenyl-1,3,8-triazaspiro[4.5]decan-4-one | 4.9 | 612.3 |
| 4 | H₂N⌒NH—* | 1-(piperidin-4-yl)-1,3-dihydro-2H-benzimidazol-2-one | 4.8 | 598.3 |
| 5 | H₂N⌒NH—* | 4-(piperidin-1-yl)piperidine | 3.8 | 549.4 |

-continued
FORMULA 2
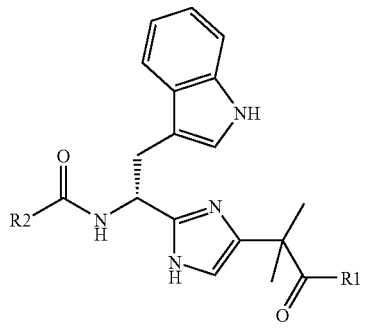
| | R1 | R3 | Rt (min.) | [M + H]+ |
|---|---|---|---|---|
| 6 | H₂N~NH-* | 4-benzylpiperidine | 5.6 | 556.3 |
| 7 | H₂N~NH-* | 4-phenyl-1,2,3,6-tetrahydropyridine | 5.3 | 540.3 |
| 8 | H₂N~NH-* | 1-phenylpiperazine | 4.9 | 543.3 |
| 9 | H₂N~NH-* | 1-(2-fluorophenyl)piperazine | 5.1 | 561.3 |
| 10 | H₂N~NH-* | 1-(2-methylthiophenyl)piperazine | 5.4 | 589.3 |
| 11 | H₂N~NH-* | 1-(2-furoyl)piperazine | 4.3 | 561.3 |
| 12 | H₂N~NH-* | 1-benzylpiperazine | 4.1 | 557.3 |

-continued
FORMULA 2
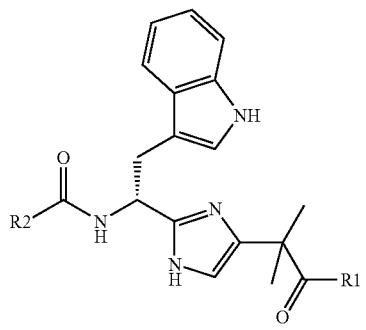
| | R1 | R3 | Rt (min.) | [M + H]+ |
|---|---|---|---|---|
| 13 | H₂N~~NH-* | benzodioxole-CH₂-piperazine-* | 4.1 | 601.3 |
| 14 | H₂N~~NH-* | diphenylmethyl-piperazine-* | 4.9 | 633.4 |
| 15 | H₂N~~NH-* | tetrahydro-β-carboline-* | 5.3 | 533.3 |
| 16 | H₂N~~NH-* | benzyl-N(*)-CH₂CH₂-N(CH₃)₂ | 4.2 | 559.3 |
| 17 | H₂N~~NH-* | *-piperazine-CH₂CH₂-OH | 3.5 | 511.3 |
| 18 | H₂N~~NH-* | 4-amino-piperidine-* | 3.5 | 481.3 |
| 19 | H₂N~~NH-* | piperazine-* | 3.5 | 467.3 |

-continued
FORMULA 2
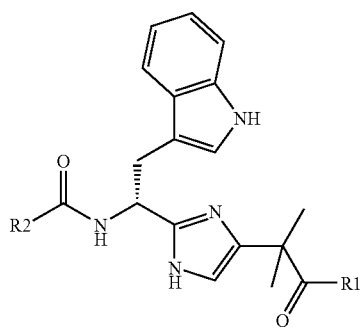
| | R1 | R3 | Rt (min.) | [M + H]+ |
|---|---|---|---|---|
| 20 | H₂N〜NH→* | 1-benzylpiperidin-4-ylamino | 4.1 | 571.3 |
| 21 | H₂N〜〜NH→* | spiro[indene-1,4'-piperidine] | 5.6 | 580.4 |
| 22 | H₂N〜〜NH→* | spiro[indane-1,4'-piperidine] | 5.6 | 582.4 |
| 23 | H₂N〜〜NH→* | 1-phenyl-1,3,8-triazaspiro[4.5]decan-4-one | 4.9 | 626.4 |

-continued
FORMULA 2
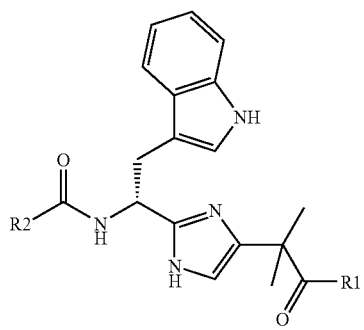
| | R1 | R3 | Rt (min.) | [M + H]+ |
|---|---|---|---|---|
| 24 | H₂N~~~NH* | benzimidazolone-piperidine | 4.8 | 612.4 |
| 25 | H₂N~~~NH* | piperidinyl-piperidine | 3.8 | 563.4 |
| 26 | H₂N~~~NH* | 4-benzylpiperidine | 5.6 | 570.4 |
| 27 | H₂N~~~NH* | 4-phenyl-tetrahydropyridine | 5.4 | 554.3 |
| 28 | H₂N~~~NH* | 4-phenylpiperazine | 4.9 | 557.3 |
| 29 | H₂N~~~NH* | 4-(2-fluorophenyl)piperazine | 5.1 | 575.3 |

-continued
FORMULA 2
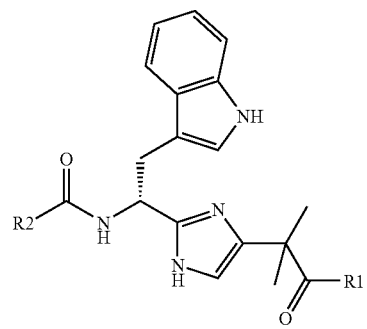
| | R1 | R3 | Rt (min.) | [M + H]+ |
|---|---|---|---|---|
| 30 | H₂N⌒⌒NH→* | 2-(methylthio)phenyl-piperazinyl | 5.4 | 603.3 |
| 31 | H₂N⌒⌒NH→* | furan-2-carbonyl-piperazinyl | 4.4 | 575.3 |
| 32 | H₂N⌒⌒NH→* | benzyl-piperazinyl | 4.1 | 571.3 |
| 33 | H₂N⌒⌒NH→* | benzo[1,3]dioxol-5-ylmethyl-piperazinyl | 4.1 | 615.4 |
| 34 | H₂N⌒⌒NH→* | diphenylmethyl-piperazinyl | 4.9 | 647.4 |
| 35 | H₂N⌒⌒NH→* | 2,3,4,9-tetrahydro-1H-β-carbolin-2-yl | 5.3 | 567.3 |
| 36 | H₂N⌒⌒NH→* | N-benzyl-N-(2-dimethylaminoethyl)amino | 4.2 | 573.3 |
| 37 | H₂N⌒⌒NH→* | 4-(2-hydroxyethyl)piperazin-1-yl | 3.5 | 525.3 |

-continued

FORMULA 2

[Structure of Formula 2: R2-C(=O)-NH-CH(CH2-indol-3-yl)-[imidazole]-C(CH3)2-C(=O)-R1]

| | R1 | R3 | Rt (min.) | [M + H]+ |
|---|---|---|---|---|
| 38 | H2N~~~NH-* | H2N-[4-piperidinyl]-N-* | 3.5 | 495.3 |
| 39 | H2N~~~NH-* | HN-[piperazine]-N-* | 3.5 | 481.3 |
| 40 | H2N~~~NH-* | 1-benzyl-piperidin-4-yl-NH-* | 4.1 | 585.4 |
| 41 | H2N~~~~NH-* | spiro[indene-1,4'-piperidine]-N-* | 5.6 | 594.4 |
| 42 | H2N~~~~NH-* | spiro[indane-1,4'-piperidine]-N-* | 5.6 | 596.4 |
| 43 | H2N~~~~NH-* | 1-phenyl-1,3,8-triazaspiro[4.5]decan-4-one-8-yl-* | 5.0 | 640.4 |

-continued
FORMULA 2
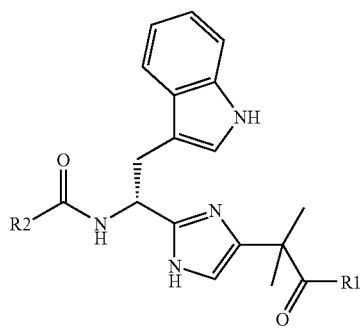
| | R1 | R3 | Rt (min.) | [M + H]+ |
|---|---|---|---|---|
| 44 | H₂N~~~NH–* | benzimidazolone-piperidinyl | 4.8 | 626.4 |
| 45 | H₂N~~~NH–* | 4-benzylpiperidinyl | 5.6 | 584.4 |
| 46 | H₂N~~~NH–* | 4-phenyl-tetrahydropyridinyl | 5.7 | 568.3 |
| 47 | H₂N~~~NH–* | 4-phenylpiperazinyl | 5 | 571.3 |
| 48 | H₂N~~~NH–* | 4-(2-fluorophenyl)piperazinyl | 5.1 | 589.4 |
| 49 | H₂N~~~NH–* | 4-(2-methylthiophenyl)piperazinyl | 5.5 | 617.4 |

-continued
FORMULA 2
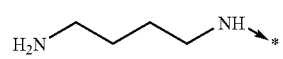
| | R1 | R3 | Rt (min.) | [M + H]+ |
|---|---|---|---|---|
| 50 | 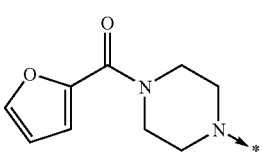 | 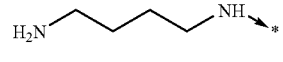 | 4.4 | 589.3 |
| 51 | 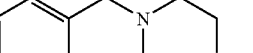 | 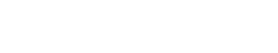 | 4.1 | 585.4 |
| 52 | 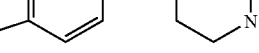 | 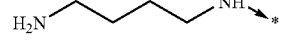 | 4.2 | 629.4 |
| 53 | 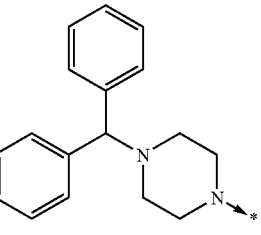 | 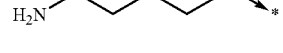 | 4.9 | 661.5 |
| 54 | 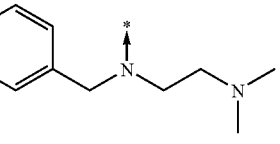 | 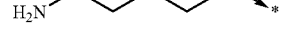 | 4.3 | 587.4 |
| 55 | 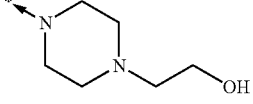 | 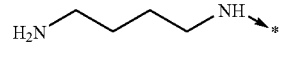 | 3.6 | 539.4 |
| 56 | 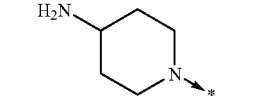 | 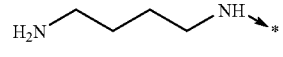 | 3.6 | 509.4 |
| 57 | 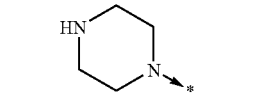 | | 3.5 | 495.3 |

-continued
FORMULA 2
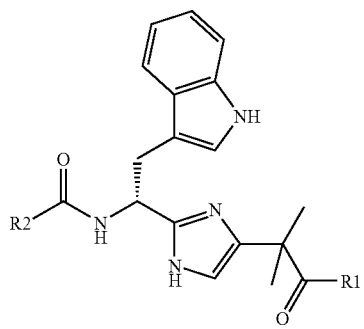
| | R1 | R3 | Rt (min.) | [M + H]+ |
|---|---|---|---|---|
| 58 | H₂N−(CH₂)₄−NH−* | 1-benzylpiperidin-4-yl-NH−* | 4.1 | 599.3 |
| 59 | H₂N−CH₂−(cyclohexyl)−CH₂−NH−* | spiro[indene-1,4'-piperidine]−N−* | 5.8 | 648.5 |
| 60 | H₂N−CH₂−(cyclohexyl)−CH₂−NH−* | spiro[indane-1,4'-piperidine]−N−* | 5.9 | 650.5 |
| 61 | H₂N−CH₂−(cyclohexyl)−CH₂−NH−* | 1-phenyl-1,3,8-triazaspiro[4.5]decan-4-one−N−* | 5.2 | 694.5 |

-continued
FORMULA 2
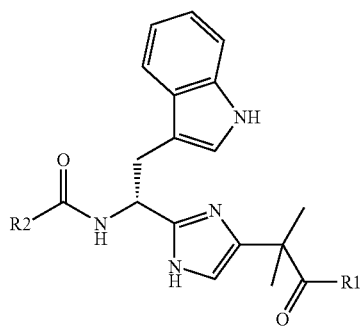
| | R1 | R3 | Rt (min.) | [M + H]+ |
|---|---|---|---|---|
| 62 | H₂N–[cyclohexyl]–NH–* | benzimidazolone-piperidine | 5 | 680.5 |
| 63 | H₂N–[cyclohexyl]–NH–* | 4-benzylpiperidine | 5.9 | 638.5 |
| 64 | H₂N–[cyclohexyl]–NH–* | 4-phenylpiperazine | 5.2 | 625.5 |
| 65 | H₂N–[cyclohexyl]–NH–* | 4-(2-fluorophenyl)piperazine | 5.4 | 643.5 |
| 66 | H₂N–[cyclohexyl]–NH–* | 4-(2-methylthiophenyl)piperazine | 5.7 | 671.4 |
| 67 | H₂N–[cyclohexyl]–NH–* | 4-(2-furoyl)piperazine | 4.6 | 643.4 |

-continued
FORMULA 2
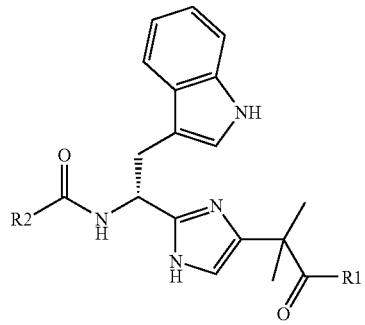
| | R1 | R3 | Rt (min.) | [M + H]+ |
|---|---|---|---|---|
| 68 | H₂N-cyclohexyl-NH-* | benzyl-piperazinyl-* | 4.4 | 639.5 |
| 69 | H₂N-cyclohexyl-NH-* | (1,3-benzodioxol-5-ylmethyl)-piperazinyl-* | 4.4 | 689.5 |
| 70 | H₂N-cyclohexyl-NH-* | (diphenylmethyl)-piperazinyl-* | 5.2 | 715.5 |
| 71 | H₂N-cyclohexyl-NH-* | N-benzyl-N-(2-dimethylaminoethyl)amino-* | 4.5 | 641.5 |
| 72 | H₂N-cyclohexyl-NH-* | 4-(2-hydroxyethyl)piperazin-1-yl-* | 3.9 | 593.4 |

FORMULA 3
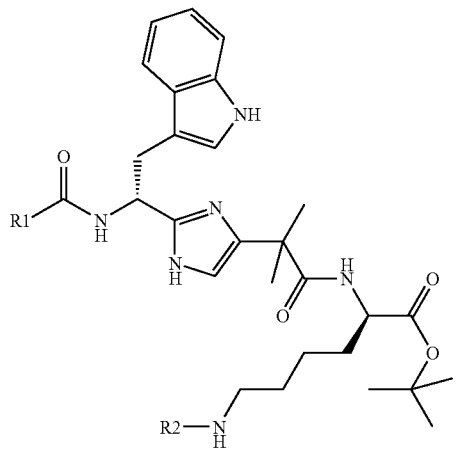
| | Structure | Analysis | |
|---|---|---|---|
| | | Rt (min) | [M + H]+ |
| 1 | 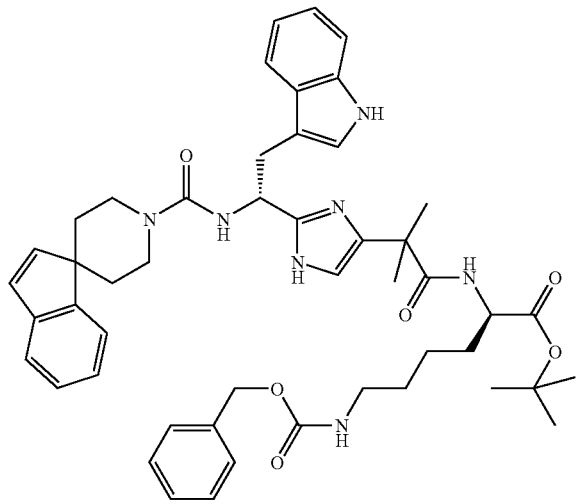 | 9.1 | 842.5 |
| 2 | 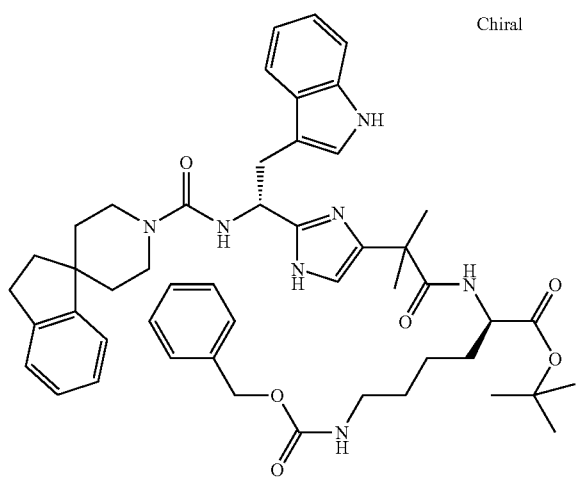 Chiral | 9.2 | 844.5 |

FORMULA 3
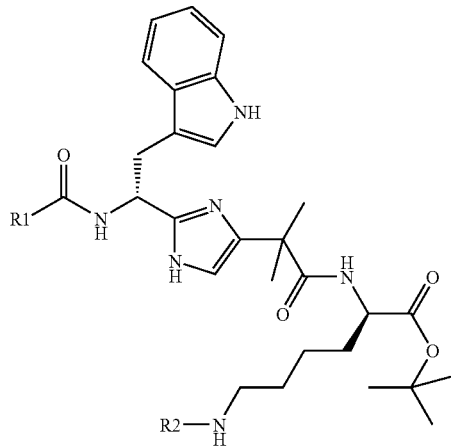
| | Structure | Analysis Rt (min) | [M + H]+ |
|---|---|---|---|
| 3 | Chiral 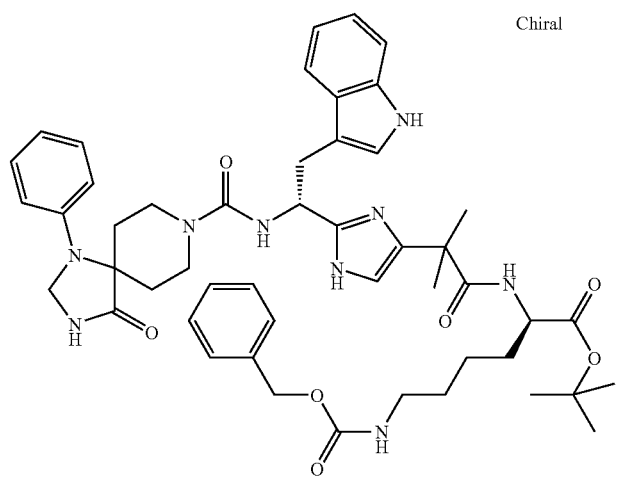 | 8.3 | 888.5 |
| 4 | Chiral 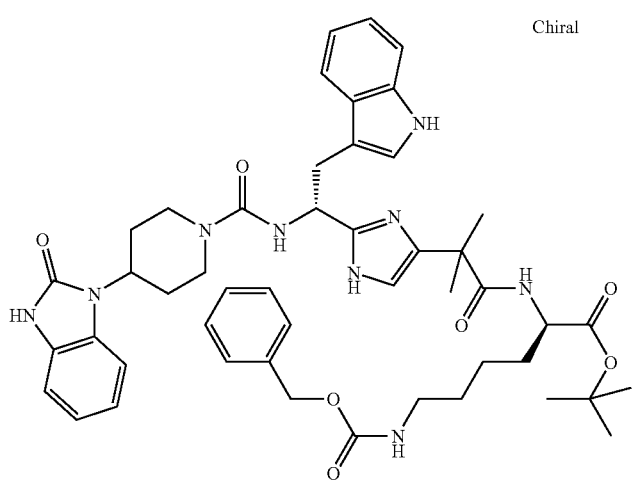 | 8.1 | 874.5 |

FORMULA 3
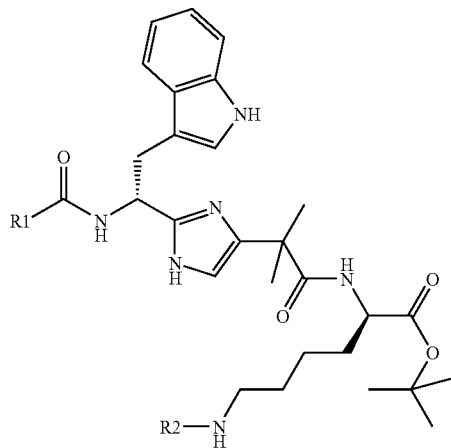
|   | Structure | Analysis | |
|---|---|---|---|
|   |   | Rt (min) | [M + H]+ |
| 5 | Chiral | 6.9 | 825.5 |
| 6 | Chiral | 9.2 | 832.5 |

-continued
FORMULA 3
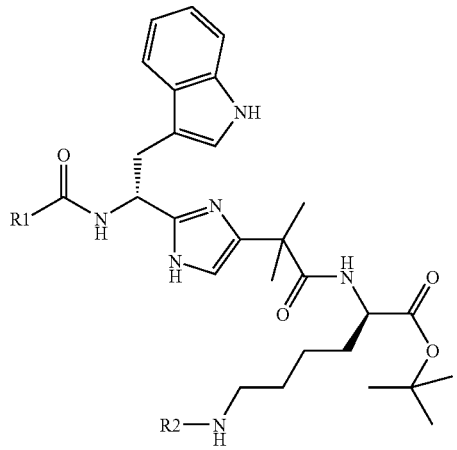
| | Structure | | Analysis | |
|---|---|---|---|---|
| | | | Rt (min) | [M + H]+ |
| 7 | 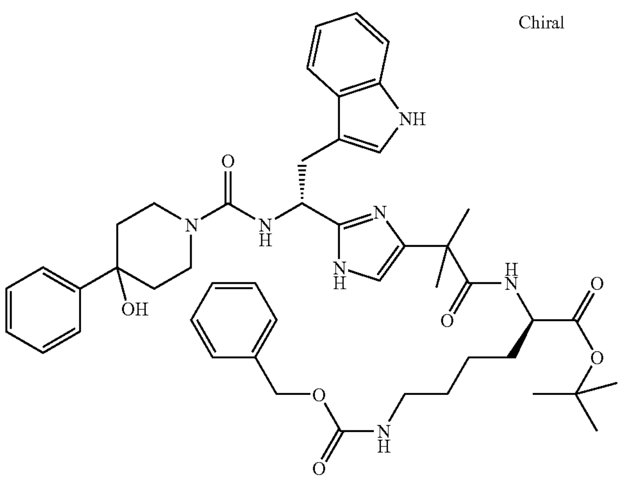 | Chiral | 8.2 | 834.5 |
| 8 | 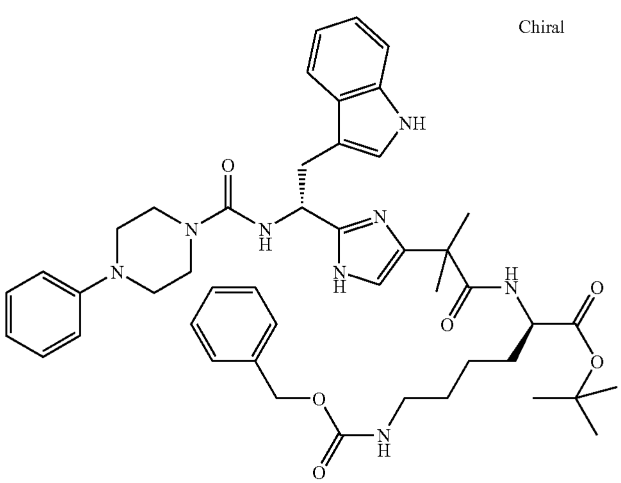 | Chiral | 8.6 | 819.4 |

FORMULA 3

| | Structure | | Analysis | |
|---|---|---|---|---|
| | | | Rt (min) | [M + H]+ |
| 9 | 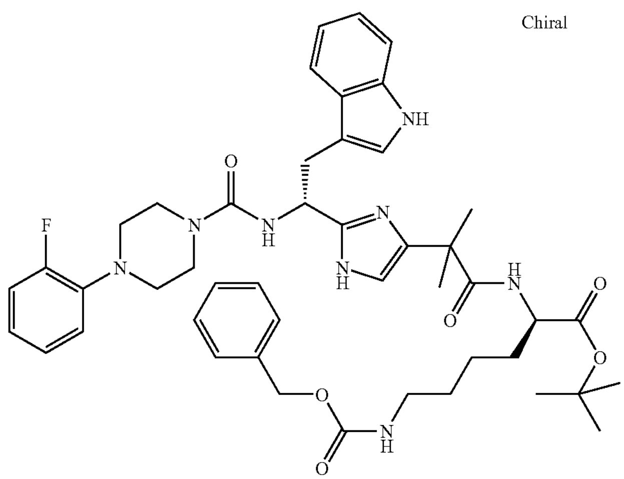 | Chiral | 8.7 | 837.5 |
| 10 | 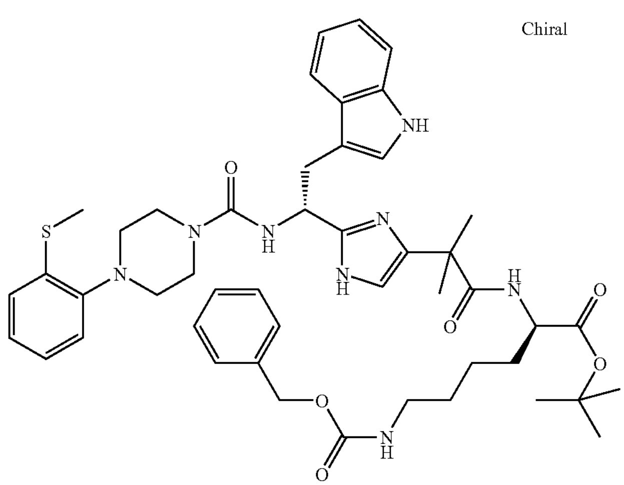 | Chiral | 9 | 865.5 |

-continued
FORMULA 3
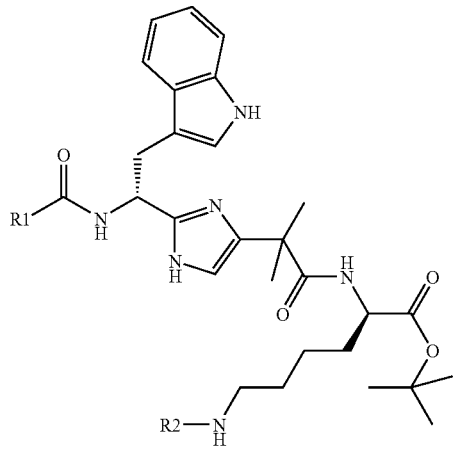
| | Structure | Analysis | |
|---|---|---|---|
| | | Rt (min) | [M + H]+ |
| 11 | Chiral 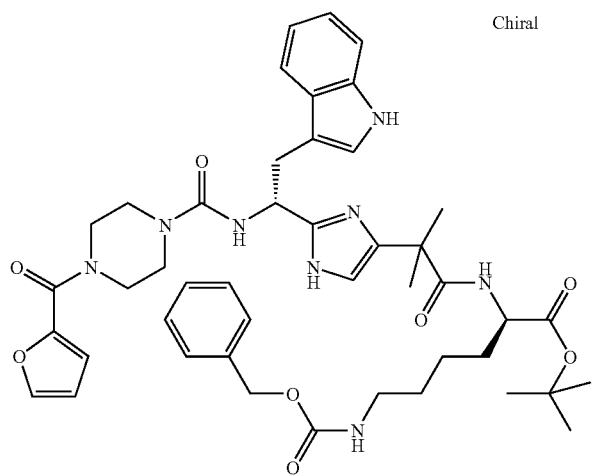 | 7.8 | 837.4 |
| 12 | Chiral 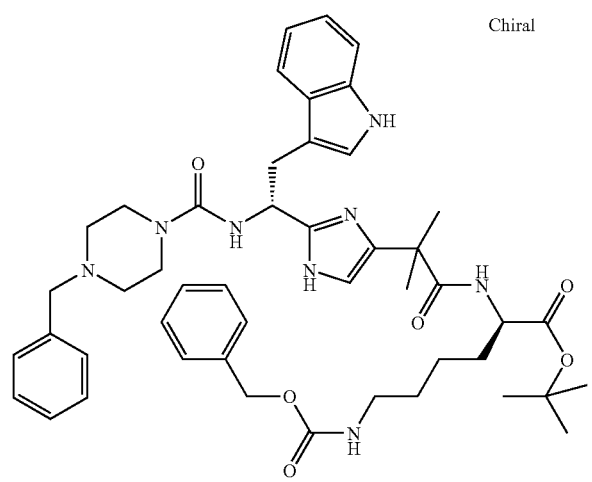 | 7.1 | 833.5 |

-continued
FORMULA 3
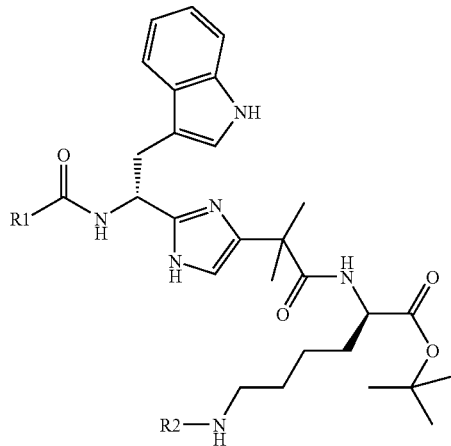
| | Structure | Analysis | |
|---|---|---|---|
| | | Rt (min) | [M + H]+ |
| 13 | 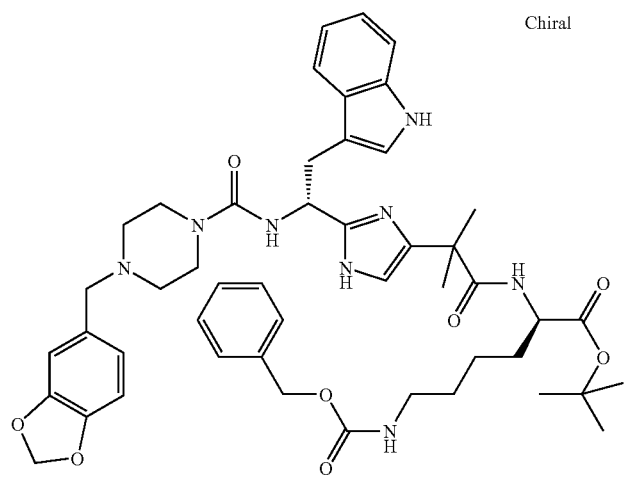 Chiral | 7.1 | 877.5 |
| 14 | 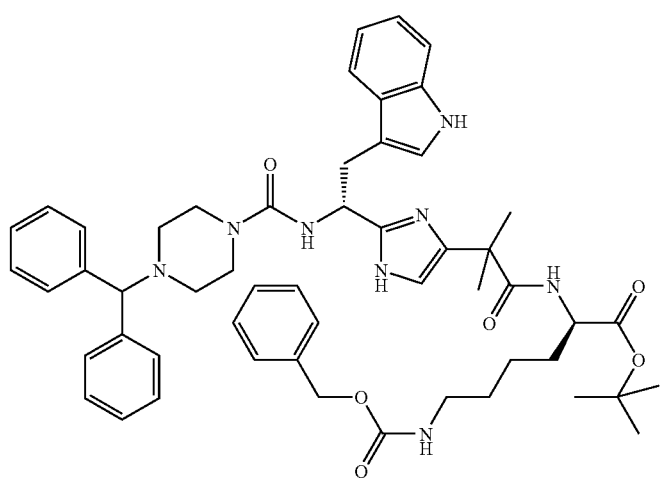 | 8.1 | 909.5 |

-continued
FORMULA 3
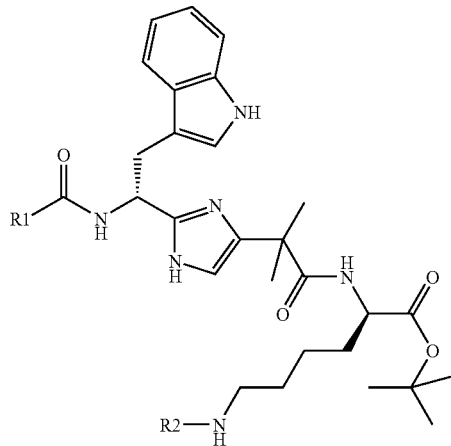
| | Structure | Analysis | |
|---|---|---|---|
| | | Rt (min) | [M + H]+ |
| 15 | 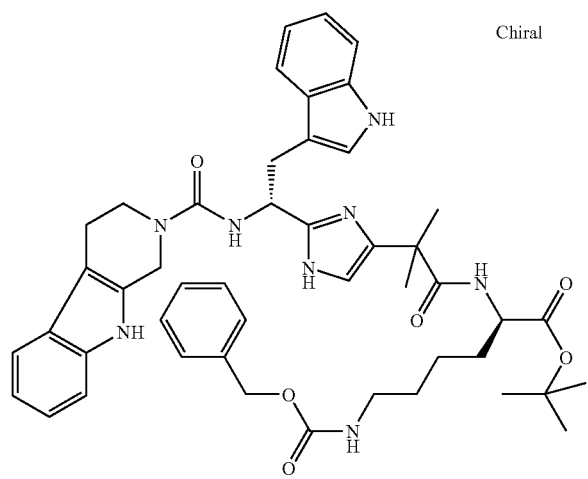 Chiral | 8.7 | 829.5 |
| 16 | 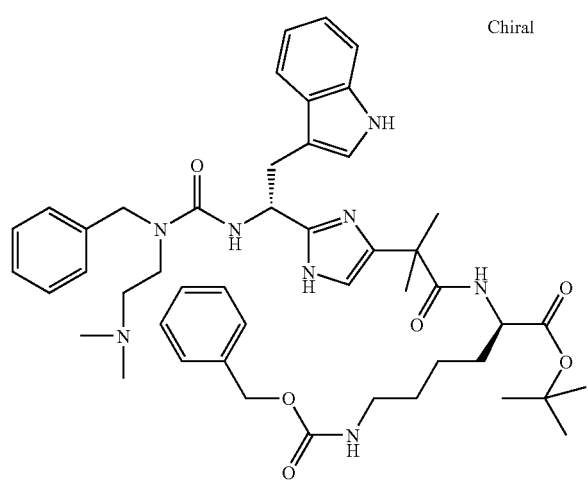 Chiral | 7.2 | 835.5 |

-continued
FORMULA 3
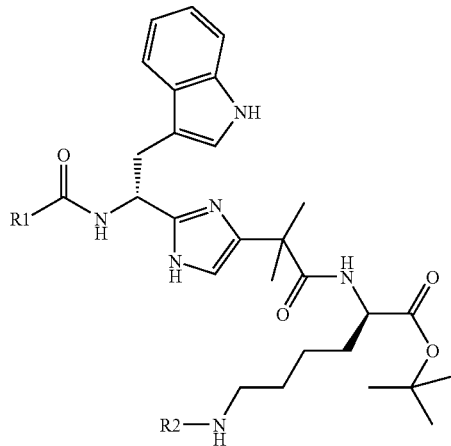
|    | Structure | Analysis |  |
|----|-----------|----------|----------|
|    |           | Rt (min) | [M + H]+ |
| 17 | 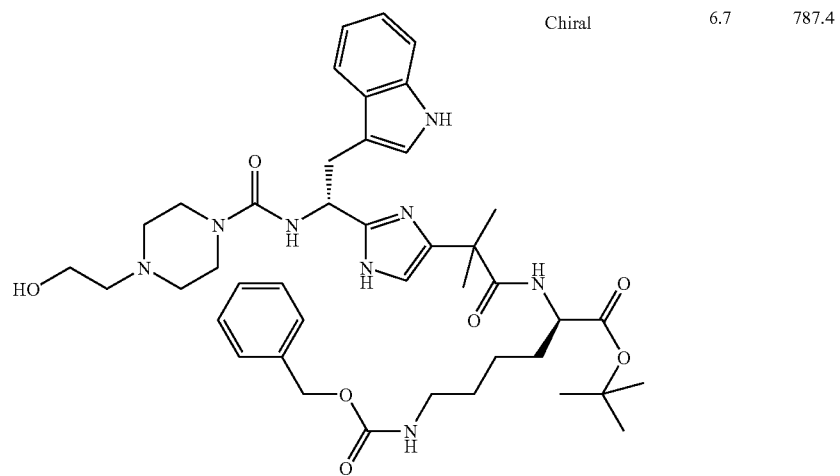 Chiral | 6.7 | 787.4 |
| 18 | 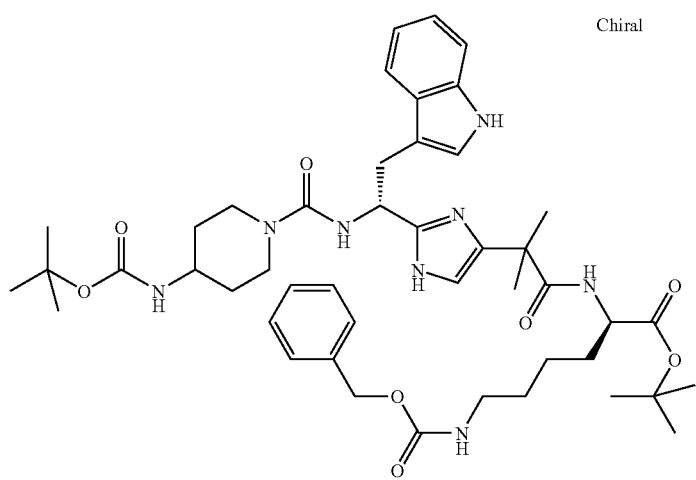 Chiral | 8.5 | 843.5 |

-continued
FORMULA 3
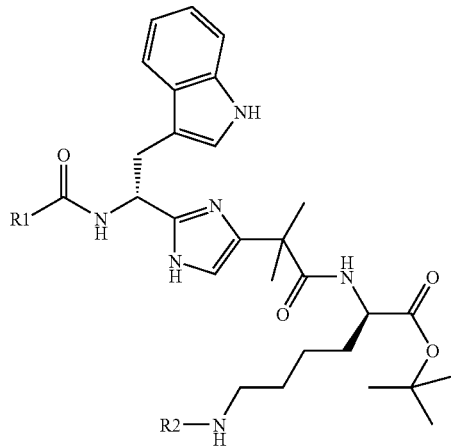
| | Structure | Analysis | |
|---|---|---|---|
| | | Rt (min) | [M + H]+ |
| 19 | 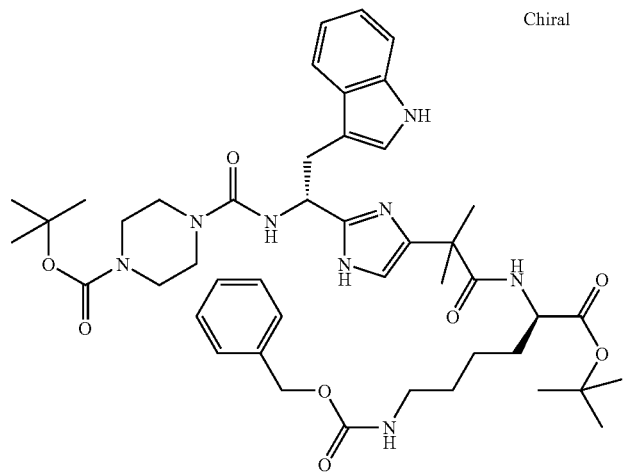 Chiral | 8.5 | 857.5 |
| 20 | 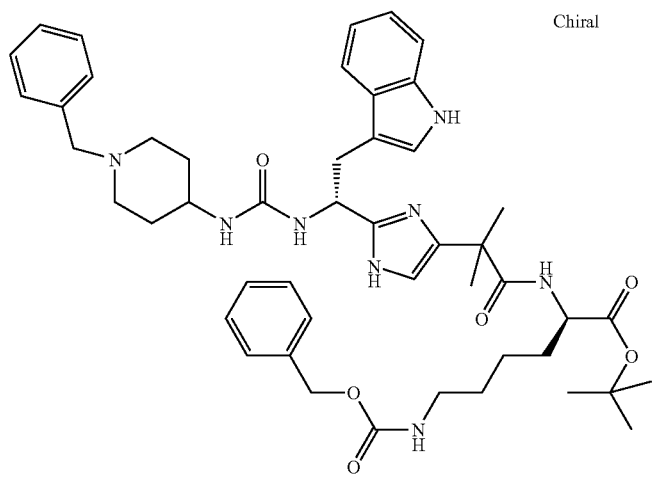 Chiral | 7.1 | 847.5 |

-continued
FORMULA 3
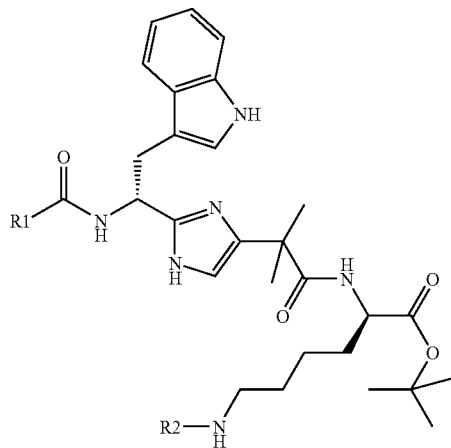
| | Structure | | Analysis | |
|---|---|---|---|---|
| | | | Rt (min) | [M + H]+ |
| 21 | 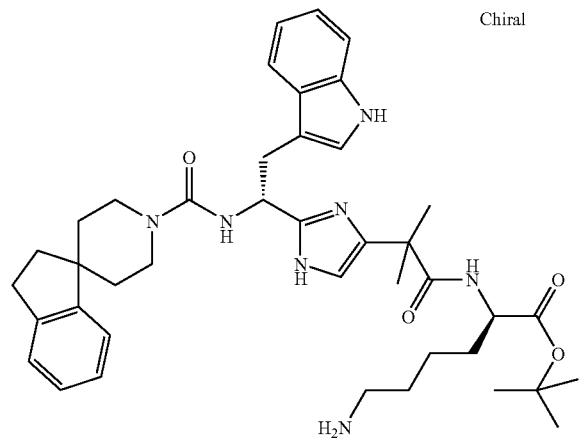 | Chiral | 4.5 | 710.5 |
| 22 | 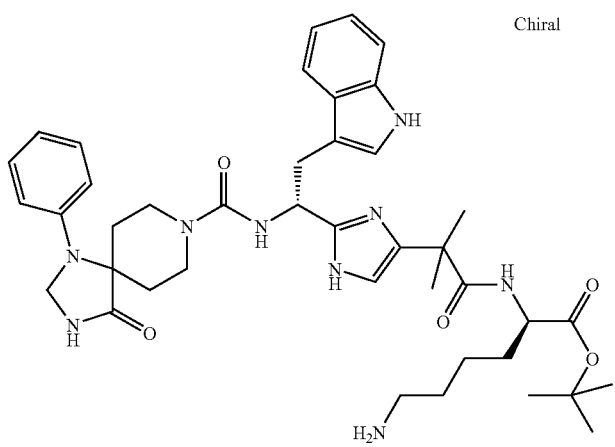 | Chiral | 4.1 | 754.5 |

-continued
FORMULA 3
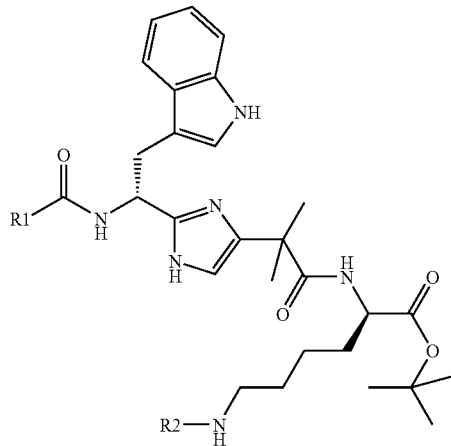
| | Structure | Analysis | |
|---|---|---|---|
| | | Rt (min) | [M + H]+ |
| 23 | 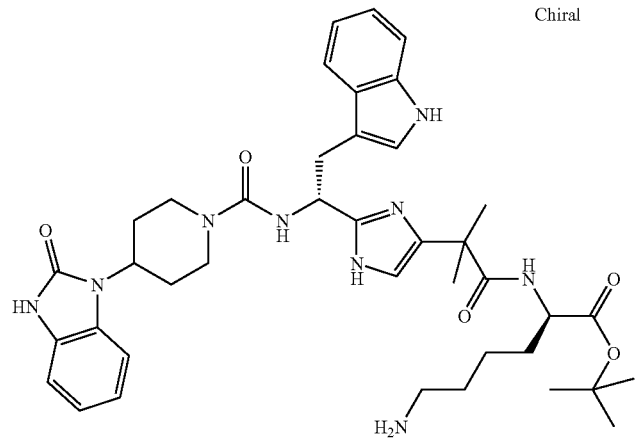 Chiral | 4 | 740.5 |
| 24 | 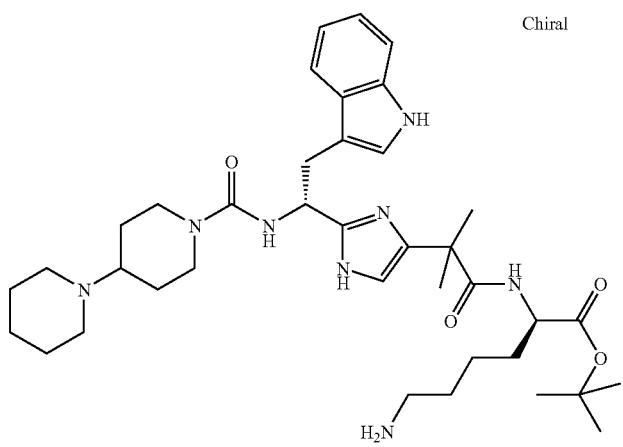 Chiral | 3.1 | 691.6 |

-continued
FORMULA 3
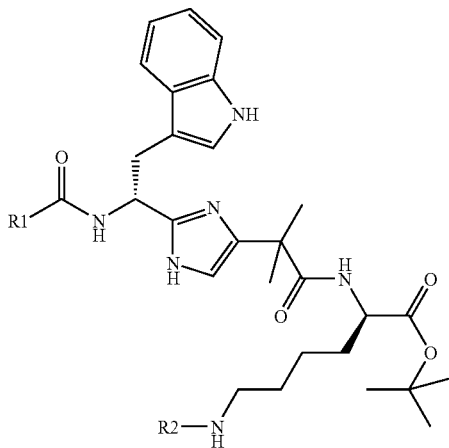
| | Structure | | Analysis | |
|---|---|---|---|---|
| | | | Rt (min) | [M + H]+ |
| 25 | 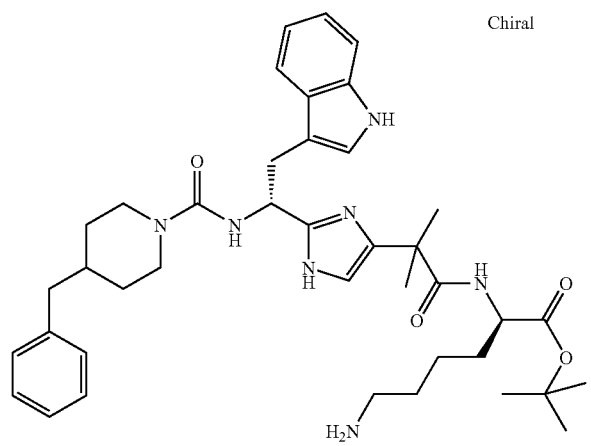 | Chiral | 4.5 | 698.5 |
| 26 | 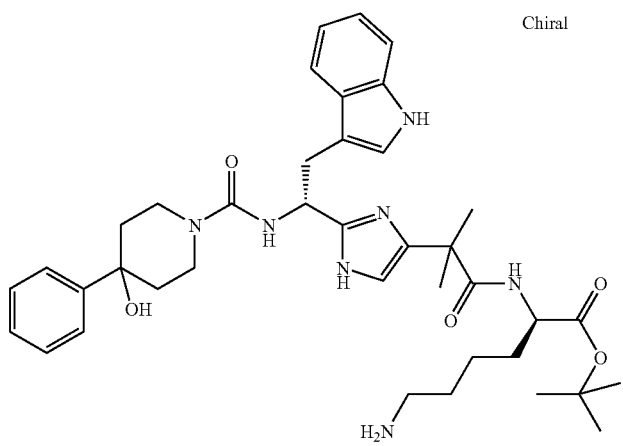 | Chiral | 3.9 | 700.5 |

-continued
FORMULA 3
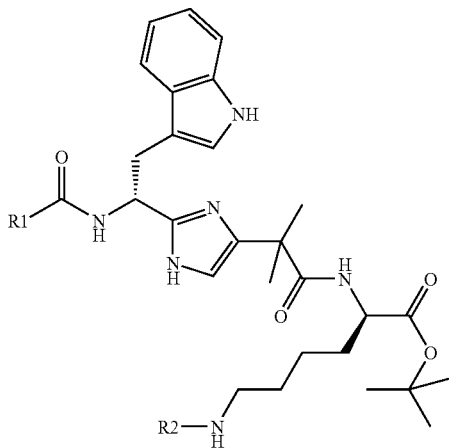
| | Structure | Analysis | |
|---|---|---|---|
| | | Rt (min) | [M + H]+ |
| 27 | 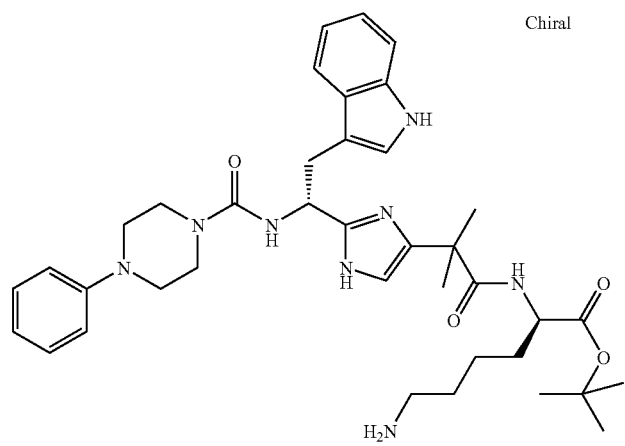 Chiral | 4.1 | 685.5 |
| 28 | 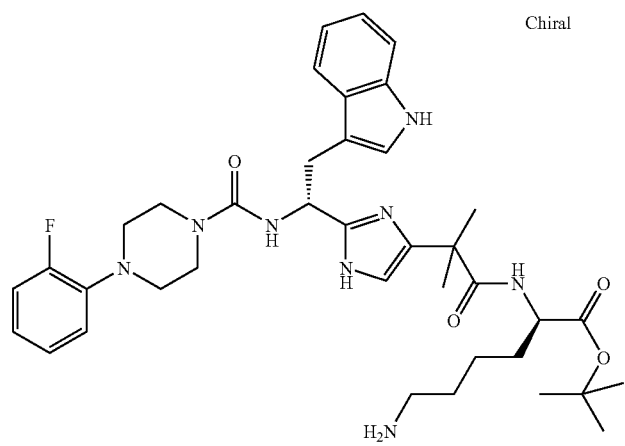 Chiral | 4.2 | 703.5 |

-continued
FORMULA 3
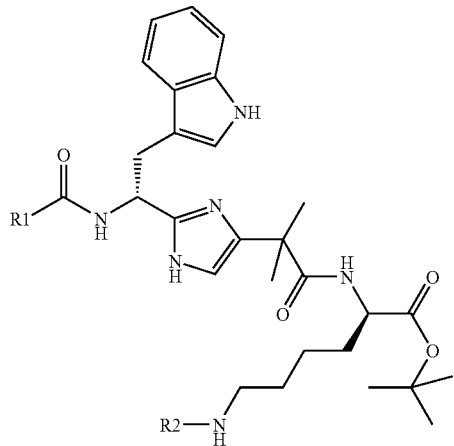
| | Structure | | Analysis | |
|---|---|---|---|---|
| | | | Rt (min) | [M + H]+ |
| 29 | 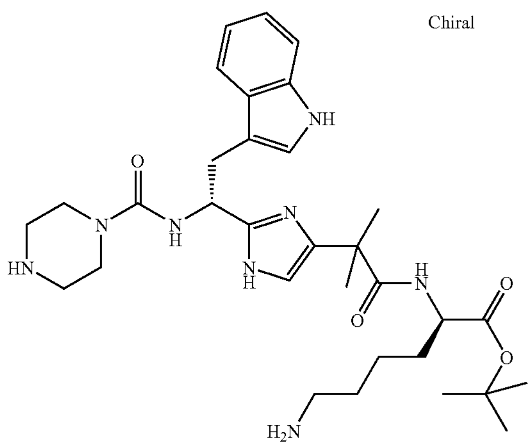 | Chiral | 3.1 | 721.4 |
| 30 | 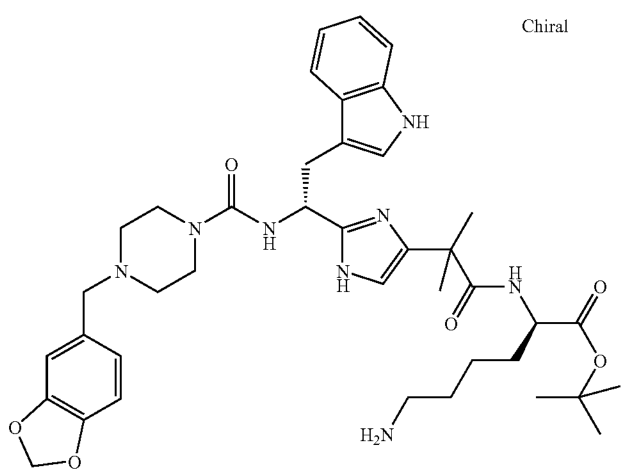 | Chiral | 3.3 | 743.5 |

FORMULA 3
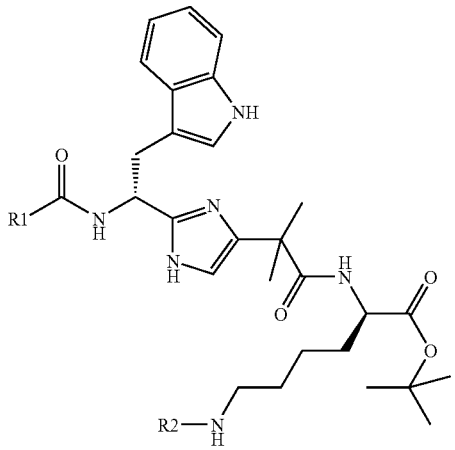
| | Structure | | Analysis | |
|---|---|---|---|---|
| | | | Rt (min) | [M + H]+ |
| 31 | 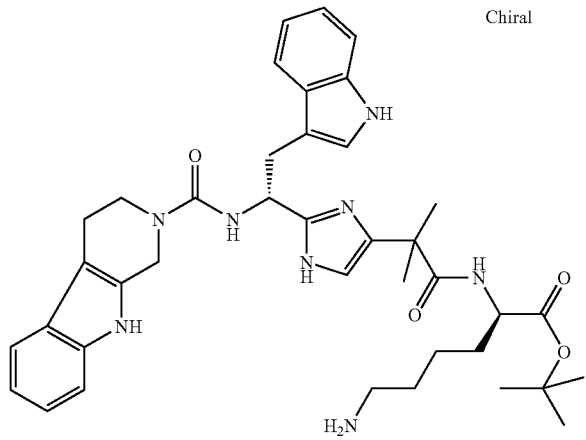 | Chiral | 4.2 | 695.5 |
| 32 | 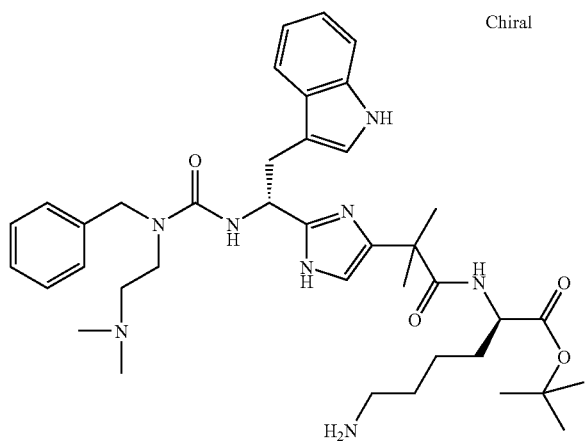 | Chiral | 3.4 | 701.5 |

FORMULA 3
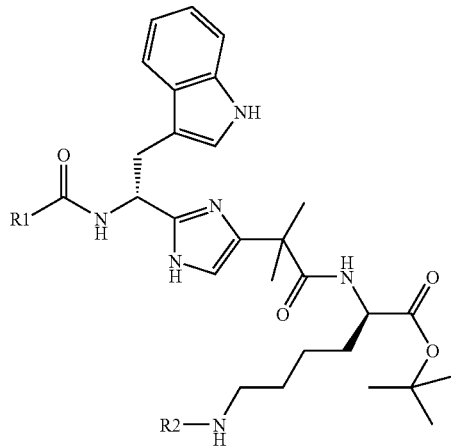
| | Structure | Analysis | |
|---|---|---|---|
| | | Rt (min) | [M + H]+ |
| 33 | 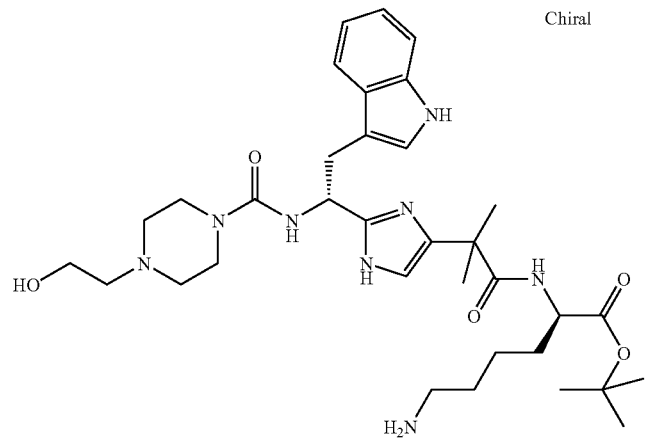 Chiral | 3 | 653.4 |
| 34 | 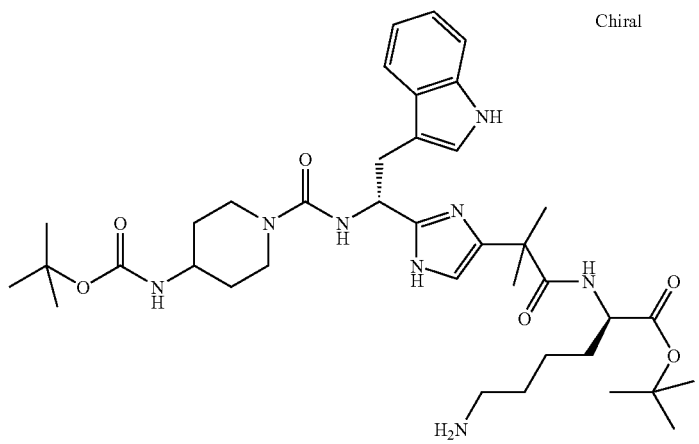 Chiral | 4.1 | 709.5 |

-continued
FORMULA 3
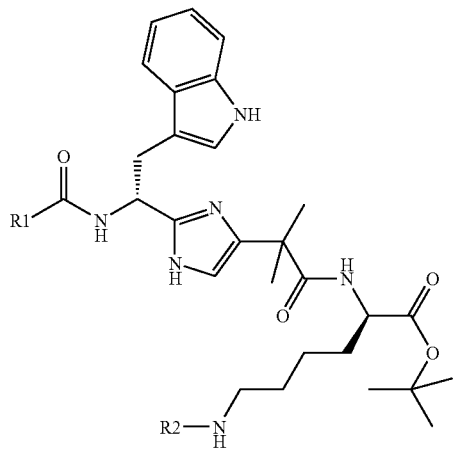
| | Structure | | Analysis | |
|---|---|---|---|---|
| | | | Rt (min) | [M + H]+ |
| 35 | 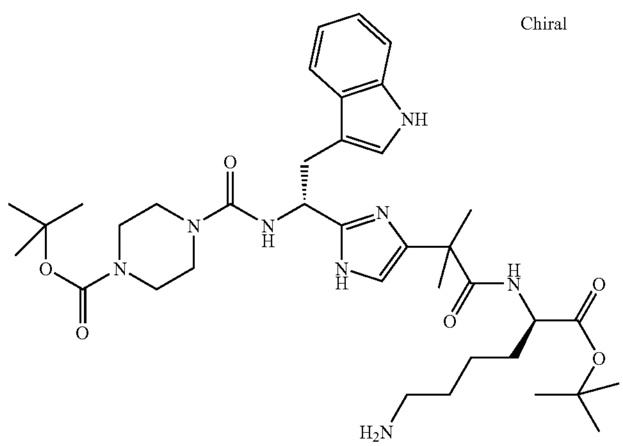 | Chiral | 4 | 723.5 |
| 36 | 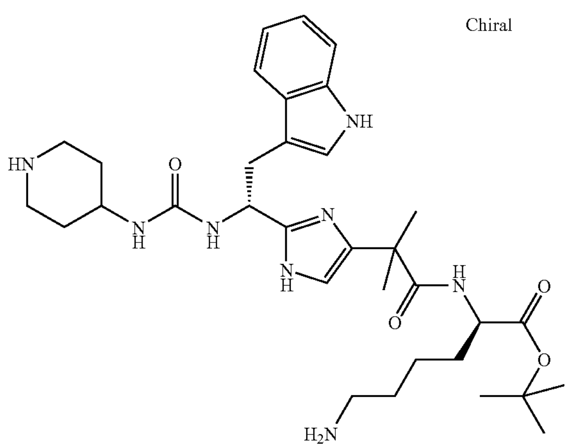 | Chiral | 3.2 | 623.4 |

FORMULA 4
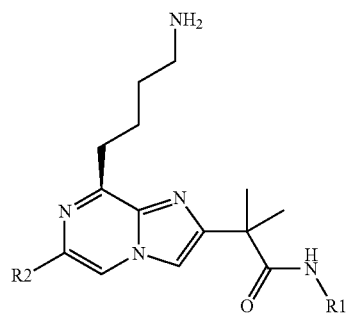
| | R1 | R2 | Tr (min) | (M + H)+ |
|---|---|---|---|---|
| 1 | *–N–⌢⌢–N | 3-NO2-phenyl | 4.53 | 454.24 |
| 2 | *–N–⌢⌢–N | 4-Cl-3-NO2-phenyl | 4.87 | 488.21 |
| 3 | *–N–⌢⌢–N | benzothiophen-3-yl | 4.79 | 465.24 |
| 4 | *–N–⌢⌢–N | 4-NO2-phenyl | 4.53 | 454.25 |

FORMULA 5
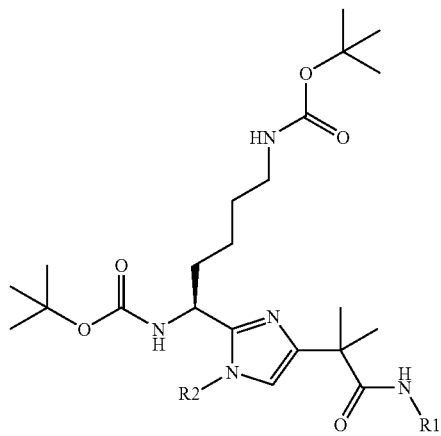
| | R1 | R2 | Tr (min) | [M + H]+ |
|---|---|---|---|---|
| 1 | N-cyclohexyl (N-*) | Br-C6H4-* | 8.0 | 732.2 |
| 2 | *-N-butyl | Br-C6H4-* | 7.7 | 706.2 |
| 3 | *-N-CH2CH2-(2-pyridyl) | Br-C6H4-* | 6.4 | 755.2 |
| 4 | furfuryl-N-* | *-C6H4-3-NO2 | 7.3 | 697.3 |
| 5 | furfuryl-N-* | *-C6H3-4-Cl-3-NO2 | 7.6 | 731.2 |
| 6 | tryptamine-N-* | *-C6H4-3-NO2 | 7.6 | 760.3 |
| 7 | tryptamine-N-* | *-C6H3-4-Cl-3-NO2 | 7.9 | 794.3 |

-continued
FORMULA 5
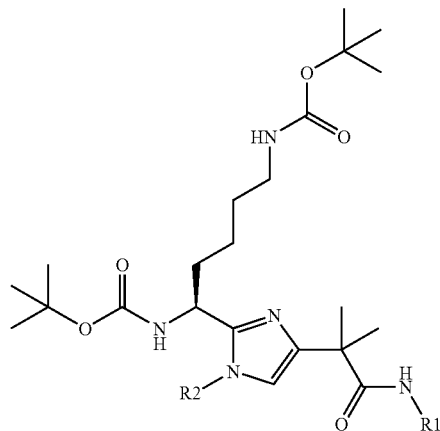
| | R1 | R2 | Tr (min) | [M + H]+ |
|---|---|---|---|---|
| 8 | tryptamine-derived | phenethyl | 7.8 | 743.4 |
| 9 | Boc-aminopropyl-N | 3-NO$_2$-phenyl | 7.5 | 774.4 |
| 10 | Boc-aminopropyl-N | 4-Cl-3-NO$_2$-phenyl | 7.8 | 808.3 |
| 11 | Boc-aminopropyl-N | phenethyl | 7.8 | 757.4 |
| 12 | Boc-aminopropyl-N | benzyl | 7.6 | 743.4 |

-continued
FORMULA 5
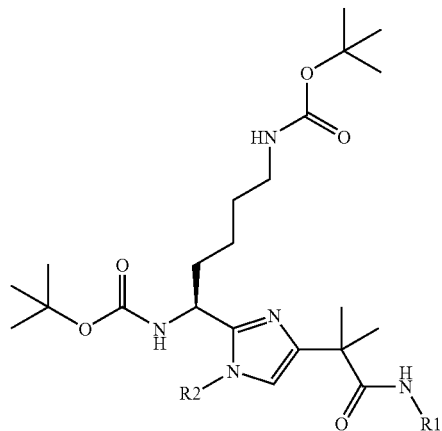
| | R1 | R2 | Tr (min) | [M + H]+ |
|---|---|---|---|---|
| 13 | | | 7.8 | 785.4 |
| 14 | | | 7.6 | 774.4 |
| 15 | | | 7.8 | 763.4 |
| 16 | | | 8.5 | 783.3 |
| 17 | | | 8.9 | 817.3 |

FORMULA 6

| | R2 | Tr (min) | [M + H]+ |
|---|---|---|---|
| 1 | dimethylaminoethylamino | 4.7 | 525.3 |
| 2 | furfurylamino | 6.0 | 534.3 |
| 3 | cyclohexylamino | 6.4 | 536.3 |
| 4 | tryptamino (indol-3-ylethylamino) | 6.5 | 597.3 |
| 5 | n-butylamino | 6.1 | 510.4 |
| 6 | 2-(pyridin-2-yl)ethylamino | 4.9 | 559.3 |
| 7 | 3-(Boc-amino)propylamino | 6.4 | 611.4 |
| *8 | benzhydrylamino | 7.1 | 620.4 |

FORMULA 7

| | R2 | Tr (min) | [M + H]+ |
|---|---|---|---|
| 1 | benzyl | 4.6 | 469.4 |
| 2 | 4-bromophenyl | 5.0 | 533.3 |
| 3 | 4-methoxyphenyl | 4.6 | 485.4 |
| 4 | 4-chlorophenyl | 4.9 | 489.4 |
| 5 | 3,4-dichlorophenyl | 5.3 | 523.3 |

FORMULA 8
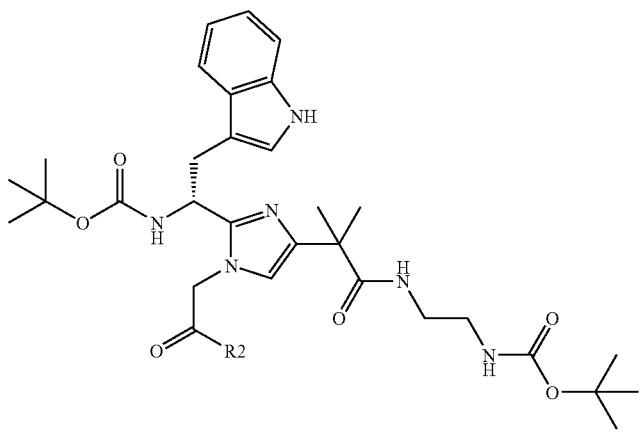
| | R2 | Tr (min) | [M + H]+ |
|---|---|---|---|
| 1 | benzyl | 7.0 | 687.5 |
| 2 | 4-Br-phenyl | 7.3 | 751.3 |
| 3 | 4-OMe-phenyl | 6.9 | 703.4 |
| 4 | 4-Cl-phenyl | 7.2 | 707.4 |
| 5 | 3,4-diCl-phenyl | 7.5 | 741.3 |

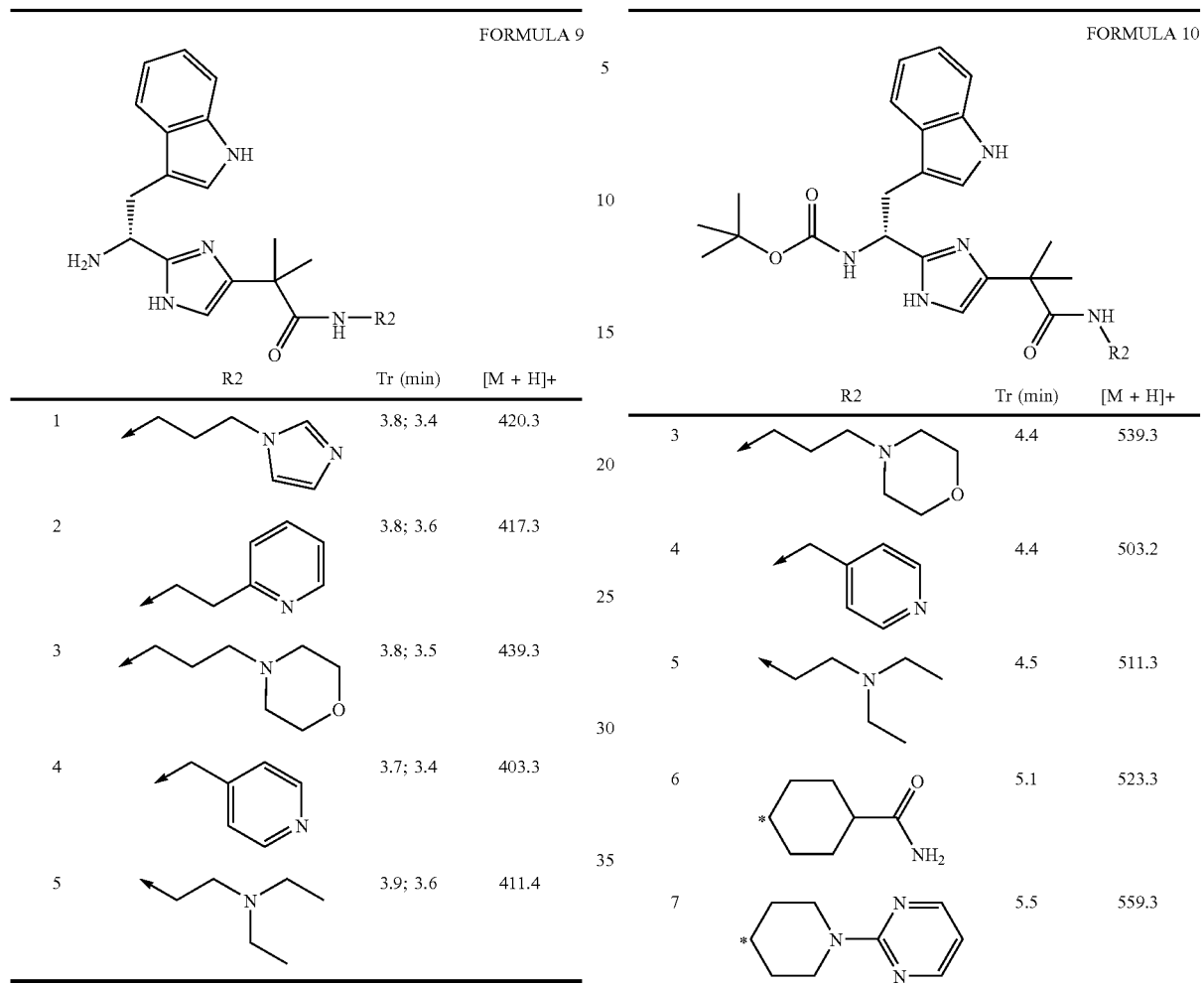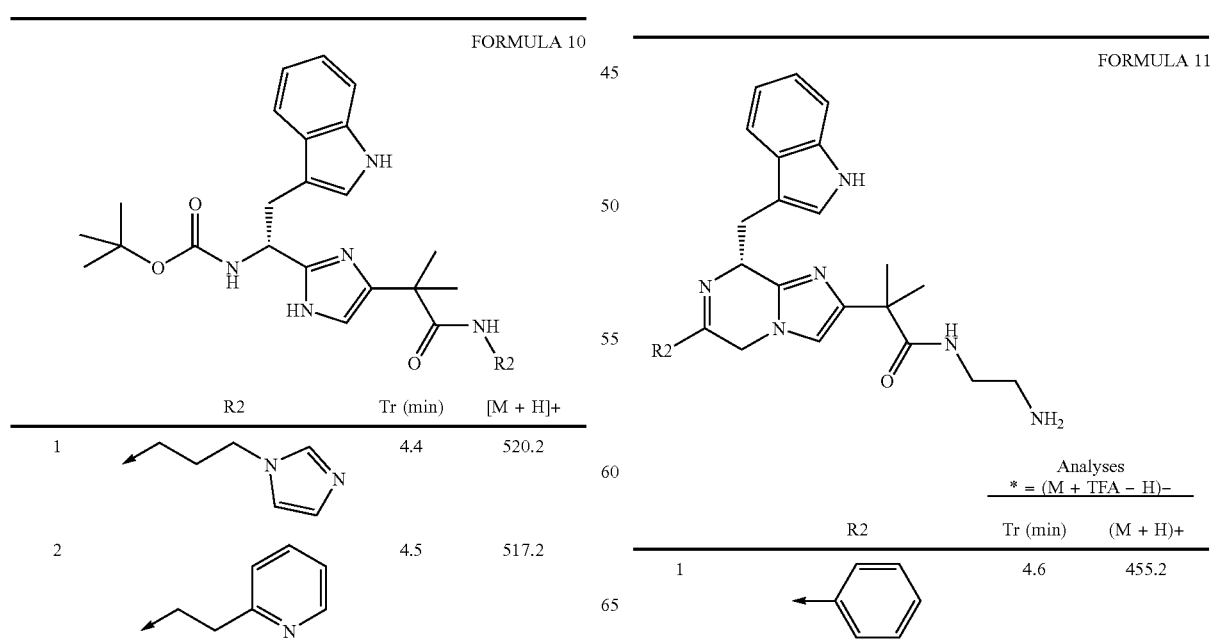

-continued
FORMULA 11
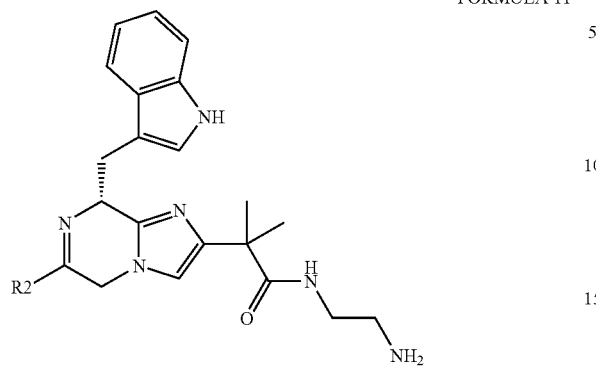
| | R2 | Analyses * = (M + TFA − H)− Tr (min) | (M + H)+ |
|---|---|---|---|
| 2 | 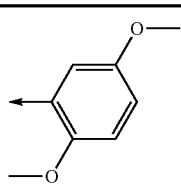 | 4.9 | 515.2 |
| 3 |  | 4.8 | 473.2 |
| 4 | 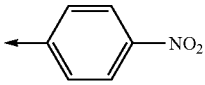 | 4.9 | 612.2* |
| 5 | 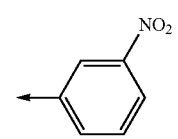 | 4.8 | 500.2 |
| 6 | 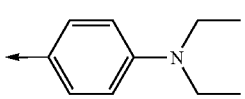 | 4.2 | 526.3 |
| 7 | 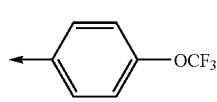 | 5.4 | 539.2 |
-continued
FORMULA 11
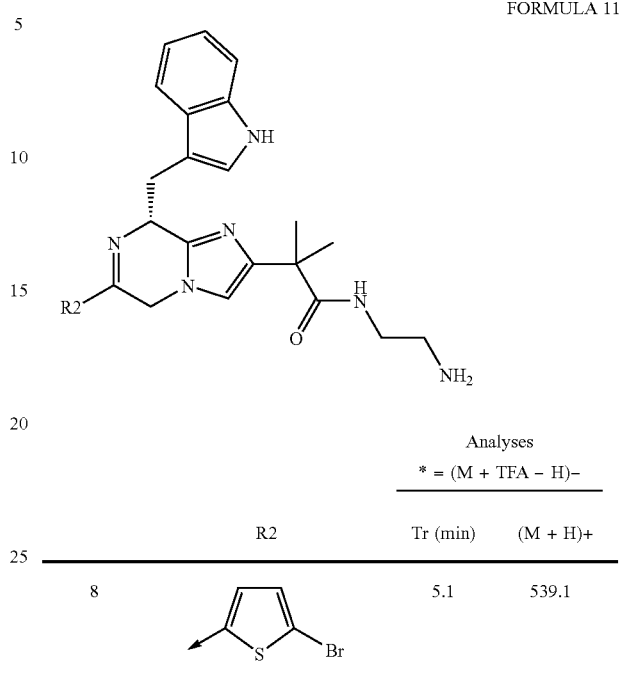
| | R2 | Analyses * = (M + TFA − H)− Tr (min) | (M + H)+ |
|---|---|---|---|
| 8 | 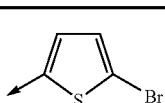 | 5.1 | 539.1 |
| 9 | 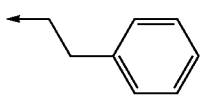 | 5.1 | 483.3 |
| 10 | 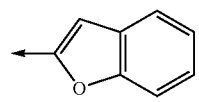 | 5.0 | 495.2 |
| 11 |  | 4.1 | 519.2* |
| 12 | 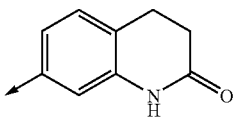 | 4.4 | 524.3 |

FORMULA 12
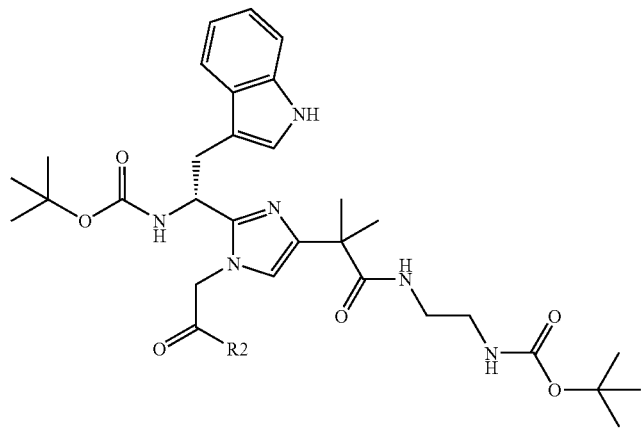
| | R2 | Tr (min) | [M + H]+ |
|---|---|---|---|
| 1 | phenyl | 6.9 | 673.3 |
| 2 | 2,5-dimethoxyphenyl | 7.0 | 733.3 |
| 3 | 4-fluorophenyl | 7.0 | 691.3 |
| 4 | 4-nitrophenyl | 7.1 | 718.3 |
| 5 | 3-nitrophenyl | 7.0 | 718.3 |
| 6 | 4-(diethylamino)phenyl | 7.4 | 744.4 |
| 7 | 4-(trifluoromethoxy)phenyl | 7.6 | 757.3 |
| 8 | 5-bromothiophen-2-yl | 7.3 | 757.2 |
| 9 | benzyl | 7.3 | 701.3 |

FORMULA 12
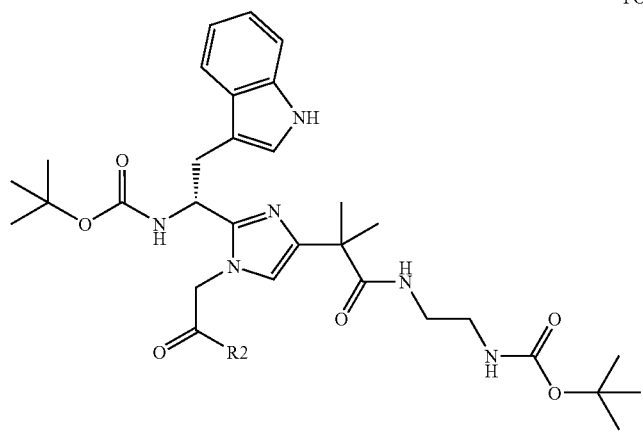
| | R2 | Tr (min) | [M + H]+ |
|---|---|---|---|
| 10 | benzofuran-2-yl | 7.2 | 713.3 |
| 11 | propyl | 6.5 | 625.3 |
| 12 | 2-oxo-1,2,3,4-tetrahydroquinolin-7-yl | 6.3 | 742.3 |
FORMULA 13
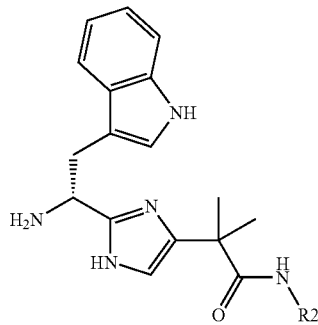
| | R2 | Tr (min) | [M + H]+ |
|---|---|---|---|
| 1 | 2-morpholinoethyl | 3.8 | 425.3 |
| 2 | 1-benzylpiperidin-4-yl | 4.2 | 485.4 |
FORMULA 13
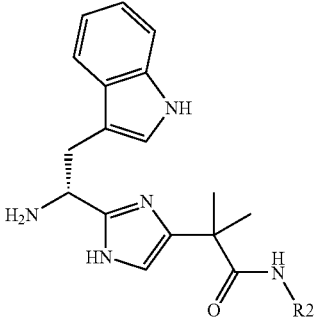
| | R2 | Tr (min) | [M + H]+ |
|---|---|---|---|
| 3 | 1,2-diethylpyrazolidin-4-yl | 4.0 | 438.4 |

-continued
FORMULA 13
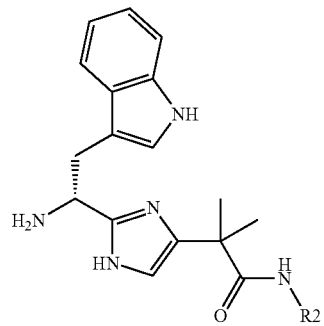
| | R2 | Tr (min) | [M + H]+ |
|---|---|---|---|
| 4 | 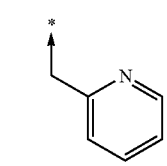 | 4.0 | 403.3 |
| 5 | 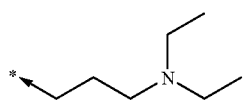 | 3.9 | 425.4 |
| 6 | 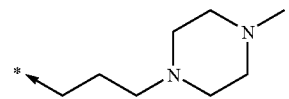 | 3.6 | 452.4 |
| 7 | 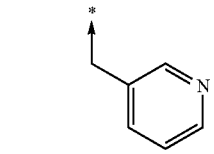 | 3.8 | 403.3 |
| 8 | 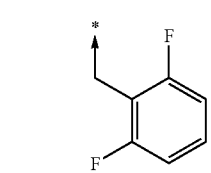 | 5.1 | 438.3 |
| 9 | 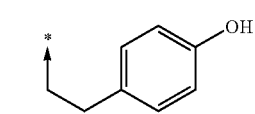 | 4.6 | 432.3 |
-continued
FORMULA 13
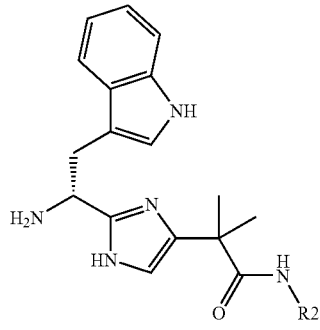
| | R2 | Tr (min) | [M + H]+ |
|---|---|---|---|
| 10 | 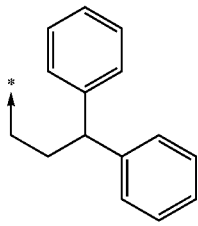 | 6.2 | 506.4 |
| 11 | 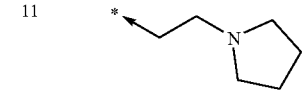 | 3.8 | 409.3 |
FORMULA 14
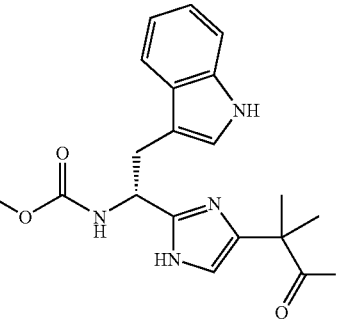
| | R2 | Tr (min) | [M + H]+ |
|---|---|---|---|
| 1 | 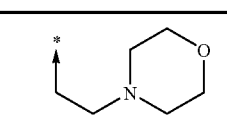 | 4.6 | 525.3 |
| 2 | 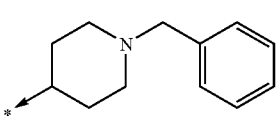 | 5.0 | 585.3 |
| 3 | 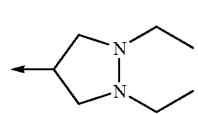 | 4.8 | 538.3 |

187
-continued
FORMULA 14
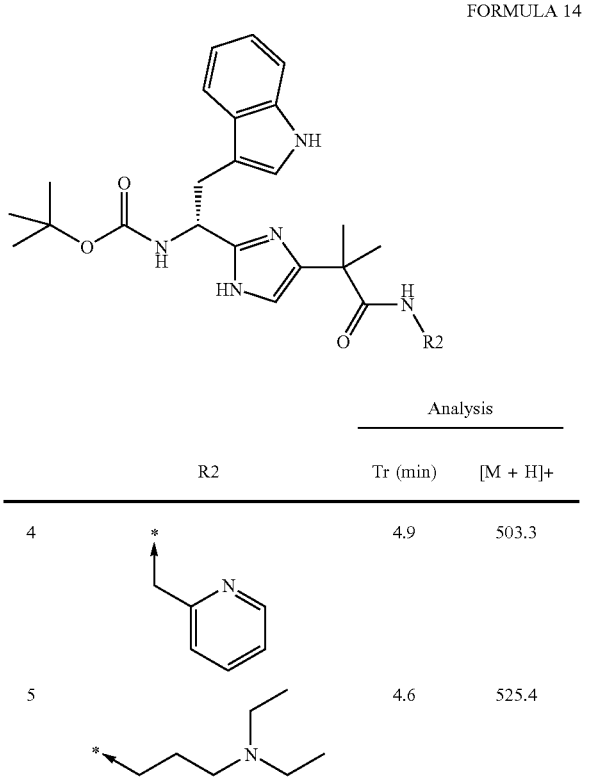
| | R2 | Analysis Tr (min) | [M + H]+ |
|---|---|---|---|
| 4 | *-CH2-(2-pyridyl) | 4.9 | 503.3 |
| 5 | *-(CH2)3-N(Et)2 | 4.6 | 525.4 |
188
-continued
FORMULA 14
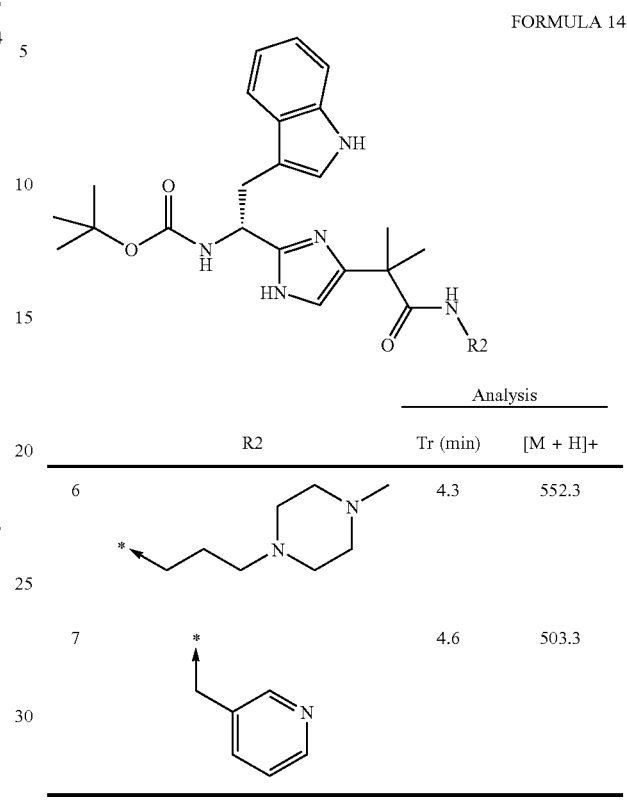
| | R2 | Analysis Tr (min) | [M + H]+ |
|---|---|---|---|
| 6 | *-(CH2)4-N-methylpiperazine | 4.3 | 552.3 |
| 7 | *-CH2-(3-pyridyl) | 4.6 | 503.3 |
FORMULA 15
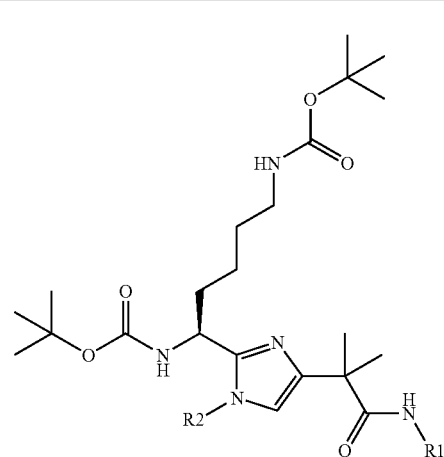
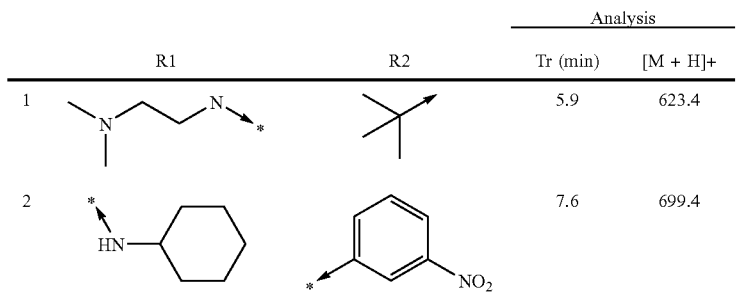
| | R1 | R2 | Analysis Tr (min) | [M + H]+ |
|---|---|---|---|---|
| 1 | Me2N-CH2CH2-N(Me)-* | tert-butyl | 5.9 | 623.4 |
| 2 | *-NH-cyclohexyl | *-C6H4-3-NO2 | 7.6 | 699.4 |

-continued
FORMULA 15
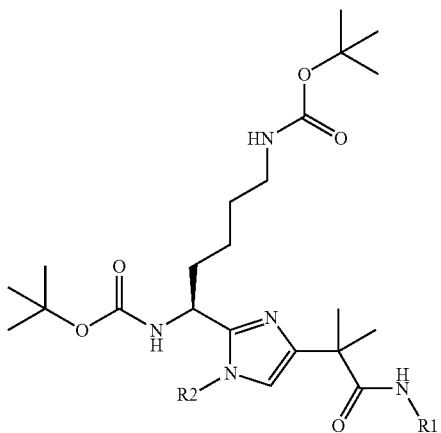
|   | R1 | R2 | Analysis Tr (min) | [M + H]+ |
|---|---|---|---|---|
| 3 | HN–cyclohexyl | 4-Cl, 3-NO₂ phenyl | 7.9 | 733.3 |
| 4 | HN–cyclohexyl | phenethyl | 7.9 | 682.4 |
| 5 | HN–cyclohexyl | benzyl | 7.7 | 668.4 |
| 6 | HN–cyclohexyl | benzothiophen-3-yl | 7.9 | 710.3 |
| 7 | HN–cyclohexyl | 4-NO₂ phenyl | 7.7 | 699.4 |
| 8 | HN–cyclohexyl | 4-Cl phenyl | 7.9 | 688.3 |
| 9 | HN–cyclohexyl | 3,4-diCl phenyl | 8.2 | 722.3 |

-continued
FORMULA 15
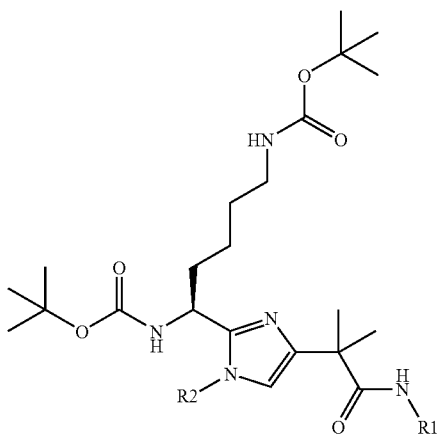
| | R1 | R2 | Tr (min) | [M + H]+ |
|---|---|---|---|---|
| 10 | *-HN-cyclohexyl | 2,3-dihydro-1,4-benzodioxin-6-yl-* | 7.5 | 712.4 |
| 11 | *-HN-cyclohexyl | tert-butyl-* | 7.6 | 634.4 |
| 12 | *-HN-butyl | 3-nitrophenyl-* | 7.3 | 673.3 |
| 13 | *-HN-butyl | 4-chloro-3-nitrophenyl-* | 7.6 | 707.3 |
| 14 | *-HN-butyl | 2-phenylethyl-* | 7.6 | 656.4 |
| 15 | *-HN-butyl | benzyl-* | 7.4 | 642.4 |
| 16 | *-HN-butyl | benzo[b]thiophen-3-yl-* | 7.6 | 684.3 |
| 17 | *-HN-butyl | 4-nitrophenyl-* | 7.4 | 673.3 |

-continued
FORMULA 15
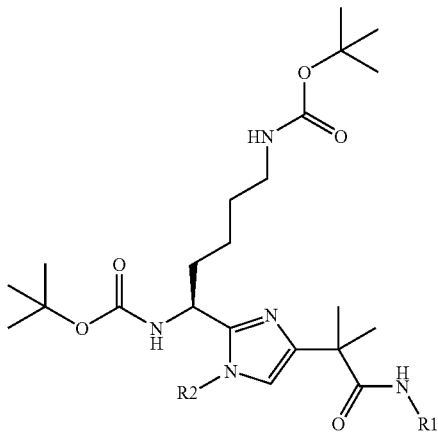
|  | R1 | R2 | Analysis Tr (min) | [M + H]+ |
|---|---|---|---|---|
| 18 | HN-butyl | 4-Cl-C6H4 | 7.6 | 662.3 |
| 19 | HN-butyl | 3,4-diCl-C6H3 | 7.9 | 696.3 |
| 20 | HN-butyl | 2,3-dihydrobenzo[1,4]dioxin-6-yl | 7.2 | 686.4 |
| 21 | HN-butyl | tert-butyl | 7.3 | 608.4 |
| 22 | HN-CH2CH2-(2-pyridyl) | 3-NO2-C6H4 | 6.0 | 722.3 |
| 23 | HN-CH2CH2-(2-pyridyl) | 4-Cl-3-NO2-C6H3 | 6.4 | 756.3 |
| 24 | HN-CH2CH2-(2-pyridyl) | CH2CH2-C6H5 | 6.3 | 705.4 |
| 25 | HN-CH2CH2-(2-pyridyl) | CH2-C6H5 | 6.1 | 691.4 |

-continued
FORMULA 15
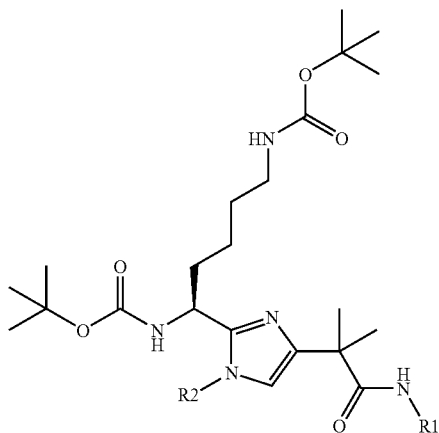
| | R1 | R2 | Analysis | |
|---|---|---|---|---|
| | | | Tr (min) | [M + H]+ |
| 26 | *-HN-CH2CH2-(2-pyridyl) | 3-benzothienyl | 6.4 | 733.3 |
| 27 | *-HN-CH2CH2-(2-pyridyl) | 4-nitrophenyl | 6.1 | 722.3 |
| 28 | *-HN-CH2CH2-(2-pyridyl) | 4-chlorophenyl | 6.3 | 711.3 |
| 29 | *-HN-CH2CH2-(2-pyridyl) | 3,4-dichlorophenyl | 6.7 | 745.2 |
| 30 | *-HN-CH2CH2-(2-pyridyl) | 2,3-dihydrobenzo[1,4]dioxin-6-yl | 5.9 | 735.3 |
| 31 | *-HN-CH2CH2-(2-pyridyl) | tert-butyl | 6.0 | 657.4 |

FORMULA 16
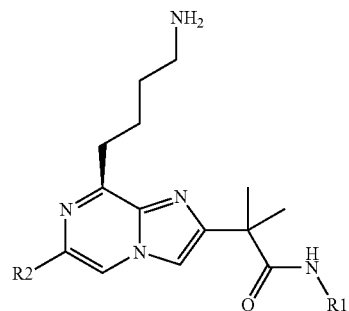
| | R1 | R2 | Tr (min) | [M + H]+ |
|---|---|---|---|---|
| 1 | furan-2-ylmethyl-NH-* | *-C6H4-NO2 (meta) | 5.7 | 477.2 |
| 2 | furan-2-ylmethyl-NH-* | *-C6H3(Cl)(NO2) | 6.0 | 511.1 |
| 3 | indol-3-yl-ethyl-NH-* | *-C6H4-NO2 (meta) | 6.1 | 540.2 |
| 4 | indol-3-yl-ethyl-NH-* | *-C6H3(Cl)(NO2) | 6.3 | 574.1 |
| 5 | indol-3-yl-ethyl-NH-* | phenethyl-* | 6.0 | 523.3 |
| 6 | *-HN-(CH2)4-NH2 | phenethyl-* | 4.4 | 437.3 |
| 7 | *-HN-(CH2)3-NH2 | benzyl-* | 4.2 | 423.3 |

-continued

FORMULA 16

| | R1 | R2 | Analysis Tr (min) | [M + H]+ |
|---|---|---|---|---|
| 8 | *–HN–(CH2)4–NH2 | 4-Cl-C6H4–* | 4.8 | 443.3 |
| 9 | diphenylmethyl-NH–* | 3-NO2-C6H4–* | 6.8 | 563.2 |
| 10 | diphenylmethyl-NH–* | 4-Cl-3-NO2-C6H3–* | 7.0 | 597.2 |
| 11 | cyclohexyl-NH–* | 3-NO2-C6H4–* | 6.1 | 479.3 |
| 12 | cyclohexyl-NH–* | 4-Cl-3-NO2-C6H3–* | 6.5 | 513.2 |
| 13 | cyclohexyl-NH–* | PhCH2CH2–* | 6.0 | 462.3 |
| 14 | cyclohexyl-NH–* | PhCH2–* | 5.8/5.9 | 448.3 |
| 15 | cyclohexyl-NH–* | benzothiophen-3-yl–* | 6.4 | 490.2 |

-continued
FORMULA 16
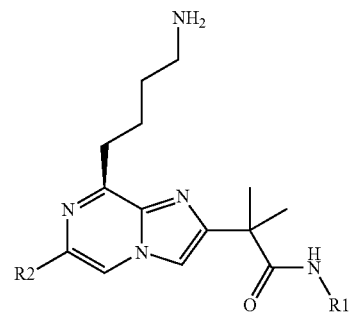
| | R1 | R2 | Analysis Tr (min) | [M + H]+ |
|---|---|---|---|---|
| 16 | HN-cyclohexyl | 4-NO2-phenyl | 6.1 | 479.3 |
| 17 | HN-cyclohexyl | 4-Cl-phenyl | 6.4 | 468.2 |
| 18 | HN-cyclohexyl | 3,4-diCl-phenyl | 6.8 | 502.2 |
| 19 | HN-cyclohexyl | 2,3-dihydrobenzo[1,4]dioxin-6-yl | 6.0 | 492.3 |
| 20 | HN-cyclohexyl | 4-Br-phenyl | 6.5 | 512.2 |
| 21 | HN-butyl | 3-NO2-phenyl | 5.9 | 453.3 |
| 22 | HN-butyl | 4-Cl-3-NO2-phenyl | 6.2 | 487.2 |
| 23 | HN-butyl | phenethyl | 5.7 | 436.3 |
| 24 | HN-butyl | benzyl | 5.5/5.6 | 422.3 |

-continued

FORMULA 16

|    | R1 | R2 | Tr (min) | [M + H]+ |
|----|----|----|----------|----------|
| 25 | HN—butyl | benzothiophen-3-yl | 6.2 | 464.2 |
| 26 | HN—butyl | 4-nitrophenyl | 5.9/6.0 | 453.3 |
| 27 | HN—butyl | 4-chlorophenyl | 6.1 | 442.2 |
| 28 | HN—butyl | 3,4-dichlorophenyl | 6.5 | 476.2 |
| 29 | HN—butyl | 2,3-dihydrobenzo[1,4]dioxin-6-yl | 5.7 | 466.3 |
| 30 | HN—butyl | 4-bromophenyl | 6.2 | 486.2 |
| 31 | HN—CH₂CH₂-(2-pyridyl) | 3-nitrophenyl | 4.7 | 502.2 |
| 32 | HN—CH₂CH₂-(2-pyridyl) | 4-chloro-3-nitrophenyl | 5.0 | 536.2 |
| 33 | HN—CH₂CH₂-(2-pyridyl) | phenethyl | 4.6 | 485.3 |

FORMULA 16
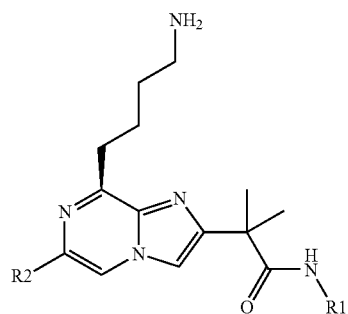
| | R1 | R2 | Tr (min) | [M + H]+ |
|---|---|---|---|---|
| 34 | *-HN-CH2CH2-(2-pyridyl) | *-CH2-phenyl | 4.5 | 471.3 |
| 35 | *-HN-CH2CH2-(2-pyridyl) | benzothiophen-3-yl* | 5.0 | 513.2 |
| 36 | *-HN-CH2CH2-(2-pyridyl) | O2N-C6H4-* (4-nitrophenyl) | 4.7 | 502.2 |
| 37 | *-HN-CH2CH2-(2-pyridyl) | Cl-C6H4-* (4-chlorophenyl) | 4.9 | 491.2 |
| 38 | *-HN-CH2CH2-(2-pyridyl) | 3,4-dichlorophenyl-* | 5.3 | 525.2 |
| 39 | *-HN-CH2CH2-(2-pyridyl) | 2,3-dihydro-1,4-benzodioxin-6-yl* | 4.6 | 515.2 |
| 40 | *-HN-CH2CH2-(2-pyridyl) | Br-C6H4-* (4-bromophenyl) | 5.0 | 535.1 |

FORMULA 17
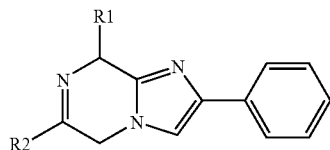
| | R1 | R2 | Tr (min) | [M + H]+ |
|---|---|---|---|---|
| 1 | (S)-1H-indol-3-ylmethyl | phenyl | 14.3 | 403.2 |
| 2 | (S)-1H-indol-3-ylmethyl | biphenyl-4-yl | 15.0 | 479.2 |
| 3 | (S)-1H-indol-3-ylmethyl | naphthalen-2-yl | 14.8 | 453.2 |
| 4 | (S)-1H-indol-3-ylmethyl | 2,5-dimethoxyphenyl | 14.4 | 463.2 |
| 5 | (S)-1H-indol-3-ylmethyl | 4-chlorophenyl | 14.6 | 437.1 |
| 6 | (S)-1H-indol-3-ylmethyl | 3,4-dichlorophenyl | 15.0 | 471.1 |
| 7 | (S)-1H-indol-3-ylmethyl | 4-chloro-3-methylphenyl | 14.8 | 451.1 |

-continued
FORMULA 17
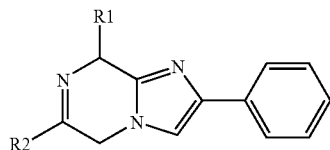
| | R1 | R2 | Analysis | |
|---|---|---|---|---|
| | | | Tr (min) | [M + H]+ |
| 8 | 1H-indol-3-ylmethyl (S) | 4-Br-phenyl | 14.8 | 481.0 |
| 9 | 1H-indol-3-ylmethyl (S) | 4-F-phenyl | 14.5 | 421.2 |
| 10 | 1H-indol-3-ylmethyl (S) | 4-CN-phenyl | 14.3 | 428.1 |
| 11 | 1H-indol-3-ylmethyl (S) | 4-N$_3$-phenyl | 14.6 | 444.2 |
| 12 | 1H-indol-3-ylmethyl (S) | 4-NO$_2$-phenyl | 14.5 | 448.1 |
| 13 | 1H-indol-3-ylmethyl (S) | 3-NO$_2$-phenyl | 14.5 | 448.1 |
| 14 | 1H-indol-3-ylmethyl (S) | propyl | 14.0 | 355.2 |

-continued

FORMULA 17

| | R1 | R2 | Analysis Tr (min) | [M + H]+ |
|---|---|---|---|---|
| 15 | (R)-1H-indol-3-ylmethyl | phenyl | 14.3 | 403.2 |
| 16 | (R)-1H-indol-3-ylmethyl | biphenyl-4-yl | 15.2 | 479.2 |
| 17 | (R)-1H-indol-3-ylmethyl | naphthalen-2-yl | 14.9 | 453.2 |
| 18 | (R)-1H-indol-3-ylmethyl | 4-methoxyphenyl | 14.4 | 433.2 |
| 19 | (R)-1H-indol-3-ylmethyl | 2,5-dimethoxyphenyl | 14.5 | 463.2 |
| 20 | (R)-1H-indol-3-ylmethyl | 4-chlorophenyl | 14.8 | 437.1 |
| 21 | (R)-1H-indol-3-ylmethyl | 3,4-dichlorophenyl | 15.1 | 474.1 |

-continued

FORMULA 17

[Structure: imidazo-pyrazine core with R1 and R2 substituents, and 2-phenyl group]

| | R1 | R2 | Analysis Tr (min) | [M + H]+ |
|---|---|---|---|---|
| 22 | 1H-indol-3-ylmethyl (R) | 4-chloro-3-methylphenyl | 15.0 | 451.1 |
| 23 | 1H-indol-3-ylmethyl (R) | 4-bromophenyl | 14.8 | 481.0 |
| 24 | 1H-indol-3-ylmethyl (R) | 4-fluorophenyl | 14.5 | 421.2 |
| 25 | 1H-indol-3-ylmethyl (R) | 4-cyanophenyl | 14.4 | 428.1 |
| 26 | 1H-indol-3-ylmethyl (R) | 4-azidophenyl | 14.7 | 444.1 |
| 27 | 1H-indol-3-ylmethyl (R) | 4-nitrophenyl | 14.6 | 448.1 |
| 28 | 1H-indol-3-ylmethyl (R) | 3-nitrophenyl | 14.5 | 448.1 |

-continued
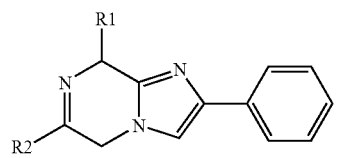
FORMULA 17
| | R1 | R2 | Tr (min) | [M + H]+ |
|---|---|---|---|---|
| 29 | 1H-indol-3-ylmethyl (R) | propyl | 13.9 | 355.2 |
| 30 | benzyl | phenyl | 15.2 | 364.2 |
| 31 | benzyl | 4-biphenyl | 16.3 | 440.2 |
| 32 | benzyl | 2-naphthyl | 15.9 | 414.2 |
| 33 | benzyl | 4-methoxyphenyl | 15.1 | 394.2 |
| 34 | benzyl | 2,5-dimethoxyphenyl | 15.1 | 424.2 |
| 35 | benzyl | 4-(diethylamino)phenyl | 15.1 | 435.2 |
| 36 | benzyl | 4-chlorophenyl | 15.8 | 398.1 |
| 37 | benzyl | 3,4-dichlorophenyl | 16.8 | 432.1 |
| 38 | benzyl | 4-chloro-3-methylphenyl | 16.3 | 412.1 |

-continued
FORMULA 17
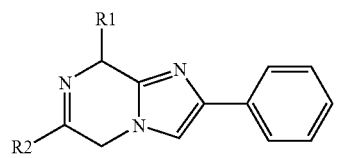
| | R1 | R2 | Tr (min) | [M + H]+ |
|---|---|---|---|---|
| 39 | benzyl | 4-bromophenyl | 16.1 | 442.0 |
| 40 | benzyl | 4-nitrophenyl | 15.6 | 409.1 |
| 41 | benzyl | 3-nitrophenyl | 15.6 | 409.1 |
| 42 | benzyl | propyl | 14.4 | 316.2 |
| 43 | butyl-NH-C(O)-O-CH2-phenyl | phenyl | 15.1 | 479.2 |
| 44 | butyl-NH-C(O)-O-CH2-phenyl | naphthyl | 15.6 | 529.2 |
| 45 | butyl-NH-C(O)-O-CH2-phenyl | 4-methoxyphenyl | 15.0 | 509.2 |
| 46 | butyl-NH-C(O)-O-CH2-phenyl | 2,5-dimethoxyphenyl | 15.2 | 539.2 |
| 47 | butyl-NH-C(O)-O-CH2-phenyl | 4-(diethylamino)phenyl | 15.2 | 550.2 |
| 48 | butyl-NH-C(O)-O-CH2-phenyl | 4-chlorophenyl | 15.6 | 513.1 |

FORMULA 17
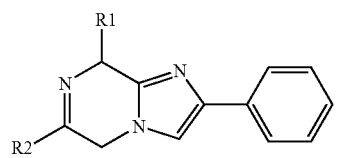
| | R1 | R2 | Tr (min) | [M + H]+ |
|---|---|---|---|---|
| 49 | ⟵(CH2)4NHC(O)OCH2Ph | 3,4-diCl-C6H3 | 16.0 | 547.1 |
| 50 | ⟵(CH2)4NHC(O)OCH2Ph | 3-Me-4-Cl-C6H3 | 15.8 | 527.2 |
| 51 | ⟵(CH2)4NHC(O)OCH2Ph | 4-Br-C6H4 | 15.6 | 557.0 |
| 52 | ⟵(CH2)4NHC(O)OCH2Ph | 4-F-C6H4 | 15.2 | 497.2 |
| 53 | ⟵(CH2)4NHC(O)OCH2Ph | 4-N3-C6H4 | 15.7 | 520.2 |
| 54 | ⟵(CH2)4NHC(O)OCH2Ph | 3-NO2-C6H4 | 15.4 | 524.2 |
| 55 | ⟵(CH2)4NHC(O)OCH2Ph | n-propyl | 14.5 | 431.2 |

FORMULA 18
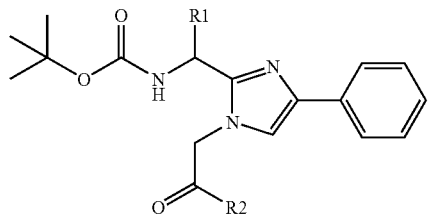
| | R1 | R2 | Analyses | |
|---|---|---|---|---|
| | | | Tr (min) | [M + H]+ |
| 1 | (S)-indol-3-ylmethyl | phenyl | 15.4 | 521.2 |
| 2 | (S)-indol-3-ylmethyl | biphenyl-4-yl | 16.5 | 597.1 |
| 3 | (S)-indol-3-ylmethyl | naphthalen-2-yl | 16.1 | 571.2 |
| 4 | (S)-indol-3-ylmethyl | 4-methoxyphenyl | 15.3 | 551.2 |
| 5 | (S)-indol-3-ylmethyl | 2,5-dimethoxyphenyl | 15.3 | 581.2 |
| 6 | (S)-indol-3-ylmethyl | 4-(diethylamino)phenyl | 15.8 | 592.2 |
| 7 | (S)-indol-3-ylmethyl | 4-chlorophenyl | 16.1 | 555.1 |
| 8 | (S)-indol-3-ylmethyl | 3,4-dichlorophenyl | 16.7 | 589.0 |

-continued
FORMULA 18
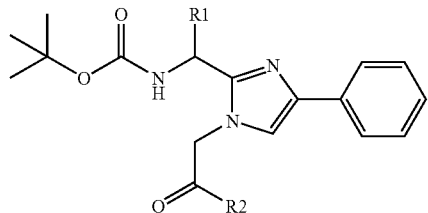
| | R1 | R2 | Tr (min) | [M + H]+ |
|---|---|---|---|---|
| 9 | (S)-1H-indol-3-ylmethyl | 4-chloro-3-methylphenyl | 16.4 | 569.1 |
| 10 | (S)-1H-indol-3-ylmethyl | 4-bromophenyl | 16.1 | 599.0 |
| 11 | (S)-1H-indol-3-ylmethyl | 4-fluorophenyl | 15.6 | 539.1 |
| 12 | (S)-1H-indol-3-ylmethyl | 4-cyanophenyl | 15.4 | 546.2 |
| 13 | (S)-1H-indol-3-ylmethyl | 4-azidophenyl | 15.8 | 562.1 |
| 14 | (S)-1H-indol-3-ylmethyl | 4-nitrophenyl | 15.8 | 566.1 |
| 15 | (S)-1H-indol-3-ylmethyl | 3-nitrophenyl | 15.7 | 566.1 |
| 16 | (S)-1H-indol-3-ylmethyl | propyl | 14.8 | 473.2 |

-continued
FORMULA 18
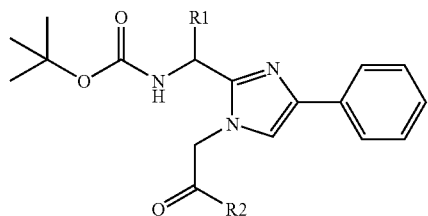
| | R1 | R2 | Tr (min) | [M + H]+ |
|---|---|---|---|---|
| 17 | 1H-indol-3-yl-methyl (S) | phenyl | 15.5 | 521.2 |
| 18 | 1H-indol-3-yl-methyl (R) | biphenyl | 16.5 | 597.1 |
| 19 | 1H-indol-3-yl-methyl (R) | naphthyl | 16.1 | 571.1 |
| 20 | 1H-indol-3-yl-methyl (R) | 4-methoxyphenyl | 15.4 | 551.2 |
| 21 | 1H-indol-3-yl-methyl (R) | 2,5-dimethoxyphenyl | 15.4 | 581.1 |
| 22 | 1H-indol-3-yl-methyl (R) | 4-(diethylamino)phenyl | 15.9 | 592.2 |
| 23 | 1H-indol-3-yl-methyl (R) | 4-chlorophenyl | 16.3 | 555.1 |

-continued
FORMULA 18
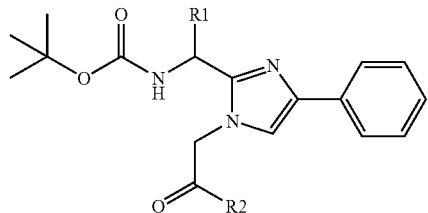
| | R1 | R2 | Tr (min) | [M + H]+ |
|---|---|---|---|---|
| 24 | (R)-1H-indol-3-ylmethyl | 3,4-dichlorophenyl | 16.8 | 589.0 |
| 25 | (R)-1H-indol-3-ylmethyl | 3-methyl-4-chlorophenyl | 16.7 | 569.1 |
| 26 | (R)-1H-indol-3-ylmethyl | 4-bromophenyl | 16.4 | 599.0 |
| 27 | (R)-1H-indol-3-ylmethyl | 4-fluorophenyl | 15.8 | 539.1 |
| 28 | (R)-1H-indol-3-ylmethyl | 4-cyanophenyl | 15.6 | 546.1 |
| 29 | (R)-1H-indol-3-ylmethyl | 4-azidophenyl | 16.0 | 562.1 |
| 30 | (R)-1H-indol-3-ylmethyl | 4-nitrophenyl | 15.9 | 566.1 |

-continued
FORMULA 18
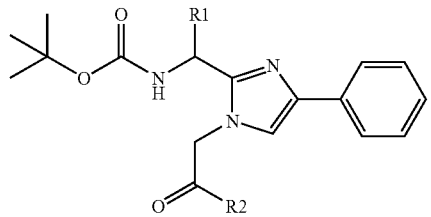
| | R1 | R2 | Tr (min) | [M + H]+ |
|---|---|---|---|---|
| 31 | (R)-3-indolylmethyl | 3-nitrophenyl | 15.8 | 566.1 |
| 32 | (R)-3-indolylmethyl | propyl | 15.0 | 473.2 |
| 33 | benzyl | phenyl | 16.7 | 482.2 |
| 34 | benzyl | 4-biphenyl | 18.0 | 558.2 |
| 35 | benzyl | 4-methoxyphenyl | 16.4 | 512.2 |
| 36 | benzyl | 2,5-dimethoxyphenyl | 16.5 | 542.2 |
| 37 | benzyl | 4-(diethylamino)phenyl | 17.0 | 553.2 |
| 38 | benzyl | 4-chlorophenyl | 17.6 | 516.1 |
| 39 | benzyl | 3,4-dichlorophenyl | 18.2 | 550.1 |

-continued
FORMULA 18
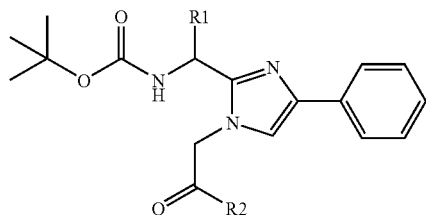
| | R1 | R2 | Analyses | |
|---|---|---|---|---|
| | | | Tr (min) | [M + H]+ |
| 40 | benzyl | 2-methyl-4-chlorophenyl | 18.0 | 530.1 |
| 41 | benzyl | 4-bromophenyl | 17.7 | 560.0 |
| 42 | benzyl | 4-fluorophenyl | 16.9 | 500.2 |
| 43 | benzyl | 4-cyanophenyl | 16.7 | 507.2 |
| 44 | benzyl | 4-azidophenyl | 17.2 | 523.2 |
| 45 | benzyl | 4-nitrophenyl | 16.9 | 527.2 |
| 46 | benzyl | 3-nitrophenyl | 16.8 | 527.2 |
| 47 | benzyl | propyl | 15.8 | 434.2 |
| 48 | 4-(Cbz-amino)butyl | phenyl | 15.8 | 597.2 |
| 49 | 4-(Cbz-amino)butyl | 4-biphenyl | 16.8 | 673.2 |

-continued
FORMULA 18
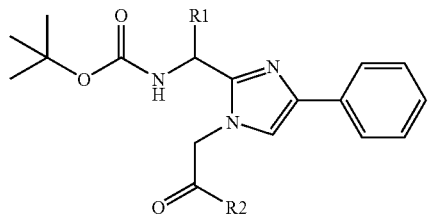
| | R1 | R2 | Tr (min) | [M + H]+ |
|---|---|---|---|---|
| 50 | ~~~NHC(O)OCH2Ph | 2-naphthyl | 16.5 | 647.2 |
| 51 | ~~~NHC(O)OCH2Ph | 4-methoxyphenyl | 15.8 | 627.2 |
| 52 | ~~~NHC(O)OCH2Ph | 2,5-dimethoxyphenyl | 15.8 | 657.2 |
| 53 | ~~~NHC(O)OCH2Ph | 4-chlorophenyl | 16.5 | 631.1 |
| 54 | ~~~NHC(O)OCH2Ph | 3,4-dichlorophenyl | 17.2 | 665.1 |
| 55 | ~~~NHC(O)OCH2Ph | 4-chloro-3-methylphenyl | 16.7 | 645.1 |
| 56 | ~~~NHC(O)OCH2Ph | 4-bromophenyl | 16.5 | 675.1 |
| 57 | ~~~NHC(O)OCH2Ph | 4-fluorophenyl | 16.0 | 615.1 |
| 58 | ~~~NHC(O)OCH2Ph | 4-cyanophenyl | 15.9 | 622.1 |

-continued
FORMULA 18
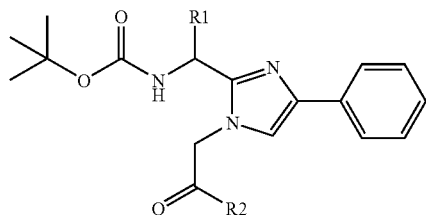
| | R1 | R2 | Tr (min) | [M + H]+ |
|---|---|---|---|---|
| 59 | (pentyl-NH-C(O)-O-benzyl) | (4-azidophenyl) | 16.1 | 638.2 |
| 60 | (pentyl-NH-C(O)-O-benzyl) | (4-nitrophenyl) | 16.1 | 642.1 |
| 61 | (pentyl-NH-C(O)-O-benzyl) | (3-nitrophenyl) | 16.2 | 642.1 |
| 62 | (pentyl-NH-C(O)-O-benzyl) | (propyl) | 15.4 | 549.2 |
| 63 | (pentyl-NH-C(O)-O-tBu) | (phenyl) | 15.9 | 563.2 |
| 64 | (pentyl-NH-C(O)-O-tBu) | (biphenyl) | 17.0 | 639.2 |
| 65 | (pentyl-NH-C(O)-O-tBu) | (2-naphthyl) | 16.5 | 613.2 |
| 66 | (pentyl-NH-C(O)-O-tBu) | (4-methoxyphenyl) | 15.7 | 593.2 |
| 67 | (pentyl-NH-C(O)-O-tBu) | (2,5-dimethoxyphenyl) | 15.8 | 623.2 |

FORMULA 18
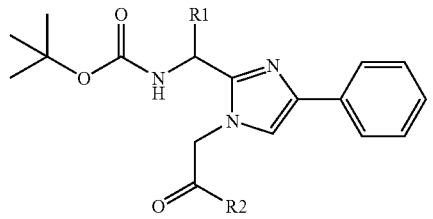
| | R1 | R2 | Tr (min) | [M + H]+ |
|---|---|---|---|---|
| 68 | ←∽∽NHC(O)OC(CH3)3 | ←C6H4-N(Et)2 (para) | 16.2 | 634.2 |
| 69 | ←∽∽NHC(O)OC(CH3)3 | ←C6H4-Cl (para) | 16.6 | 597.1 |
| 70 | ←∽∽NHC(O)OC(CH3)3 | ←C6H3-(Cl)2 (3,4) | 17.4 | 631.1 |
| 71 | ←∽∽NHC(O)OC(CH3)3 | ←C6H3-(CH3)(Cl) | 17.0 | 611.1 |
| 72 | ←∽∽NHC(O)OC(CH3)3 | ←C6H4-Br (para) | 16.7 | 641.1 |
| 73 | ←∽∽NHC(O)OC(CH3)3 | ←C6H4-F (para) | 16.1 | 581.2 |
| 74 | ←∽∽NHC(O)OC(CH3)3 | ←C6H4-CN (para) | 15.9 | 588.2 |
| 75 | ←∽∽NHC(O)OC(CH3)3 | ←C6H4-N3 (para) | 16.2 | 604.2 |
| 76 | ←∽∽NHC(O)OC(CH3)3 | ←C6H4-NO2 (para) | 16.2 | 608.2 |
| 77 | ←∽∽NHC(O)OC(CH3)3 | ←C6H4-NO2 (meta) | 16.1 | 608.2 |

-continued
FORMULA 18
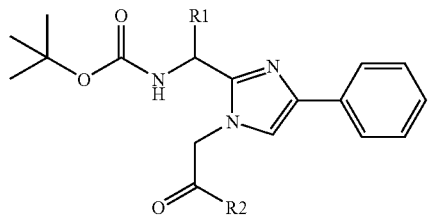
| | R1 | R2 | Tr (min) | [M + H]+ |
|---|---|---|---|---|
| 78 | 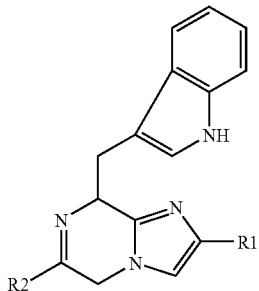 | ![propyl] | 15.3 | 515.3 |
FORMULA 19
| | R1 | R2 | Tr | [M + H]+ |
|---|---|---|---|---|
| 1 | 2-methoxyphenyl | phenyl | 6.2 | 433.2 |
| 2 | 2-methoxyphenyl | 4-biphenyl | 7.0 | 509.2 |
| 3 | 2-methoxyphenyl | 2-naphthyl | 6.8 | 483.2 |
Analyses * = [M + TFA − H]−

-continued
FORMULA 19
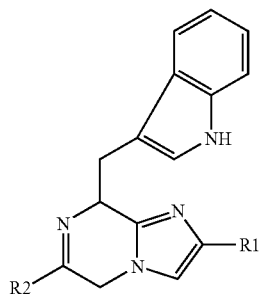
| | R1 | R2 | Tr | [M + H]+ |
|---|---|---|---|---|
| | | | Analyses * = [M + TFA − H]− | |
| 4 | 2-OMe-phenyl | 4-OMe-phenyl | 6.2 | 463.2 |
| 5 | 2-OMe-phenyl | 2,5-diOMe-phenyl | 6.5 | 493.2 |
| 6 | 2-OMe-phenyl | 4-NEt₂-phenyl | 5.4 | 504.3 |
| 7 | 2-OMe-phenyl | 4-Cl-phenyl | 6.5 | 467.2 |
| 8 | 2-OMe-phenyl | 3,4-diCl-phenyl | 6.9 | 501.1 |
| 9 | 2-OMe-phenyl | 3-Me-4-Cl-phenyl | 6.8 | 481.2 |

-continued
FORMULA 19
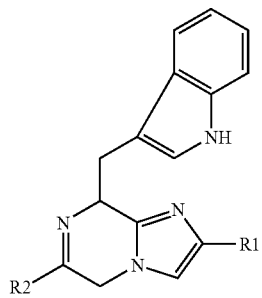
| | R1 | R2 | Tr | Analyses<br>* = [M + TFA − H]−<br>[M + H]+ |
|---|---|---|---|---|
| 10 | 2-methoxyphenyl | 4-bromophenyl | 6.6 | 511.1 |
| 11 | 2-methoxyphenyl | 4-fluorophenyl | 6.3 | 451.2 |
| 12 | 2-methoxyphenyl | 4-cyanophenyl | 6.2 | 458.2 |
| 13 | 2-methoxyphenyl | 4-azidophenyl | 6.5 | 474.2 |
| 14 | 2-methoxyphenyl | 4-nitrophenyl | 6.3 | 478.2 |
| 15 | 2-methoxyphenyl | 3-nitrophenyl | 6.3 | 478.2 |
| 16 | 2-methoxyphenyl | ethyl | 5.7 | 385.2 |

-continued
FORMULA 19
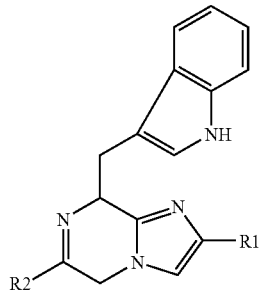
| | R1 | R2 | Tr | [M + H]+ |
|---|---|---|---|---|
| | | | Analyses * = [M + TFA − H]− | |
| 17 | (S) 4-methoxyphenyl | phenyl | 6.9 | 433.2 |
| 18 | (S) 4-methoxyphenyl | 4-biphenyl | 7.0 | 509.2 |
| 19 | (S) 4-methoxyphenyl | 2-naphthyl | 6.7 | 483.2 |
| 20 | (S) 4-methoxyphenyl | 4-methoxyphenyl | 6.2 | 463.2 |
| 21 | (S) 4-methoxyphenyl | 2,5-dimethoxyphenyl | 6.3 | 493.2 |
| 22 | (S) 4-methoxyphenyl | 4-(diethylamino)phenyl | 5.3 | 504.3 |
| 23 | (S) 4-methoxyphenyl | 4-chlorophenyl | 6.5 | 467.2 |
| 24 | (S) 4-methoxyphenyl | 3,4-dichlorophenyl | 6.8 | 501.1 |
| 25 | (S) 4-methoxyphenyl | 4-chloro-3-methylphenyl | 6.7 | 481.2 |

-continued
FORMULA 19
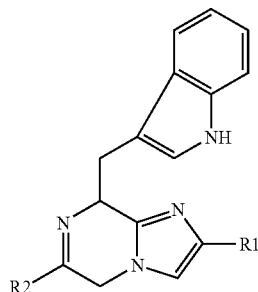
| | R1 | R2 | Tr | [M + H]+ Analyses * = [M + TFA − H]− |
|---|---|---|---|---|
| 26 | (S) 4-methoxyphenyl | 4-bromophenyl | 6.5 | 511.1 |
| 27 | (S) 4-methoxyphenyl | 4-fluorophenyl | 6.2 | 451.2 |
| 28 | (S) 4-methoxyphenyl | 4-cyanophenyl | 6.1 | 458.2 |
| 29 | (S) 4-methoxyphenyl | 4-azidophenyl | 6.4 | 474.2 |
| 30 | (S) 4-methoxyphenyl | 4-nitrophenyl | 6.3 | 478.2 |
| 31 | (S) 4-methoxyphenyl | 3-nitrophenyl | 6.3 | 478.2 |
| 32 | (S) 4-methoxyphenyl | isopropyl | 5.6 | 385.2 |
| 33 | 4-bromophenyl | phenyl | 6.5 | 481.1 |
| 34 | 4-bromophenyl | 4-biphenyl | 7.4 | 557.1 |
| 35 | 4-bromophenyl | 2-naphthyl | 7.1 | 531.1 |
| 36 | 4-bromophenyl | 4-methoxyphenyl | 6.6 | 511.1 |

-continued
FORMULA 19
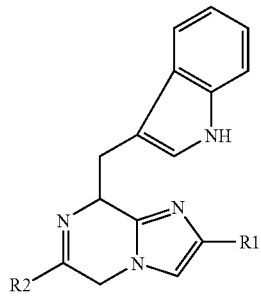
Analyses
* = [M + TFA − H]−
| | R1 | R2 | Tr | [M + H]+ |
|---|---|---|---|---|
| 37 | -C6H4-Br | 2,5-dimethoxyphenyl | 6.8 | 541.1 |
| 38 | -C6H4-Br | 4-(N,N-diethylamino)phenyl | 5.7 | 552.2 |
| 39 | -C6H4-Br | 4-Cl-C6H4 | 6.9 | 515.0 |
| 40 | -C6H4-Br | 3,4-diCl-C6H3 | 7.3 | 549.0 |
| 41 | -C6H4-Br | 3-methyl-4-Cl-C6H3 | 7.1 | 529.1 |
| 42 | -C6H4-Br | -C6H4-Br | 7.0 | 670.1* |
| 43 | -C6H4-Br | -C6H4-F | 6.6 | 499.1 |
| 44 | -C6H4-Br | -C6H4-CN | 6.6 | 506.1 |
| 45 | -C6H4-Br | -C6H4-N3 | 6.8 | 522.1 |
| 46 | -C6H4-Br | -C6H4-NO2 | 6.8 | 526.1 |

-continued
FORMULA 19
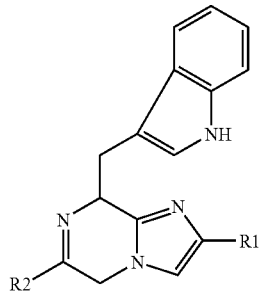
| | R1 | R2 | Tr | [M + H]+ |
|---|---|---|---|---|
| 47 | 4-Br-C6H4 | 3-NO2-C6H4 | 6.7 | 526.1 |
| 48 | 4-Br-C6H4 | ethyl | 6.0 | 433.1 |
| 49 | 4-NO2-C6H4 | C6H5 | 6.6 | 448.2 |
| 50 | 4-NO2-C6H4 | 4-phenyl-C6H4 | 7.7 | 524.2 |
| 51 | 4-NO2-C6H4 | 2-naphthyl | 7.4 | 498.2 |
| 52 | 4-NO2-C6H4 | 4-OMe-C6H4 | 6.6 | 478.2 |
| 53 | 4-NO2-C6H4 | 2,5-(OMe)2-C6H3 | 6.7 | 508.2 |
| 54 | 4-NO2-C6H4 | 4-NEt2-C6H4 | 5.8 | 519.2 |
| 55 | 4-NO2-C6H4 | 4-Cl-C6H4 | 7.2 | 482.1 |
Analyses
* = [M + TFA − H]−

-continued
FORMULA 19
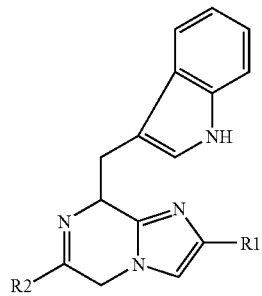
| | R1 | R2 | Tr | [M + H]+ |
|---|---|---|---|---|
| 56 | 4-NO2-C6H4 | 3,4-diCl-C6H3 | 7.7 | 516.1 |
| 57 | 4-NO2-C6H4 | 3-Me-4-Cl-C6H3 | 7.5 | 496.2 |
| 58 | 4-NO2-C6H4 | 4-Br-C6H4 | 7.3 | 526.1 |
| 59 | 4-NO2-C6H4 | 4-F-C6H4 | 6.8 | 466.2 |
| 60 | 4-NO2-C6H4 | 4-CN-C6H4 | 6.8 | 473.2 |
| 61 | 4-NO2-C6H4 | 4-N3-C6H4 | 7.1 | 489.2 |
| 62 | 4-NO2-C6H4 | 4-NO2-C6H4 | 7.1 | 493.1 |
| 63 | 4-NO2-C6H4 | 3-NO2-C6H4 | 7.0 | 493.2 |
| 64 | 4-NO2-C6H4 | Et | 5.8 | 400.2 |
| 65 | t-Bu | C6H5 | 5.8 | 383.2 |

-continued
FORMULA 19
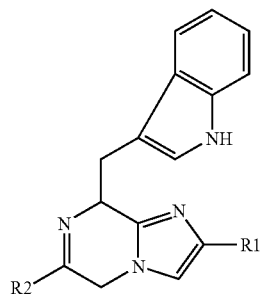
| | R1 | R2 | Analyses<br>* = [M + TFA − H]− | |
|---|---|---|---|---|
| | | | Tr | [M + H]+ |
| 66 | *tert*-butyl | biphenyl-4-yl | 6.8 | 459.2 |
| 67 | *tert*-butyl | naphthalen-2-yl | 6.5 | 433.2 |
| 68 | *tert*-butyl | 4-methoxyphenyl | 5.9 | 413.2 |
| 69 | *tert*-butyl | 2,5-dimethoxyphenyl | 6.2 | 443.3 |
| 70 | *tert*-butyl | 4-(diethylamino)phenyl | 5.0 | 454.3 |
| 71 | *tert*-butyl | 4-chlorophenyl | 6.3 | 417.2 |
| 72 | *tert*-butyl | 3,4-dichlorophenyl | 6.6 | 451.1 |
| 73 | *tert*-butyl | 4-chloro-3-methylphenyl | 6.5 | 431.2 |

-continued
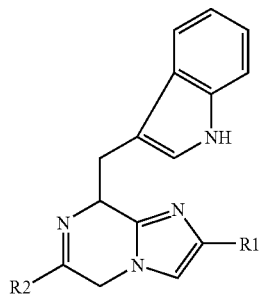
FORMULA 19
Analyses
* = [M + TFA − H]−
| | R1 | R2 | Tr | [M + H]+ |
|---|---|---|---|---|
| 74 | t-Bu | 4-Br-C6H4 | 6.3 | 461.1 |
| 75 | t-Bu | 4-F-C6H4 | 6.0 | 401.2 |
| 76 | t-Bu | 4-CN-C6H4 | 5.8 | 408.2 |
| 77 | t-Bu | 4-N3-C6H4 | 6.2 | 424.2 |
| 78 | t-Bu | 4-NO2-C6H4 | 6.0 | 428.2 |
| 79 | t-Bu | 3-NO2-C6H4 | 6.0 | 428.2 |
| 80 | t-Bu | Et | 5.3 | 335.3 |

FORMULA 20
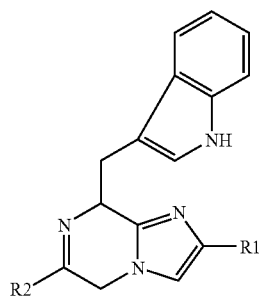
| | R1 | R2 | Tr (min) | [M+H]+ |
|---|---|---|---|---|
| 1 | (R) phenyl | 4-(OCF3)phenyl | 6.9 | 487.2 |
| 2 | (R) phenyl | 2,3-dihydro-1,4-benzodioxin-6-yl | 6.3 | 461.3 |
| 3 | (R) phenyl | 1,3-benzodioxol-5-yl | 6.3 | 447.3 |
| 4 | (R) phenyl | 3,4,5-trimethoxyphenyl | 6.2 | 493.3 |
| 5 | (R) phenyl | 4-chloro-3-nitrophenyl | 6.7 | 482.2 |
| 6 | (R) phenyl | 4-(benzyloxy)phenyl | 7.2 | 509.3 |
| 7 | (R) phenyl | 4-pentylphenyl | 7.7 | 473.4 |

-continued
FORMULA 20
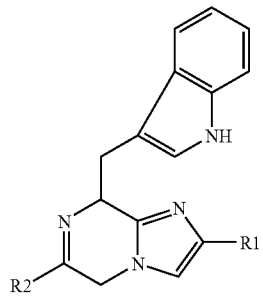
| | R1 | R2 | LFPlb2-02fon/xls Analyses | |
|---|---|---|---|---|
| | | | Tr (min) | [M+H]+ |
| 8 | (R) phenyl | 7-(3,4-dihydroquinolin-2(1H)-one) | 5.8 | 472.3 |
| 9 | (R) phenyl | 5-chloro-3-methylbenzo[b]thiophen-2-yl | 7.3 | 507.2 |
| 10 | (R) phenyl | benzo[b]thiophen-3-yl | 6.6 | 459.3 |
| 11 | (R) phenyl | 5-bromothiophen-2-yl | 6.6 | 487.2 |
| 12 | (R) phenyl | 3-phenylisoxazol-5-yl | 6.7 | 470.3 |
| 13 | (R) phenyl | 3-(2,4-dichlorophenyl)isoxazol-5-yl | 7.2 | 538.2 |
| 14 | (R) phenyl | 1H-indol-3-ylmethyl | 6.6 | 456.3 |
| 15 | (R) phenyl | phenethyl | 6.6 | 431.3 |

-continued
FORMULA 20
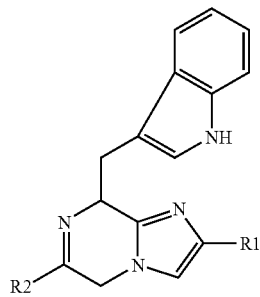
| | R1 | R2 | Tr (min) | [M+H]+ |
|---|---|---|---|---|
| | | | LFPlb2-02fon/xls Analyses | |
| 16 | phenyl (R) | 3,4-difluorophenyl | 6.5 | 439.3 |
| 17 | 2-methoxyphenyl | 4-trifluoromethoxyphenyl | 7.1 | 517.3 |
| 18 | 2-methoxyphenyl | 2,3-dihydro-1,4-benzodioxin-6-yl | 6.5 | 491.3 |
| 19 | 2-methoxyphenyl | 1,3-benzodioxol-5-yl | 6.4 | 477.3 |
| 20 | 2-methoxyphenyl | 3,4,5-trimethoxyphenyl | 6.4 | 523.3 |
| 21 | 2-methoxyphenyl | 4-chloro-3-nitrophenyl | 6.9 | 512.3 |
| 22 | 2-methoxyphenyl | 4-benzyloxyphenyl | 7.3 | 539.3 |

-continued
FORMULA 20
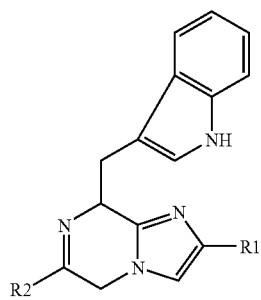
| | R1 | R2 | Tr (min) | [M+H]+ |
|---|---|---|---|---|
| 23 | 2-methoxyphenyl | 4-pentylphenyl | 7.8 | 503.4 |
| 24 | 2-methoxyphenyl | 3,4-dihydro-2(1H)-quinolinon-7-yl | 6.0 | 502.3 |
| 25 | 2-methoxyphenyl | 5-chloro-3-methylbenzo[b]thiophen-2-yl | 7.4 | 537.3 |
| 26 | 2-methoxyphenyl | benzo[b]thiophen-3-yl | 6.8 | 489.3 |
| 27 | 2-methoxyphenyl | 5-bromothiophen-2-yl | 6.8 | 517.2 |
| 28 | 2-methoxyphenyl | 3-phenylisoxazol-5-yl | 6.8 | 500.3 |

-continued
FORMULA 20
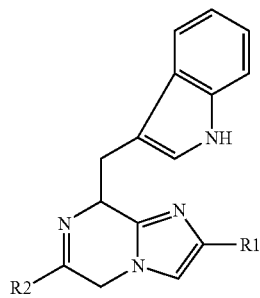
| | R1 | R2 | Tr (min) | [M+H]+ |
|---|---|---|---|---|
| 29 | 2-methoxyphenyl | 3-(2,4-dichlorophenyl)isoxazol-5-yl | 7.4 | 562.2 |
| 30 | 2-methoxyphenyl | 1H-indol-3-ylmethyl | 6.7 | 486.4 |
| 31 | 2-methoxyphenyl | phenethyl | 6.8 | 461.3 |
| 32 | 2-methoxyphenyl | 3,4-difluorophenyl | 6.7 | 469.3 |
| 33 | 4-nitrophenyl | 4-(trifluoromethoxy)phenyl | 7.4 | 532.3 |
| 34 | 4-nitrophenyl | 2,3-dihydrobenzo[1,4]dioxin-6-yl | 6.6 | 506.3 |
| 35 | 4-nitrophenyl | benzo[1,3]dioxol-5-yl | 6.6 | 492.3 |
Analyses header: LFPlb2-02fon/xls -continued
FORMULA 20
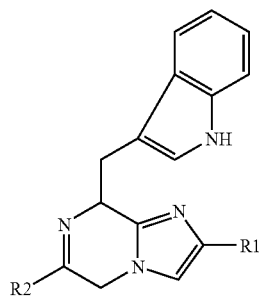
| | R1 | R2 | Tr (min) | [M+H]+ |
|---|---|---|---|---|
| | | | LFPlb2-02fon/xls Analyses | |
| 36 | -C₆H₄-NO₂ (4) | 3,4,5-trimethoxyphenyl | 6.6 | 538.3 |
| 37 | -C₆H₄-NO₂ (4) | 4-Cl, 3-NO₂-phenyl | 7.3 | 527.2 |
| 38 | -C₆H₄-NO₂ (4) | 4-benzyloxyphenyl | 7.5 | 554.3 |
| 39 | -C₆H₄-NO₂ (4) | 4-pentylphenyl | 8.1 | 518.3 |
| 40 | -C₆H₄-NO₂ (4) | 3,4-dihydroquinolin-2(1H)-on-7-yl | 6.1 | 517.3 |
| 41 | -C₆H₄-NO₂ (4) | 5-chloro-3-methylbenzothiophen-2-yl | 8.1 | 552.2 |
| 42 | -C₆H₄-NO₂ (4) | benzothiophen-3-yl | 7.0 | 504.3 |
| 43 | -C₆H₄-NO₂ (4) | 5-bromothiophen-2-yl | 7.2 | 532.1 |

-continued
FORMULA 20
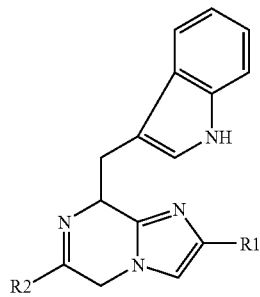
| | R1 | R2 | Tr (min) | [M+H]+ |
|---|---|---|---|---|
| | | | LFPlb2-02fon/xls Analyses | |
| 44 | 4-NO₂-phenyl | 3-phenyl-isoxazol-5-yl | 7.4 | 515.3 |
| 45 | 4-NO₂-phenyl | 3-(2,4-dichlorophenyl)-isoxazol-5-yl | 8.1 | 583.2 |
| 46 | 4-NO₂-phenyl | 1H-indol-3-ylmethyl | 6.8 | 501.3 |
| 47 | 4-NO₂-phenyl | 2-phenylethyl | 6.9 | 476.3 |
| 48 | 4-NO₂-phenyl | 3,4-difluorophenyl | 7.0 | 484.3 |
| 49 | 4-Br-phenyl | 4-(trifluoromethoxy)phenyl | 7.3 | 565.2 |
| 50 | 4-Br-phenyl | 2,3-dihydro-1,4-benzodioxin-6-yl | 6.7 | 539.2 |
| 51 | 4-Br-phenyl | 1,3-benzodioxol-5-yl | 6.7 | 525.2 |

-continued
FORMULA 20
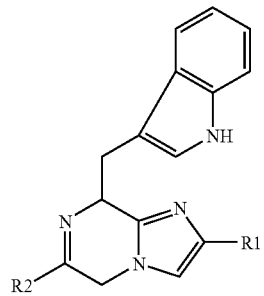
|  | R1 | R2 | Tr (min) | [M+H]+ |
|---|---|---|---|---|
| | | | LFPlb2-02fon/xls Analyses | |
| 52 | 4-Br-phenyl | 3,4,5-trimethoxyphenyl | 6.7 | 571.2 |
| 53 | 4-Br-phenyl | 4-Cl-3-NO2-phenyl | 7.1 | 560.1 |
| 54 | 4-Br-phenyl | 4-benzyloxyphenyl | 7.6 | 587.2 |
| 55 | 4-Br-phenyl | 4-pentylphenyl | 8.0 | 551.3 |
| 56 | 4-Br-phenyl | 3,4-dihydroquinolin-2(1H)-on-7-yl | 6.3 | 550.2 |
| 57 | 4-Br-phenyl | 5-chloro-3-methylbenzo[b]thiophen-2-yl | 7.7 | 585.1 |
| 58 | 4-Br-phenyl | benzo[b]thiophen-3-yl | 7.0 | 537.2 |
| 59 | 4-Br-phenyl | 5-bromothiophen-2-yl | 7.0 | 565.0 |

-continued
FORMULA 20
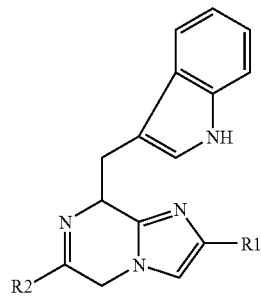
| | R1 | R2 | Tr (min) | [M+H]+ |
|---|---|---|---|---|
| 60 | 4-Br-phenyl | 3-phenyl-isoxazol-5-yl | 7.2 | 548.2 |
| 61 | 4-Br-phenyl | 3-(2,4-dichlorophenyl)-isoxazol-5-yl | 7.7 | 616.1 |
| 62 | 4-Br-phenyl | 1H-indol-3-ylmethyl | 7.0 | 534.2 |
| 63 | 4-Br-phenyl | 2-phenylethyl | 7.0 | 509.2 |
| 64 | 4-Br-phenyl | 3,4-difluorophenyl | 6.9 | 517.2 |
| 65 | tert-butyl | 4-(trifluoromethoxy)phenyl | 6.8 | 467.3 |
| 66 | tert-butyl | 2,3-dihydro-1,4-benzodioxin-6-yl | 6.1 | 444.3 |
| 67 | tert-butyl | 1,3-benzodioxol-5-yl | 6.1 | 427.3 |

-continued
FORMULA 20
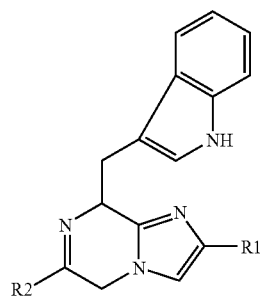
| | R1 | R2 | Tr (min) | [M+H]+ |
|---|---|---|---|---|
| 68 | tBu | 3,4,5-trimethoxyphenyl | 6.1 | 473.4 |
| 69 | tBu | 4-chloro-3-nitrophenyl | 6.6 | 462.3 |
| 70 | tBu | 4-benzyloxyphenyl | 7.1 | 489.4 |
| 71 | tBu | 4-pentylphenyl | 7.6 | 453.4 |
| 72 | tBu | 2-oxo-1,2,3,4-tetrahydroquinolin-7-yl | 5.6 | 452.3 |
| 73 | tBu | 5-chloro-3-methylbenzo[b]thiophen-2-yl | 7.2 | 487.3 |
| 74 | tBu | benzo[b]thiophen-3-yl | 6.5 | 439.3 |

-continued
FORMULA 20
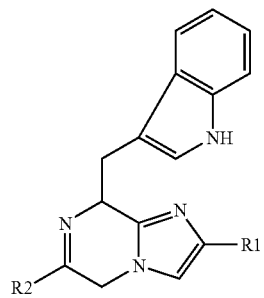
| | R1 | R2 | Tr (min) | [M+H]+ |
|---|---|---|---|---|
| 75 | tert-butyl | 5-bromothiophen-2-yl | 6.5 | 467.2 |
| 76 | tert-butyl | 3-phenylisoxazol-5-yl | 6.5 | 450.3 |
| 77 | tert-butyl | 3-(2,4-dichlorophenyl)isoxazol-5-yl | 7.1 | 518.2 |
| 78 | tert-butyl | (1H-indol-3-yl)methyl | 6.3 | 436.3 |
| 79 | tert-butyl | phenethyl | 6.5 | 411.3 |
| 80 | tert-butyl | 3,4-difluorophenyl | 6.4 | 419.3 |

FORMULA 21
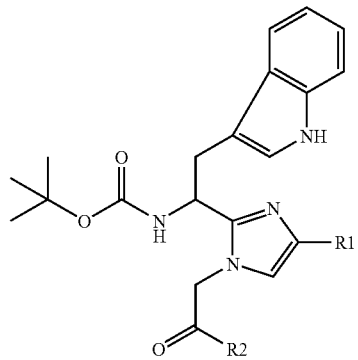
| | R1 | R2 | Tr (min) | [M + H]+ |
|---|---|---|---|---|
| | | | Analyses * = [M + TFA − H] | |
| 1 | 2-methoxyphenyl | phenyl | 7.0 | 551.2 |
| 2 | 2-methoxyphenyl | 4-biphenyl | 7.8 | 627.2 |
| 3 | 2-methoxyphenyl | 2-naphthyl | 7.5 | 601.2 |
| 4 | 2-methoxyphenyl | 4-methoxyphenyl | 7.1 | 581.2 |
| 5 | 2-methoxyphenyl | 2,5-dimethoxyphenyl | 7.1 | 611.2 |
| 6 | 2-methoxyphenyl | 4-(diethylamino)phenyl | 7.5 | 622.3 |

FORMULA 21
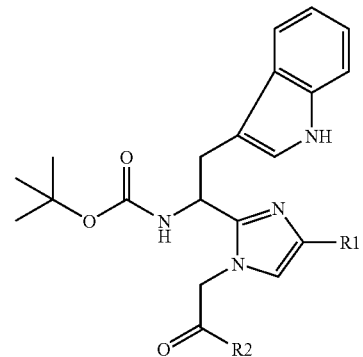
|   | R1 | R2 | Tr (min) | [M + H]+ |
|---|---|---|---|---|
| 7 | 2-OMe-C6H4 | 4-Cl-C6H4 | 7.4 | 585.2 |
| 8 | 2-OMe-C6H4 | 3,4-diCl-C6H3 | 7.7 | 619.1 |
| 9 | 2-OMe-C6H4 | 3-Me-4-Cl-C6H3 | 7.7 | 599.2 |
| 10 | 2-OMe-C6H4 | 4-Br-C6H4 | 7.4 | 629.1 |
| 11 | 2-OMe-C6H4 | 4-F-C6H4 | 7.1 | 569.2 |
| 12 | 2-OMe-C6H4 | 4-CN-C6H4 | 7.0 | 576.2 |
Analyses * = [M + TFA − H]

-continued
FORMULA 21
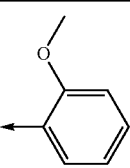
| | R1 | R2 | Tr (min) | [M + H]+ |
|---|---|---|---|---|
| | | | Analyses * = [M + TFA − H] | |
| 13 |  | 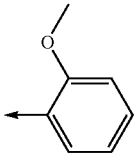 | 7.3 | 592.2 |
| 14 | 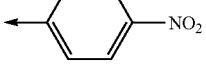 | 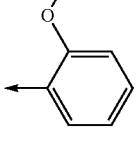 | 7.2 | 596.2 |
| 15 | 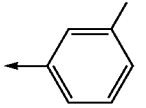 | 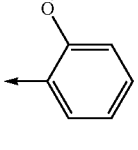 | 7.1 | 596.2 |
| 16 |  | 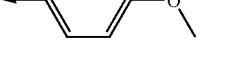 | 6.6 | 503.3 |
| 17 (S) | 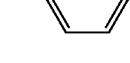 | 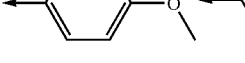 | 7.0 | 551.2 |
| 18 (S) | 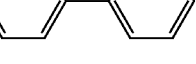 | 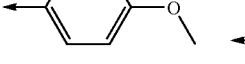 | 7.8 | 627.2 |
| 19 (S) | 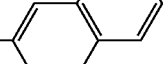 | 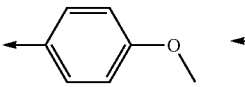 | 7.5 | 601.2 |
| 20 (S) | 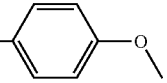 | | 7.0 | 581.2 |

FORMULA 21
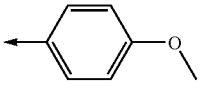
| | R1 | R2 | Tr (min) | [M + H]+ |
|---|---|---|---|---|
| 21 (S) | 4-methoxyphenyl | 2,5-dimethoxyphenyl | 7.1 | 611.2 |
| 22 (S) | 4-methoxyphenyl | 4-(diethylamino)phenyl | 7.5 | 622.3 |
| 23 (S) | 4-methoxyphenyl | 4-chlorophenyl | 7.4 | 585.2 |
| 24 (S) | 4-methoxyphenyl | 3,4-dichlorophenyl | 7.7 | 619.1 |
| 25 (S) | 4-methoxyphenyl | 4-chloro-3-methylphenyl | 7.6 | 599.2 |
| 26 (S) | 4-methoxyphenyl | 4-bromophenyl | 7.4 | 629.1 |
| 27 (S) | 4-methoxyphenyl | 4-fluorophenyl | 7.1 | 569.2 |
| 28 (S) | 4-methoxyphenyl | 4-cyanophenyl | 6.9 | 576.2 |
| 29 (S) | 4-methoxyphenyl | 4-azidophenyl | 7.3 | 704.2* |
Analyses * = [M + TFA − H]

-continued
FORMULA 21
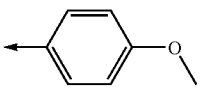
| | R1 | R2 | Tr (min) | [M + H]+ |
|---|---|---|---|---|
| | | | Analyses * = [M + TFA − H] | |
| 30 (S) | 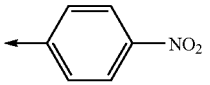 4-OMe-C6H4 | 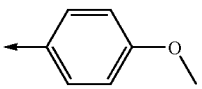 4-NO2-C6H4 | 7.1 | 596.2 |
| 31 (S) | 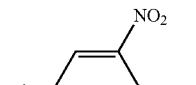 4-OMe-C6H4 | 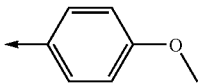 3-NO2-C6H4 | 7.0 | 596.2 |
| 32 (S) | 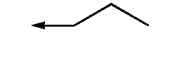 4-OMe-C6H4 | 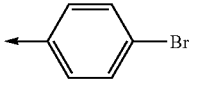 | 6.5 | 503.2 |
| 33 | 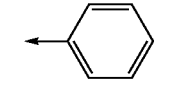 4-Br-C6H4 | 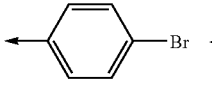 | 8.1 | 599.1 |
| 34 | 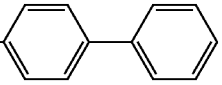 4-Br-C6H4 | 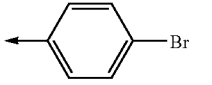 | 9.0 | 675.1 |
| 35 | 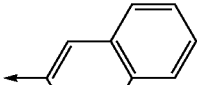 4-Br-C6H4 | 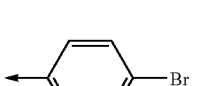 | 8.7 | 649.1 |
| 36 | 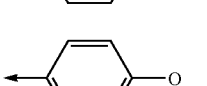 4-Br-C6H4 | 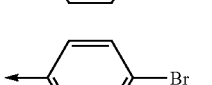 4-OMe-C6H4 | 8.1 | 629.1 |
| 37 | 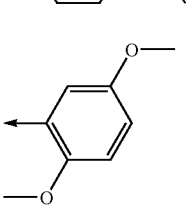 4-Br-C6H4 | 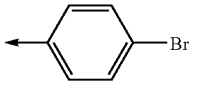 2,5-diOMe-C6H3 | 8.0 | 659.1 |
| 38 | 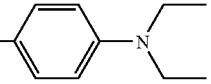 4-Br-C6H4 | 4-NEt2-C6H4 | 8.4 | 670.2 |

-continued
FORMULA 21
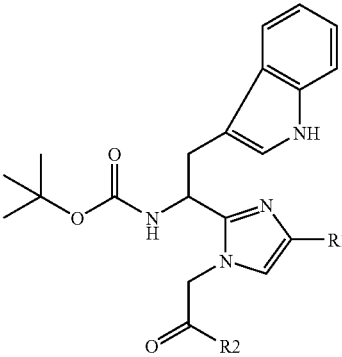
| | R1 | R2 | Tr (min) | [M + H]+ |
|---|---|---|---|---|
| | | | Analyses * = [M + TFA − H] | |
| 39 | 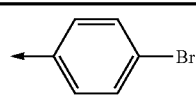—Br | 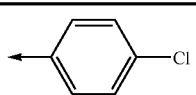—Cl | 8.6 | 633.1 |
| 40 | 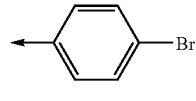—Br | 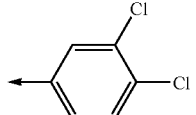 Cl, Cl | 9.0 | 667.0 |
| 41 | 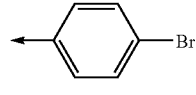—Br | 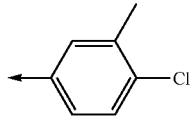 CH₃, Cl | 8.8 | 647.1 |
| 42 | 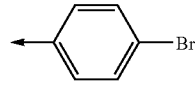—Br | 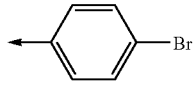—Br | 8.6 | 677.0 |
| 43 | 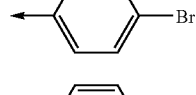—Br | 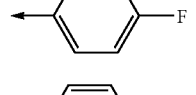—F | 8.3 | 617.1 |
| 44 | 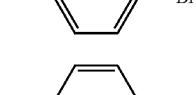—Br | —CN | 8.2 | 624.1 |
| 45 | —Br | 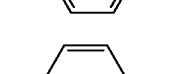—N₃ | 8.4 | 640.1 |
| 46 | 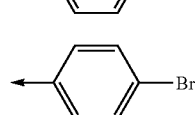—Br | 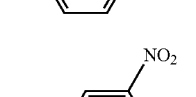—NO₂ | 8.4 | 644.1 |
| 47 | —Br | 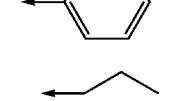 NO₂ | 8.3 | 644.1 |
| 48 | 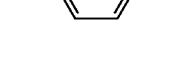—Br |  | 7.6 | 551.1 |

-continued
FORMULA 21
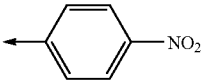
| | R1 | R2 | Tr (min) | [M + H]+ |
|---|---|---|---|---|
| | | | Analyses * = [M + TFA − H] | |
| 49 | 4-NO2-C6H4- | C6H5- | 8.7 | 566.2 |
| 50 | 4-NO2-C6H4- | 4-biphenyl | 9.7 | 542.2 |
| 51 | 4-NO2-C6H4- | 2-naphthyl | 9.3 | 616.2 |
| 52 | 4-NO2-C6H4- | 4-MeO-C6H4- | 8.6 | 596.2 |
| 53 | 4-NO2-C6H4- | 2,5-(MeO)2-C6H3- | 8.7 | 626.2 |
| 54 | 4-NO2-C6H4- | 4-(NEt2)-C6H4- | 9.1 | 637.2 |
| 55 | 4-NO2-C6H4- | 4-Cl-C6H4- | 9.2 | 600.1 |
| 56 | 4-NO2-C6H4- | 3,4-Cl2-C6H3- | 9.6 | 634.1 |
| 57 | 4-NO2-C6H4- | 2-Me-4-Cl-C6H3- | 9.5 | 614.1 |

-continued
FORMULA 21
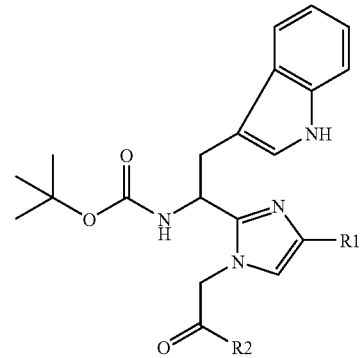
| | R1 | R2 | Tr (min) | [M + H]+ |
|---|---|---|---|---|
| | | | Analyses *=[M + TFA − H] | |
| 58 | 4-NO₂-phenyl | 4-Br-phenyl | 9.3 | 644.1 |
| 59 | 4-NO₂-phenyl | 4-F-phenyl | 8.8 | 584.2 |
| 60 | 4-NO₂-phenyl | 4-CN-phenyl | 8.7 | 591.2 |
| 61 | 4-NO₂-phenyl | 4-N₃-phenyl | 9.0 | 607.2 |
| 62 | 4-NO₂-phenyl | 4-NO₂-phenyl | 8.9 | 611.1 |
| 63 | 4-NO₂-phenyl | 3-NO₂-phenyl | 8.8 | 611.1 |
| 64 | 4-NO₂-phenyl | propyl | 8.2 | 518.2 |
| 65 | tert-butyl | phenyl | 6.7 | 501.3 |
| 66 | tert-butyl | 4-biphenyl | 7.5 | 577.2 |
| 67 | tert-butyl | 2-naphthyl | 7.2 | 551.3 |

-continued
FORMULA 21
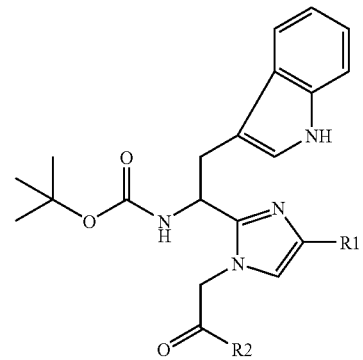
| | R1 | R2 | Tr (min) | [M + H]+ |
|---|---|---|---|---|
| | | | Analyses * = [M + TFA − H] | |
| 68 | t-Bu | 4-methoxyphenyl | 6.8 | 531.3 |
| 69 | t-Bu | 2,5-dimethoxyphenyl | 6.9 | 561.2 |
| 70 | t-Bu | 4-(diethylamino)phenyl | 7.3 | 572.3 |
| 71 | t-Bu | 4-chlorophenyl | 7.0 | 535.2 |
| 72 | t-Bu | 3,4-dichlorophenyl | 7.3 | 569.1 |
| 73 | t-Bu | 4-chloro-3-methylphenyl | 7.3 | 549.2 |
| 74 | t-Bu | 4-bromophenyl | 7.1 | 579.1 |
| 75 | t-Bu | 4-fluorophenyl | 6.8 | 519.2 |
| 76 | t-Bu | 4-cyanophenyl | 6.6 | 526.3 |

FORMULA 21

| | R1 | R2 | Tr (min) | [M + H]+ |
|---|---|---|---|---|
| 77 | tBu | 4-N₃-C₆H₄- | 7.0 | 542.2 |
| 78 | tBu | 4-NO₂-C₆H₄- | 6.8 | 546.2 |
| 79 | tBu | 3-NO₂-C₆H₄- | 6.7 | 546.2 |
| 80 | tBu | n-propyl | 6.2 | 453.3 |

Analyses * = [M + TFA − H]

FORMULA 22

| | R1 | R2 | Tr (min) | [M + H]+ |
|---|---|---|---|---|
| 1 | Ph (R) | 4-OCF₃-C₆H₄- | 6.6 | 605.3 |

-continued
FORMULA 22
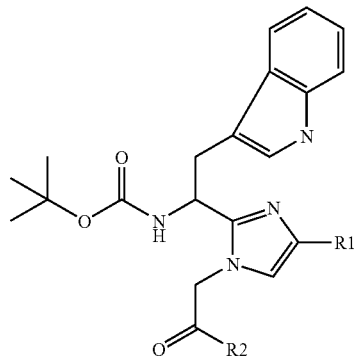
| | R1 | R2 | Tr (min) | [M + H]+ |
|---|---|---|---|---|
| 2 | (R) phenyl | 2,3-dihydrobenzo[1,4]dioxin-6-yl | 6.3 | 579.3 |
| 3 | (R) phenyl | benzo[1,3]dioxol-5-yl | 6.3 | 565.3 |
| 4 | (R) phenyl | 3,4,5-trimethoxyphenyl | 6.3 | 611.3 |
| 5 | (R) phenyl | 4-chloro-3-nitrophenyl | 6.5 | 600.2 |
| 6 | (R) phenyl | 4-benzyloxyphenyl | 6.6 | 627.3 |
| 7 | (R) phenyl | 4-pentylphenyl | 6.9 | |
| 8 | (R) phenyl | 2-oxo-1,2,3,4-tetrahydroquinolin-7-yl | 5.9 | 590.3 |

-continued
FORMULA 22
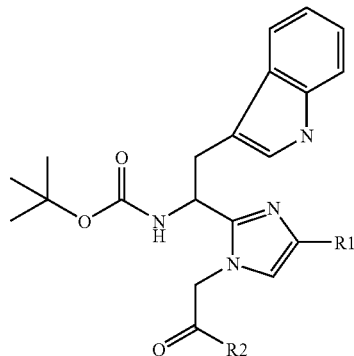
| | R1 | R2 | Analysis | |
|---|---|---|---|---|
| | | | Tr (min) | [M + H]+ |
| 9 | (R) phenyl | 3-methyl-5-chloro-benzothiophen-2-yl | 6.9 | 625.2 |
| 10 | (R) phenyl | benzothiophen-3-yl | 6.5 | 577.3 |
| 11 | (R) phenyl | 5-bromothiophen-2-yl | 6.6 | (605.12) THEO |
| 12 | (R) phenyl | 3-phenylisoxazol-5-yl | 6.6 | 588.3 |
| 13 | (R) phenyl | 3-(2,4-dichlorophenyl)isoxazol-5-yl | 7.0 | 656.2 |
| 14 | (R) phenyl | 1H-indol-3-ylmethyl | 6.4 | 574.3 |
| 15 | (R) phenyl | phenethyl | 6.5 | 549.3 |
| 16 | (R) phenyl | 3,4-difluorophenyl | 6.5 | 557.3 |

-continued
FORMULA 22
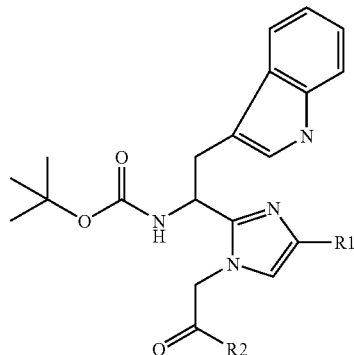
| | R1 | R2 | Tr (min) | [M + H]+ |
|---|---|---|---|---|
| 17 | 2-methoxyphenyl | 4-(trifluoromethoxy)phenyl | 6.5 | 635.3 |
| 18 | 2-methoxyphenyl | 2,3-dihydro-1,4-benzodioxin-6-yl | 6.2 | 609.3 |
| 19 | 2-methoxyphenyl | 1,3-benzodioxol-5-yl | 6.2 | 595.3 |
| 20 | 2-methoxyphenyl | 3,4,5-trimethoxyphenyl | 6.2 | 641.3 |
| 21 | 2-methoxyphenyl | 4-chloro-3-nitrophenyl | 6.4 | 630.2 |
| 22 | 2-methoxyphenyl | 4-(benzyloxy)phenyl | 6.5 | 657.3 |

-continued
FORMULA 22
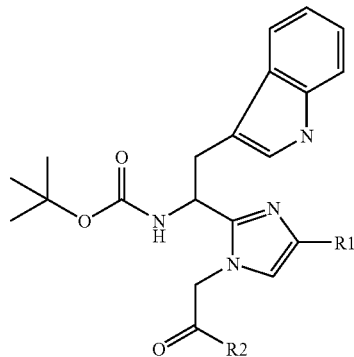
|    | R1 | R2 | Tr (min) | [M + H]+ |
|----|----|----|----------|----------|
| 23 | 2-methoxyphenyl | 4-pentylphenyl | 6.8 | 621.4 |
| 24 | 2-methoxyphenyl | 3,4-dihydroquinolin-2(1H)-one-7-yl | 5.9 | |
| 25 | 2-methoxyphenyl | 5-chloro-3-methylbenzo[b]thiophen-2-yl | 6.7 | 655.2 |
| 26 | 2-methoxyphenyl | benzo[b]thiophen-3-yl | 6.4 | 607.2 |
| 27 | 2-methoxyphenyl | 5-bromothiophen-2-yl | 6.4 | 635.2 |
| 28 | 2-methoxyphenyl | 3-phenylisoxazol-5-yl | 6.5 | 618.3 |

-continued
FORMULA 22
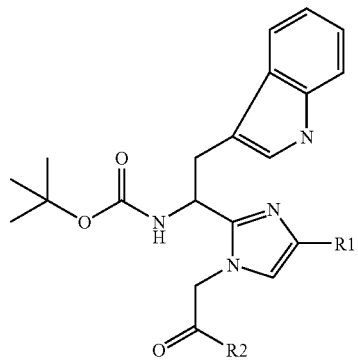
| | R1 | R2 | Analysis Tr (min) | [M + H]+ |
|---|---|---|---|---|
| 29 | 2-methoxyphenyl | 3-(2,4-dichlorophenyl)isoxazol-5-yl | 6.7 | 686.2 |
| 30 | 2-methoxyphenyl | 1H-indol-3-ylmethyl | .2 OU 6.3 ? | 604.3 |
| 31 | 2-methoxyphenyl | phenethyl | 6.4 | 579.3 |
| 32 | 2-methoxyphenyl | 3,4-difluorophenyl | 6.3 | 587.2 |
| 33 | 4-nitrophenyl | 4-(trifluoromethoxy)phenyl | 7.3 | 650.2 |
| 34 | 4-nitrophenyl | 2,3-dihydrobenzo[1,4]dioxin-6-yl | 7.0 | 624.2 |
| 35 | 4-nitrophenyl | benzo[1,3]dioxol-5-yl | 7.0 | 610.2 |

-continued
FORMULA 22
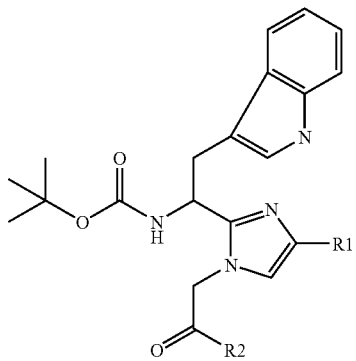
| | R1 | R2 | Tr (min) | [M + H]+ |
|---|---|---|---|---|
| 36 | -C6H4-NO2 (para) | 3,4,5-trimethoxyphenyl | 7.0 | 656.3 |
| 37 | -C6H4-NO2 (para) | 4-chloro-3-nitrophenyl | 7.0 | 645.1 |
| 38 | -C6H4-NO2 (para) | 4-benzyloxyphenyl | 7.3 | 672.3 |
| 39 | -C6H4-NO2 (para) | 4-pentylphenyl | 7.6 | 636.3 |
| 40 | -C6H4-NO2 (para) | 2-oxo-1,2,3,4-tetrahydroquinolin-7-yl | 7.8 | 635.2 |
| 41 | -C6H4-NO2 (para) | 5-chloro-3-methylbenzo[b]thiophen-2-yl | 7.5 ? | 670.2 ? |
| 42 | -C6H4-NO2 (para) | benzo[b]thiophen-3-yl | 7.3 ? | 622.2 ? |
| 43 | -C6H4-NO2 (para) | 5-bromothiophen-2-yl | 7.3 | 650.1 |

-continued
FORMULA 22
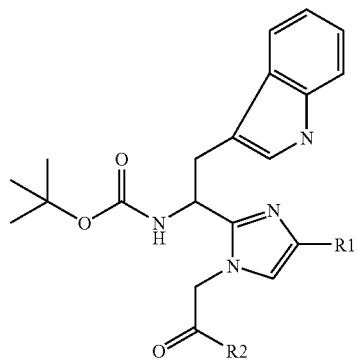
| | R1 | R2 | Analysis | |
|---|---|---|---|---|
| | | | Tr (min) | [M + H]+ |
| 44 | —⟨⟩—NO₂ | 3-phenylisoxazol-5-yl | 7.3 | 633.2 |
| 45 | —⟨⟩—NO₂ | 3-(2,4-dichlorophenyl)isoxazol-5-yl | 7.6 | 701.2 |
| 46 | —⟨⟩—NO₂ | phenethyl | 7.2 | 594.3 |
| 47 | —⟨⟩—NO₂ | 3,4-difluorophenyl | 7.2 | 602.2 |
| 48 | —⟨⟩—Br | 4-(trifluoromethoxy)phenyl | 7.0 | (683.14) THEO |
| 49 | —⟨⟩—Br | 2,3-dihydrobenzo[1,4]dioxin-6-yl | 6.7 | 657.2 |
| 50 | —⟨⟩—Br | benzo[1,3]dioxol-5-yl | 6.7 | 643.1 |

-continued
FORMULA 22
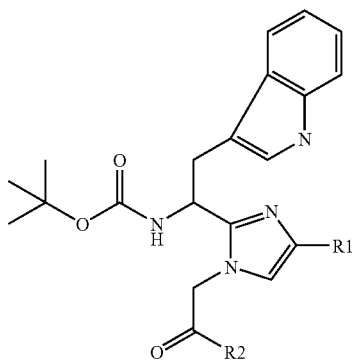
| | R1 | R2 | Analysis Tr (min) | [M + H]+ |
|---|---|---|---|---|
| 51 | -C6H4-Br | 3,4,5-trimethoxyphenyl | 6.7 | 689.2 |
| 52 | -C6H4-Br | 4-Cl-3-NO2-phenyl | 7.0 ? | 678.1 ? |
| 53 | -C6H4-Br | 4-(benzyloxy)phenyl | 7.0 | 705.2 |
| 54 | -C6H4-Br | 4-pentylphenyl | 7.2 | 699.3 |
| 55 | -C6H4-Br | 2-oxo-1,2,3,4-tetrahydroquinolin-7-yl | 7.3 | 668.1 |
| 56 | -C6H4-Br | 5-chloro-3-methylbenzo[b]thiophen-2-yl | 9.5 | 703.0 |
| 57 | -C6H4-Br | benzo[b]thiophen-3-yl | 8.6 | 655.0 |
| 58 | -C6H4-Br | 5-bromothiophen-2-yl | 8.7 | 683.0 |

-continued
FORMULA 22
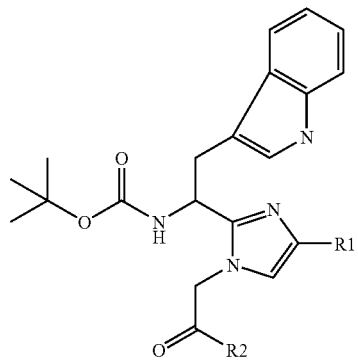
| | R1 | R2 | Analysis Tr (min) | [M + H]+ |
|---|---|---|---|---|
| 59 | -C6H4-Br | 3-phenyl-isoxazol-5-yl | 9.0 | 666.1 |
| 60 | -C6H4-Br | 3-(2,4-dichlorophenyl)-isoxazol-5-yl | 9.8 | 734.0 |
| 61 | -C6H4-Br | 1H-indol-3-yl-methyl | 8.0 | 652.1 |
| 62 | -C6H4-Br | 2-phenylethyl | 8.5 | 627.1 |
| 63 | -C6H4-Br | 3,4-difluorophenyl | 8.5 | 635.1 |
| 64 | tert-butyl | 4-(trifluoromethoxy)phenyl | 7.3 | 585.2 |
| 65 | tert-butyl | 2,3-dihydro-1,4-benzodioxin-6-yl | 6.7 | 559.2 |
| 66 | tert-butyl | 1,3-benzodioxol-5-yl | 6.7 | 545.2 |

-continued
FORMULA 22
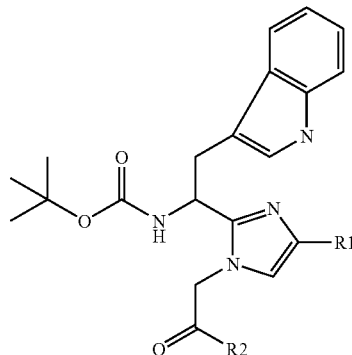
| | R1 | R2 | Tr (min) | [M + H]+ |
|---|---|---|---|---|
| 67 | tBu | 3,4,5-trimethoxyphenyl | 6.7 | 591.3 |
| 68 | tBu | 4-chloro-3-nitrophenyl | 7.0 | 580.2 |
| 69 | tBu | 4-benzyloxyphenyl | 7.6 | 607.3 |
| 70 | tBu | 4-pentylphenyl | 8.0 | 571.3 |
| 71 | tBu | 2-oxo-1,2,3,4-tetrahydroquinolin-7-yl | 6.1 | 570.3 |
| 72 | tBu | 5-chloro-3-methylbenzo[b]thiophen-2-yl | 7.6 | 605.2 |
| 73 | tBu | benzo[b]thiophen-3-yl | 7.1 | 557.2 |

-continued
FORMULA 22
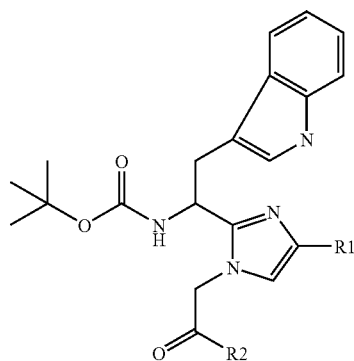
| | R1 | R2 | Analysis Tr (min) | [M + H]+ |
|---|---|---|---|---|
| 74 | tBu | 5-bromothiophen-2-yl | 7.0 | 585.1 |
| 75 | tBu | 3-phenylisoxazol-5-yl | 7.1 | 568.2 |
| 76 | tBu | 3-(2,4-dichlorophenyl)isoxazol-5-yl | 7.6 | 636.2 |
| 77 | tBu | 1H-indol-3-ylmethyl | 6.8 | 554.2 |
| 78 | tBu | benzyl (phenethyl) | 7.1 | 529.3 |
| 79 | tBu | 3,4-difluorophenyl | 6.9 | 537.2 |

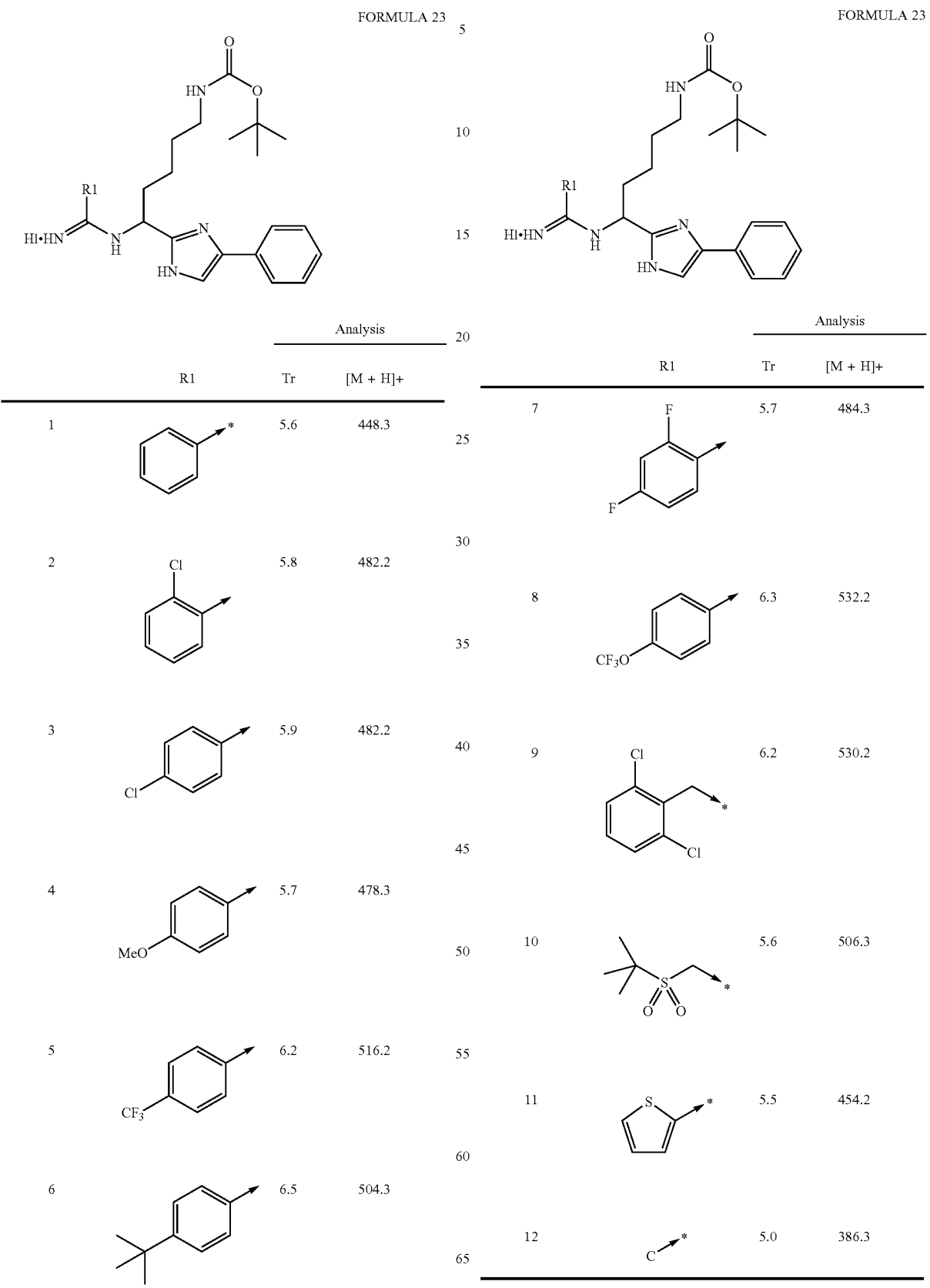
FORMULA 23
| | R1 | Analysis | |
|---|---|---|---|
| | | Tr | [M + H]+ |
| 1 | phenyl* | 5.6 | 448.3 |
| 2 | 2-Cl-phenyl | 5.8 | 482.2 |
| 3 | 4-Cl-phenyl | 5.9 | 482.2 |
| 4 | 4-MeO-phenyl | 5.7 | 478.3 |
| 5 | 4-CF3-phenyl | 6.2 | 516.2 |
| 6 | 4-tBu-phenyl | 6.5 | 504.3 |
| 7 | 2,4-diF-phenyl | 5.7 | 484.3 |
| 8 | 4-CF3O-phenyl | 6.3 | 532.2 |
| 9 | 2,6-diCl-benzyl* | 6.2 | 530.2 |
| 10 | tBu-SO2-CH2* | 5.6 | 506.3 |
| 11 | 2-thienyl* | 5.5 | 454.2 |
| 12 | C* | 5.0 | 386.3 |

FORMULA 24
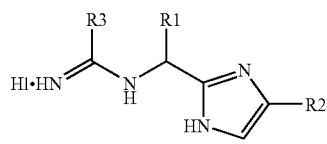
| | R1 | R2 | R3 | Analysis Tr | [M + H]+ |
|---|---|---|---|---|---|
| 1 (S) | PhCH2OCH2– | Ph– | 2-thienyl– | 5.6 | 403.1 |
| 2 (S) | PhCH2OCH2– | Ph– | C– | 4.9 | 335.2 |
| 3 (S) | 4-MeO-C6H4-CH2– | Ph– | 2-thienyl– | 5.3 | 403.2 |
| 4 (S) | 4-MeO-C6H4-CH2– | Ph– | C– | 4.8 | 335.3 |
| 5 (R) | indol-3-yl-CH2– | 4-MeO-C6H4– | 2-thienyl– | 5.1 | 442.2 |
| 6 (R) | indol-3-yl-CH2– | 4-MeO-C6H4– | C– | 4.7 | 374.2 |
| 7 (R,S) | indol-3-yl-CH2– | 2-MeO-C6H4– | 2-thienyl– | 5.2 | 442.2 |

-continued
FORMULA 24
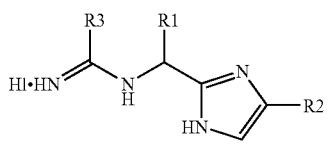
| | R1 | R2 | R3 | Analysis Tr | [M + H]+ |
|---|---|---|---|---|---|
| 8 (R,S) | indol-3-ylmethyl | 2-OMe-phenyl | C | 4.7 | 374.2 |
| 9 (R,S) | indol-3-ylmethyl | tert-butyl | thiophen-2-yl | 4.5 | 392.2 |
| 10 (R,S) | indol-3-ylmethyl | tert-butyl | C | 4.3 | 324.3 |
| 11 (S) | 1-benzylimidazol-4-ylmethyl | phenyl | thiophen-2-yl | 4.8 | 455.2 |
| 12 (S) | 1-benzylimidazol-4-ylmethyl | phenyl | C | 4.5 | 387.2 |
| 13 (S) | benzyl | phenyl | thiophen-2-yl | 5.3 | 373.2 |
| 14 (S) | benzyl | phenyl | C | 4.7 | 305.2 |

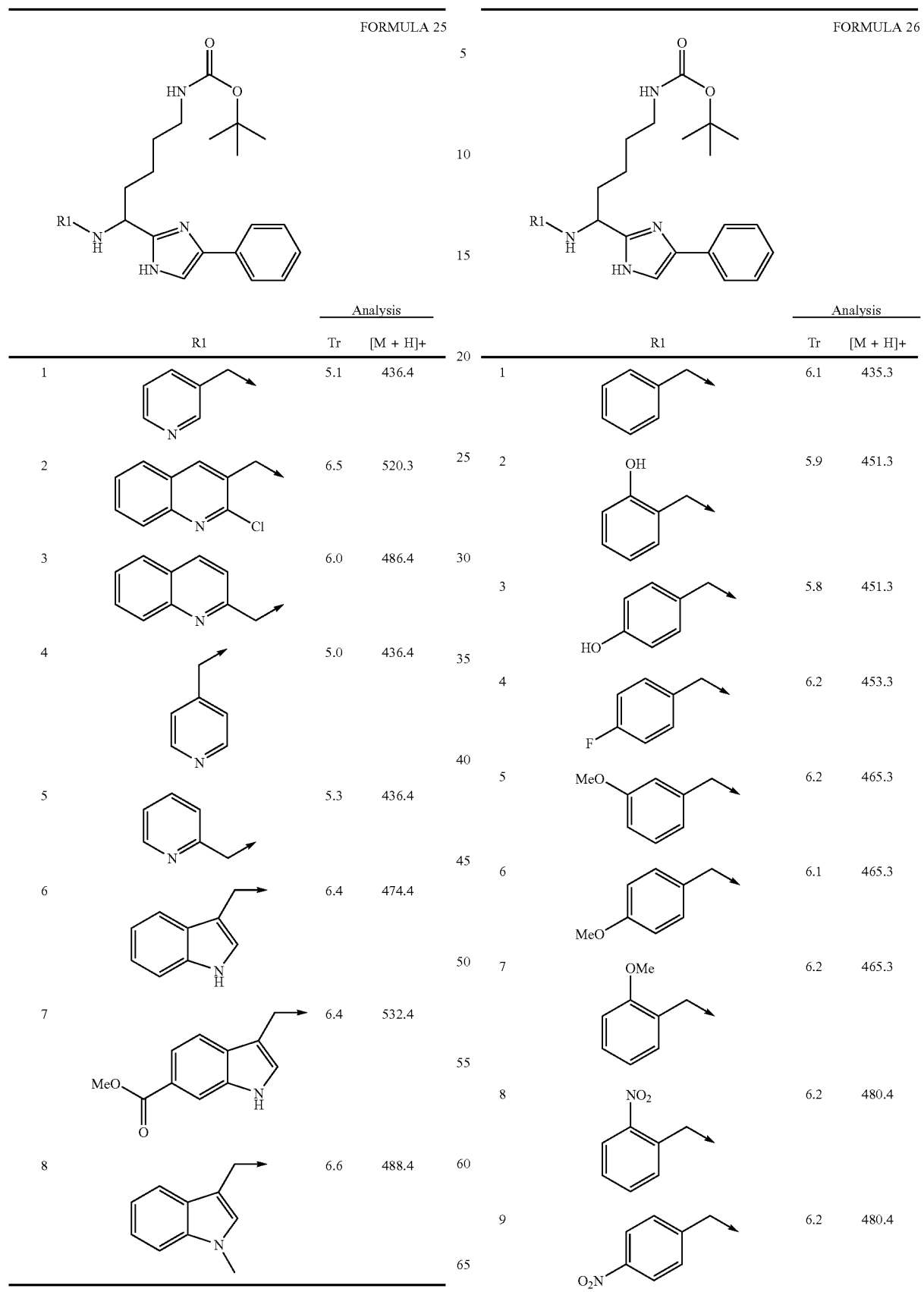

-continued
FORMULA 26
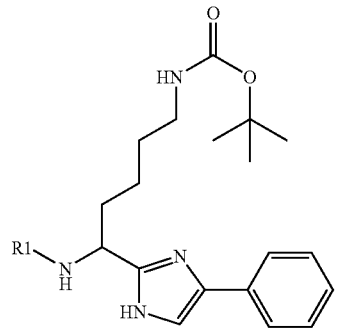
| | R1 | Analysis | |
|---|---|---|---|
| | | Tr | [M + H]+ |
| 10 | 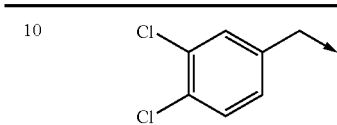 3,4-diCl-benzyl | 6.7 | 503.3 |
| 11 | 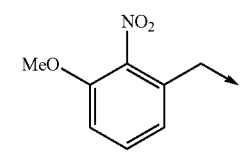 3-MeO-2-NO2-benzyl | 6.4 | 510.4 |
| 12 | 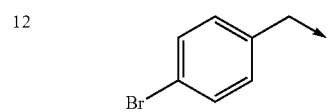 4-Br-benzyl | 6.5 | 513.3 |
| 13 | 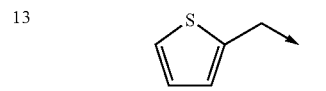 thiophen-2-ylmethyl | 6.0 | 441.3 |
| 14 | 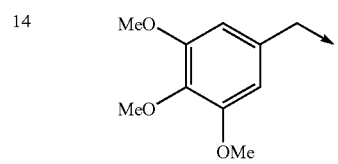 3,4,5-triMeO-benzyl | 6.1 | 525.4 |
| 15 | 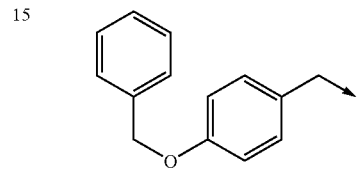 4-benzyloxy-benzyl | 7.0 | 541.4 |
| 16 | 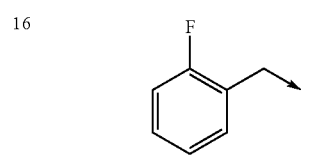 2-F-benzyl | 6.1 | 453.4 |
| 17 | 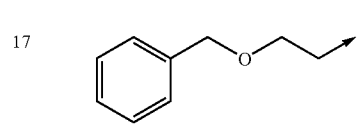 2-benzyloxy-ethyl | 6.5 | 479.4 |
-continued
FORMULA 26
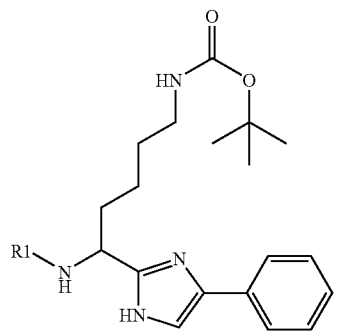
| | R1 | Analysis | |
|---|---|---|---|
| | | Tr | [M + H]+ |
| 18 | 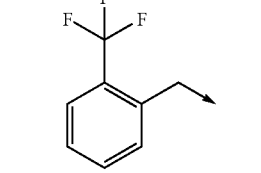 | 6.6 | 503.4 |
| 19 | 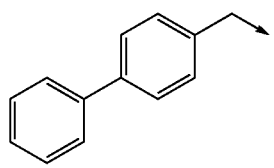 | 6.9 | 511.4 |
| 20 | 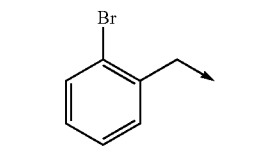 | 6.4 | 513.3 |
| 21 | 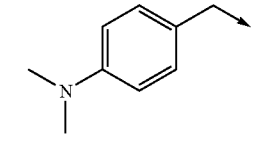 | 5.8 | 478.4 |
| 22 | 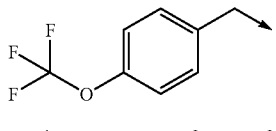 | 6.8 | 519.3 |
| 23 | 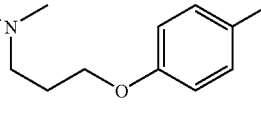 | 5.1 | 536.5 |
| 24 | 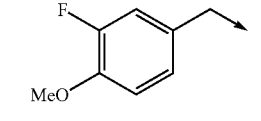 | 6.2 | 483.4 |
| 25 | 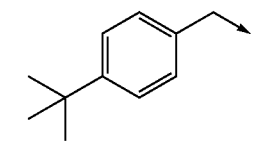 | 7.0 | 491.4 |

-continued
FORMULA 26
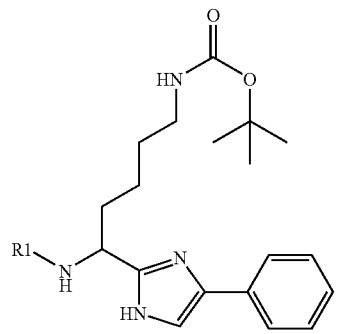
| | R1 | Analysis Tr | [M + H]+ |
|---|---|---|---|
| 26 | 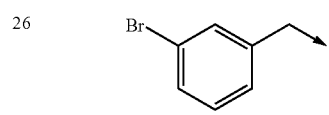 | 6.5 | 513.3 |
| 27 | 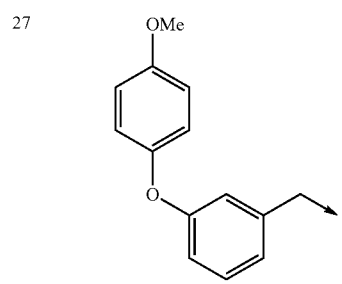 | 6.9 | 557.4 |
FORMULA 27
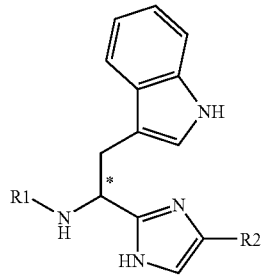
| | R1 | R2 | Analysis Tr | [M + H]+ |
|---|---|---|---|---|
| 1 | 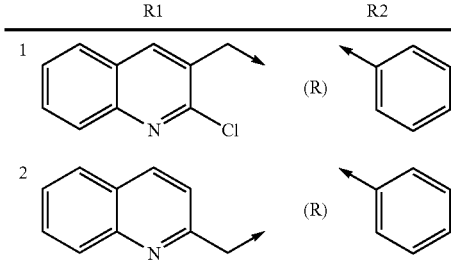 (R) | | 6.4 | 478.3 |
| 2 | (R) | | 5.6 | 444.3 |
-continued
FORMULA 27
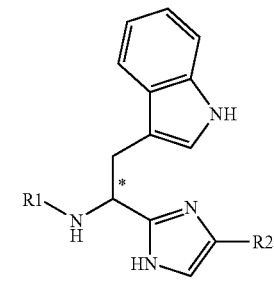
| | R1 | R2 | Analysis Tr | [M + H]+ |
|---|---|---|---|---|
| 3 | 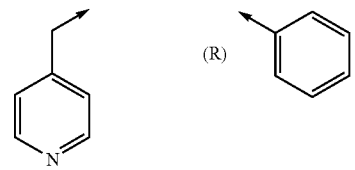 (R) | | 4.8 | 394.3 |
| 4 | 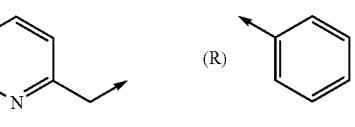 (R) | | 4.9 | 394.3 |
| 5 | 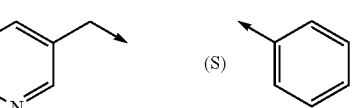 (S) | | 4.8 | 394.3 |
| 6 | 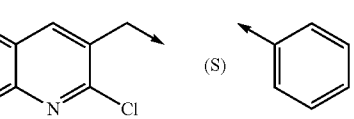 (S) | | 6.4 | 478.3 |
| 7 | 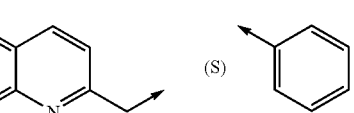 (S) | | 5.6 | 444.3 |
| 8 | 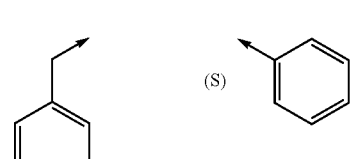 (S) | | 4.7 | 394.3 |
| 9 |  (S) | | 4.9 | 394.3 |
| 10 |  (R,S) | | 4.9 | 424.3 |

-continued
FORMULA 27
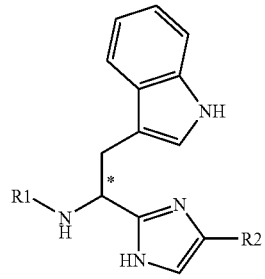
| | R1 | R2 | Analysis Tr | [M+H]+ |
|---|---|---|---|---|
| 11 | 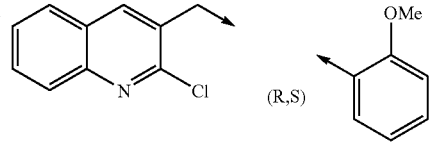 | | 6.6 | 508.3 |
| 12 | 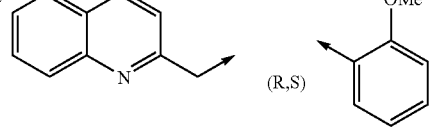 | | 5.7 | 474.3 |
| 13 | 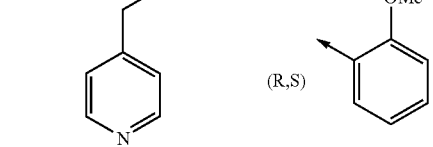 | | 4.9 | 424.3 |
| 14 | 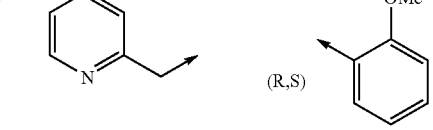 | | 5.0 | 424.3 |
| 15 | 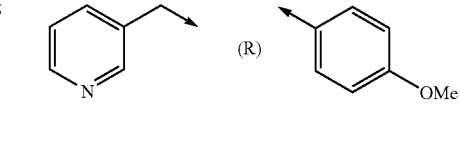 | | 4.9 | 424.3 |
| 16 | 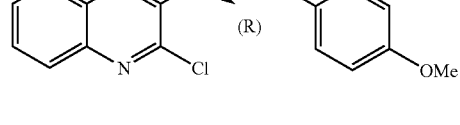 | | 6.5 | 508.3 |
| 17 | 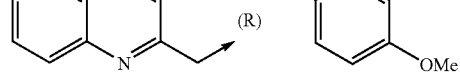 | | 5.6 | 474.3 |
-continued
FORMULA 27
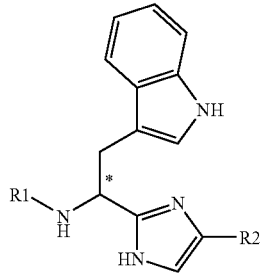
| | R1 | R2 | Analysis Tr | [M+H]+ |
|---|---|---|---|---|
| 18 | 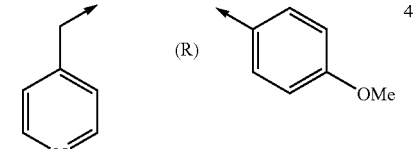 | | 4.9 | 424.3 |
| 19 | 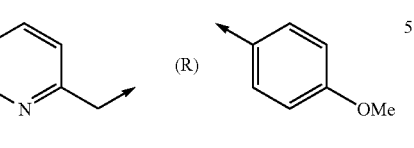 | | 5.0 | 424.3 |
| 20 | 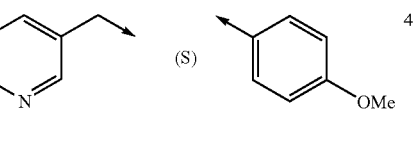 | | 4.9 | 424.3 |
| 21 | 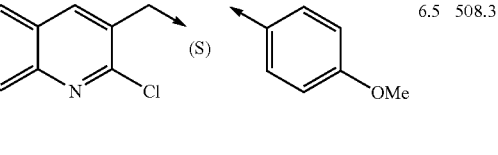 | | 6.5 | 508.3 |
| 22 | 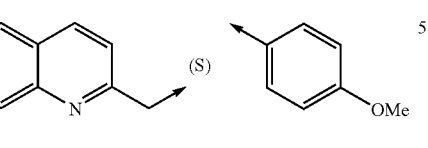 | | 5.6 | 474.3 |
| 23 | 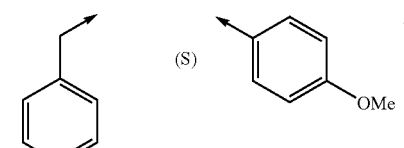 | | 4.9 | 424.3 |
| 24 | 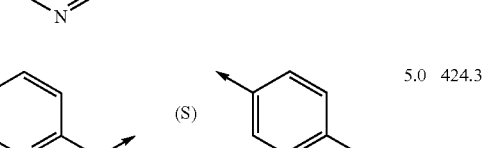 | | 5.0 | 424.3 |

FORMULA 28
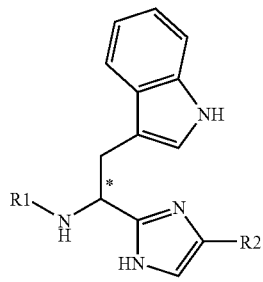
| | R1 | R2 | Tr | [M + H]+ |
|---|---|---|---|---|
| 1 | F, MeO-phenyl-CH2 | (S) phenyl | 6.1 | 441.2 |
| 2 | Br-phenyl-CH2 | (S) phenyl | 6.4 | 471.1 |
| 3 | propyl | (S) phenyl | 5.8 | 359.3 |
| 4 | butyl | (S) phenyl | 6.1 | 373.3 |
| 5 | MeS-CH2CH2 | (S) phenyl | 5.8 | 391.2 |
| 6 | neopentyl-CH2 | (S) phenyl | 6.2 | 387.3 |
| 7 | BnO-CH2CH2 | (S) phenyl | 7.1 | 437.5 |
| 8 | cyclohexyl-CH2 | (S) phenyl | 6.3 | 399.3 |
| 9 | 4-tBu-phenyl-CH2 | (S) phenyl | 6.8 | 449.3 |
| 10 | hexyl | (S) phenyl | 6.4 | 387.3 |

-continued
FORMULA 28
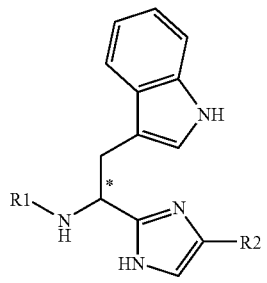
| | R1 | R2 | Analysis | |
|---|---|---|---|---|
| | | | Tr | [M + H]+ |
| 11 | F, MeO-phenyl-CH2- | OMe (R,S) | 6.1 | 471.2 |
| 12 | Br-phenyl-CH2- | OMe (R,S) | 6.5 | 501.1 |
| 13 | n-butyl- | OMe (R,S) | 5.8 | 389.3 |
| 14 | n-pentyl- | OMe (R,S) | 6.1 | 403.3 |
| 15 | MeS-CH2CH2CH2- | OMe (R,S) | 5.8 | 421.2 |
| 16 | (CH3)3C-CH2CH2- | OMe (R,S) | 6.2 | 417.3 |
| 17 | PhCH2-O-CH2CH2- | OMe (R,S) | 7.0 | 467.2 |

-continued
FORMULA 28
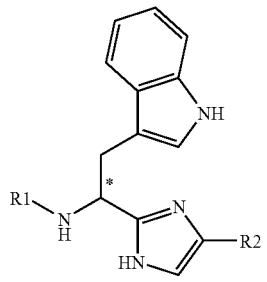
| | R1 | R2 | Tr | [M + H]+ |
|---|---|---|---|---|
| 18 | cyclohexylmethyl (R,S) | 2-OMe-phenyl | 6.3 | 429.3 |
| 19 | 4-tert-butylbenzyl (R,S) | 2-OMe-phenyl | 6.9 | 479.3 |
| 20 | n-heptyl (R,S) | 2-OMe-phenyl | 6.4 | 417.3 |
| 21 | 3-fluoro-4-methoxybenzyl (R) | 4-OMe-phenyl | 6.0 | 471.2 |
| 22 | 3-bromobenzyl (R) | 4-OMe-phenyl | 6.4 | 501.1 |
| 23 | n-hexyl (R) | 4-OMe-phenyl | 6.0 | 403.3 |
| 24 | 3,3-dimethylbutyl (R) | 4-OMe-phenyl | 6.1 | 417.3 |
| 25 | 2-benzyloxyethyl (R) | 4-OMe-phenyl | 6.9 | 467.1 |
| 26 | cyclohexylmethyl (R) | 4-OMe-phenyl | 6.3 | 429.3 |

-continued
FORMULA 28
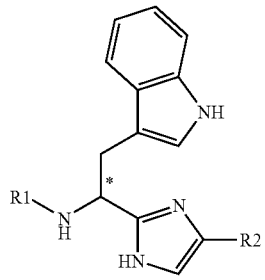
| | R1 | R2 | Analysis Tr | [M + H]+ |
|---|---|---|---|---|
| 27 | 4-tert-butylbenzyl (R) | 4-MeO-phenyl | 6.8 | 479.3 |
| 28 | n-heptyl (R) | 4-MeO-phenyl | 6.4 | 417.3 |
| 29 | 3-fluoro-4-methoxybenzyl (S) | 4-MeO-phenyl | 6.0 | 471.2 |
| 30 | 3-bromobenzyl (S) | 4-MeO-phenyl | 6.4 | 501.1 |
| 31 | n-pentyl (S) | 4-MeO-phenyl | 5.8 | 389.3 |
| 32 | 3,3-dimethylbutyl (S) | 4-MeO-phenyl | 6.2 | 417.3 |
| 33 | 2-(benzyloxy)ethyl (S) | 4-MeO-phenyl | 6.9 | 467.1 |
| 34 | cyclohexylmethyl (S) | 4-MeO-phenyl | 6.3 | 429.3 |
| 35 | 4-tert-butylbenzyl (S) | 4-MeO-phenyl | 6.8 | 479.3 |

-continued
FORMULA 28
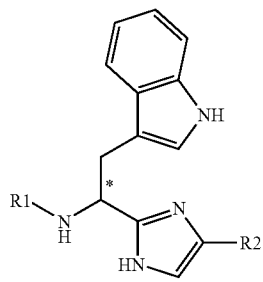
| | R1 | R2 | Analysis Tr | [M + H]+ |
|---|---|---|---|---|
| 36 | hexyl | (S) 4-OMe-phenyl | 6.4 | 417.3 |
FORMULA 29
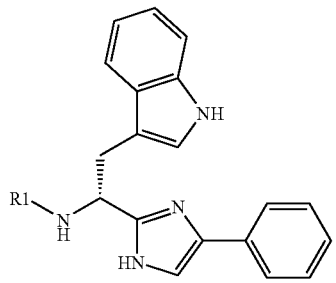
| | R1 | Analysis Tr | [M + H]+ |
|---|---|---|---|
| 1 | benzyl | 5.9 | 393.3 |
| 2 | 2-OH-benzyl | 5.7 | 409.3 |
| 3 | 4-OH-benzyl | 5.6 | 409.3 |
| 4 | 4-F-benzyl | 6.1 | 411.3 |
| 5 | 3-MeO-benzyl | 6.0 | 423.3 |
-continued
FORMULA 29
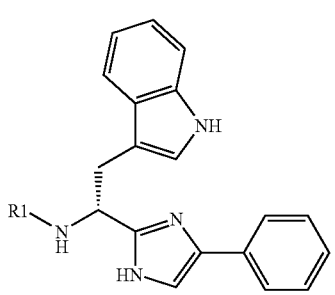
| | R1 | Analysis Tr | [M + H]+ |
|---|---|---|---|
| 6 | 2-OMe-benzyl | 6.1 | 423.3 |
| 7 | 4-NO2-benzyl | 6.1 | 438.3 |
| 8 | 3,4-diCl-benzyl | 6.6 | 461.2 |
| 9 | 2-NO2-3-MeO-benzyl | 6.2 | 468.3 |

-continued
FORMULA 29
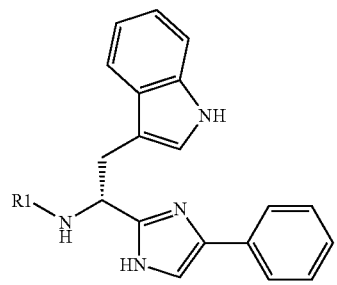
| | R1 | Analysis Tr | [M + H]+ |
|---|---|---|---|
| 10 | 4-Br-benzyl | 6.4 | 471.2 |
| 11 | 2-thienylmethyl | 5.9 | 399.3 |
| 12 | 3,4,5-triMeO-benzyl | 5.9 | 483.4 |
| 13 | 2-Br-benzyl | 6.3 | 471.2 |
| 14 | 4-OCF3-benzyl | 6.7 | 477.3 |
| 15 | 4-(3-dimethylaminopropoxy)-benzyl | 6.5 | 494.4 |
-continued
FORMULA 29
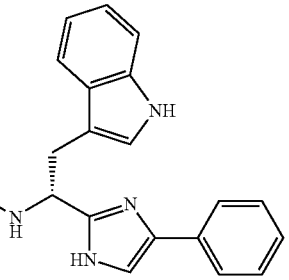
| | R1 | Analysis Tr | [M + H]+ |
|---|---|---|---|
| 16 | 3-F-4-MeO-benzyl | 6.1 | 441.3 |
| 17 | neohexyl (3,3-dimethylbutyl) | 6.3 | 387.3 |
| 18 | 2-(benzyloxy)ethyl | 6.4 | 437.3 |
| 19 | cyclohexylmethyl | 6.4 | 399.4 |
| 20 | 4-tert-butylbenzyl | 6.9 | 449.4 |
| 21 | hexyl | 6.5 | 387.4 |

FORMULA 30
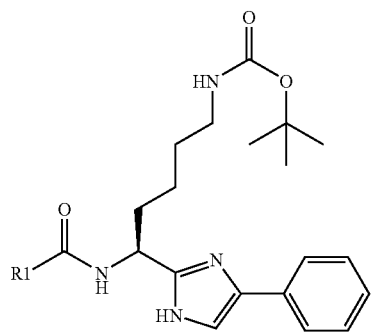
| | R1 | Tr | [M + H]+ |
|---|---|---|---|
| 1 | morpholine | 5.4 | 458.2 |
| 2 | thiazolidine | 5.7 | 460.2 |
| 3 | piperidine-4-carboxamide | 5.3 | 499.3 |
| 4 | N-benzyl-N-(2-hydroxyethyl)amino | 6.1 | 522.3 |
| 5 | tryptamine | 6.3 | 531.3 |
| 6 | 4-phenylpiperazine | 6.4 | 533.3 |
| 7 | 2,3,4,9-tetrahydro-1H-β-carboline | 6.6 | 543.3 |
| 8 | 4-benzylpiperazine | 5.1 | 547.3 |
| 9 | 4-(4-fluorophenyl)piperazine | 6.5 | 551.3 |

-continued
FORMULA 30
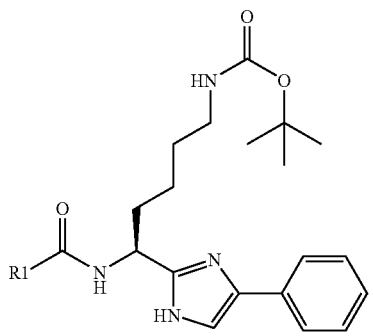
| | R1 | Analysis | |
|---|---|---|---|
| | | Tr | [M + H]+ |
| 10 | *←N(piperazine)N-(2-methoxyphenyl) | 6.1 | 563.3 |
| 11 | *←N(piperazine)N-(3-chlorophenyl) | 6.9 | 567.2 |
| 12 | dibenzylamine-* | 7.2 | 568.2 |
| 13 | *←N(piperazine)N-(4-nitrophenyl) | 6.5 | 578.2 |
| 14 | 6,7-dimethoxy-tetrahydroisoquinoline-* | 6.1 | 564.3 |
| 15 | *←N(piperazine)N-(4-chlorophenyl) | 6.8 | 567.2 |
| 16 | *←N(piperazine)N-(2-pyridyl) | 4.9 | 534.3 |
| 17 | *←N(piperidine)-4-benzyl | 7.0 | 546.3 |

-continued
FORMULA 30
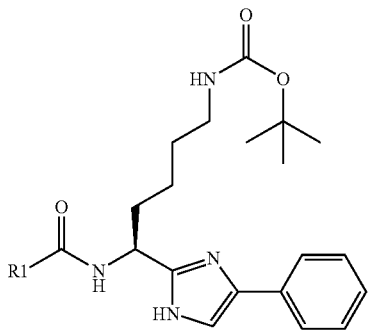
| | R1 | Analysis Tr | [M + H]+ |
|---|---|---|---|
| 18 | 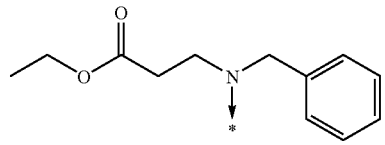 | 6.8 | 578.3 |
| 19 | 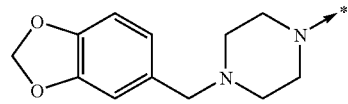 | 5.1 | 591.3 |
| 20 | 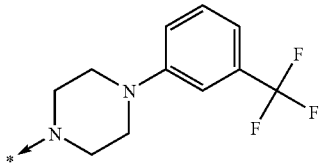 | 7.1 | 601.3 |
| 21 | 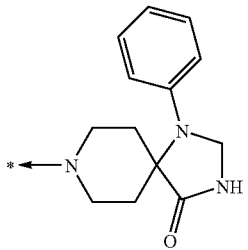 | 6.2 | 602.3 |
| 22 | 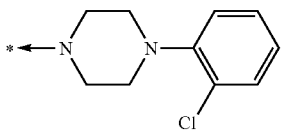 | 6.9 | 567.2 |
| 23 | 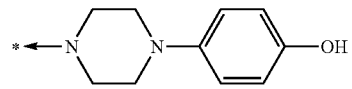 | 5.2 | 549.2 |
| 24 | 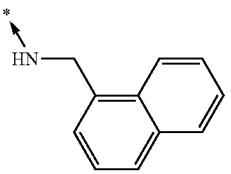 | 6.7 | 528.2 |

-continued
FORMULA 30
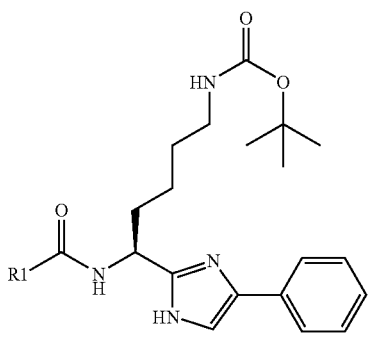
| | R1 | Analysis Tr | [M + H]+ |
|---|---|---|---|
| 25 | | 7.1 | 561.3 |
| 26 | | 7.0 | 568.2 |
| 27 | | 6.5 | 591.3 |
| 28 | | 6.0 | 588.2 |
| 29 | | 5.7 | 571.2 |
| 30 | | 5.7 | 551.2 |

-continued
FORMULA 30
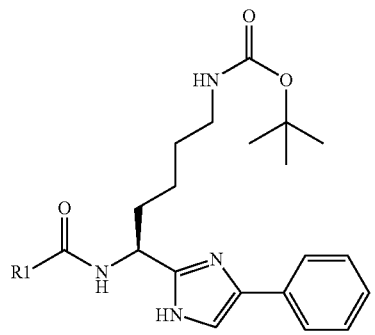
| | R1 | Analysis | |
|---|---|---|---|
| | | Tr | [M + H]+ |
| 31 | 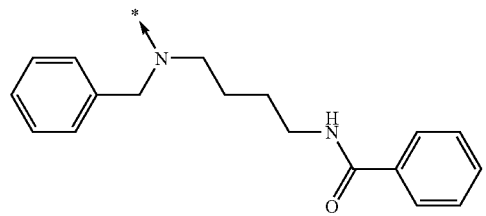 | 6.9 | 653.3 |
| 32 | 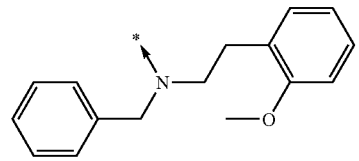 | 7.4 | 612.3 |
| 33 | 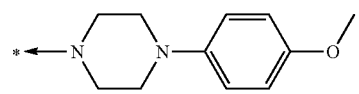 | 6.0 | 563.3 |
| 34 | 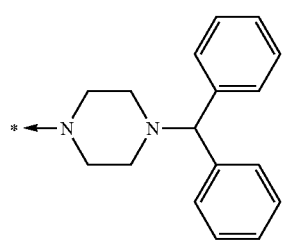 | 6.0 | 623.3 |
| 35 | 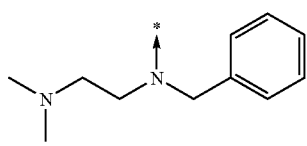 | 5.2 | 549.3 |
| 36 | 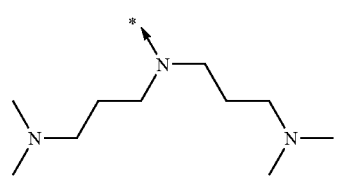 | 4.4 | 558.3 |

-continued
FORMULA 30
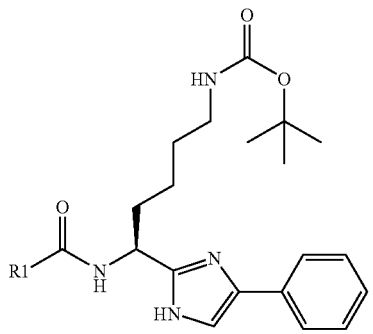
| | R1 | Analysis | |
|---|---|---|---|
| | | Tr | [M + H]+ |
| 37 | 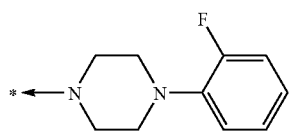 | 6.6 | 551.3 |
FORMULA 31
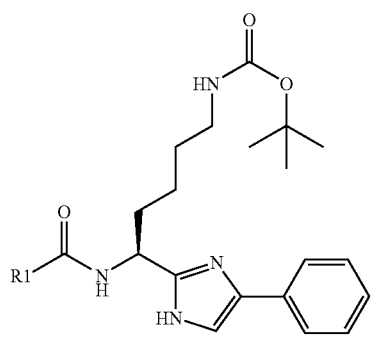
| | R1 | Analysis | |
|---|---|---|---|
| | | Tr | [M + H]+ |
| 1 | 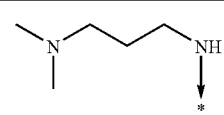 | 4.7 | 473.3 |
| 2 | 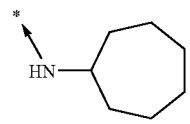 | 6.6 | 484.3 |
| 3 | 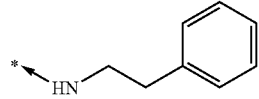 | 6.3 | 492.3 |
-continued
FORMULA 31
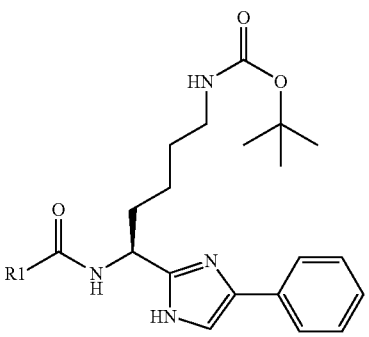
| | R1 | Analysis | |
|---|---|---|---|
| | | Tr | [M + H]+ |
| 4 | 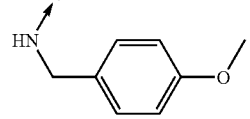 | 6.2 | 508.3 |
| 5 | 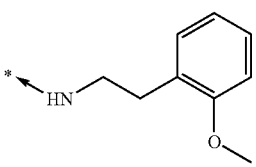 | 6.5 | 522.3 |
| 6 | 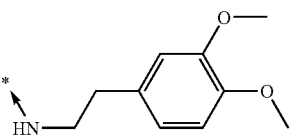 | 6.1 | 552.3 |

-continued

FORMULA 31

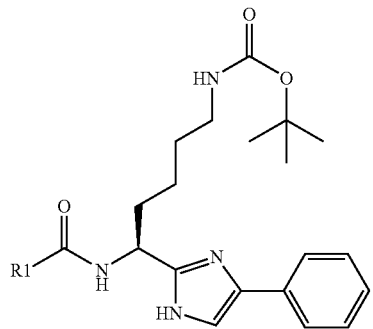

| R1 | Analysis Tr | [M + H]+ |
|---|---|---|
| 7 (imidazole-ethyl-NH-*) | 4.8 | 482.3 |
| 8 (3,4,5-trimethoxybenzyl-NH-*) | 6.0 | 568.2 |
| 9 (4-nitrophenethyl-NH-*) | 6.4 | 537.2 |
| 10 (neopentyl-NH-*) | 6.5 | 472.3 |
| 11 (4-pyridylmethyl-NH-*) | 4.7 | 479.3 |
| 12 (2-(2-pyridyl)ethyl-NH-*) | 4.8 | 493.3 |
| 13 (3-morpholinopropyl-NH-*) | 4.8 | 515.3 |
| 14 (1-ethoxycarbonylpiperidin-4-yl-NH-*) | 5.9 | 543.3 |

-continued

FORMULA 31

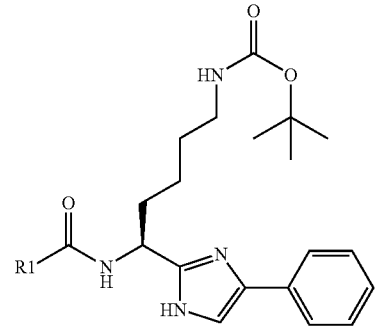

| R1 | Analysis Tr | [M + H]+ |
|---|---|---|
| 15 (2-(5-nitropyridin-2-ylamino)ethyl-NH-*) | 6.0 | 553.2 |
| 16 (2-(benzylthio)ethyl-NH-*) | 6.6 | 538.2 |
| 17 (3,4-dihydroxybenzyl-NH-*) | 5.5 | 510.3 |
| 18 (1,2-diethylpyrazolidin-4-yl-NH-*) | 4.9 | 514.3 |
| 19 (tert-butyl-NH-*) | 6.1 | 444.3 |
| 20 (2-(4-(3-chlorophenyl)piperazin-1-yl)ethyl-NH-*) | 5.8 | 610.3 |
| 21 (diphenylmethyl-NH-*) | 7.0 | 554.3 |

-continued
FORMULA 31
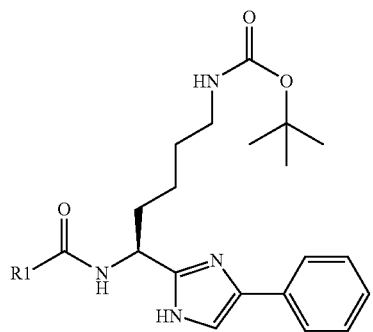
| | R1 | Analysis | |
|---|---|---|---|
| | | Tr | [M + H]+ |
| 22 | 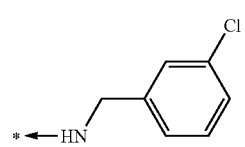 | 4.9 | 479.3 |
| 23 | 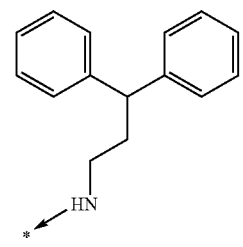 | 6.5 | 512.2 |
| 24 | 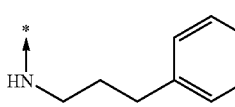 | 7.2 | 582.3 |
| 25 | 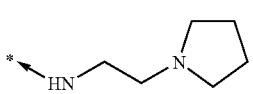 | 6.6 | 506.3 |
| 26 | 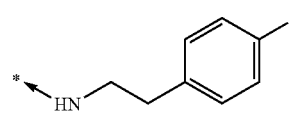 | 4.8 | 485.3 |
| 27 | 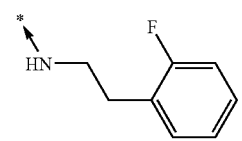 | 6.7 | 526.2 |
| 28 | 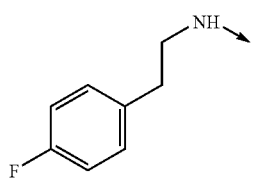 | 6.4 | 510.3 |
| 29 | 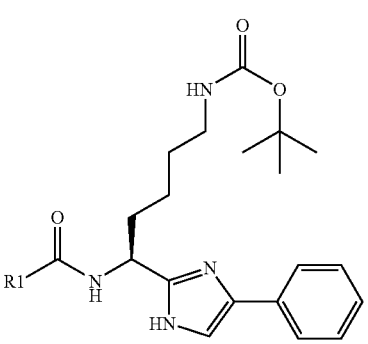 | 6.4 | 510.3 |
-continued
FORMULA 31
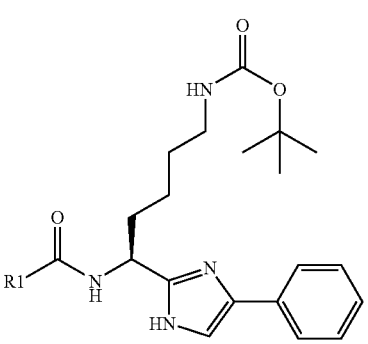
| | R1 | Analysis | |
|---|---|---|---|
| | | Tr | [M + H]+ |
| 30 | 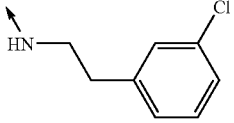 | 6.7 | 526.2 |
| 31 | 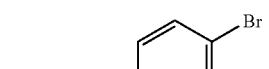 | 6.8 | 570.2 |
| 32 | 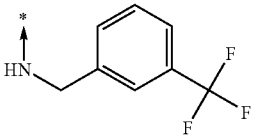 | 6.7 | 546.2 |
| 33 | 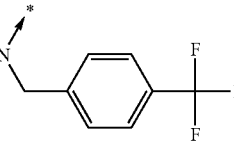 | 6.8 | 546.2 |
| 34 | 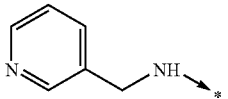 | 4.8 | 479.3 |
| 35 | 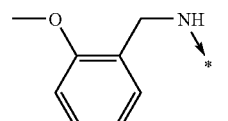 | 6.3 | 508.3 |
| 36 | 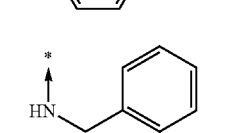 | 6.4 | 512.2 |
| 37 | 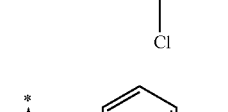 | 6.3 | 496.3 |

-continued
FORMULA 31
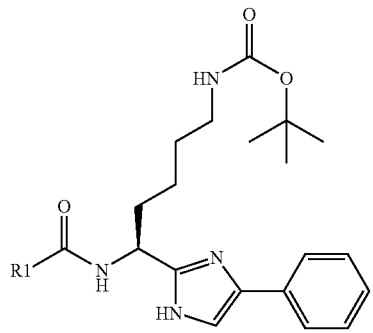
| | R1 | Analysis Tr | [M + H]+ |
|---|---|---|---|
| 38 | 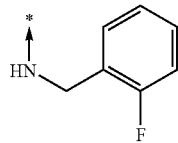 | 6.2 | 496.3 |
| 39 | 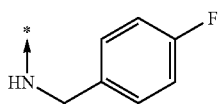 | 6.3 | 496.3 |
| 40 | 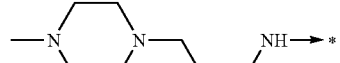 | 4.5 | 528.3 |
FORMULA 32
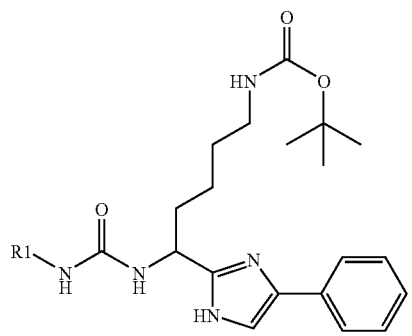
| | R1 | Analysis Tr | [M + H]+ |
|---|---|---|---|
| 1 | 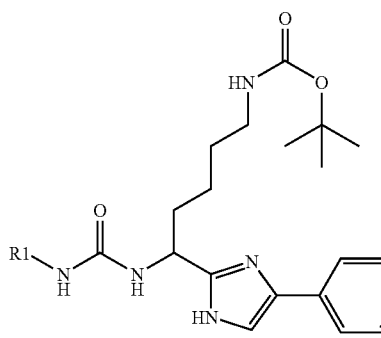 (Cl) | 6.4 | 498.2 |
| 2 | 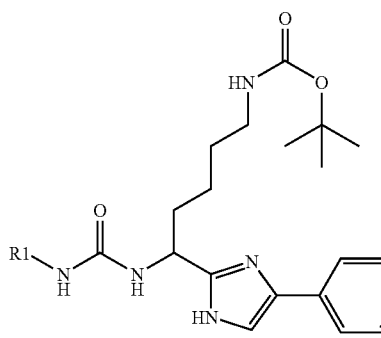 (Cl) | 6.6 | 498.2 |
-continued
FORMULA 32
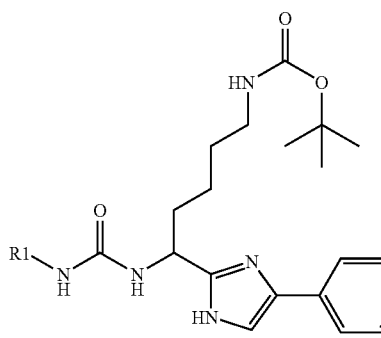
| | R1 | Analysis Tr | [M + H]+ |
|---|---|---|---|
| 3 | 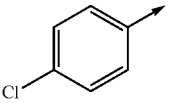 (Cl) | 6.6 | 498.2 |
| 4 | 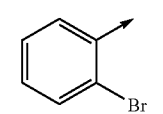 (Br) | 6.4 | 542.1 |
| 5 | (Br) | 6.6 | 542.1 |
| 6 | (Br) | 6.7 | 542.1 |
| 7 | 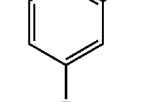 (F) | 6.3 | 482.2 |
| 8 | 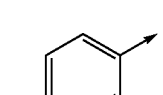 (F, F) | 6.3 | 500.2 |
| 9 | 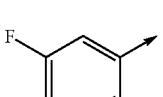 (F, F) | 6.4 | 500.2 |
| 10 | 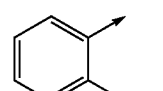 (NO₂) | 6.3 | 509.2 |

-continued
FORMULA 32
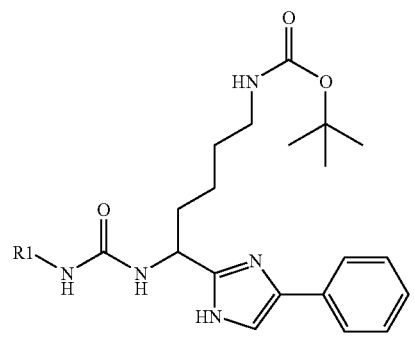
| | R1 | Analysis Tr | [M + H]+ |
|---|---|---|---|
| 11 | 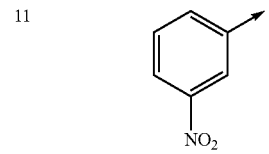 | 6.4 | 509.2 |
| 12 | 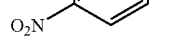 | 6.4 | 509.2 |
| 13 | 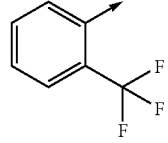 | 6.5 | 532.2 |
| 14 | 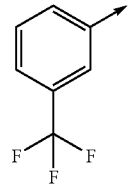 | 6.8 | 532.2 |
| 15 | 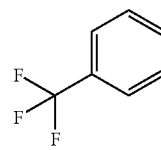 | 6.8 | 532.2 |
| 16 | 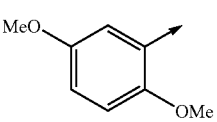 | 6.3 | 524.2 |
| 17 | 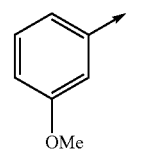 | 6.2 | 494.2 |
| 18 | 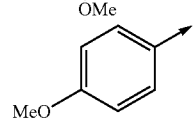 | 6.1 | 494.2 |
-continued
FORMULA 32
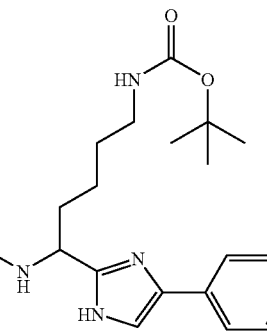
| | R1 | Analysis Tr | [M + H]+ |
|---|---|---|---|
| 19 | 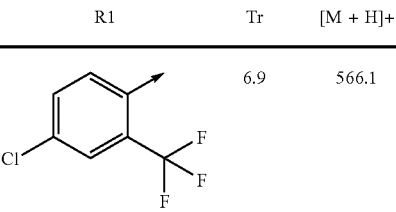 | 6.9 | 566.1 |
| 20 | | 6.4 | 527.2 |
FORMULA 33
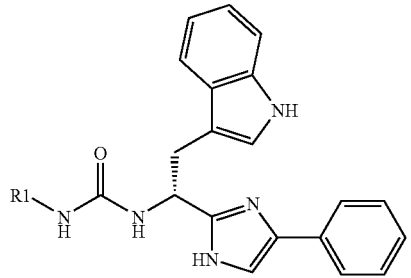
| | R1 | Analysis Tr | [M + H]+ |
|---|---|---|---|
| 1 | 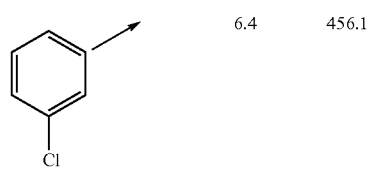 | 6.4 | 456.1 |

-continued
FORMULA 33
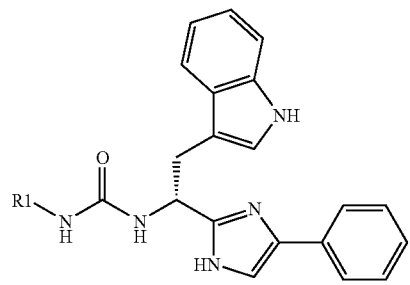
| | R1 | Tr | [M + H]⁺ |
|---|---|---|---|
| 2 | 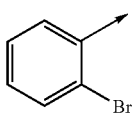 | 6.2 | 500.1 |
| 3 | 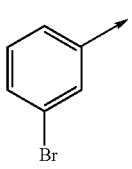 | 6.4 | 500.1 |
| 4 | 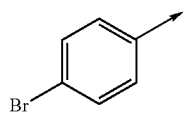 | 6.4 | 500.1 |
| 5 | 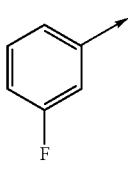 | 6.1 | 440.1 |
| 6 | 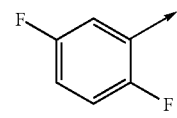 | 6.2 | 458.1 |
| 7 | 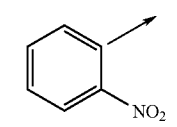 | 6.1 | 467.1 |
| 8 | 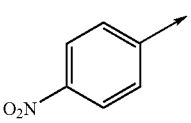 | 6.2 | 467.1 |
| 9 | 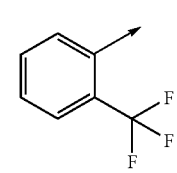 | 6.2 | 490.1 |
-continued
FORMULA 33
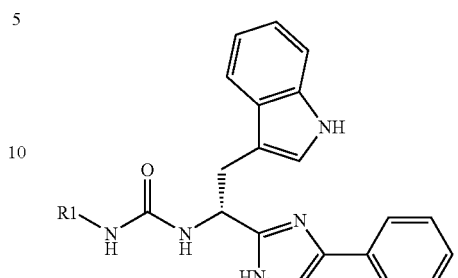
| | R1 | Tr | [M + H]⁺ |
|---|---|---|---|
| 10 | 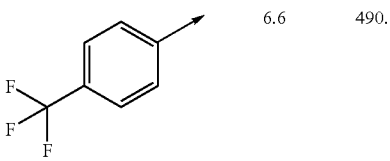 | 6.6 | 490.1 |
| 11 | 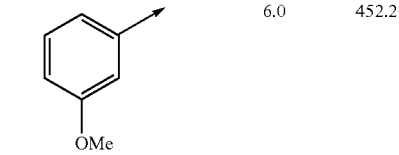 | 6.1 | 482.2 |
| 12 | 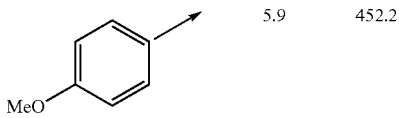 | 6.0 | 452.2 |
| 13 | 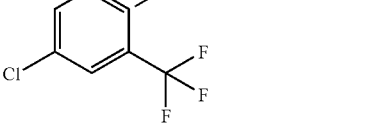 | 5.9 | 452.2 |
| 14 | 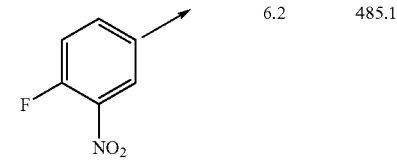 | 6.7 | 524.1 |
| 15 | | 6.2 | 485.1 |

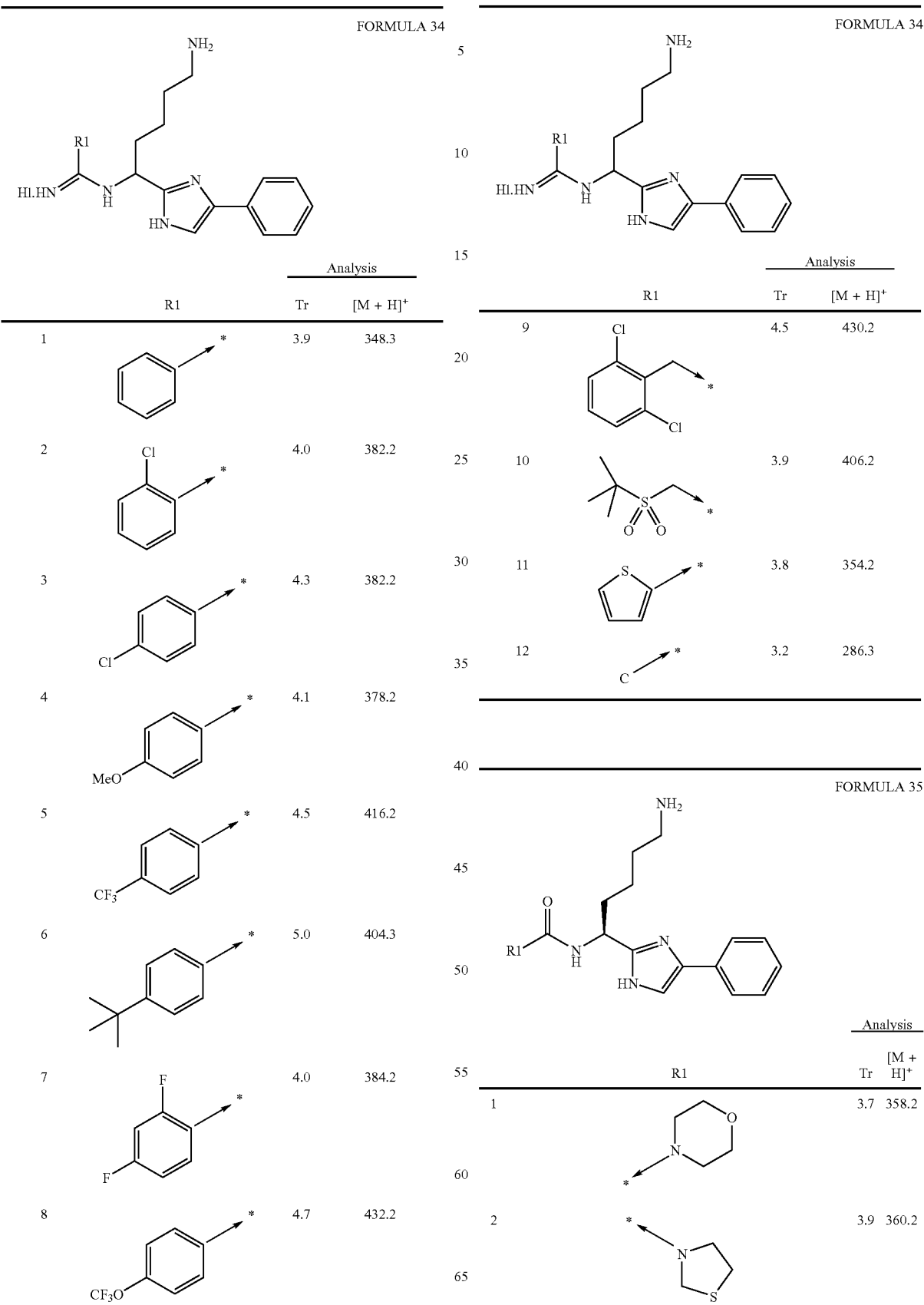

-continued

FORMULA 35

| | R1 | Tr | [M+H]+ |
|---|---|---|---|
| 3 | H2N-C(O)-piperidine-N-* (carboxamide piperidine) | 3.5 | 399.2 |
| 4 | HO-CH2CH2-N(*)-CH2-Ph | 4.4 | 422.2 |
| 5 | *-NH-CH2CH2-(indol-3-yl) | 4.7 | 431.2 |
| 6 | *-N(piperazine)N-Ph | 4.7 | 433.2 |
| 7 | *-N(piperazine)N-Ph | 5.0 | 443.2 |
| 8 | *-N(piperazine)N-CH2-Ph | 3.8 | 447.3 |
| 9 | *-N(piperazine)N-(4-F-C6H4) | 4.8 | 451.2 |
| 10 | *-N(piperazine)N-(2-OMe-C6H4) | 4.6 | 463.2 |
| 11 | *-N(piperazine)N-(3-Cl-C6H4) | 5.2 | 467.2 |

-continued

FORMULA 35

| | R1 | Tr | [M+H]+ |
|---|---|---|---|
| 12 | (PhCH2)2N-* | 5.4 | 468.2 |
| 13 | *-N(piperazine)N-(4-NO2-C6H4) | 4.9 | 478.2 |
| 14 | 6,7-dimethoxy-1,2,3,4-tetrahydroisoquinolin-2-yl-* | 4.6 | 464.2 |
| 15 | *-N(piperazine)N-(4-Cl-C6H4) | 5.2 | 467.2 |
| 16 | *-N(piperazine)N-(2-pyridyl) | 3.5 | 434.2 |
| 17 | *-N(piperidine)-4-CH2-Ph | 5.3 | 446.2 |
| 18 | EtO2C-CH2CH2-N(*)-CH2-Ph | 5.0 | 478.2 |
| 19 | (1,3-benzodioxol-5-yl)-CH2-N(piperazine)N-* | 3.8 | 491.2 |

-continued
FORMULA 35
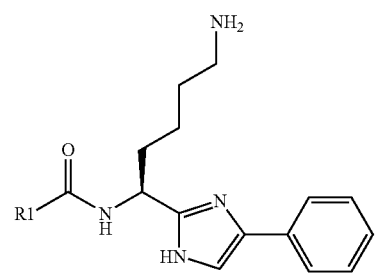
| | R1 | Analysis Tr | [M + H]+ |
|---|---|---|---|
| 20 | 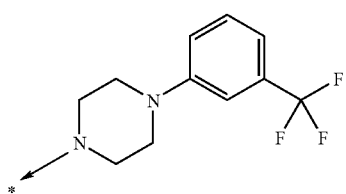 | 5.5 | 501.2 |
| 21 | 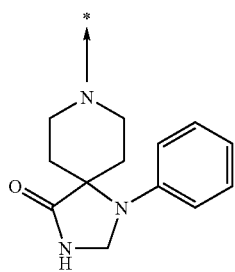 | 4.6 | 502.3 |
| 22 | 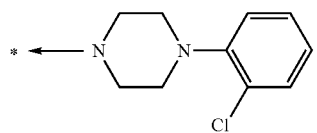 | 5.1 | 467.2 |
| 23 | 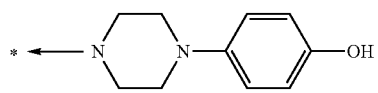 | 3.8 | 449.2 |
| 24 | 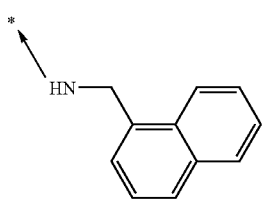 | 5.0 | 428.2 |
| 25 | 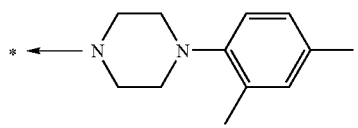 | 5.4 | 461.2 |
-continued
FORMULA 35
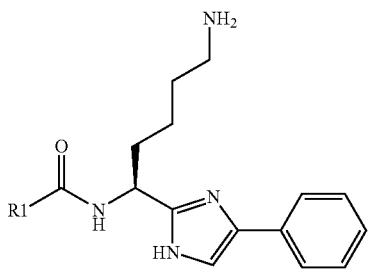
| | R1 | Analysis Tr | [M + H]+ |
|---|---|---|---|
| 26 | 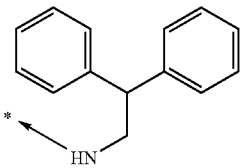 | 5.4 | 468.2 |
| 27 | 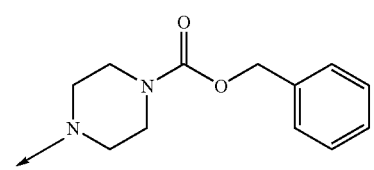 | 5.0 | 491.2 |
| 28 | 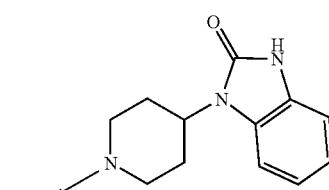 | 4.5 | 488.2 |
| 29 | 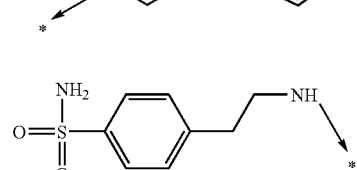 | 4.0 | 471.2 |
| 30 | 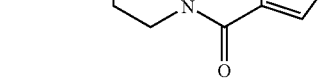 | 4.1 | 451.2 |
| 31 | 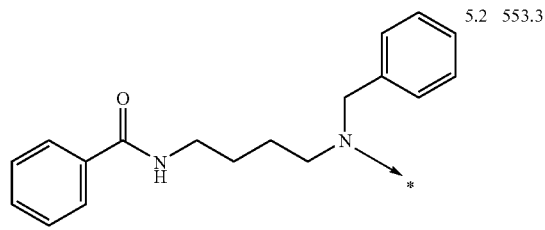 | 5.2 | 553.3 |

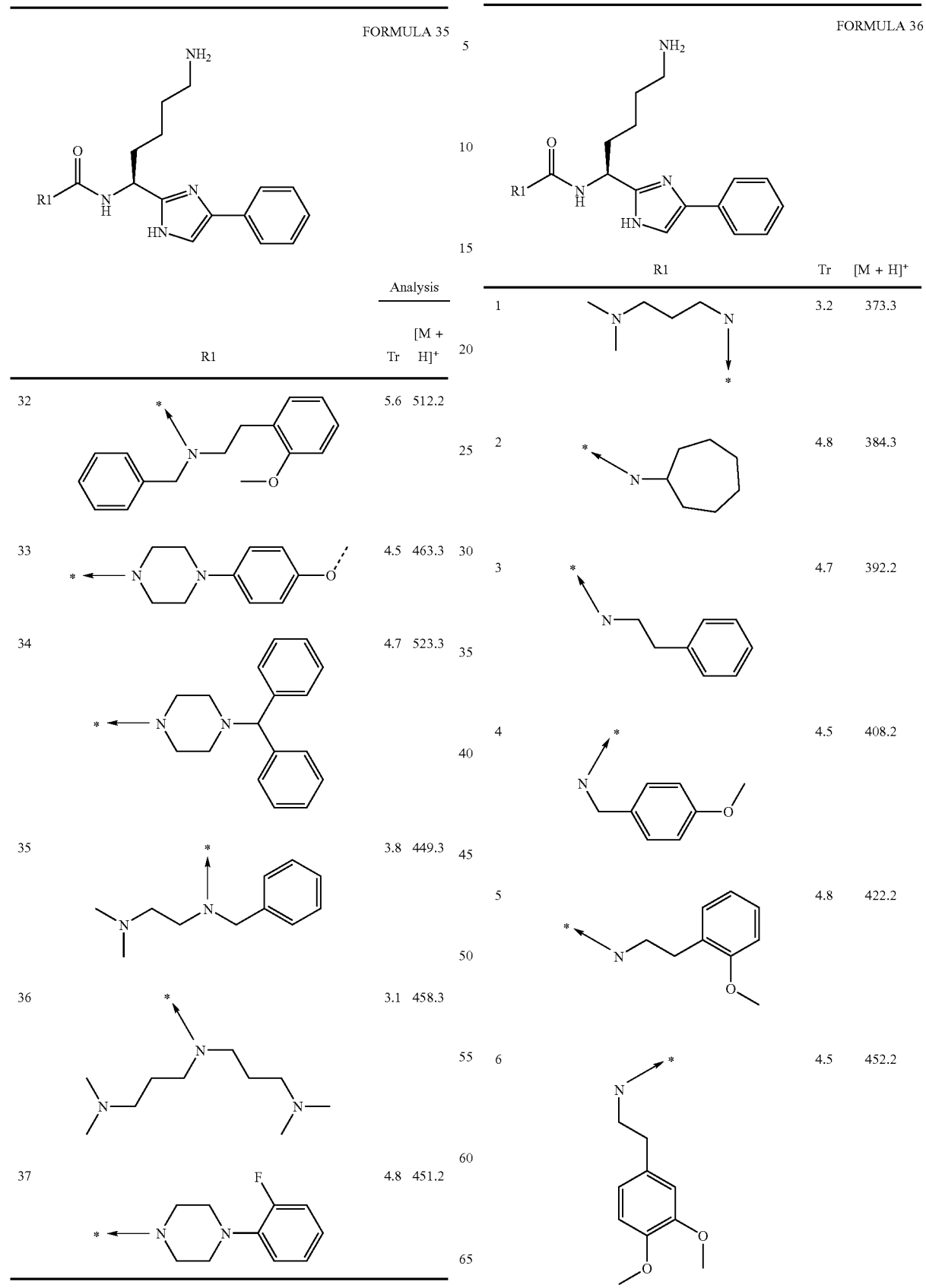

-continued
FORMULA 36
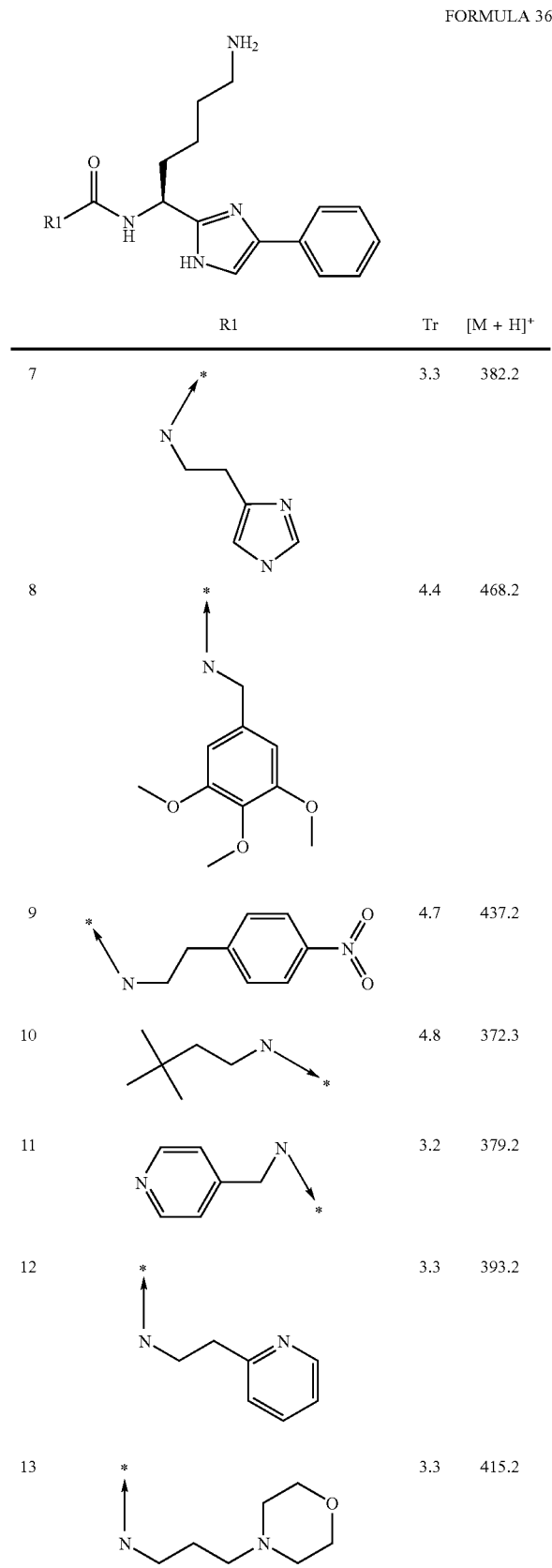
| | R1 | Tr | [M + H]+ |
|---|---|---|---|
| 7 | | 3.3 | 382.2 |
| 8 | | 4.4 | 468.2 |
| 9 | | 4.7 | 437.2 |
| 10 | | 4.8 | 372.3 |
| 11 | | 3.2 | 379.2 |
| 12 | | 3.3 | 393.2 |
| 13 | | 3.3 | 415.2 |
-continued
FORMULA 36
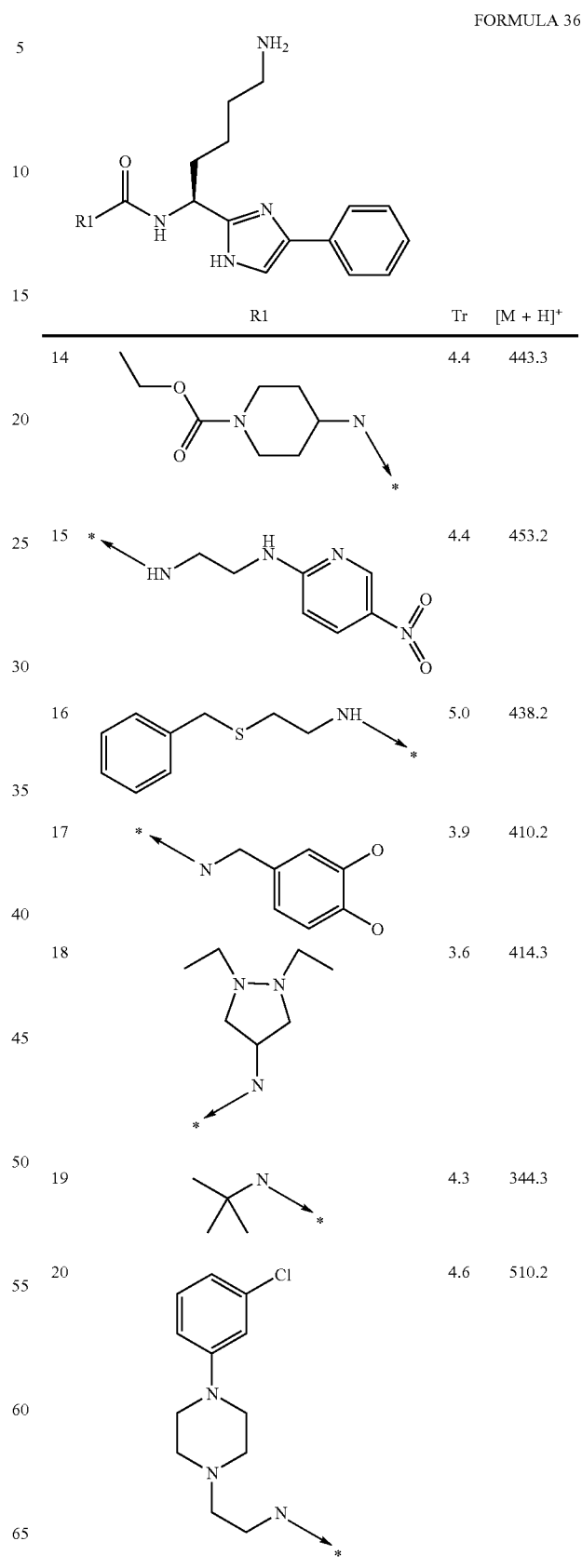
| | R1 | Tr | [M + H]+ |
|---|---|---|---|
| 14 | | 4.4 | 443.3 |
| 15 | | 4.4 | 453.2 |
| 16 | | 5.0 | 438.2 |
| 17 | | 3.9 | 410.2 |
| 18 | | 3.6 | 414.3 |
| 19 | | 4.3 | 344.3 |
| 20 | | 4.6 | 510.2 |

-continued
FORMULA 36
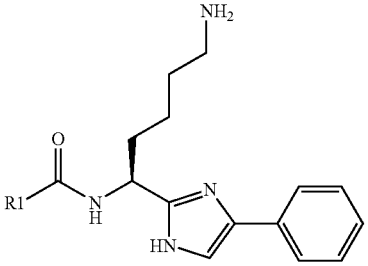
| | R1 | Tr | [M + H]+ |
|---|---|---|---|
| 21 | 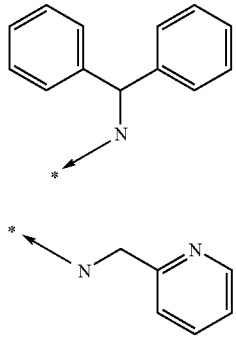 | 5.3 | 454.2 |
| 22 | 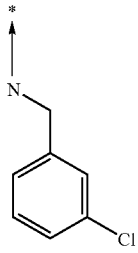 | 3.4 | 379.2 |
| 23 | 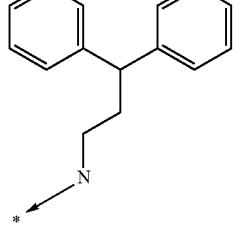 | 4.8 | 412.1 |
| 24 | 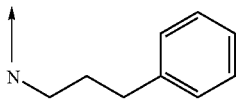 | 5.6 | 482.3 |
| 25 | 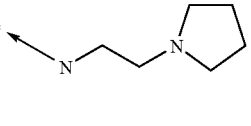 | 5.0 | 406.2 |
| 26 | 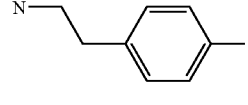 | 3.3 | 385.2 |
| 27 | 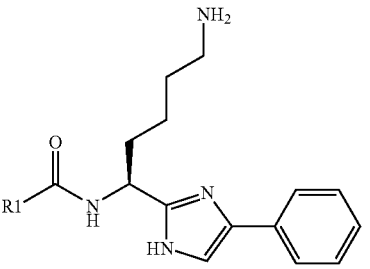 | 5.0 | 426.2 |
-continued
FORMULA 36
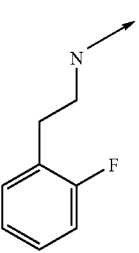
| | R1 | Tr | [M + H]+ |
|---|---|---|---|
| 28 | 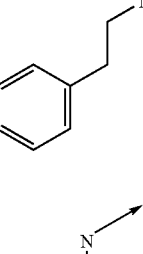 | 4.7 | 410.2 |
| 29 | 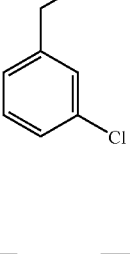 | 4.8 | 410.2 |
| 30 | 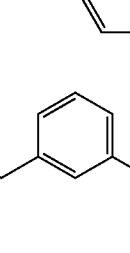 | 5.0 | 426.2 |
| 31 | 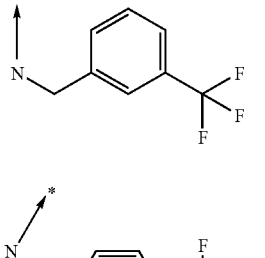 | 5.1 | 470.2 |
| 32 | 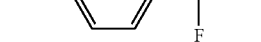 | 5.1 | 446.2 |
| 33 | | 5.1 | 446.2 |

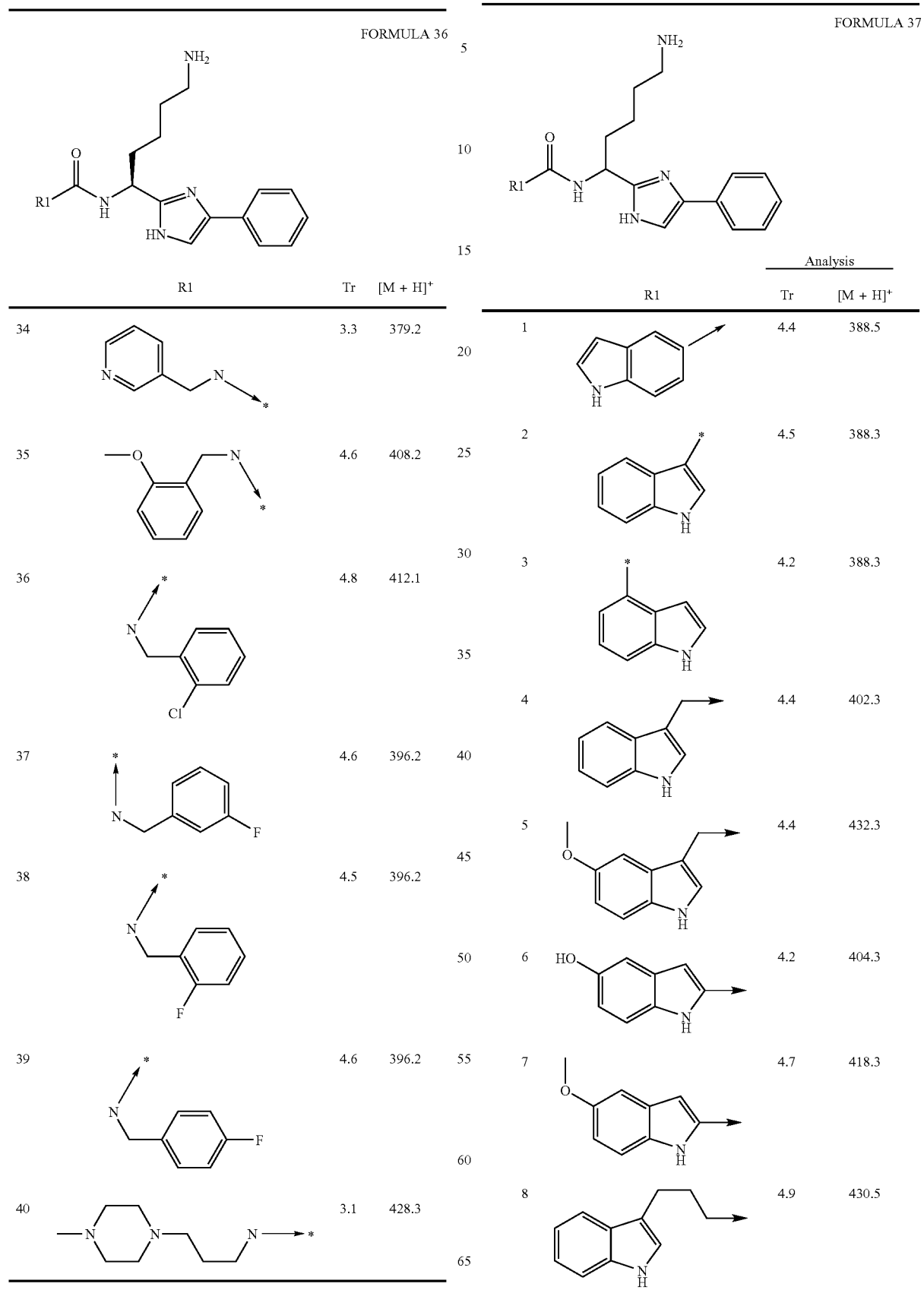

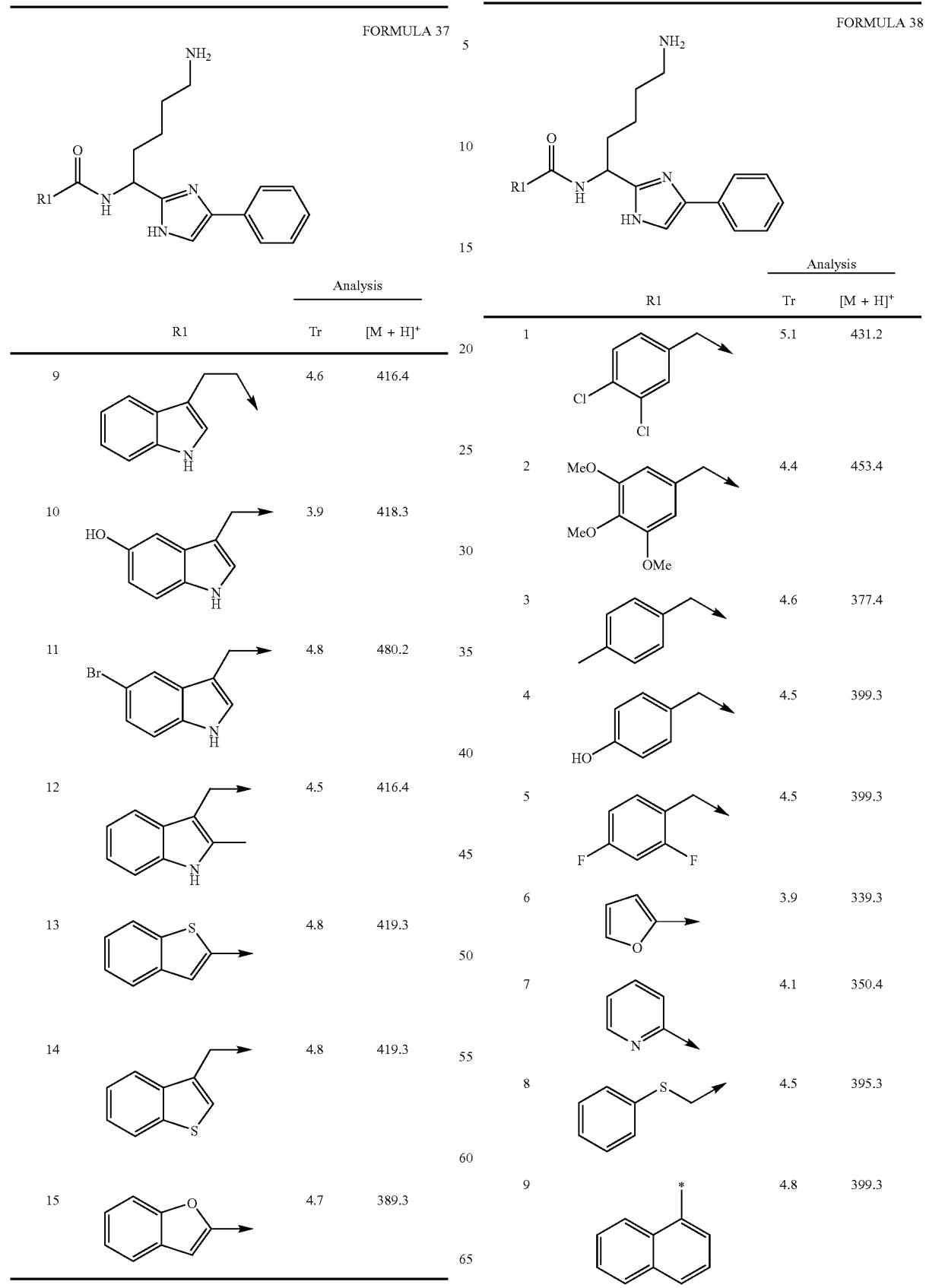

-continued
FORMULA 38
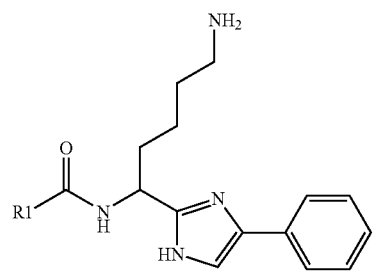
| R1 | | Analysis | |
|---|---|---|---|
| | | Tr | [M + H]⁺ |
| 10 | quinolin-2-yl-methyl | 4.7 | 400.3 |
| 11 | quinolin-8-yl-methyl | 4.5 | 400.3 |
| 12 | quinolin-3-yl-methyl | 4.4 | 400.3 |
| 13 | quinolin-4-yl-methyl | 4.2 | 400.3 |
| 14 | isoquinolin-1-yl-methyl | 4.3 | 441.3 |
| 15 | phenylsulfonyl-ethyl | 4.3 | 441.3 |
| 16 | thiophen-2-yl-methyl | 4.2 | 369.3 |
| 17 | pyrimidin-2-yl-thio-ethyl | 3.9 | 397.3 |
-continued
FORMULA 38
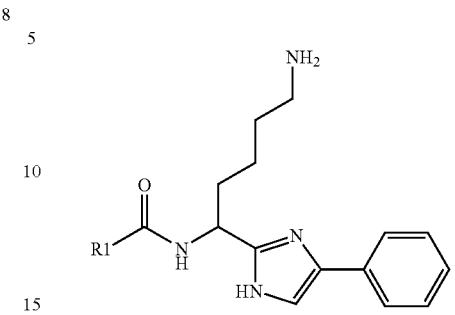
| R1 | | Analysis | |
|---|---|---|---|
| | | Tr | [M + H]⁺ |
| 18 | pyridin-3-yl | 3.8 | 350.3 |
FORMULA 39
| R1 | | Analysis | |
|---|---|---|---|
| | | Tr | [M + H]⁺ |
| 1 | 2-chlorobenzyl | 4.5 | 397.3 |
| 2 | 3-chlorobenzyl | 4.7 | 397.3 |
| 3 | 4-chlorobenzyl | 4.7 | 397.3 |
| 4 | 2-bromobenzyl | 4.6 | 441.2 |

-continued
FORMULA 39
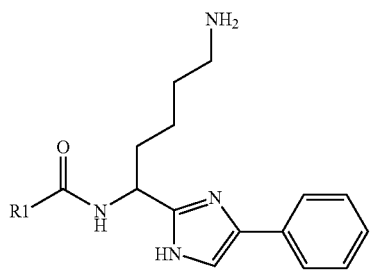
| | R1 | Tr | [M + H]+ |
|---|---|---|---|
| 5 | 3-Br-benzyl | 4.8 | 441.2 |
| 6 | 4-Br-benzyl | 4.8 | 441.2 |
| 7 | 2-F-benzyl | 4.3 | 381.3 |
| 8 | 3-F-benzyl | 4.4 | 381.3 |
| 9 | 4-F-benzyl | 4.4 | 381.3 |
| 10 | 2-NO2-benzyl | 4.3 | 408.3 |
| 11 | 3-NO2-benzyl | 4.4 | 408.3 |
| 12 | 4-NO2-benzyl | 4.5 | 408.3 |
| 13 | 2-CF3-benzyl | 4.7 | 431.3 |
-continued
FORMULA 39
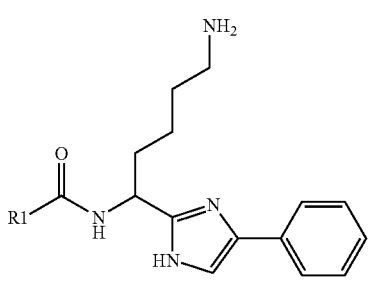
| | R1 | Tr | [M + H]+ |
|---|---|---|---|
| 14 | 3-CF3-benzyl | 4.9 | 431.3 |
| 15 | 4-CF3-benzyl | 5.0 | 431.3 |
| 16 | 2-OMe-benzyl | 4.4 | 393.3 |
| 17 | 3-OMe-benzyl | 4.4 | 393.4 |
| 18 | 4-OMe-benzyl | 4.4 | 393.3 |
| 19 | benzyl | 4.3 | 363.4 |
| 20 | 4-NMe2-benzyl | 3.7 | 406.3 |

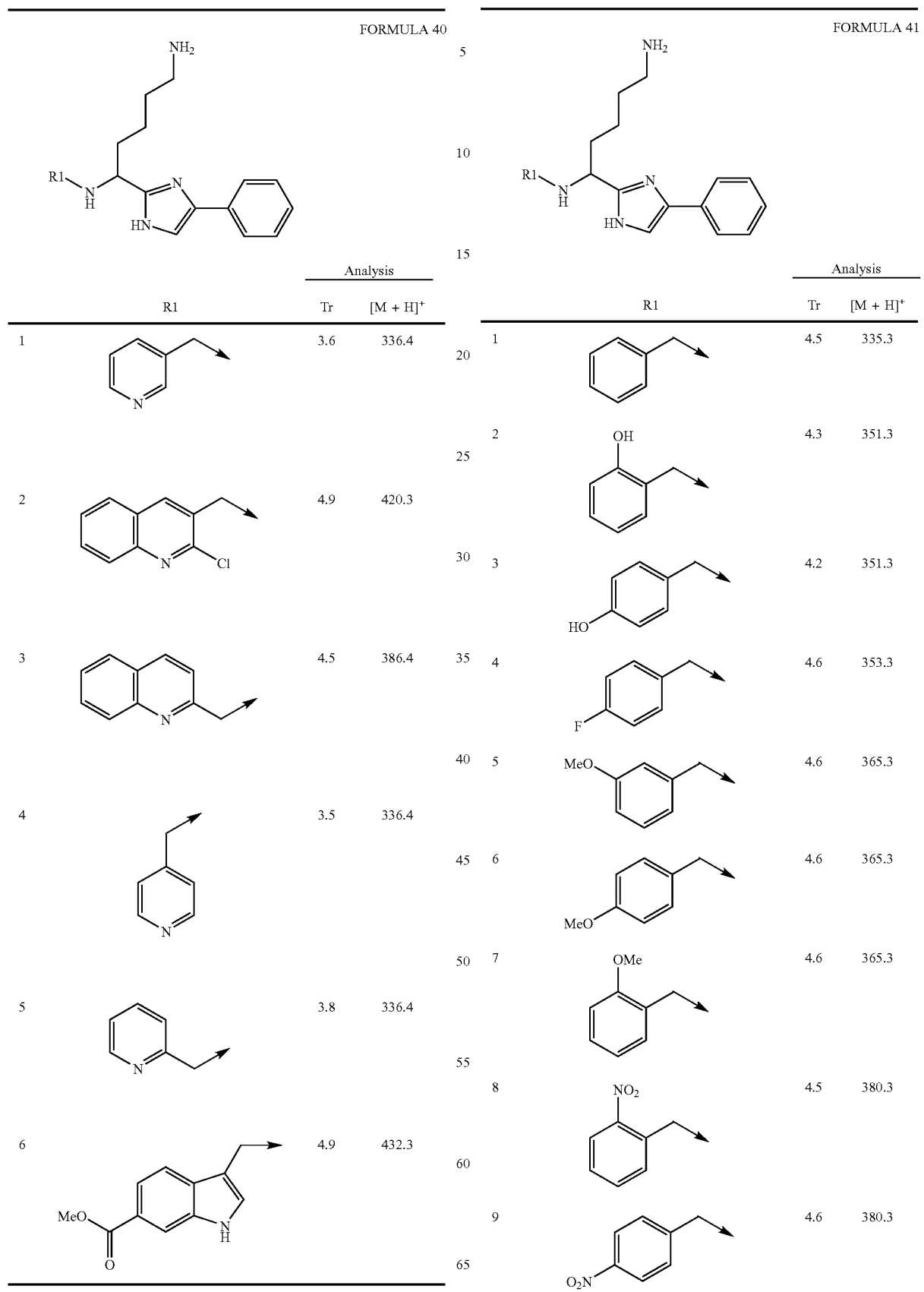

-continued

FORMULA 41

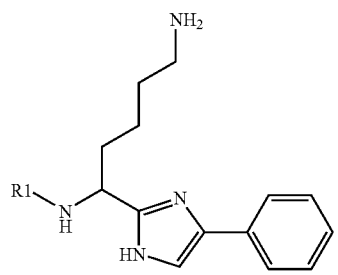

| | R1 | Analysis Tr | [M + H]+ |
|---|---|---|---|
| 10 | 3,4-dichlorobenzyl | 5.1 | 403.2 |
| 11 | 3-methoxy-2-nitrobenzyl | 4.7 | 410.3 |
| 12 | 4-bromobenzyl | 4.9 | 413.2 |
| 13 | thiophen-2-ylmethyl | 4.3 | 341.3 |
| 14 | 3,4,5-trimethoxybenzyl | 4.6 | 425.3 |
| 15 | 4-benzyloxybenzyl | 5.4 | 441.3 |
| 16 | 2-fluorobenzyl | 4.5 | 353.3 |
| 17 | 2-(trifluoromethyl)benzyl | 4.9 | 403.3 |

-continued

FORMULA 41

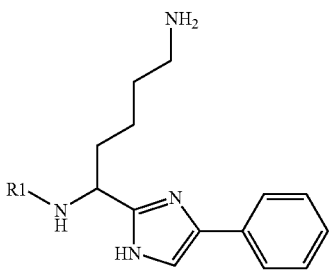

| | R1 | Analysis Tr | [M + H]+ |
|---|---|---|---|
| 18 | biphenyl-4-ylmethyl | 5.3 | 411.3 |
| 19 | 2-bromobenzyl | 4.7 | 415.2 |
| 20 | 4-(trifluoromethoxy)benzyl | 5.2 | 419.3 |
| 21 | 4-(3-(dimethylamino)propoxy)benzyl | 3.9 | 436.4 |
| 22 | 3-fluoro-4-methoxybenzyl | 4.6 | 383.3 |
| 23 | 4-tert-butylbenzyl | 5.4 | 391.4 |
| 24 | 3-bromobenzyl | 4.9 | 413.2 |

-continued
FORMULA 41
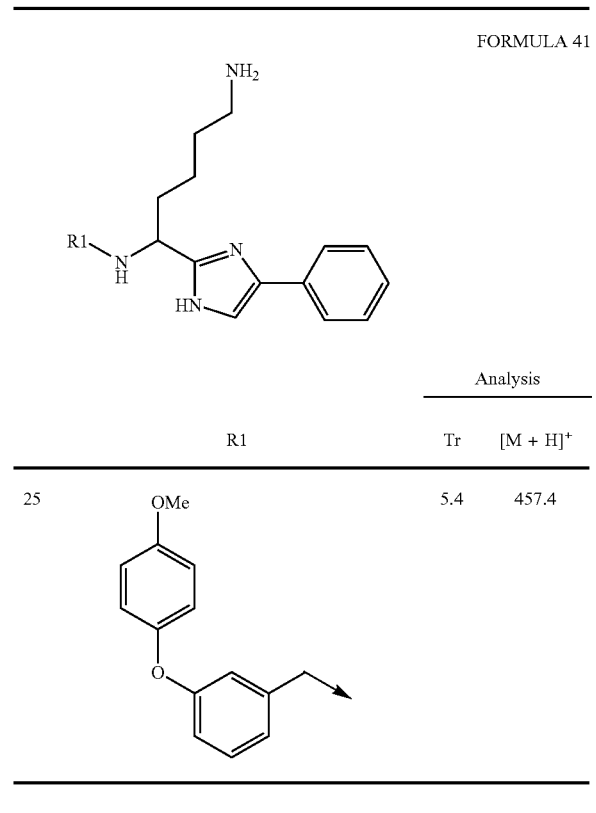
| R1 | Analysis | |
|---|---|---|
| | Tr | [M + H]⁺ |
| OMe-C₆H₄-O-C₆H₄-CH₂- | 5.4 | 457.4 |
FORMULA 42
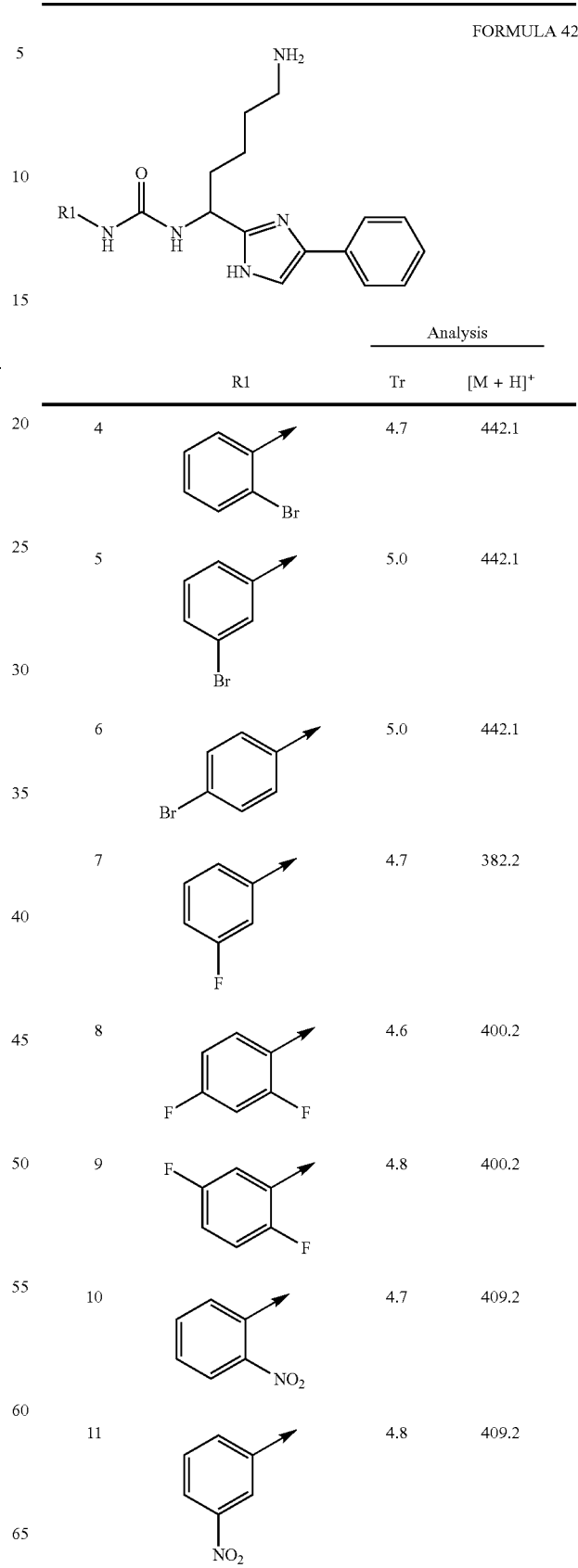
| | R1 | Analysis | |
|---|---|---|---|
| | | Tr | [M + H]⁺ |
| 1 | 2-Cl-C₆H₄- | 4.7 | 398.1 |
| 2 | 3-Cl-C₆H₄- | 4.9 | 398.1 |
| 3 | 4-Cl-C₆H₄- | 4.9 | 398.1 |
| 4 | 2-Br-C₆H₄- | 4.7 | 442.1 |
| 5 | 3-Br-C₆H₄- | 5.0 | 442.1 |
| 6 | 4-Br-C₆H₄- | 5.0 | 442.1 |
| 7 | 3-F-C₆H₄- | 4.7 | 382.2 |
| 8 | 2,4-F₂-C₆H₃- | 4.6 | 400.2 |
| 9 | 2,5-F₂-C₆H₃- | 4.8 | 400.2 |
| 10 | 2-NO₂-C₆H₄- | 4.7 | 409.2 |
| 11 | 3-NO₂-C₆H₄- | 4.8 | 409.2 |

-continued
FORMULA 42
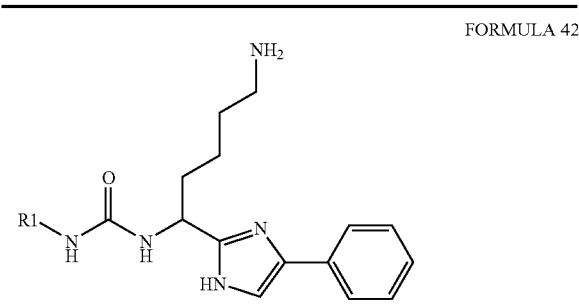
| | R1 | Analysis Tr | [M + H]+ |
|---|---|---|---|
| 12 | 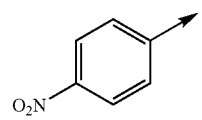 | 5.0 | 409.2 |
| 13 | 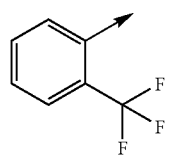 | 4.8 | 432.2 |
| 14 | 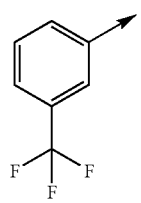 | 5.2 | 432.2 |
| 15 | 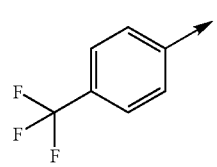 | 5.3 | 432.2 |
| 16 | 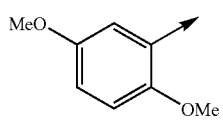 | 4.7 | 424.2 |
| 17 | 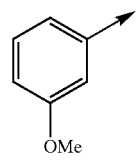 | 4.6 | 394.2 |
| 18 | 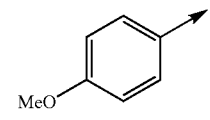 | 4.5 | 394.2 |
| 19 | 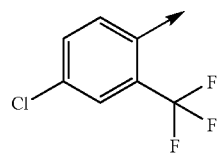 | 5.2 | 466.1 |
-continued
FORMULA 42
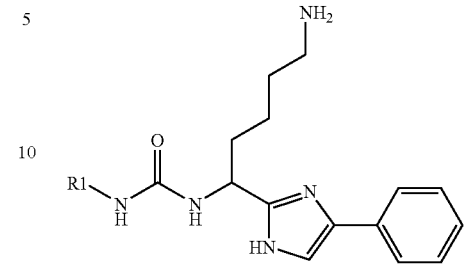
| | R1 | Analysis Tr | [M + H]+ |
|---|---|---|---|
| 20 | 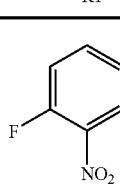 | 4.9 | 427.2 |
FORMULA 43
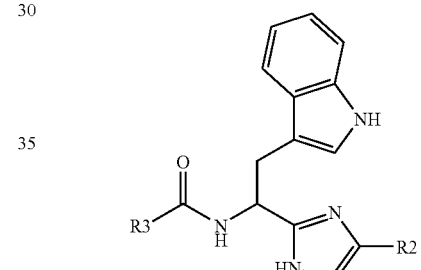
| | R3 | R2 | Analysis Tr | [M + H]+ |
|---|---|---|---|---|
| 1 |  | 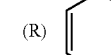 (R) | 5.5 | 374.2 |
| 2 | 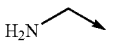 | 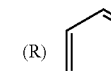 (R) | 5.4 | 360.2 |
| 3 | 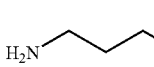 | 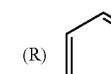 (R) | 5.4 | 388.2 |
| 4 |  | 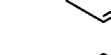 (R) | 5.5 | 416.3 |
| 5 |  | 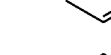 (R) | 5.4 | 374.2 |

-continued
FORMULA 43
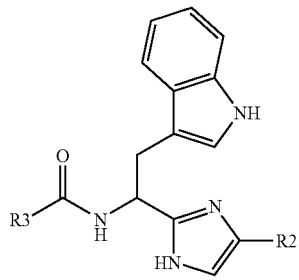
| | R3 | | R2 | Tr | [M+H]+ |
|---|---|---|---|---|---|
| 6 | H₂N-C₆H₄- | (R) | phenyl | 6.1 | 422.2 |
| 7 | tBu-NH₂ | (R) | phenyl | 5.5 | 388.2 |
| 8 | H₂N-(CH₂)₃- | (R) | phenyl | 5.5 | 402.2 |
| 9 | H₂N-CH₂-C₆H₄- | (R) | phenyl | 5.5 | 436.2 |
| 10 | H₂N-C₆H₄-CH₂- | (R) | phenyl | 5.7 | 436.2 |
| 11 | H₂N-CH₂CH₂- | (R,S) | tBu | | |
| 12 | H₂N-CH₂- | (R,S) | tBu | 5.3 | 340.3 |
| 13 | H₂N-(CH₂)₃- | (R,S) | tBu | 5.4 | 368.3 |
| 14 | H₂N-(CH₂)₅- | (R,S) | tBu | 5.4 | 396.3 |
| 15 | CH₃-NH-CH₂- | (R,S) | tBu | 5.3 | 354.3 |
| 16 | H₂N-C₆H₄- | (R,S) | tBu | 6.0 | 402.2 |
-continued
FORMULA 43
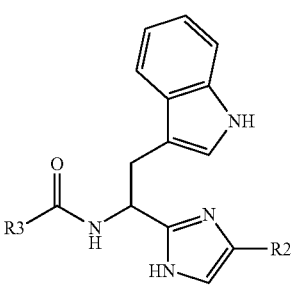
| | R3 | | R2 | Tr | [M+H]+ |
|---|---|---|---|---|---|
| 17 | tBu-NH₂ | (R,S) | tBu | 5.5 | 368.3 |
| 18 | H₂N-(CH₂)₃- | (R,S) | tBu | 5.4 | 382.3 |
| 19 | H₂N-CH₂-C₆H₄- | (R,S) | tBu | 5.5 | 416.3 |
| 20 | H₂N-C₆H₄-CH₂- | (R,S) | tBu | | 416.3 |
FORMULA 44
Analysis  
* = [M + TFA − H]−
| | R1 | R2 | Tr | [M+H]+ |
|---|---|---|---|---|
| 1 | 2-Cl-C₆H₄-CH₂- | (R) 4-MeO-C₆H₄- | 6.0 | 485.3 |

-continued
FORMULA 44
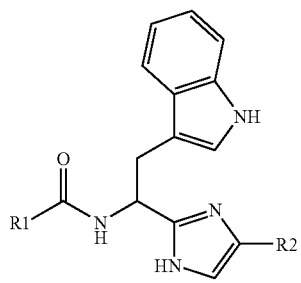
Analysis
* = [M + TFA − H]−
| | R1 | | R2 | Tr | [M + H]+ |
|---|---|---|---|---|---|
| 2 | 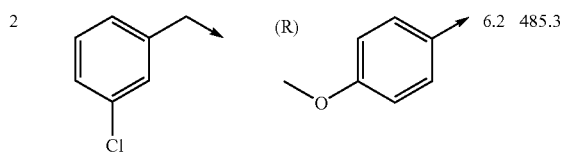 | (R) | | 6.2 | 485.3 |
| 3 | 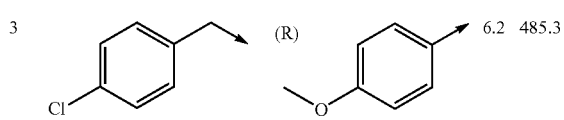 | (R) | | 6.2 | 485.3 |
| 4 | 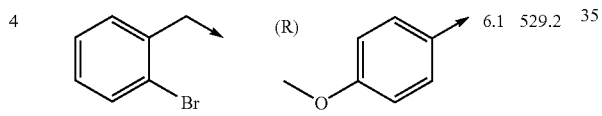 | (R) | | 6.1 | 529.2 |
| 5 | 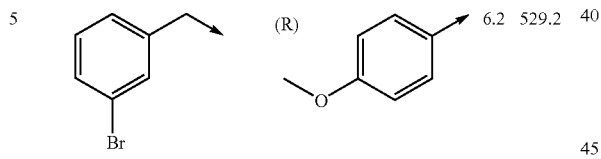 | (R) | | 6.2 | 529.2 |
| 6 | | | | 6.3 | 529.2 |
| 7 | 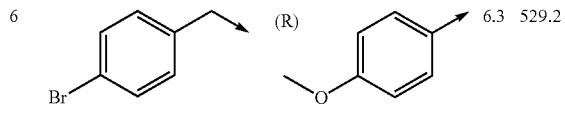 | (R) | | 5.9 | 469.3 |
| 8 | 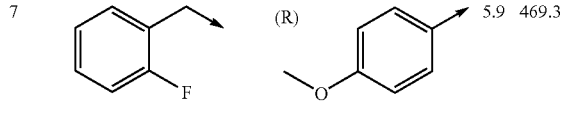 | (R) | | 5.9 | 469.3 |
| 9 | 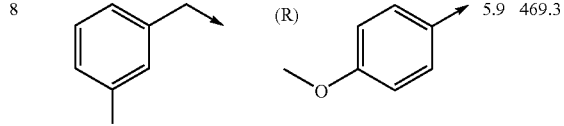 | (R) | | 5.9 | 469.3 |
-continued
FORMULA 44
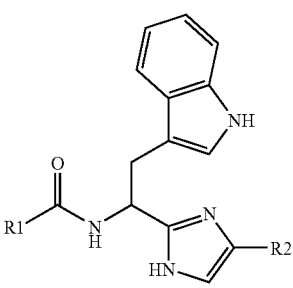
Analysis
* = [M + TFA − H]−
| | R1 | | R2 | Tr | [M + H]+ |
|---|---|---|---|---|---|
| 10 | 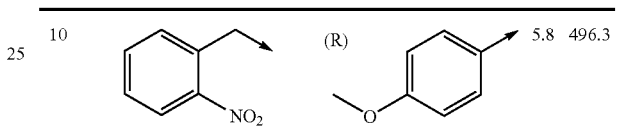 | (R) | | 5.8 | 496.3 |
| 11 | 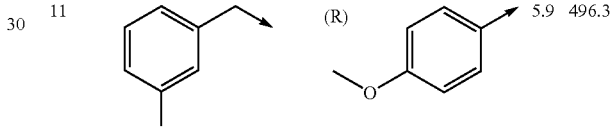 | (R) | | 5.9 | 496.3 |
| 12 | 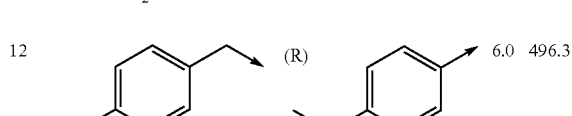 | (R) | | 6.0 | 496.3 |
| 13 | 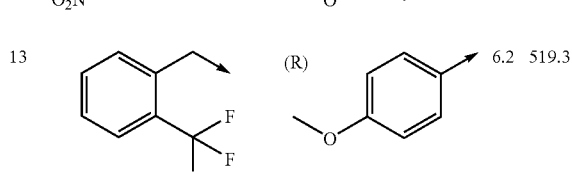 | (R) | | 6.2 | 519.3 |
| 14 | 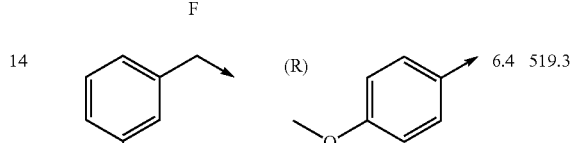 | (R) | | 6.4 | 519.3 |
| 15 | 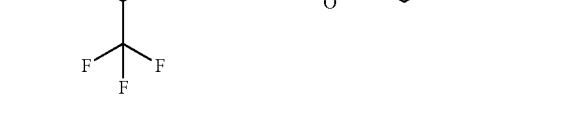 | (R) | | 6.4 | 519.3 |
| 16 | 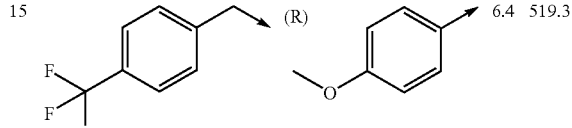 | (R) | | 5.9 | 481.3 |
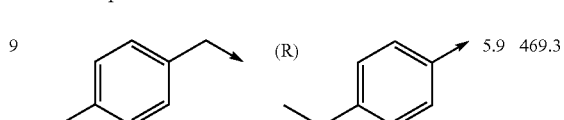

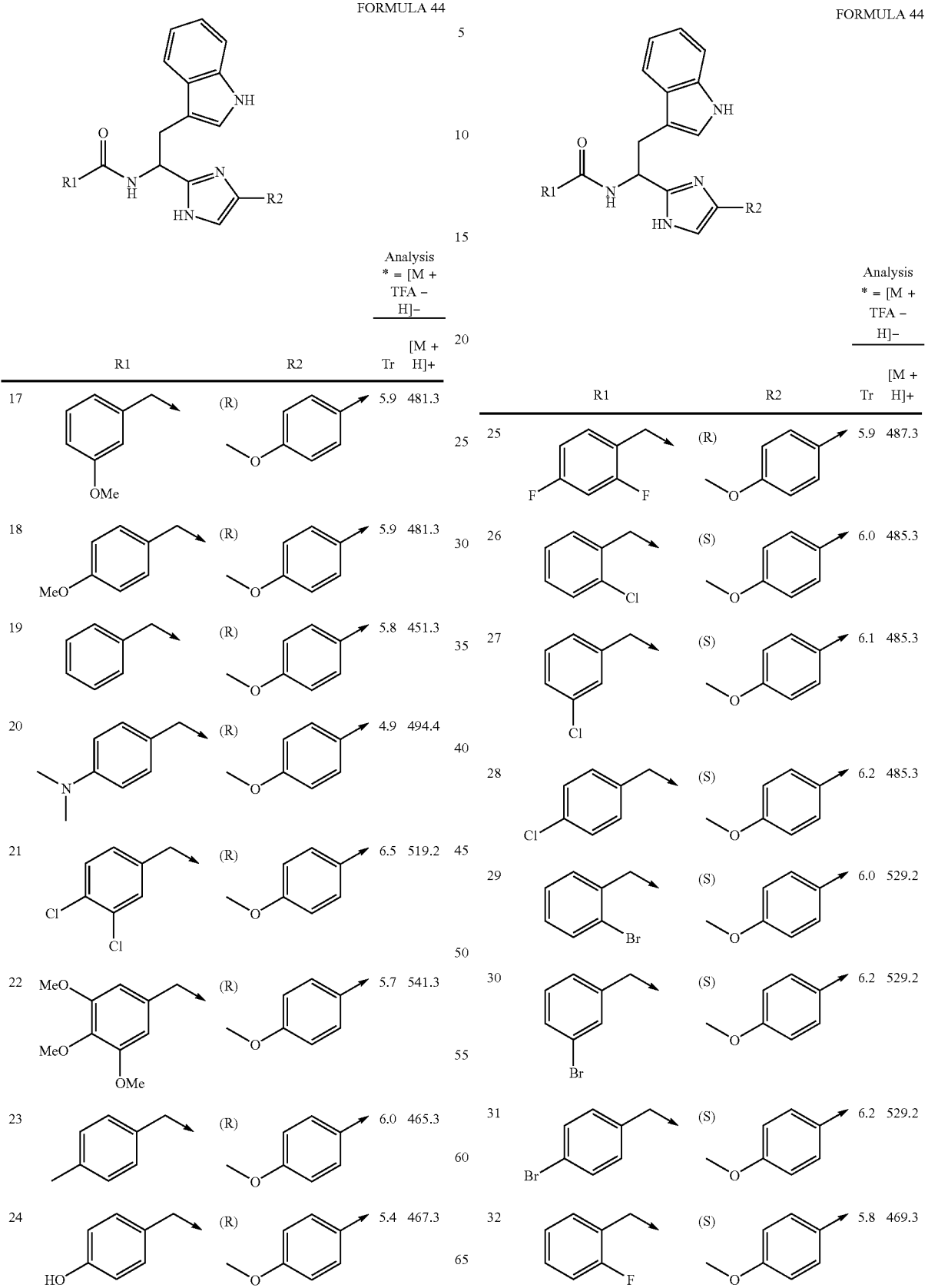

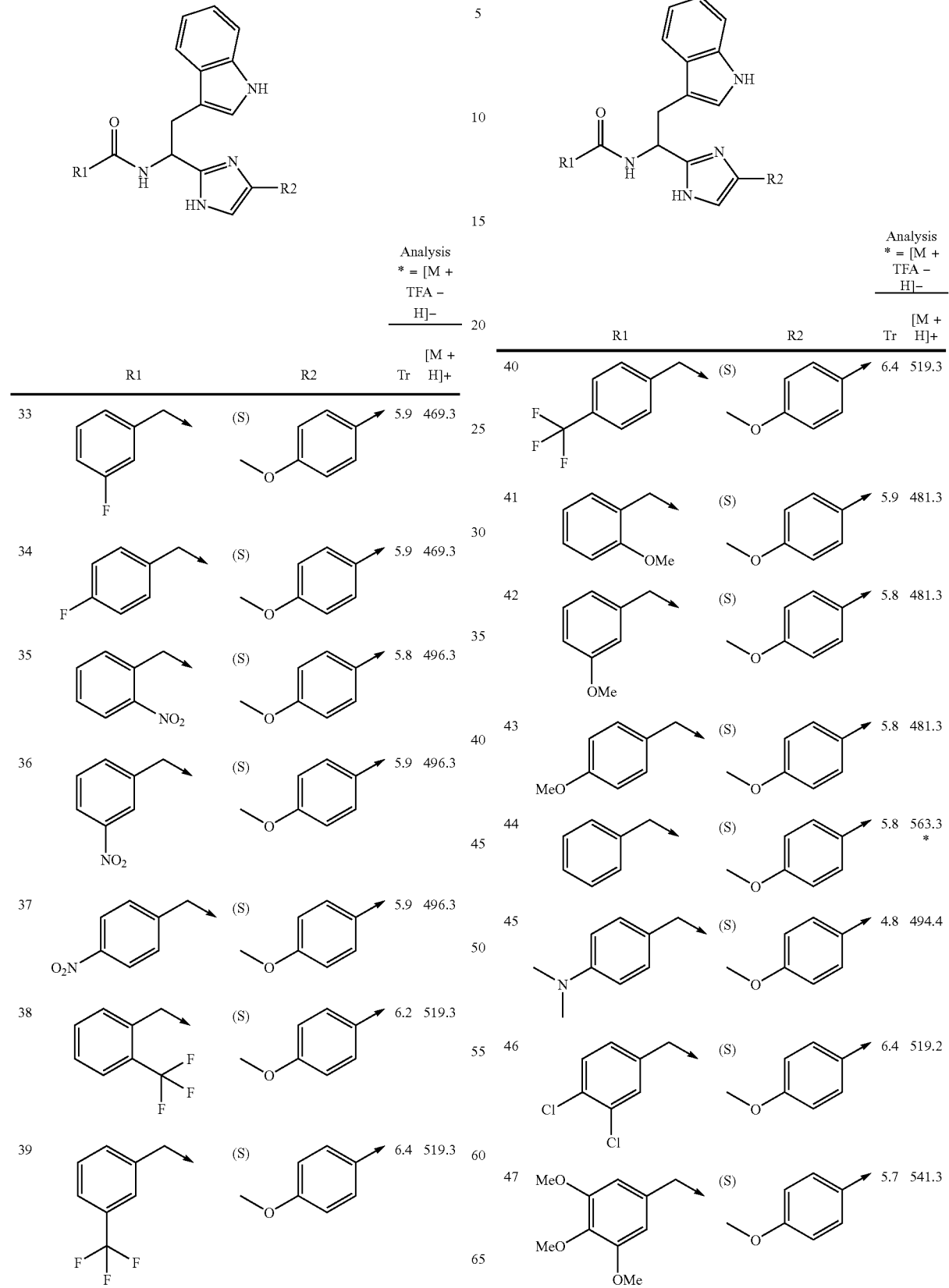

-continued
FORMULA 44
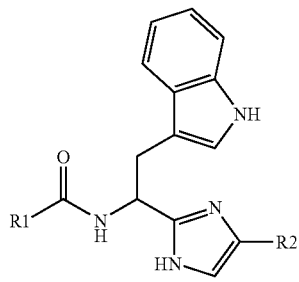
Analysis
* = [M + TFA − H]−
| | R1 | R2 | Tr | [M + H]+ |
|---|---|---|---|---|
| 48 | 4-methylbenzyl | (S) 4-methoxyphenyl | 6.0 | 465.3 |
| 49 | 4-hydroxybenzyl | (S) 4-methoxyphenyl | 5.4 | 467.3 |
| 50 | 2,4-difluorobenzyl | (S) 4-methoxyphenyl | 6.0 | 487.3 |
FORMULA 45
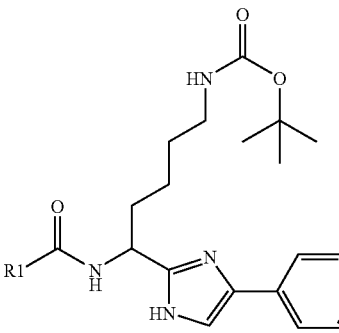
Analysis
| | R1 | Tr | [M + H]+ |
|---|---|---|---|
| 1 | 5-indolyl | 5.9 | 488.4 |
| 2 | 3-indolyl | 6.1 | 488.4 |
-continued
FORMULA 45
Analysis
| | R1 | Tr | [M + H]+ |
|---|---|---|---|
| 3 | 4-indolyl | 5.9 | 488.4 |
| 4 | 2-indolyl | 6.0 | 502.4 |
| 5 | 3-indolylmethyl | 6.0 | 502.4 |
| 6 | 5-methoxy-3-indolylmethyl | 6.0 | 532.4 |
| 7 | 5-hydroxy-2-indolyl | 5.7 | 504.4 |
| 8 | 5-methoxy-2-indolyl | 6.3 | 518.4 |
| 9 | 3-indolylethyl | 6.4 | 530.4 |

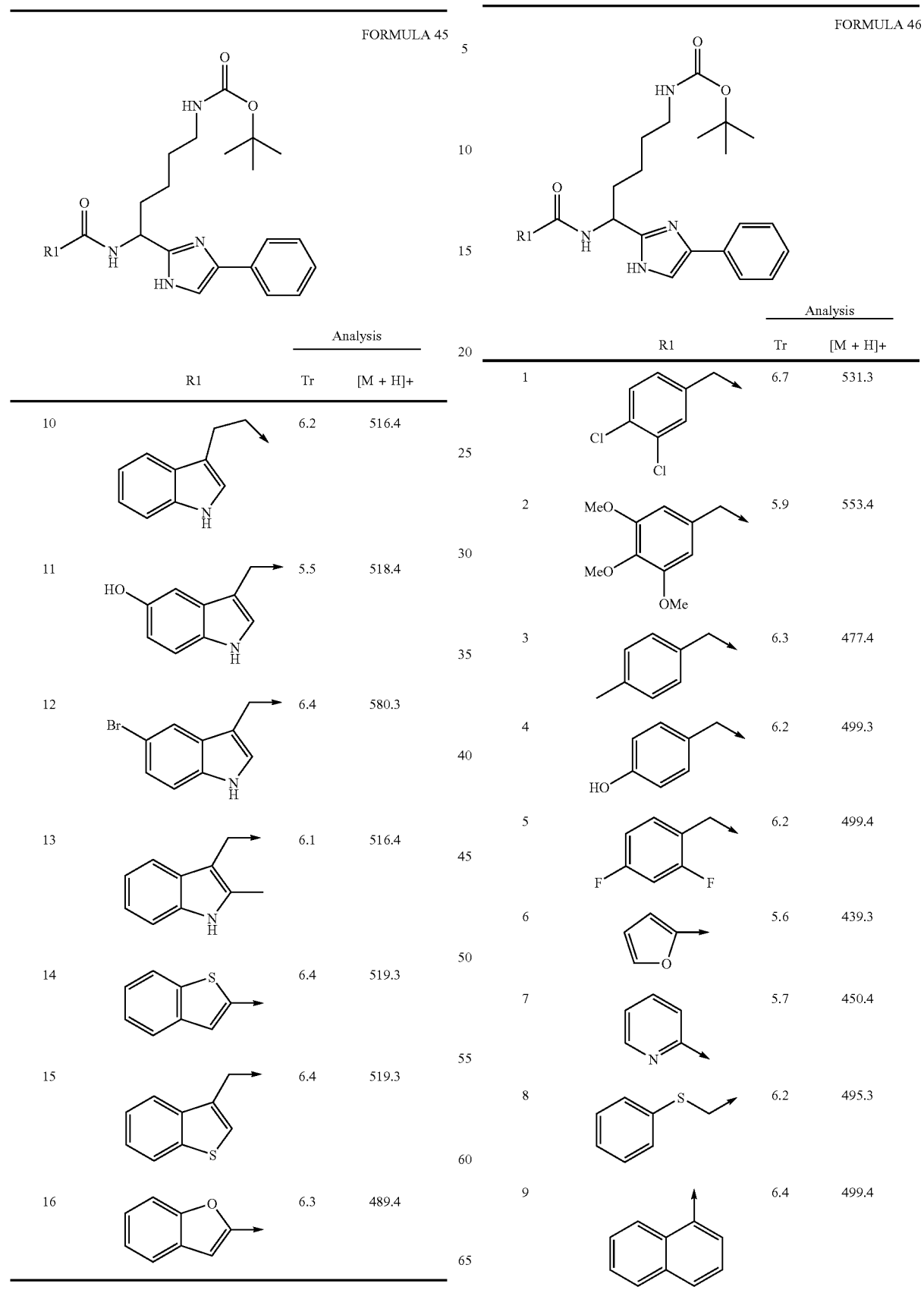

411                                                                 412
-continued                                                          -continued
FORMULA 46                                                          FORMULA 46
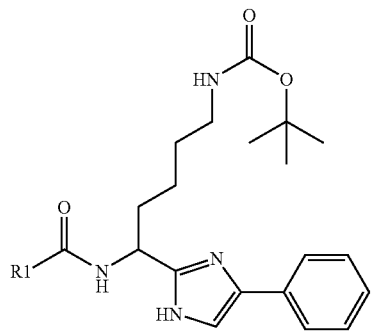
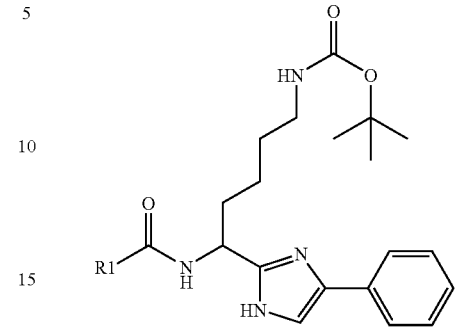
| | R1 | Analysis Tr | [M + H]+ |
|---|---|---|---|
| 10 | quinolin-2-yl | 6.4 | 500.4 |
| 11 | quinolin-8-yl | 6.2 | 500.4 |
| 12 | quinolin-3-yl | 5.9 | 500.4 |
| 13 | quinolin-4-yl | 5.7 | 500.4 |
| 14 | isoquinolin-1-yl | 5.9 | 541.3 |
| 15 | PhSO2CH2CH2- | 5.9 | 541.3 |
| 16 | thiophen-2-ylmethyl | 5.9 | 469.3 |
| 17 | pyrimidin-2-ylthiomethyl | 5.5 | 497.4 |
| | R1 | Analysis Tr | [M + H]+ |
|---|---|---|---|
| 18 | pyridin-3-yl | 5.3 | 450.4 |
FORMULA 47
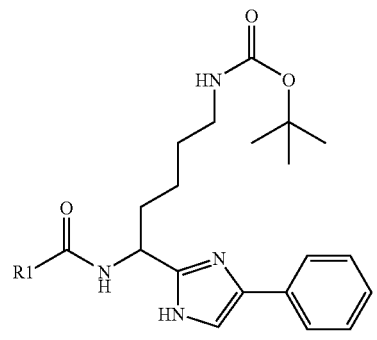
| | R1 | Analysis Tr | [M + H]+ |
|---|---|---|---|
| 1 | 2-chlorobenzyl | 6.2 | 497.3 |
| 2 | 3-chlorobenzyl | 6.3 | 497.3 |
| 3 | 4-chlorobenzyl | 6.4 | 497.3 |
| 4 | 2-bromobenzyl | 6.2 | 541.2 |

-continued
FORMULA 47
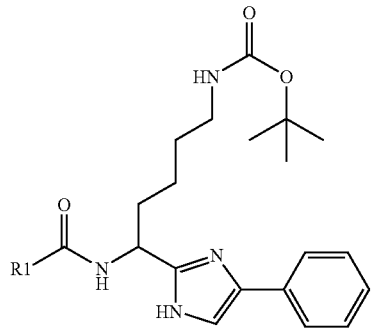
| | R1 | Tr | [M + H]+ |
|---|---|---|---|
| 5 | 3-Br-benzyl | 6.4 | 541.2 |
| 6 | 4-Br-benzyl | 6.5 | 541.2 |
| 7 | 2-F-benzyl | 6.0 | 481.3 |
| 8 | 3-F-benzyl | 6.1 | 481.3 |
| 9 | 4-F-benzyl | 6.1 | 481.3 |
| 10 | 2-NO2-benzyl | 6.0 | 508.3 |
| 11 | 3-NO2-benzyl | 6.1 | 508.3 |
| 12 | 4-NO2-benzyl | 6.1 | 508.3 |
-continued
FORMULA 47
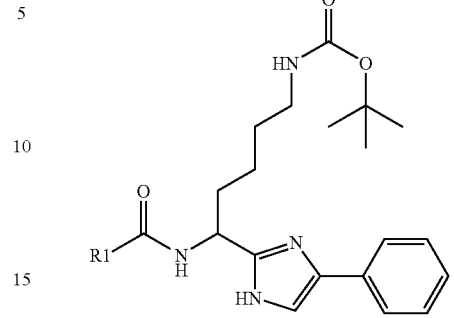
| | R1 | Tr | [M + H]+ |
|---|---|---|---|
| 13 | 2-CF3-benzyl | 6.4 | 531.3 |
| 14 | 3-CF3-benzyl | 6.6 | 531.3 |
| 15 | 4-CF3-benzyl | 6.6 | 531.3 |
| 16 | 2-OMe-benzyl | 6.1 | 493.4 |
| 17 | 3-OMe-benzyl | 6.0 | 493.4 |
| 18 | 4-OMe-benzyl | 6.0 | 493.4 |
| 19 | benzyl | 6.0 | 463.4 |
| 20 | 4-NMe2-benzyl | 5.0 | 506.4 |

FORMULA 48
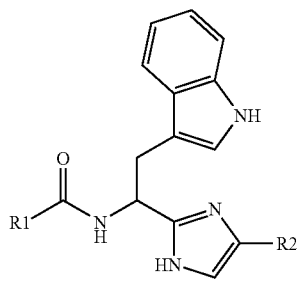
| | R1 | R2 | Analysis Tr | [M + H]+ |
|---|---|---|---|---|
| 1 | 3,4-dichlorobenzyl (R, S) | 2-OMe-phenyl | 6.9 | 519.2 |
| 2 | 3,4,5-trimethoxybenzyl (R, S) | 2-OMe-phenyl | 6.5 | 541.3 |
| 3 | 4-methylbenzyl (R, S) | 2-OMe-phenyl | 6.7 | 465.3 |
| 4 | 4-hydroxybenzyl (R, S) | 2-OMe-phenyl | 6.3 | 467.3 |
| 5 | 2,4-difluorobenzyl (R, S) | 2-OMe-phenyl | 6.6 | 487.2 |
| 6 | 3,4-dichlorobenzyl (R, S) | 4-Br-phenyl | 7.0 | 567.0 |
| 7 | 3,4,5-trimethoxybenzyl (R, S) | 4-Br-phenyl | 6.7 | 589.1 |
| 8 | 4-methylbenzyl (R, S) | 4-Br-phenyl | 6.9 | 513.2 |

-continued
FORMULA 48
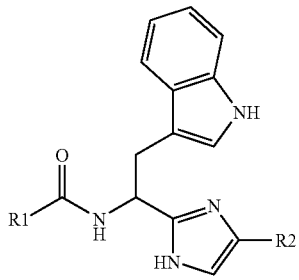
| | R1 | | R2 | Analysis | |
|---|---|---|---|---|---|
| | | | | Tr | [M + H]+ |
| 9 | 4-HO-C6H4-CH2- | (R, S) | 4-Br-C6H4- | 6.5 | 515.1 |
| 10 | 2,4-F2-C6H3-CH2- | (R, S) | 4-Br-C6H4- | 6.8 | 535.1 |
| 11 | 3,4-Cl2-C6H3-CH2- | (R, S) | 4-O2N-C6H4- | 7.2 | 534.1 |
| 12 | 3,4,5-(MeO)3-C6H2-CH2- | (R, S) | 4-O2N-C6H4- | 6.8 | 556.2 |
| 13 | 4-Me-C6H4-CH2- | (R, S) | 4-O2N-C6H4- | 6.8 | 480.1 |
| 14 | 4-HO-C6H4-CH2- | (R, S) | 4-O2N-C6H4- | 5.8 | 482.1 |
| 15 | 2,4-F2-C6H3-CH2- | (R, S) | 4-O2N-C6H4- | 6.7 | 502.1 |
| 16 | 3,4-Cl2-C6H3-CH2- | (R, S) | 4-(Et2N)-C6H4- | 6.3 | 560.1 |

-continued

FORMULA 48

| | R1 | R2 | Tr | [M + H]+ |
|---|---|---|---|---|
| 17 | 3,4,5-tri-MeO-benzyl | (R,S) 4-(NEt₂)-phenyl | 5.5 | 582.2 |
| 18 | 4-Me-benzyl | (R,S) 4-(NEt₂)-phenyl | 5.8 | 506.3 |
| 19 | 4-HO-benzyl | (R,S) 4-(NEt₂)-phenyl | 5.1 | 508.2 |
| 20 | 2,4-di-F-benzyl | (R,S) 4-(NEt₂)-phenyl | 5.7 | 528.2 |
| 21 | 3,4-di-Cl-benzyl | (R) phenyl | 6.5 | 489.1 |
| 22 | 3,4,5-tri-MeO-benzyl | (R) phenyl | 5.7 | 511.2 |
| 23 | 4-Me-benzyl | (R) phenyl | 6.1 | 435.2 |
| 24 | 4-HO-benzyl | (R) phenyl | 5.4 | 437.2 |

-continued
FORMULA 48
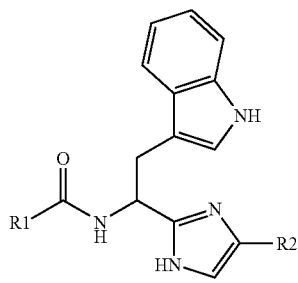
| | R1 | R2 | Tr | [M + H]+ |
|---|---|---|---|---|
| 25 | 2,4-difluorobenzyl | (R) phenyl | 6.0 | 457.2 |
FORMULA 49
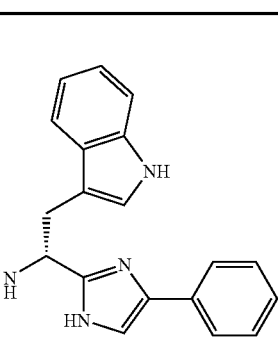
| | R1 | (min) | [M + H]+ |
|---|---|---|---|
| 1 | 2-Cl-benzyl | 6.6 | 455.2 |
| 2 | 3-Cl-benzyl | 6.6 | 455.2 |
| 3 | 4-Cl-benzyl | 6.6 | 455.2 |
| 4 | 2-Br-benzyl | 6.6 | 499.2 |
-continued
FORMULA 49
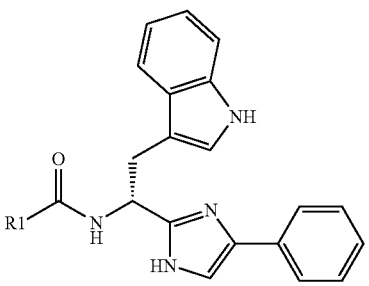
| | R1 | (min) | [M + H]+ |
|---|---|---|---|
| 5 | 3-Br-benzyl | 6.7 | 499.2 |
| 6 | 4-Br-benzyl | 6.7 | 499.2 |
| 7 | 2-F-benzyl | 6.5 | 439.2 |
| 8 | 3-F-benzyl | 6.5 | 439.2 |

-continued
FORMULA 49
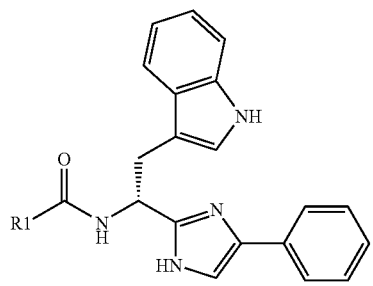
| | R1 | Analysis (min) | [M + H]+ |
|---|---|---|---|
| 9 | 4-F-C6H4-CH2- | 6.5 | 439.2 |
| 10 | 2-NO2-C6H4-CH2- | 6.5 | 466.2 |
| 11 | 3-NO2-C6H4-CH2- | 6.5 | 466.2 |
| 12 | 4-NO2-C6H4-CH2- | 6.5 | 466.2 |
| 13 | 2-CF3-C6H4-CH2- | 6.7 | 489.2 |
| 14 | 3-CF3-C6H4-CH2- | 6.7 | 489.2 |
| 15 | 4-CF3-C6H4-CH2- | 6.8 | 489.2 |
-continued
FORMULA 49
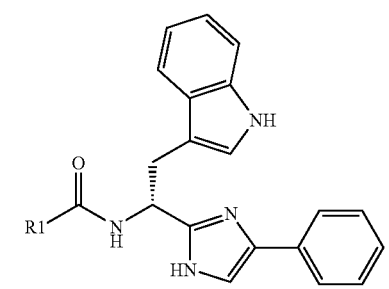
| | R1 | Analysis (min) | [M + H]+ |
|---|---|---|---|
| 16 | 2-OMe-C6H4-CH2- | 6.5 | 451.3 |
| 17 | 3-OMe-C6H4-CH2- | 6.5 | 451.3 |
| 18 | 4-OMe-C6H4-CH2- | 6.5 | 451.3 |
| 19 | C6H5-CH2- | 6.5 | 421.3 |
| 20 | 4-NMe2-C6H4-CH2- | 5.8 | 464.3 |

FORMULA 50
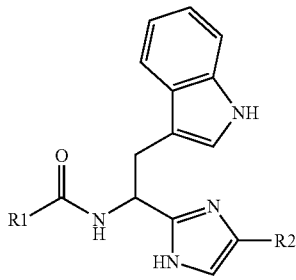
| | R1 | R2 | Tr | [M + H]+ |
|---|---|---|---|---|
| 1 | tert-butyl N-ethyl carbamate | (R) Ph | 6.3 | 474.3 |
| 2 | tert-butyl N-methyl carbamate | (R) Ph | 6.3 | 460.3 |
| 3 | tert-butyl N-propyl carbamate | (R) Ph | 6.3 | 488.3 |
| 4 | tert-butyl N-pentyl carbamate | (R) Ph | 6.4 | 516.3 |
| 5 | tert-butyl N-methyl-N-ethyl carbamate | (R) Ph | 6.3 | 474.3 |
| 6 | tert-butyl N-phenyl carbamate | (R) Ph | 6.5 | 522.3 |
| 7 | tert-butyl N-(tert-butyl) carbamate | (R) Ph | 6.5 | 488.3 |
| 8 | tert-butyl N-butyl carbamate | (R) Ph | 6.4 | 502.3 |
| 9 | tert-butyl N-benzyl carbamate | (R) Ph | 6.5 | 536.3 |

-continued
FORMULA 50
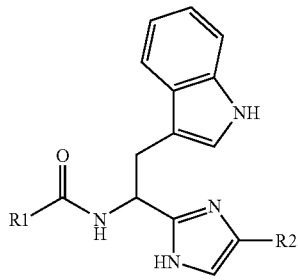
| | R1 | R2 | Tr | [M + H]+ |
|---|---|---|---|---|
| 10 | tert-butyl (4-methylphenyl)carbamate-CH2- | (R) phenyl | 6.5 | 536.3 |
| 11 | Boc-NH-CH2CH2- | (R, S) tBu | 6.2 | 454.3 |
| 12 | Boc-NH-CH2- | (R, S) tBu | 6.2 | 440.3 |
| 13 | Boc-NH-(CH2)3- | (R, S) tBu | 6.3 | 468.3 |
| 14 | Boc-NH-(CH2)5- | (R, S) tBu | 6.4 | 496.3 |
| 15 | Boc-N(CH3)-CH2- | (R, S) tBu | 6.2 | 454.3 |
| 16 | Boc-NH-(4-methylphenyl)- | (R, S) tBu | 6.5 | 502.3 |
| 17 | Boc-NH-C(CH3)3- | (R, S) tBu | 6.4 | 468.3 |
| 18 | Boc-NH-(CH2)4- | (R, S) tBu | 6.3 | 482.3 |

FORMULA 50
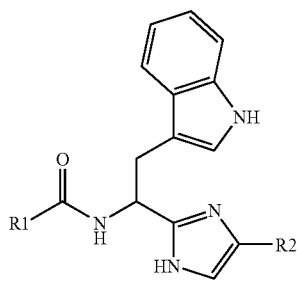
| | R1 | | R2 | Analysis | |
|---|---|---|---|---|---|
| | | | | Tr | [M + H]+ |
| 19 | Boc-NH-CH2-C6H4- | (R, S) | tBu | 6.4 | 516.3 |
| 20 | Boc-NH-C6H4-CH2- | (R, S) | tBu | 6.4 | 516.3 |
FORMULA 51
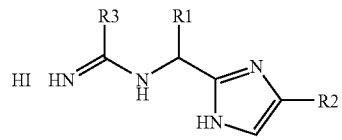
| | R1 | R2 | R3 | Analysis | |
|---|---|---|---|---|---|
| | | | | Tr | [M + H]+ |
| 1 (S) | BnOCH2-* | Ph-* | Ph-* | 5.6 | 397.2 |
| 2 (S) | BnOCH2-* | Ph-* | 2-Cl-C6H4-* | 5.9 | 431.2 |
| 3 (S) | BnOCH2-* | Ph-* | 4-Cl-C6H4-* | 6.0 | 431.2 |
| 4 (S) | BnOCH2-* | Ph-* | 4-MeO-C6H4-* | 5.8 | 427.2 |

-continued
FORMULA 51
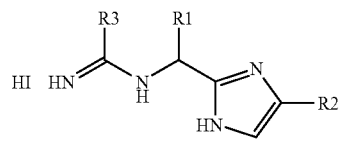
| | R1 | R2 | R3 | Tr | [M + H]+ |
|---|---|---|---|---|---|
| 5 (S) | BnOCH2- | Ph | 4-CF3-C6H4 | 6.3 | 465.2 |
| 6 (S) | BnOCH2- | Ph | 4-tBu-C6H4 | 6.7 | 453.3 |
| 7 (S) | BnOCH2- | Ph | 2,4-F2-C6H3 | 5.8 | 433.2 |
| 8 (S) | BnOCH2- | Ph | 4-CF3O-C6H4 | 6.4 | 481.2 |
| 9 (S) | BnOCH2- | Ph | 2,6-Cl2-C6H3-CH2 | 6.3 | 479.1 |
| 10 (S) | BnOCH2- | Ph | tBu-SO2-CH2 | 5.7 | 455.2 |
| 11 (S) | 4-MeO-C6H4-CH2 | Ph | Ph | 5.4 | 397.2 |
| 12 (S) | 4-MeO-C6H4-CH2 | Ph | 2-Cl-C6H4 | 5.0 | 431.2 |
| 13 (S) | 4-MeO-C6H4-CH2 | Ph | 4-Cl-C6H4 | 5.8 | 431.2 |

FORMULA 51
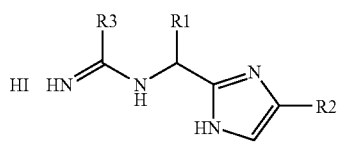
| | R1 | R2 | R3 | Tr | [M + H]+ |
|---|---|---|---|---|---|
| 14 (S) | 4-MeO-benzyl | phenyl | 4-MeO-phenyl | 5.5 | 427.2 |
| 15 (S) | 4-MeO-benzyl | phenyl | 4-CF3-phenyl | 6.0 | 465.2 |
| 16 (S) | 4-MeO-benzyl | phenyl | 4-tBu-phenyl | 6.5 | 453.3 |
| 17 (S) | 4-MeO-benzyl | phenyl | 2,4-diF-phenyl | 5.5 | 433.2 |
| 18 (S) | 4-MeO-benzyl | phenyl | 4-CF3O-phenyl | 6.2 | 481.2 |
| 19 (S) | 4-MeO-benzyl | phenyl | 2,6-diCl-benzyl | 6.1 | 479.1 |
| 20 (S) | 4-MeO-benzyl | phenyl | tBu-SO2-CH2 | 5.5 | 455.2 |
| 21 (R) | indol-3-yl-methyl | phenyl | phenyl | 5.3 | 406.2 |
| 22 (R) | indol-3-yl-methyl | phenyl | 2-Cl-phenyl | 5.5 | 440.1 |

-continued
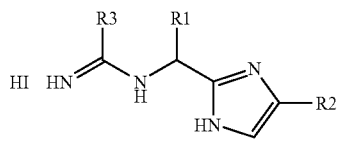
FORMULA 51
| | R1 | R2 | R3 | Tr | [M + H]+ |
|---|---|---|---|---|---|
| 23 (R) | indol-3-ylmethyl | phenyl | 4-Cl-phenyl | 5.7 | 440.2 |
| 24 (R) | indol-3-ylmethyl | phenyl | 4-MeO-phenyl | 5.5 | 436.2 |
| 25 (R) | indol-3-ylmethyl | phenyl | 4-CF3-phenyl | 6.0 | 474.2 |
| 26 (R) | indol-3-ylmethyl | phenyl | 4-tBu-phenyl | 6.4 | 462.3 |
| 27 (R) | indol-3-ylmethyl | phenyl | 2,4-diF-phenyl | 5.5 | 442.2 |
| 28 (R) | indol-3-ylmethyl | phenyl | 4-CF3O-phenyl | 6.1 | 490.2 |
| 29 (R) | indol-3-ylmethyl | phenyl | 2,6-diCl-benzyl | 6.0 | 488.1 |
| 30 (R) | indol-3-ylmethyl | phenyl | tBu-SO2-CH2 | 5.4 | 464.2 |

-continued
FORMULA 51
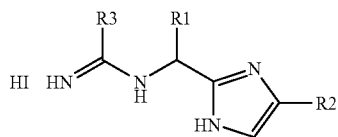
|    | R1 | R2 | R3 | Tr | [M + H]+ |
|----|----|----|----|-----|----------|
| 31 | (R) indol-3-yl | 4-MeO-C6H4 | C6H5 | 5.2 | 436.2 |
| 32 | (R) indol-3-yl | 4-MeO-C6H4 | 2-Cl-C6H4 | 5.4 | 470.2 |
| 33 | (R) indol-3-yl | 4-MeO-C6H4 | 4-Cl-C6H4 | 5.6 | 470.2 |
| 34 | (R) indol-3-yl | 4-MeO-C6H4 | 4-MeO-C6H4 | 5.4 | 466.2 |
| 35 | (R) indol-3-yl | 4-MeO-C6H4 | 4-CF3-C6H4 | 5.9 | 504.2 |
| 36 | (R) indol-3-yl | 4-MeO-C6H4 | 4-tBu-C6H4 | 6.2 | 492.3 |
| 37 | (R) indol-3-yl | 4-MeO-C6H4 | 2,4-F2-C6H3 | 5.4 | 472.2 |
| 38 | (R) indol-3-yl | 4-MeO-C6H4 | 4-CF3O-C6H4 | 6.0 | 520.1 |

-continued

FORMULA 51

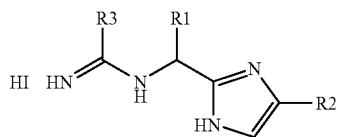

| | R1 | R2 | R3 | Tr | [M + H]+ |
|---|---|---|---|---|---|
| 39 | indol-3-ylmethyl (R) | 4-MeO-phenyl | 2,6-dichlorobenzyl | 5.8 | 518.1 |
| 40 | indol-3-ylmethyl (R) | 4-MeO-phenyl | tert-butylsulfonylmethyl | 5.3 | 494.2 |
| 41 | indol-3-ylmethyl (R, S) | 2-OMe-phenyl | phenyl | 5.2 | 436.2 |
| 42 | indol-3-ylmethyl (R, S) | 2-OMe-phenyl | 2-Cl-phenyl | 5.4 | 470.2 |
| 43 | indol-3-ylmethyl (R, S) | 2-OMe-phenyl | 4-Cl-phenyl | 5.6 | 470.2 |
| 44 | indol-3-ylmethyl (R, S) | 2-OMe-phenyl | 4-MeO-phenyl | 5.4 | 466.2 |
| 45 | indol-3-ylmethyl (R, S) | 2-OMe-phenyl | 4-CF3-phenyl | 5.9 | 504.2 |
| 46 | indol-3-ylmethyl (R, S) | 2-OMe-phenyl | 4-tert-butyl-phenyl | 6.2 | 492.3 |

FORMULA 51

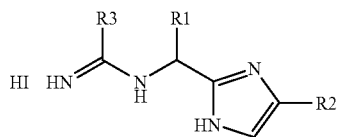

| | R1 | R2 | R3 | Tr | [M + H]+ |
|---|---|---|---|---|---|
| 47 (R, S) | 3-indolylmethyl | 2-OMe-phenyl | 2,4-difluorophenyl | 5.4 | 472.2 |
| 48 (R, S) | 3-indolylmethyl | 2-OMe-phenyl | 4-OCF3-phenyl | 6.0 | 520.1 |
| 49 (R, S) | 3-indolylmethyl | 2-OMe-phenyl | 2,6-dichlorobenzyl | 5.9 | 518.1 |
| 50 (R, S) | 3-indolylmethyl | 2-OMe-phenyl | tert-butylsulfonylmethyl | 5.3 | 494.2 |
| 51 (R, S) | 3-indolylmethyl | tert-butyl | phenyl | 4.6 | 386.2 |
| 52 (R, S) | 3-indolylmethyl | tert-butyl | 2-chlorophenyl | 4.7 | 420.2 |
| 53 (R, S) | 3-indolylmethyl | tert-butyl | 4-chlorophenyl | 4.9 | 420.2 |
| 54 (R, S) | 3-indolylmethyl | tert-butyl | 4-methoxyphenyl | 4.8 | 416.2 |

US 7,238,695 B2
-continued
FORMULA 51
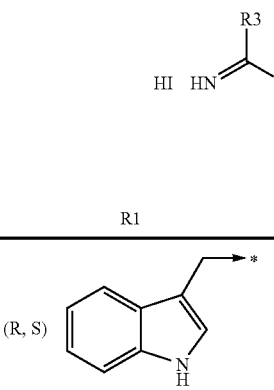
| | R1 | R2 | R3 | Analysis Tr | [M + H]+ |
|---|---|---|---|---|---|
| 55 (R, S) | 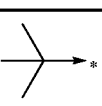 | 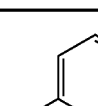 | 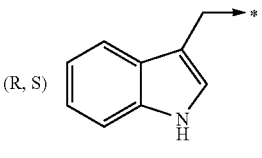 | 5.2 | 454.2 |
| 56 (R, S) | 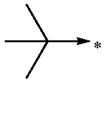 | 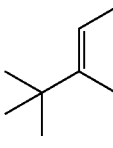 | 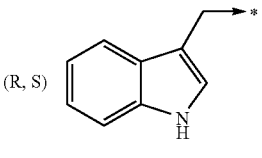 | 5.6 | 442.3 |
| 57 (R, S) | 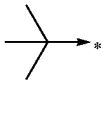 | 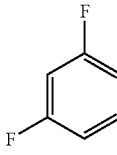 | 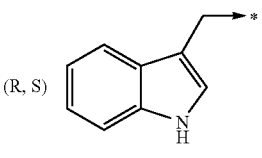 | 4.7 | 422.2 |
| 58 (R, S) | 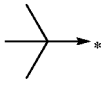 | 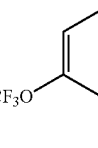 | 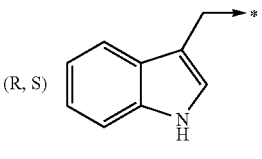 | 5.3 | 470.2 |
| 59 (R, S) | 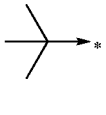 | 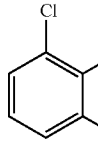 | 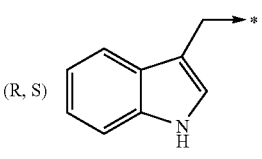 | 5.2 | 468.2 |
| 60 (R, S) | 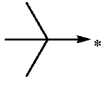 | 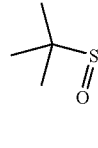 | 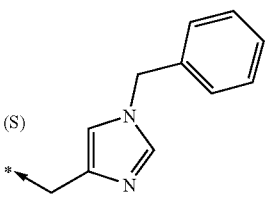 | 4.8 | 444.2 |
| 61 (S) | 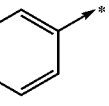 | 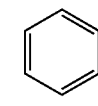 | 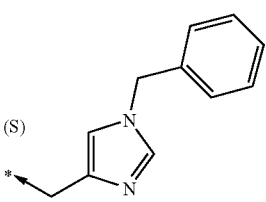 | 4.9 | 449.2 |
| 62 (S) | 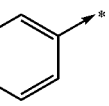 | | 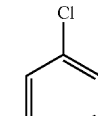 | 5.0 | 483.2 |

-continued
FORMULA 51
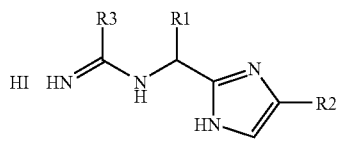
| | R1 | R2 | R3 | Tr | [M + H]+ |
|---|---|---|---|---|---|
| 63 | (S)-1-benzyl-imidazol-4-ylmethyl | phenyl | 4-chlorophenyl | 5.2 | 483.2 |
| 64 | (S)-1-benzyl-imidazol-4-ylmethyl | phenyl | 4-methoxyphenyl | 5.0 | 477.2 |
| 65 | (S)-1-benzyl-imidazol-4-ylmethyl | phenyl | 4-CF3-phenyl | 5.4 | 515.1 |
| 66 | (S)-1-benzyl-imidazol-4-ylmethyl | phenyl | 4-tert-butylphenyl | 5.8 | 503.3 |
| 67 | (S)-1-benzyl-imidazol-4-ylmethyl | phenyl | 2,4-difluorophenyl | 4.9 | 483.2 |
| 68 | (S)-1-benzyl-imidazol-4-ylmethyl | phenyl | 4-CF3O-phenyl | 5.5 | 531.2 |

-continued
FORMULA 51
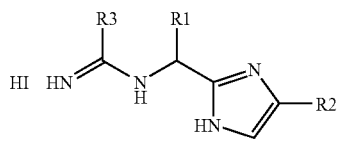
| | R1 | R2 | R3 | Tr | [M + H]+ |
|---|---|---|---|---|---|
| 69 | (S) 1-benzyl-imidazol-4-ylmethyl | phenyl | 2,6-dichlorobenzyl | 5.4 | 531.1 |
| 70 | (S) 1-benzyl-imidazol-4-ylmethyl | phenyl | tert-butylsulfonylmethyl | 4.9 | 507.2 |
| 71 | (S) benzyl | phenyl | phenyl | 5.3 | 367.2 |
| 72 | (S) benzyl | phenyl | 2-chlorophenyl | 5.6 | 401.2 |
| 73 | (S) benzyl | phenyl | 4-chlorophenyl | 5.7 | 401.1 |
| 74 | (S) benzyl | phenyl | 4-methoxyphenyl | 5.5 | 397.2 |
| 75 | (S) benzyl | phenyl | 4-trifluoromethylphenyl | 6.0 | 435.2 |
| 76 | (S) benzyl | phenyl | 4-tert-butylphenyl | 6.5 | 423.3 |

FORMULA 51
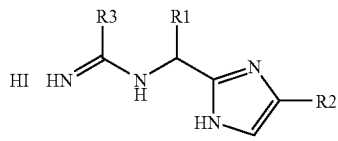
| | R1 | R2 | R3 | Tr | [M + H]+ |
|---|---|---|---|---|---|
| 77 | benzyl (S) | phenyl | 2,4-difluorophenyl | 5.5 | 403.2 |
| 78 | benzyl (S) | phenyl | 4-(CF3O)phenyl | 6.2 | 451.2 |
| 79 | benzyl (S) | phenyl | 2,6-dichlorobenzyl | 6.1 | 449.1 |
| 80 | benzyl (S) | phenyl | tert-butylsulfonylmethyl | 5.4 | 425.2 |
FORMULA 52
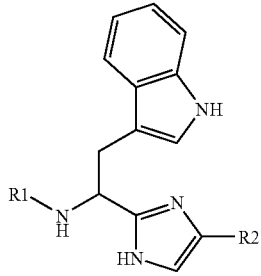
| | R1 | R2 | Tr | [M + H]+ |
|---|---|---|---|---|
| 1 | benzyl | phenyl (S) | 5.9 | 393.2 |
| 2 | 2-hydroxybenzyl | phenyl (S) | 5.7 | 409.2 |

-continued
FORMULA 52
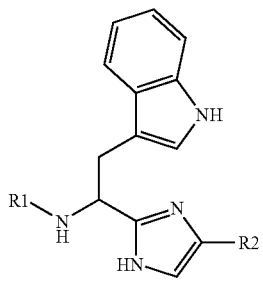
| | R1 | R2 | Analysis Tr | [M + H]+ |
|---|---|---|---|---|
| 3 | 4-HO-C6H4-CH2- | (S) Ph | 5.6 | 409.2 |
| 4 | 4-F-C6H4-CH2- | (S) Ph | 6.0 | 411.2 |
| 5 | 3-MeO-C6H4-CH2- | (S) Ph | 6.0 | 423.2 |
| 6 | 4-MeO-C6H4-CH2- (SH2) | (S) Ph | 6.0 | 423.2 |
| 7 | 2-MeO-C6H4-CH2- | (S) Ph | 6.0 | 423.2 |
| 8 | 2-NO2-C6H4-CH2- | (S) Ph | 6.0 | 438.2 |
| 9 | 4-O2N-C6H4-CH2- | (S) Ph | 6.0 | 438.2 |
| 10 | 3,4-Cl2-C6H3-CH2- | (S) Ph | 6.5 | 461.1 |
| 11 | 2-NO2-3-MeO-C6H3-CH2- | (S) Ph | 6.1 | 468.2 |

-continued
FORMULA 52
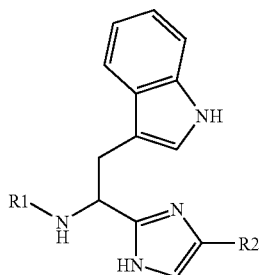
|    | R1 | R2 | Tr | [M + H]+ |
|----|----|----|----|----------|
| 12 | 4-Br-benzyl | (S) phenyl | 6.4 | 471.1 |
| 13 | 2-thienylmethyl | (S) phenyl | 5.8 | 511.2* |
| 14 | 3,4,5-trimethoxybenzyl | (S) phenyl | 5.9 | 483.3 |
| 15 | 2-F-benzyl | (S) phenyl | 5.9 | 411.2 |
| 16 | 2-CF3-benzyl | (S) phenyl | 6.4 | 461.2 |
| 17 | 2-Br-benzyl | (S) phenyl | 6.2 | 471.1 |
| 18 | 4-(NMe2)-benzyl | (S) phenyl | 5.5 | 436.3 |
| 19 | 4-(OCF3)-benzyl | (S) phenyl | 6.6 | 477.2 |

-continued
FORMULA 52
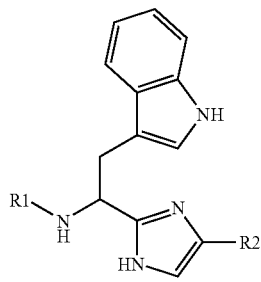
| | R1 | R2 | Analysis Tr | [M + H]+ |
|---|---|---|---|---|
| 20 | SH₂, Me₂N-(CH₂)₃-O-C₆H₄-CH₂- | Ph (S) | 4.9 | 494.3 |
| 21 | PhCH₂- | 2-MeO-C₆H₄- (R,S) | 6.0 | 423.3 |
| 22 | 2-HO-C₆H₄-CH₂- | 2-MeO-C₆H₄- (R,S) | 5.7 | 439.2 |
| 23 | 4-HO-C₆H₄-CH₂- | 2-MeO-C₆H₄- (R,S) | 5.6 | 439.2 |
| 24 | 4-F-C₆H₄-CH₂- | 2-MeO-C₆H₄- (R,S) | 6.1 | 441.2 |
| 25 | 3-MeO-C₆H₄-CH₂- | 2-MeO-C₆H₄- (R,S) | 6.0 | 453.2 |
| 26 | 4-MeO-C₆H₄-CH₂- | 2-MeO-C₆H₄- (R,S) | 5.9 | 453.2 |

-continued
FORMULA 52
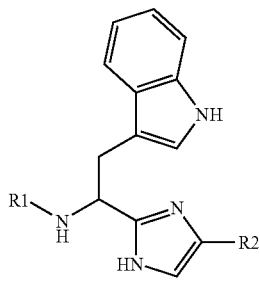
| | R1 | R2 | Analysis Tr | [M + H]+ |
|---|---|---|---|---|
| 27 | 2-OMe-benzyl | 2-OMe-phenyl (R,S) | 6.0 | 453.2 |
| 28 | 2-NO2-benzyl | 2-OMe-phenyl (R,S) | 6.2 | 468.2 |
| 29 | 4-NO2-benzyl | 2-OMe-phenyl (R,S) | 6.1 | 468.2 |
| 30 | 3,4-diCl-benzyl | 2-OMe-phenyl (R,S) | 6.7 | 491.2 |
| 31 | 3-MeO-2-NO2-benzyl | 2-OMe-phenyl (R,S) | 6.1 | 498.2 |
| 32 | 4-Br-benzyl | 2-OMe-phenyl (R,S) | 6.5 | 501.1 |
| 33 | 2-thienyl-methyl | 2-OMe-phenyl (R,S) | 6.0 | 429.2 |

-continued
FORMULA 52
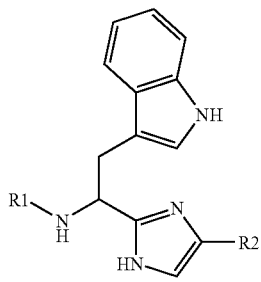
| | R1 | R2 | Tr | [M + H]+ |
|---|---|---|---|---|
| 34 | 3,4,5-trimethoxybenzyl | 2-OMe-phenyl (R,S) | 5.9 | 513.2 |
| 35 | 2-fluorobenzyl | 2-OMe-phenyl (R,S) | 6.1 | 441.2 |
| 36 | 2-trifluoromethylbenzyl | 2-OMe-phenyl (R,S) | 6.6 | 491.2 |
| 37 | 2-bromobenzyl | 2-OMe-phenyl (R,S) | 6.4 | 501.1 |
| 38 | 4-dimethylaminobenzyl | 2-OMe-phenyl (R,S) | 5.5 | 466.3 |
| 39 | 4-trifluoromethoxybenzyl | 2-OMe-phenyl (R,S) | 6.7 | 507.2 |
| 40 | 4-(3-dimethylaminopropoxy)benzyl, SH$_2$ | 2-OMe-phenyl (R,S) | 4.9 | 524.3 |

-continued
FORMULA 52
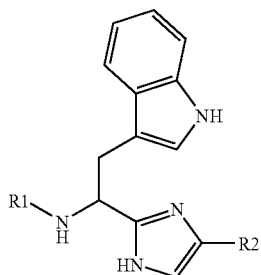
| | R1 | R2 | Tr | [M + H]+ |
|---|---|---|---|---|
| 41 | benzyl | (R) 4-OMe-benzyl | 5.9 | 423.2 |
| 42 | 2-OH-benzyl | (R) 4-OMe-benzyl | 5.6 | 439.2 |
| 43 | 4-OH-benzyl | (R) 4-OMe-benzyl | 5.5 | 439.2 |
| 44 | 4-F-benzyl | (R) 4-OMe-benzyl | 6.0 | 441.2 |
| 45 | 3-OMe-benzyl | (R) 4-OMe-benzyl | 6.0 | 453.2 |
| 46 | 4-OMe-benzyl | (R) 4-OMe-benzyl | 5.9 | 453.2 |
| 47 | 2-OMe-benzyl | (R) 4-OMe-benzyl | 6.0 | 453.2 |
| 48 | 2-NO2-benzyl | (R) 4-OMe-benzyl | 6.1 | 468.2 |
| 49 | 4-NO2-benzyl | (R) 4-OMe-benzyl | 6.1 | 468.2 |

-continued
FORMULA 52
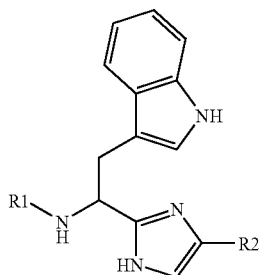
| | R1 | R2 | Tr | [M + H]+ |
|---|---|---|---|---|
| 50 | 3,4-dichlorobenzyl | (R) 4-OMe-phenyl | 6.6 | 491.1 |
| 51 | 2-nitro-3-methoxybenzyl | (R) 4-OMe-phenyl | 6.2 | 498.2 |
| 52 | 4-bromobenzyl | (R) 4-OMe-phenyl | 6.4 | 501.1 |
| 53 | 2-thienylmethyl | (R) 4-OMe-phenyl | 5.8 | 429.2 |
| 54 | 3,4,5-trimethoxybenzyl | (R) 4-OMe-phenyl | 5.8 | 513.2 |
| 55 | 2-fluorobenzyl | (R) 4-OMe-phenyl | 6.0 | 441.2 |
| 56 | 2-trifluoromethylbenzyl | (R) 4-OMe-phenyl | 6.5 | 491.2 |
| 57 | 2-bromobenzyl | (R) 4-OMe-phenyl | 6.3 | 501.1 |

-continued
FORMULA 52
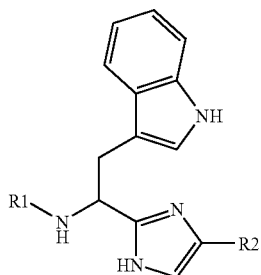
| | R1 | R2 | Analysis Tr | [M + H]+ |
|---|---|---|---|---|
| 58 | 4-(dimethylamino)benzyl, SH₂ | (R) 4-OMe-phenyl | 5.4 | 466.3 |
| 59 | 4-(trifluoromethoxy)benzyl | (R) 4-OMe-phenyl | 6.6 | 507.2 |
| 60 | 4-(3-(dimethylamino)propoxy)benzyl, SH₂ | (R) 4-OMe-phenyl | 4.9 | 524.3 |
| 61 | benzyl | (R) 4-OMe-phenyl | 5.9 | 423.2 |
| 62 | 2-hydroxybenzyl | (S) 4-OMe-phenyl | 5.6 | 439.2 |
| 63 | 4-hydroxybenzyl | (S) 4-OMe-phenyl | 5.5 | 439.2 |
| 64 | 4-fluorobenzyl | (S) 4-OMe-phenyl | 6.0 | 441.2 |
| 65 | 3-methoxybenzyl | (S) 4-OMe-phenyl | 6.0 | 453.2 |
| 66 | 4-methoxybenzyl | (S) 4-OMe-phenyl | 5.9 | 453.2 |

-continued
FORMULA 52
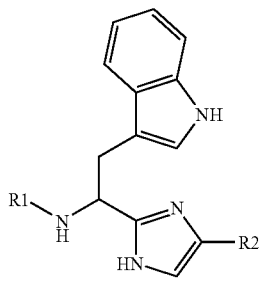
| | R1 | R2 | Analysis Tr | [M + H]+ |
|---|---|---|---|---|
| 67 | 2-OMe-benzyl | (S) 4-OMe-phenyl | 6.0 | 453.2 |
| 68 | 2-NO₂-benzyl | (S) 4-OMe-phenyl | 6.0 | 468.2 |
| 69 | 4-NO₂-benzyl | (S) 4-OMe-phenyl | 6.0 | 468.2 |
| 70 | 3,4-diCl-benzyl (SH₂) | (S) 4-OMe-phenyl | 6.6 | 491.1 |
| 71 | 3-OMe-2-NO₂-benzyl (SH₂) | (S) 4-OMe-phenyl | 6.2 | 498.2 |
| 72 | 4-Br-benzyl | (S) 4-OMe-phenyl | 6.4 | 501.1 |
| 73 | 2-thienylmethyl | (S) 4-OMe-phenyl | 5.9 | 429.2 |
| 74 | 3,4,5-triOMe-benzyl | (S) 4-OMe-phenyl | 5.8 | 513.3 |

-continued
FORMULA 52
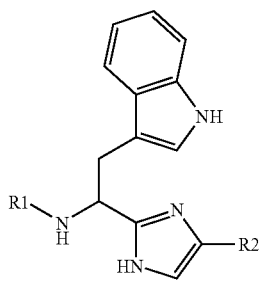
|  | R1 | R2 | Analysis Tr | [M + H]+ |
|---|---|---|---|---|
| 75 | 2-F-benzyl | (S) 4-OMe-phenyl | 6.0 | 441.2 |
| 76 | 2-CF₃-benzyl | (S) 4-OMe-phenyl | 6.5 | 491.2 |
| 77 | 2-Br-benzyl | (S) 4-OMe-phenyl | 6.3 | 501.1 |
| 78 | 4-NMe₂-benzyl | (S) 4-OMe-phenyl | 5.4 | 466.3 |
| 79 | 4-OCF₃-benzyl-SH₂ | (S) 4-OMe-phenyl | 6.6 | 507.2 |

FORMULA 53
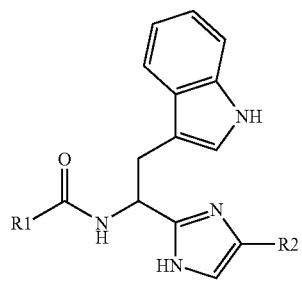
| | R1 | R2 | Analysis | |
|---|---|---|---|---|
| | | | Tr (min) | [M + H]+ |
| 1 | morpholine | (R) phenyl | 5.2 | 416.2 |
| 2 | thiazolidine | (R) phenyl | 5.5 | 418.1 |
| 3 | 4-hydroxypiperidine | (R) phenyl | 5.0 | 430.2 |
| 4 | piperidine-4-carboxamide | (R) phenyl | 5.0 | 457.2 |
| 5 | N-benzyl-N-(2-hydroxyethyl)amine | (R) phenyl | 5.9 | 480.2 |
| 6 | 4-phenylpiperazine | (R) phenyl | 6.1 | 491.2 |
| 7 | 2,3,4,9-tetrahydro-1H-β-carboline | (R) phenyl | 6.4 | 501.2 |
| 8 | 4-benzylpiperazine | (R) phenyl | 4.9 | 505.2 |
| 9 | 4-(4-fluorophenyl)piperazine | (R) phenyl | 6.3 | 509.2 |
| 10 | 4-(2-methoxyphenyl)piperazine | (R) phenyl | 5.9 | 521.2 |

-continued
FORMULA 53
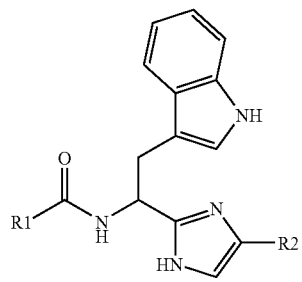
| | R1 | R2 | Analysis Tr (min) | [M + H]+ |
|---|---|---|---|---|
| 11 | N-piperazinyl-(3-chlorophenyl) | (R) phenyl | 6.7 | 525.2 |
| 12 | N(CH2Ph)2 * | (R) phenyl | 7.0 | 526.2 |
| 13 | N-piperazinyl-(4-nitrophenyl) | (R) phenyl | 6.3 | 536.2 |
| 14 | 6,7-dimethoxy-tetrahydroisoquinolinyl | (R) phenyl | 5.9 | 522.2 |
| 15 | N-piperazinyl-(4-chlorophenyl) | (R) phenyl | 6.7 | 525.2 |
| 16 | N-piperazinyl-(2-pyridyl) | (R) phenyl | 4.6 | 492.2 |
| 17 | 4-benzyl-piperidinyl | (R) phenyl | 6.9 | 504.2 |
| 18 | 1,4-dioxa-8-azaspiro[4.5]decyl | (R) phenyl | 5.4 | 472.2 |
| 19 | 4-hydroxy-4-phenyl-piperidinyl | (R) phenyl | 5.9 | 506.2 |

-continued

FORMULA 53

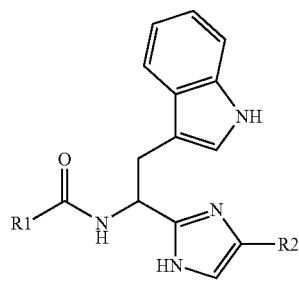

| | R1 | R2 | Analysis Tr (min) | [M + H]+ |
|---|---|---|---|---|
| 20 | ethyl 3-(N-benzyl-N-*)propanoate | (R) phenyl | 6.6 | 536.2 |
| 21 | 4-(benzo[d][1,3]dioxol-5-ylmethyl)piperazin-1-yl* | (R) phenyl | 4.9 | 549.2 |
| 22 | 4-(3-(trifluoromethyl)phenyl)piperazin-1-yl | (R) phenyl | 6.9 | 559.2 |
| 23 | 1-phenyl-4-oxo-1,3,8-triazaspiro[4.5]decan-8-yl* | (R) phenyl | 6.0 | 560.2 |
| 24 | 4-(2-chlorophenyl)piperazin-1-yl | (R) phenyl | 6.7 | 525.2 |
| 25 | 4-(4-hydroxyphenyl)piperazin-1-yl | (R) phenyl | 5.0 | 507.2 |
| 26 | 4-(2,4-dimethylphenyl)piperazin-1-yl | (R) phenyl | 6.9 | 519.2 |
| 27 | (3S)-3-hydroxypyrrolidin-1-yl, Chiral | (R) phenyl | 5.0 | 416.2 |

-continued
FORMULA 53
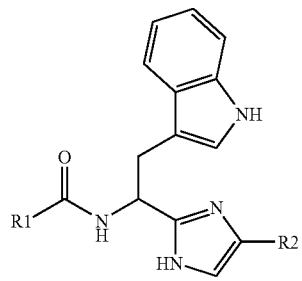
|  | R1 | R2 | Tr (min) | [M + H]+ |
|---|---|---|---|---|
| 28 | benzyl piperazine-1-carboxylate | (R) phenyl | 6.4 | 549.2 |
| 29 | 1-(piperidin-4-yl)-1,3-dihydro-2H-benzimidazol-2-one | (R) phenyl | 5.8 | 546.2 |
| 30 | furan-2-yl(piperazin-1-yl)methanone | (R) phenyl | 5.5 | 509.2 |
| 31 | N-(4-(benzylamino)butyl)benzamide | (R) phenyl | 6.8 | 611.2 |
| 32 | N-benzyl-2-(2-methoxyphenyl)ethanamine | (R) phenyl | 7.2 | 570.2 |
| 33 | 1-(4-methoxyphenyl)piperazine | (R) phenyl | 5.8 | 521.2 |

-continued
FORMULA 53
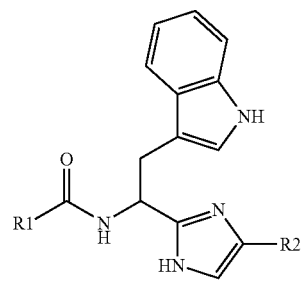
|    | R1                                    | R2       | Tr (min) | [M + H]+ |
|----|---------------------------------------|----------|----------|----------|
| 34 | piperazine-N-benzhydryl               | (R) phenyl | 5.8      | 581.2    |
| 35 | N,N-dimethylaminoethyl-N-benzyl       | (R) phenyl | 5.1      | 507.2    |
| 36 | bis(3-dimethylaminopropyl)amine       | (R) phenyl | 4.2      | 516.3    |
| 37 | 4-(2-fluorophenyl)piperazine          | (R) phenyl | 6.4      | 509.2    |
| 38 | 4-(2-methylthiophenyl)piperazine      | (R) phenyl | 6.7      | 537.2    |
| 39 | morpholine                            | (R,S) tert-butyl | 5.1 | 396.2    |
| 40 | thiazolidine                          | (R,S) tert-butyl | 5.4 | 398.2    |
| 41 | 4-hydroxypiperidine                   | (R,S) tert-butyl | 5.0 | 410.2    |

-continued
FORMULA 53
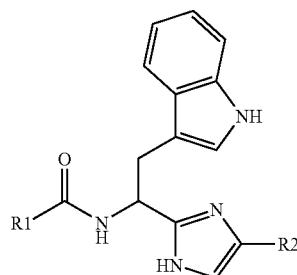
| | R1 | R2 | Tr (min) | [M + H]+ |
|---|---|---|---|---|
| 42 | H₂N-C(O)-piperidine-N→ | (R,S) tBu | 4.9 | 437.2 |
| 43 | HO-CH₂CH₂-N(*)-CH₂-Ph | (R,S) tBu | 5.8 | 460.2 |
| 44 | ←N-piperazine-N-phenyl | (R,S) tBu | 6.0 | 471.3 |
| 45 | tetrahydro-β-carboline-N→ | (R,S) tBu | 6.4 | 481.2 |
| 46 | ←N-piperazine-N-CH₂-Ph | (R,S) tBu | 4.8 | 485.3 |
| 47 | ←N-piperazine-N-C₆H₄-F | (R,S) tBu | 6.2 | 489.2 |
| 48 | ←N-piperazine-N-(2-OMe-C₆H₄) | (R,S) tBu | 5.8 | 501.3 |
| 49 | ←N-piperazine-N-(3-Cl-C₆H₄) | (R,S) tBu | 6.7 | 505.2 |
| 50 | Ph-CH₂-N(*)-CH₂-Ph | (R,S) tBu | 6.9 | 506.3 |
| 51 | ←N-piperazine-N-(4-NO₂-C₆H₄) | (R,S) tBu | 6.2 | 516.2 |

-continued

FORMULA 53

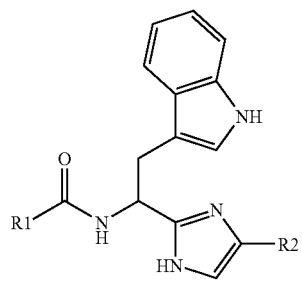

| | R1 | R2 | Analysis | |
|---|---|---|---|---|
| | | | Tr (min) | [M + H]+ |
| 52 | 6,7-dimethoxy-tetrahydroisoquinolin-2-yl | (R,S) t-Bu | 5.9 | 502.2 |
| 53 | 4-(4-chlorophenyl)piperazin-1-yl | (R,S) t-Bu | 6.6 | 505.2 |
| 54 | 4-(pyridin-2-yl)piperazin-1-yl | (R,S) t-Bu | 4.5 | 472.3 |
| 55 | 4-benzylpiperidin-1-yl | (R,S) t-Bu | 6.8 | 484.3 |
| 56 | 1,4-dioxa-8-azaspiro[4.5]decan-8-yl | (R,S) t-Bu | 5.3 | 452.3 |
| 57 | 4-hydroxy-4-phenylpiperidin-1-yl | (R,S) t-Bu | 5.8 | 486.3 |
| 58 | N-benzyl-N-(3-ethoxy-3-oxopropyl)amino | (R,S) t-Bu | 6.5 | 516.3 |
| 59 | 4-(benzo[d][1,3]dioxol-5-ylmethyl)piperazin-1-yl | (R,S) t-Bu | 4.8 | 529.2 |
| 60 | 4-(3-(trifluoromethyl)phenyl)piperazin-1-yl | (R,S) t-Bu | 6.9 | 539.2 |

-continued
FORMULA 53
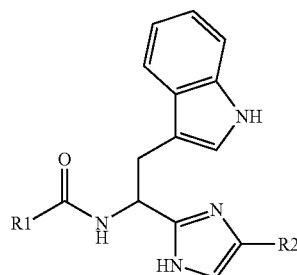
| | R1 | R2 | Tr (min) | [M + H]+ |
|---|---|---|---|---|
| 61 | piperazine-3-(trifluoromethyl)phenyl | (R,S) t-Bu | 6.0 | 540.2 |
| 62 | piperazine-2-chlorophenyl | (R,S) t-Bu | 6.6 | 505.2 |
| 63 | piperazine-4-hydroxyphenyl | (R,S) t-Bu | 4.9 | 487.3 |
| 64 | piperazine-2,4-dimethylphenyl | (R,S) t-Bu | 6.9 | 499.3 |
| 65 | (3-hydroxypyrrolidinyl) Chiral | (R,S) t-Bu | 4.9 | 396.2 |
| 66 | piperazine-N-Cbz | (R,S) t-Bu | 6.3 | 529.2 |
| 67 | 4-(2-oxo-benzimidazol-1-yl)piperidine | (R,S) t-Bu | 5.7 | 526.3 |
| 68 | piperazine-N-(2-furoyl) | (R,S) t-Bu | 5.4 | 489.2 |

-continued
FORMULA 53
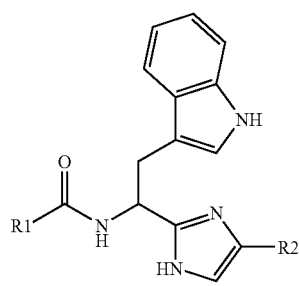
| | R1 | R2 | Analysis Tr (min) | [M + H]+ |
|---|---|---|---|---|
| 69 | ![benzamide-butyl-N-benzyl structure] | (R,S) ![t-Bu] | 6.7 | 591.3 |
| 70 | ![2-methoxyphenethyl-N-benzyl structure] | (R,S) ![t-Bu] | 7.2 | 550.3 |
| 71 | ![4-(4-methoxyphenyl)piperazine structure] | (R,S) ![t-Bu] | 5.7 | 501.3 |
| 72 | ![4-benzhydrylpiperazine structure] | (R,S) ![t-Bu] | 5.7 | 561.3 |
| 73 | ![N,N-dimethylaminoethyl-N-benzyl structure] | (R,S) ![t-Bu] | 5.0 | 487.3 |
| 74 | ![bis(3-dimethylaminopropyl)amine structure] | (R,S) ![t-Bu] | 4.1 | 496.4 |

-continued
FORMULA 53
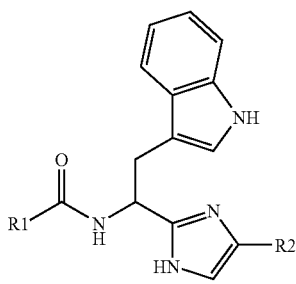
| | R1 | R2 | Analysis Tr (min) | [M + H]+ |
|---|---|---|---|---|
| 75 | (2-fluorophenyl)piperazine | (R,S) tert-butyl | 6.3 | 489.3 |
| 76 | (2-methylthiophenyl)piperazine | (R,S) tert-butyl | 6.7 | 517.2 |
FORMULA 54
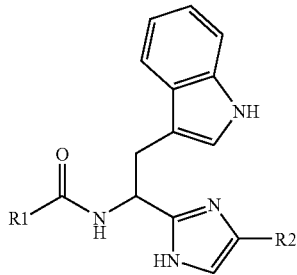
| | R1 | R2 | Analysis Tr (min) | [M + H]+ |
|---|---|---|---|---|
| 1 | 3-(dimethylamino)propylamino | (R) phenyl | 4.4 | 431.2 |
| 2 | cycloheptylamino | (R) phenyl | 6.3 | 442.2 |
| 3 | phenethylamino | (R) phenyl | 6.1 | 450.2 |

-continued
FORMULA 54
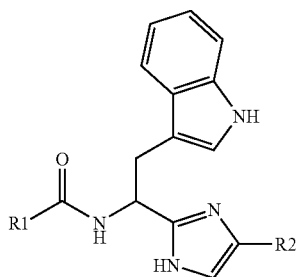
| | R1 | R2 | Analysis Tr (min) | [M + H]+ |
|---|---|---|---|---|
| 4 | HN-CH2-C6H4-OMe (4-methoxybenzyl) | (R) phenyl | 5.9 | 466.2 |
| 5 | N-CH2CH2-C6H4-OMe (2-methoxyphenethyl) | (R) phenyl | 6.2 | 480.2 |
| 6 | N-CH2CH2-C6H3(OMe)2 (3,4-dimethoxyphenethyl) | (R) phenyl | 5.9 | 510.2 |
| 7 | N-CH2CH2-imidazolyl | (R) phenyl | 4.5 | 440.2 |
| 8 | N-CH2-C6H2(OMe)3 (3,4,5-trimethoxybenzyl) | (R) phenyl | 5.8 | 526.2 |
| 9 | HN-CH2CH2-C6H4-NO2 (4-nitrophenethyl) | (R) phenyl | 6.1 | 495.2 |

-continued
FORMULA 54
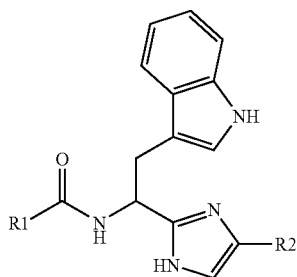
| | R1 | R2 | Analysis Tr (min) | [M + H]+ |
|---|---|---|---|---|
| 10 | neopentyl-CH2-N* | phenyl (R) | 6.3 | 430.3 |
| 11 | 4-pyridyl-CH2-N* | phenyl (R) | 4.5 | 437.2 |
| 12 | *N-CH2CH2-2-pyridyl | phenyl (R) | 4.5 | 451.2 |
| 13 | *N-(CH2)3-morpholine | phenyl (R) | 4.5 | 473.3 |
| 14 | ethyl 4-(N*)-piperidine-1-carboxylate | phenyl (R) | 5.7 | 501.3 |
| 15 | *HN-CH2CH2-NH-(5-nitro-2-pyridyl) | phenyl (R) | 5.8 | 511.2 |
| 16 | PhCH2-S-CH2CH2-N* | phenyl (R) | 6.4 | 496.2 |
| 17 | *N-CH2-(3,4-methylenedioxyphenyl) | phenyl (R) | 5.3 | 468.2 |
| 18 | 1,2-diethyl-4-(N*)-pyrazolidine | phenyl (R) | 4.7 | 472.3 |

-continued
FORMULA 54
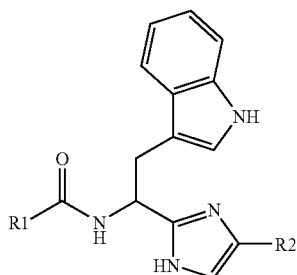
|  | R1 | R2 | Analysis Tr (min) | [M + H]+ |
|---|---|---|---|---|
| 19 | *tert*-butyl-N* | phenyl* (R) | 5.8 | 402.2 |
| 20 | 3-chlorophenyl-piperazinyl-ethyl-NH* | phenyl* (R) | 5.6 | 568.2 |
| 21 | diphenylmethyl-NH* | phenyl* (R) | 6.8 | 512.2 |
| 22 | *-HN-CH2-pyridin-2-yl | phenyl* (R) | 4.6 | 437.2 |
| 23 | *-HN-CH2-(3-chlorophenyl) | phenyl* (R) | 6.3 | 470.2 |
| 24 | 3,3-diphenylpropyl-NH* | phenyl* (R) | 7.0 | 540.2 |

FORMULA 54
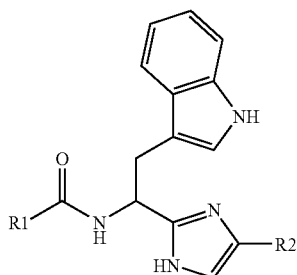
| | R1 | R2 | Tr (min) | [M + H]+ |
|---|---|---|---|---|
| 25 | HN-*-CH2CH2-C6H5 | (R) phenyl * | 6.4 | 464.2 |
| 26 | *-HN-CH2CH2-N(pyrrolidine) | (R) phenyl * | 4.5 | 443.3 |
| 27 | *-HN-CH2CH2-C6H4-Cl (4-Cl) | (R) phenyl * | 6.5 | 484.2 |
| 28 | NH-*-CH2CH2-C6H4-F (2-F) | (R) phenyl * | 6.2 | 468.2 |
| 29 | NH-*-CH2CH2-C6H4-F (4-F) | (R) phenyl * | 6.2 | 468.2 |
| 30 | NH-*-CH2CH2-C6H4-Cl (3-Cl) | (R) phenyl * | 6.5 | 484.2 |
| 31 | *-HN-CH2CH2-C6H4-Br (4-Br) | (R) phenyl * | 6.6 | 528.1 |

-continued
FORMULA 54
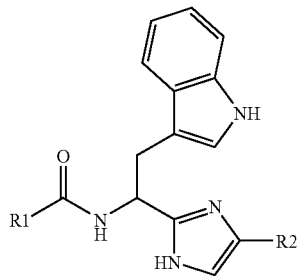
| | R1 | R2 | Tr (min) | [M + H]+ |
|---|---|---|---|---|
| 32 | HN-CH2-C6H4-CF3 (meta) * | phenyl (R) * | 6.5 | 504.2 |
| 33 | HN-CH2-C6H4-CF3 (para) * | phenyl (R) * | 6.5 | 504.2 |
| 34 | 3-pyridyl-CH2-NH * | phenyl (R) * | 4.5 | 437.2 |
| 35 | 2-methoxybenzyl-NH * | phenyl (R) * | 6.1 | 466.2 |
| 36 | HN-CH2-C6H4-Cl (ortho) * | phenyl (R) * | 6.2 | 470.2 |
| 37 | HN-CH2-C6H4-F (meta) * | phenyl (R) * | 6.0 | 454.2 |
| 38 | HN-CH2-C6H4-F (ortho) * | phenyl (R) * | 6.0 | 454.2 |
| 39 | HN-CH2-C6H4-F (para) * | phenyl (R) * | 6.0 | 454.2 |

-continued
FORMULA 54
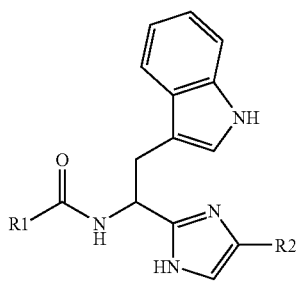
| | R1 | | R2 | Analysis | |
|---|---|---|---|---|---|
| | | | | Tr (min) | [M + H]+ |
| 40 | methylpiperazine-propyl-NH- | (R) | phenyl | 4.3 | 486.3 |
| 41 | dimethylamino-propyl-NH- | (R,S) | tert-butyl | 4.4 | 411.3 |
| 42 | cycloheptyl-NH- | (R,S) | tert-butyl | 6.3 | 422.3 |
| 43 | phenethyl-NH- | (R,S) | tert-butyl | 6.0 | 430.3 |
| 44 | (4-methoxybenzyl)-N- | (R,S) | tert-butyl | 5.9 | 446.2 |
| 45 | 2-(2-methoxyphenyl)ethyl-NH- | (R,S) | tert-butyl | 6.2 | 460.3 |
| 46 | 2-(3,4-dimethoxyphenyl)ethyl-NH- | (R,S) | tert-butyl | 5.8 | 490.3 |

-continued
FORMULA 54
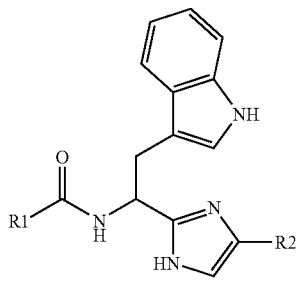
| | R1 | R2 | Analysis Tr (min) | [M + H]+ |
|---|---|---|---|---|
| 47 | HN—CH2CH2-(imidazole) | (R,S) t-Bu | 4.4 | 420.3 |
| 48 | HN—CH2-(3,4,5-trimethoxyphenyl) | (R,S) t-Bu | 5.7 | 506.3 |
| 49 | HN—CH2CH2-(4-nitrophenyl) | (R,S) t-Bu | 6.1 | 475.2 |
| 50 | neopentyl-CH2CH2-NH | (R,S) t-Bu | 6.2 | 410.3 |
| 51 | (4-pyridyl)-CH2-NH | (R,S) t-Bu | 4.4 | 417.2 |
| 52 | HN—CH2CH2-(2-pyridyl) | (R,S) t-Bu | 4.4 | 431.2 |
| 53 | HN—CH2CH2CH2-morpholine | (R,S) t-Bu | 4.4 | 453.3 |
| 54 | ethyl 4-amino-piperidine-1-carboxylate | (R,S) t-Bu | 5.7 | 481.3 |

-continued
FORMULA 54
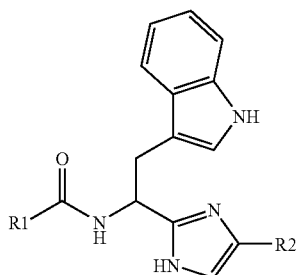
| | R1 | R2 | Analysis Tr (min) | [M + H]+ |
|---|---|---|---|---|
| 55 | (R,S) | | 5.7 | 491.2 |
| 56 | (R,S) | | 6.4 | 476.3 |
| 57 | (R,S) | | 5.2 | 448.2 |
| 58 | (R,S) | | 4.6 | 452.3 |
| 59 | (R,S) | | 5.7 | 382.3 |
| 60 | (R,S) | | 5.5 | 548.2 |
| 61 | (R,S) | | 6.7 | 492.3 |

-continued
FORMULA 54
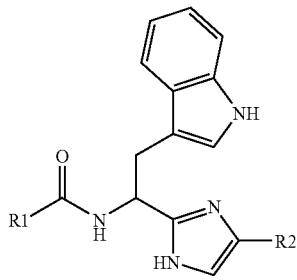
| | R1 | R2 | Tr (min) | [M + H]+ |
|---|---|---|---|---|
| 62 | *—HN—CH2-(2-pyridyl) | (R,S) tBu* | 4.5 | 417.2 |
| 63 | HN—CH2-(3-chlorophenyl)* | (R,S) tBu* | 6.2 | 450.2 |
| 64 | Ph2CH-CH2CH2-NH* | (R,S) tBu* | 7.0 | 520.3 |
| 65 | *HN-CH2CH2CH2-Ph | (R,S) tBu* | 6.3 | 444.3 |
| 66 | *HN-CH2CH2-(1-pyrrolidinyl) | (R,S) tBu* | 4.4 | 423.3 |
| 67 | *HN-CH2CH2-(4-chlorophenyl) | (R,S) tBu* | 6.4 | 464.2 |
| 68 | *NH-CH2CH2-(2-fluorophenyl) | (R,S) tBu* | 6.1 | 448.2 |

-continued
FORMULA 54
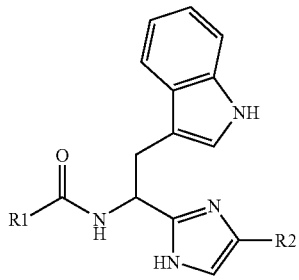
| | R1 | R2 | Analysis Tr (min) | [M + H]+ |
|---|---|---|---|---|
| 69 | 4-F-C6H4-CH2CH2-NH-* | (R,S) t-Bu-* | 6.2 | 448.2 |
| 70 | 3-Cl-C6H4-CH2CH2-NH-* | (R,S) t-Bu-* | 6.4 | 464.2 |
| 71 | 4-Br-C6H4-CH2CH2-NH-* | (R,S) t-Bu-* | 6.5 | 510.1 |
| 72 | 3-CF3-C6H4-CH2-NH-* | (R,S) t-Bu-* | 6.5 | 484.2 |
| 73 | 4-CF3-C6H4-CH2-NH-* | (R,S) t-Bu-* | 6.5 | 484.2 |
| 74 | 3-pyridyl-CH2-NH-* | (R,S) t-Bu-* | 4.4 | 417.2 |

-continued
FORMULA 54
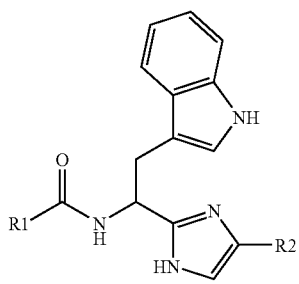
|  | R1 | | R2 | Tr (min) | [M + H]+ |
|---|---|---|---|---|---|
| 75 | 2-methoxybenzyl-NH- | (R,S) | t-Bu | 6.0 | 446.2 |
| 76 | 2-chlorobenzyl-NH- | (R,S) | t-Bu | 6.2 | 450.2 |
| 77 | 3-fluorobenzyl-NH- | (R,S) | t-Bu | 6.0 | 434.2 |
| 78 | 2-fluorobenzyl-NH- | (R,S) | t-Bu | 5.9 | 434.2 |
| 79 | 4-fluorobenzyl-NH- | (R,S) | t-Bu | 6.0 | 434.2 |
| 80 | 4-methylpiperazinyl-propyl-NH- | (R,S) | t-Bu | 4.1 | 466.3 |

FORMULA 55
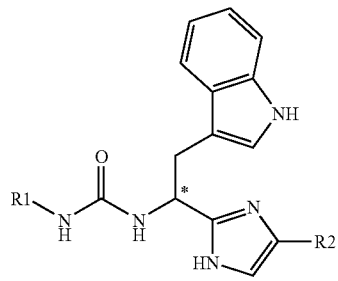
| | R1 | R2 | Analysis | |
|---|---|---|---|---|
| | | | Tr (min) | [M + H]+ |
| 1 | 2-Cl-phenyl | 2-OMe-phenyl (R, S) | 6.4 | 486.2 |
| 2 | 3-Cl-phenyl | 2-OMe-phenyl (R, S) | 6.6 | 486.2 |
| 3 | 4-Cl-phenyl | 2-OMe-phenyl (R, S) | 6.6 | 486.2 |
| 4 | 2-Br-phenyl | 2-OMe-phenyl (R, S) | 6.4 | 530.1 |
| 5 | 3-Br-phenyl | 2-OMe-phenyl (R, S) | 6.7 | 530.1 |
| 6 | 4-Br-phenyl | 2-OMe-phenyl (R, S) | 6.6 | 530.1 |
| 7 | 3-F-phenyl | 2-OMe-phenyl (R, S) | 6.3 | 470.2 |

-continued
FORMULA 55
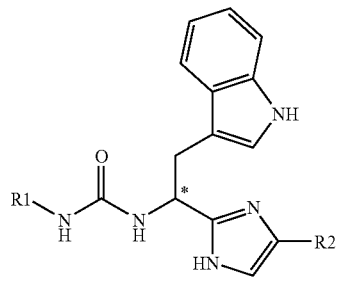
| | R1 | R2 | Analysis Tr (min) | [M + H]+ |
|---|---|---|---|---|
| 8 | 2,4-difluorophenyl (R, S) | 2-OMe-phenyl | 6.3 | 488.2 |
| 9 | 2,5-difluorophenyl (R, S) | 2-OMe-phenyl | 6.4 | 488.2 |
| 10 | 2-NO2-phenyl (R, S) | 2-OMe-phenyl | 6.3 | 497.2 |
| 11 | 3-NO2-phenyl (R, S) | 2-OMe-phenyl | 6.4 | 497.2 |
| 12 | 4-NO2-phenyl (R, S) | 2-OMe-phenyl | 6.4 | 497.2 |
| 13 | 2-CF3-phenyl (R, S) | 2-OMe-phenyl | 6.4 | 520.2 |
| 14 | 3-CF3-phenyl (R, S) | 2-OMe-phenyl | 6.8 | 520.2 |

-continued
FORMULA 55
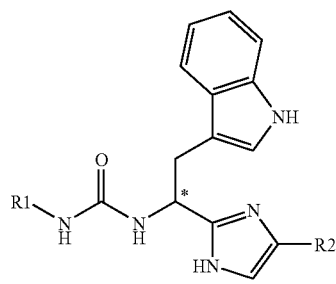
| | R1 | R2 | Tr (min) | [M + H]+ |
|---|---|---|---|---|
| 15 | 3-CF3-phenyl (R,S) | 2-OMe-phenyl | 6.8 | 520.2 |
| 16 | 2,5-diMeO-phenyl (R,S) | 2-OMe-phenyl | 6.3 | 512.2 |
| 17 | 3-OMe-phenyl (R,S) | 2-OMe-phenyl | 6.2 | 482.2 |
| 18 | 4-OMe-phenyl (R,S) | 2-OMe-phenyl | 6.1 | 482.2 |
| 19 | 4-Cl-2-CF3-phenyl (R,S) | 2-OMe-phenyl | 6.8 | 554.1 |
| 20 | 4-F-3-NO2-phenyl (R,S) | 2-OMe-phenyl | 6.4 | 515.1 |
| 21 | 2-Cl-phenyl (R,S) | 4-Br-phenyl | 6.7 | 534.0 |
| 22 | 3-Cl-phenyl (R,S) | 4-Br-phenyl | 6.9 | 534.0 |

-continued
FORMULA 55
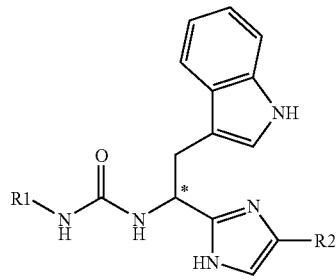
| | R1 | | R2 | Tr (min) | [M + H]+ |
|---|---|---|---|---|---|
| 23 | 4-Cl-C6H4 | (R, S) | 4-Br-C6H4 | 6.8 | 534.0 |
| 24 | 2-Br-C6H4 | (R, S) | 4-Br-C6H4 | 6.7 | 578.0 |
| 25 | 3-Br-C6H4 | (R, S) | 4-Br-C6H4 | 6.9 | 578.0 |
| 26 | 4-Br-C6H4 | (R, S) | 4-Br-C6H4 | 6.9 | 578.0 |
| 27 | 3-F-C6H4 | (R, S) | 4-Br-C6H4 | 6.6 | 518.1 |
| 28 | 2,4-F2-C6H3 | (R, S) | 4-Br-C6H4 | 6.6 | 536.1 |
| 29 | 2,5-F2-C6H3 | (R, S) | 4-Br-C6H4 | 6.7 | 536.1 |
| 30 | 2-NO2-C6H4 | (R, S) | 4-Br-C6H4 | 6.6 | 545.0 |
| 31 | 3-NO2-C6H4 | (R, S) | 4-Br-C6H4 | 6.7 | 545.0 |

-continued
FORMULA 55
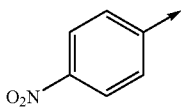
| | R1 | | R2 | Analysis | |
|---|---|---|---|---|---|
| | | | | Tr (min) | [M + H]+ |
| 32 | 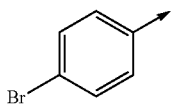 | (R, S) | 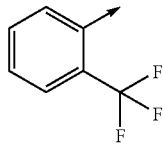 | 6.7 | 545.0 |
| 33 | 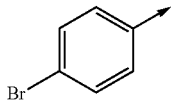 | (R, S) | 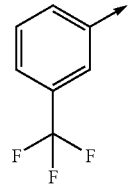 | 6.7 | 568.0 |
| 34 | 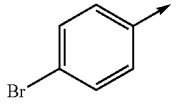 | (R, S) | 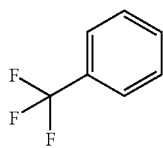 | 7.1 | 568.0 |
| 35 | 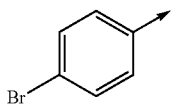 | (R, S) | 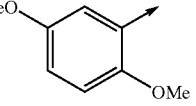 | 7.1 | 568.0 |
| 36 | 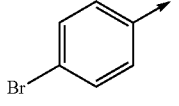 | (R, S) | 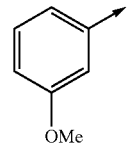 | 6.6 | 560.1 |
| 37 | 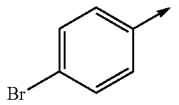 | (R, S) | 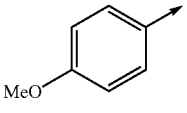 | 6.5 | 530.1 |
| 38 | 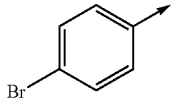 | (R, S) | 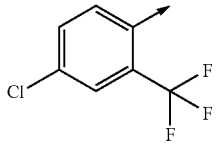 | 6.4 | 530.1 |
| 39 | 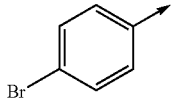 | (R, S) | | 7.1 | 602.0 |

-continued
FORMULA 55
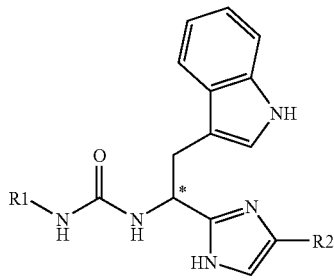
| | R1 | | R2 | Analysis | |
|---|---|---|---|---|---|
| | | | | Tr (min) | [M + H]+ |
| 40 | 4-F, 3-NO$_2$-phenyl | (R, S) | 4-Br-phenyl | 6.7 | 563.0 |
| 41 | 2-Cl-phenyl | (R, S) | 4-O$_2$N-phenyl | 6.6 | 501.1 |
| 42 | 3-Cl-phenyl | (R, S) | 4-O$_2$N-phenyl | 6.8 | 501.1 |
| 43 | 4-Cl-phenyl | (R, S) | 4-O$_2$N-phenyl | 6.8 | 501.1 |
| 44 | 2-Br-phenyl | (R, S) | 4-O$_2$N-phenyl | 6.7 | 545.0 |
| 45 | 3-Br-phenyl | (R, S) | 4-O$_2$N-phenyl | 6.9 | 545.0 |
| 46 | 4-Br-phenyl | (R, S) | 4-O$_2$N-phenyl | 6.9 | 545.0 |
| 47 | 3-F-phenyl | (R, S) | 4-O$_2$N-phenyl | 6.5 | 485.1 |

-continued
FORMULA 55
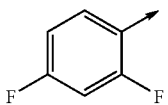
| | R1 | | R2 | Analysis | |
|---|---|---|---|---|---|
| | | | | Tr (min) | [M + H]+ |
| 48 | 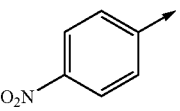 | (R, S) | 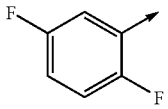 | 6.5 | 503.2 |
| 49 | 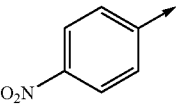 | (R, S) | 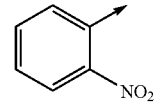 | 6.7 | 503.2 |
| 50 | 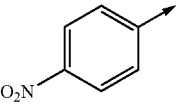 | (R, S) | 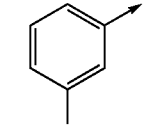 | 6.6 | 512.2 |
| 51 | 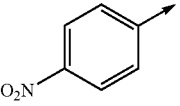 | (R, S) | 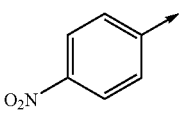 | 6.6 | 512.2 |
| 52 | 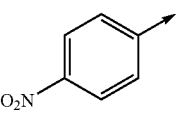 | (R, S) | 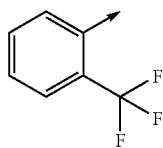 | 6.6 | 512.2 |
| 53 | 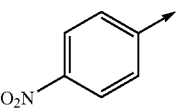 | (R, S) | 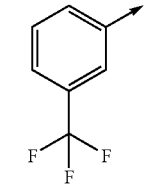 | 6.7 | 535.1 |
| 54 | 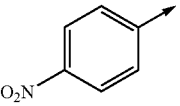 | (R, S) | 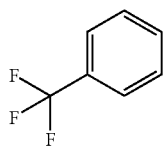 | 7.1 | 535.1 |
| 55 | 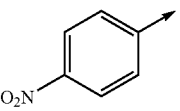 | (R, S) |  | 7.1 | 535.1 |

-continued
FORMULA 55
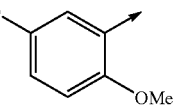
| | R1 | | R2 | Analysis Tr (min) | [M + H]+ |
|---|---|---|---|---|---|
| 56 | MeO-, OMe (phenyl) | (R, S) | O₂N-phenyl | 6.4 | 527.2 |
| 57 | OMe-phenyl (meta) | (R, S) | O₂N-phenyl | 6.3 | 497.2 |
| 58 | MeO-phenyl (para) | (R, S) | O₂N-phenyl | 6.2 | 497.2 |
| 59 | Cl, CF₃-phenyl | (R, S) | O₂N-phenyl | 7.2 | 569.1 |
| 60 | F, NO₂-phenyl | (R, S) | O₂N-phenyl | 6.7 | 530.1 |
| 61 | Cl-phenyl (ortho) | (R, S) | NEt₂-phenyl | 5.9 | 527.2 |
| 62 | Cl-phenyl (meta) | (R, S) | NEt₂-phenyl | 6.2 | 527.2 |

-continued
FORMULA 55
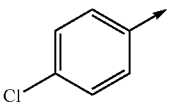
| | R1 | R2 | Analysis Tr (min) | [M + H]+ |
|---|---|---|---|---|
| 63 | 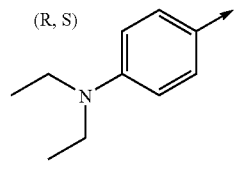 | (R, S) 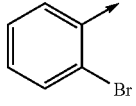 | 6.1 | 527.2 |
| 64 | 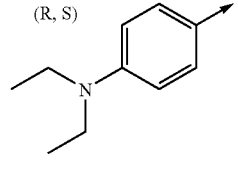 | (R, S) 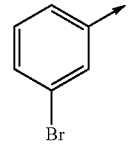 | 5.9 | 571.1 |
| 65 | 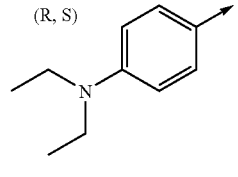 | (R, S) 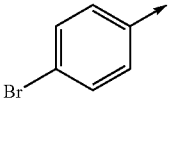 | 6.3 | 571.1 |
| 66 | 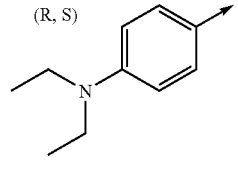 | (R, S) 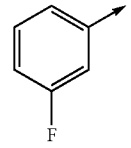 | 6.2 | 571.1 |
| 67 | 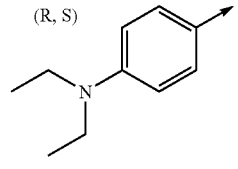 | (R, S) 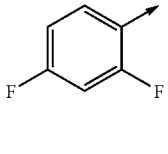 | 5.9 | 511.3 |
| 68 | 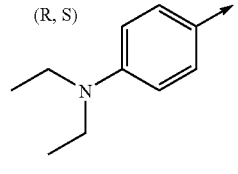 | (R, S) 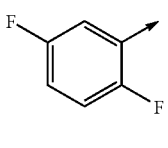 | 5.8 | 529.2 |
| 69 | 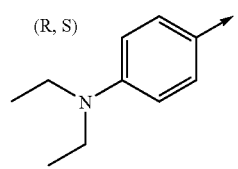 | (R, S) | 6.0 | 529.2 |

-continued
FORMULA 55
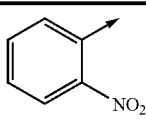
| | R1 | R2 | Analysis Tr (min) | [M + H]+ |
|---|---|---|---|---|
| 70 | 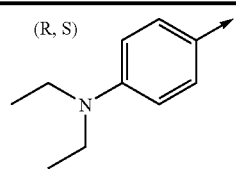 | (R, S) 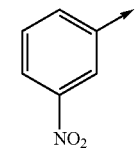 | 5.8 | 538.2 |
| 71 | 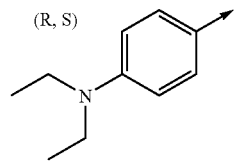 | (R, S) 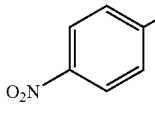 | 5.9 | 538.2 |
| 72 | 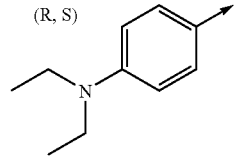 | (R, S) 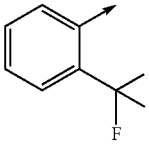 | 6.0 | 538.2 |
| 73 | 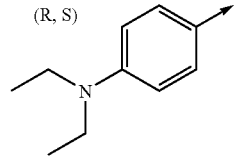 | (R, S) 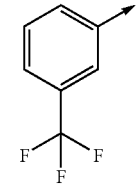 | 6.0 | 561.2 |
| 74 | 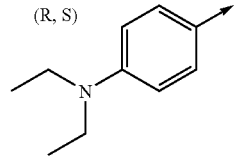 | (R, S) 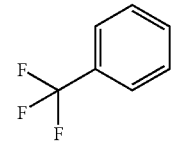 | 6.4 | 561.2 |
| 75 | 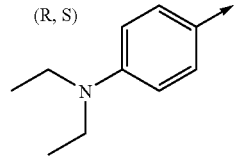 | (R, S) 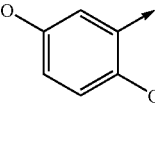 | 6.5 | 561.0 |
| 76 | MeO 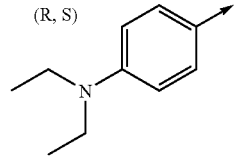 OMe | (R, S) | 5.8 | 553.3 |

-continued
FORMULA 55
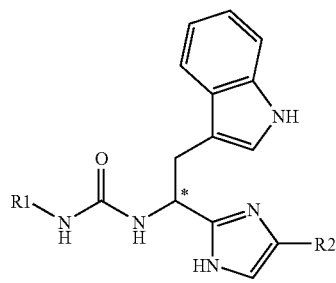
| | R1 | R2 | Analysis Tr (min) | [M + H]+ |
|---|---|---|---|---|
| 77 | 3-OMe-phenyl | (R, S) 4-(NEt₂)-phenyl | 5.7 | 523.3 |
| 78 | 4-MeO-phenyl | (R, S) 4-(NEt₂)-phenyl | 5.6 | 523.3 |
| 79 | 4-Cl-2-CF₃-phenyl | (R, S) 4-(NEt₂)-phenyl | 6.5 | 595.2 |
| 80 | 4-F-3-NO₂-phenyl | (R, S) 4-(NEt₂)-phenyl | 6.0 | 556.2 |

FORMULA 56
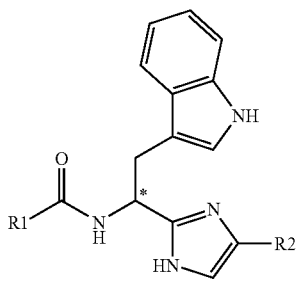
| | R1 | R2 | Tr (min) | [M + H]+ |
|---|---|---|---|---|
| 1 | 2-Cl-benzyl | 2-OMe-phenyl (R, S) | 5.6 | 485.2 |
| 2 | 3-Cl-benzyl | 2-OMe-phenyl (R, S) | 5.8 | 485.2 |
| 3 | 4-Cl-benzyl | 2-OMe-phenyl (R, S) | 6.0 | 485.2 |
| 4 | 2-Br-benzyl | 2-OMe-phenyl (R, S) | 5.8 | 529.2 |
| 5 | 3-Br-benzyl | 2-OMe-phenyl (R, S) | 6.0 | 529.2 |
| 6 | 4-Br-benzyl | 2-OMe-phenyl (R, S) | 6.0 | 529.2 |
| 7 | 2-F-benzyl | 2-OMe-phenyl (R, S) | 5.5 | 469.2 |

-continued
FORMULA 56
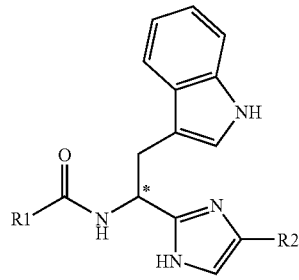
|  | R1 | R2 | Analysis Tr (min) | [M + H]+ |
|---|---|---|---|---|
| 8 | 3-F-C6H4-CH2- | 2-OMe-C6H4- (R, S) | 5.7 | 469.3 |
| 9 | 4-F-C6H4-CH2- | 2-OMe-C6H4- (R, S) | 5.6 | 469.2 |
| 10 | 2-NO2-C6H4-CH2- | 2-OMe-C6H4- (R, S) | 5.5 | 496.3 |
| 11 | 3-NO2-C6H4-CH2- | 2-OMe-C6H4- (R, S) | 5.6 | 496.3 |
| 12 | 4-NO2-C6H4-CH2- | 2-OMe-C6H4- (R, S) | 5.6 | 496.3 |
| 13 | 2-CF3-C6H4-CH2- | 2-OMe-C6H4- (R, S) | 6.0 | 519.2 |
| 14 | 3-CF3-C6H4-CH2- | 2-OMe-C6H4- (R, S) | 6.2 | 519.2 |

-continued
FORMULA 56
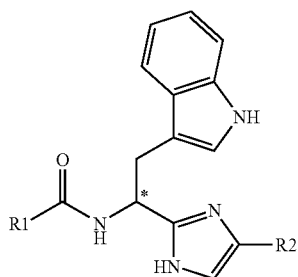
| | R1 | R2 | Tr (min) | [M + H]+ |
|---|---|---|---|---|
| 15 | 4-CF3-benzyl | 2-OMe-phenyl (R, S) | 6.2 | 519.2 |
| 16 | 2-OMe-benzyl | 2-OMe-phenyl (R, S) | 5.5 | 481.1 |
| 17 | 3-OMe-benzyl | 2-OMe-phenyl (R, S) | 5.5 | 481.2 |
| 18 | 4-OMe-benzyl | 2-OMe-phenyl (R, S) | 5.4 | 481.2 |
| 19 | benzyl | 2-OMe-phenyl (R, S) | 5.4 | 451.2 |
| 20 | 4-NMe2-benzyl | 2-OMe-phenyl (R, S) | 4.3 | 494.2 |
| 21 | 2-Cl-benzyl | 4-Br-phenyl (R, S) | 6.1 | 533.1 |
| 22 | 3-Cl-benzyl | 4-Br-phenyl (R, S) | 6.1 | 533.1 |

-continued
FORMULA 56
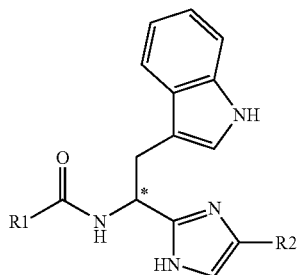
| | R1 | | R2 | Analysis | |
|---|---|---|---|---|---|
| | | | | Tr (min) | [M + H]+ |
| 23 | 4-Cl-benzyl | (R, S) | 4-Br-phenyl | 6.3 | 533.1 |
| 24 | 2-Br-benzyl | (R, S) | 4-Br-phenyl | 6.1 | 577.0 |
| 25 | 3-Br-benzyl | (R, S) | 4-Br-phenyl | 6.3 | 577.0 |
| 26 | 4-Br-benzyl | (R, S) | 4-Br-phenyl | 6.3 | 577.0 |
| 27 | 2-F-benzyl | (R, S) | 4-Br-phenyl | 5.9 | 517.1 |
| 28 | 3-F-benzyl | (R, S) | 4-Br-phenyl | 6.0 | 517.1 |
| 29 | 4-F-benzyl | (R, S) | 4-Br-phenyl | 6.0 | 517.1 |
| 30 | 2-NO2-benzyl | (R, S) | 4-Br-phenyl | 5.8 | 544.1 |
| 31 | 3-NO2-benzyl | (R, S) | 4-Br-phenyl | 6.0 | 544.1 |

-continued
FORMULA 56
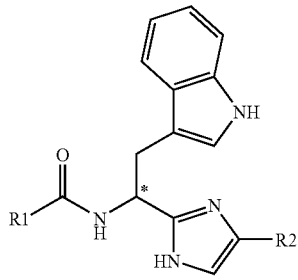
| | R1 | R2 | Tr (min) | [M + H]+ |
|---|---|---|---|---|
| 32 | 4-O₂N-C₆H₄-CH₂- (R, S) | 4-Br-C₆H₄- | 6.0 | 544.1 |
| 33 | 2-CF₃-C₆H₄-CH₂- (R, S) | 4-Br-C₆H₄- | 6.3 | 567.1 |
| 34 | 3-CF₃-C₆H₄-CH₂- (R, S) | 4-Br-C₆H₄- | 6.5 | 567.1 |
| 35 | 4-CF₃-C₆H₄-CH₂- (R, S) | 4-Br-C₆H₄- | 6.5 | 567.1 |
| 36 | 2-MeO-C₆H₄-CH₂- (R, S) | 4-Br-C₆H₄- | 5.9 | 529.1 |
| 37 | 3-MeO-C₆H₄-CH₂- (R, S) | 4-Br-C₆H₄- | 5.9 | 529.1 |
| 38 | 4-MeO-C₆H₄-CH₂- (R, S) | 4-Br-C₆H₄- | 5.9 | 529.1 |
| 39 | C₆H₅-CH₂- (R, S) | 4-Br-C₆H₄- | 5.9 | 499.1 |

-continued
FORMULA 56
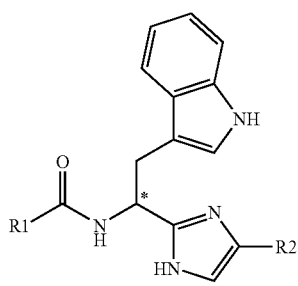
| | R1 | R2 | Tr (min) | [M + H]+ |
|---|---|---|---|---|
| 40 | 4-dimethylamino-benzyl (R, S) | 4-Br-phenyl | 4.7 | 542.1 |
| 41 | 2-Cl-benzyl (R, S) | 4-O₂N-phenyl | 6.2 | 500.2 |
| 42 | 3-Cl-benzyl (R, S) | 4-O₂N-phenyl | 6.4 | 500.2 |
| 43 | 4-Cl-benzyl (R, S) | 4-O₂N-phenyl | 6.9 | 500.1 |
| 44 | 2-Br-benzyl (R, S) | 4-O₂N-phenyl | 6.8 | 544.0 |
| 45 | 3-Br-benzyl (R, S) | 4-O₂N-phenyl | 7.0 | 544.0 |
| 46 | 4-HO-phenethyl-NHC(O)- (R, S) | 4-O₂N-phenyl | 7.0 | 544.0 |
| 47 | 2-F-benzyl (R, S) | 4-O₂N-phenyl | 6.5 | 484.2 |
| 48 | 3-F-benzyl (R, S) | 4-O₂N-phenyl | 6.6 | 484.2 |

-continued
FORMULA 56
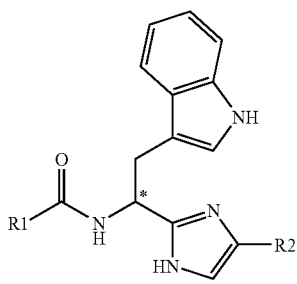
| | R1 | | R2 | Tr (min) | [M + H]+ |
|---|---|---|---|---|---|
| 49 | 4-F-benzyl | (R, S) | 4-O2N-phenyl | 6.6 | 484.2 |
| 50 | 2-NO2-benzyl | (R, S) | 4-O2N-phenyl | 6.4 | 511.2 |
| 51 | 3-NO2-benzyl | (R, S) | 4-O2N-phenyl | 6.6 | 511.2 |
| 52 | 4-NO2-benzyl | (R, S) | 4-O2N-phenyl | 6.6 | 511.2 |
| 53 | 2-CF3-benzyl | (R, S) | 4-O2N-phenyl | 7.0 | 534.1 |
| 54 | 3-CF3-benzyl | (R, S) | 4-O2N-phenyl | 7.1 | 534.1 |
| 55 | 4-CF3-benzyl | (R, S) | 4-O2N-phenyl | 7.2 | 534.1 |
| 56 | 2-OMe-benzyl | (R, S) | 4-O2N-phenyl | 6.6 | 496.2 |

-continued
FORMULA 56
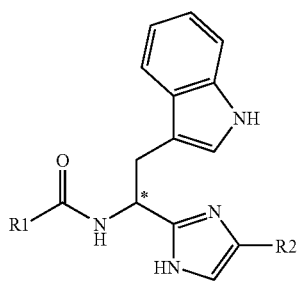
| | R1 | | R2 | Analysis Tr (min) | [M + H]+ |
|---|---|---|---|---|---|
| 57 | 3-MeO-benzyl | (R, S) | 4-O₂N-phenyl | 6.5 | 496.2 |
| 58 | 4-MeO-benzyl | (R, S) | 4-O₂N-phenyl | 6.5 | 496.2 |
| 59 | benzyl | (R, S) | 4-O₂N-phenyl | 6.5 | 466.2 |
| 60 | 4-(Me₂N)-benzyl | (R, S) | 4-O₂N-phenyl | 5.4 | 509.2 |
| 61 | 2-Cl-benzyl | (R, S) | 4-(Et₂N)-phenyl | 5.8 | 526.2 |
| 62 | 3-Cl-benzyl | (R, S) | 4-(Et₂N)-phenyl | 6.0 | 526.3 |
| 63 | 4-Cl-benzyl | (R, S) | 4-(Et₂N)-phenyl | 6.0 | 526.3 |

-continued
FORMULA 56
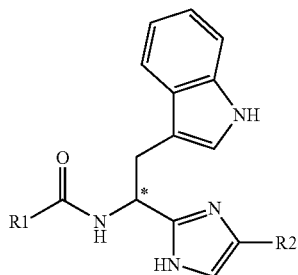
| | R1 | R2 | Analysis Tr (min) | [M + H]+ |
|---|---|---|---|---|
| 64 | 2-Br-benzyl | (R, S) 4-(N,N-diethylamino)phenyl | 5.9 | 570.2 |
| 65 | 3-Br-benzyl | (R, S) 4-(N,N-diethylamino)phenyl | 6.1 | 570.1 |
| 66 | 4-Br-benzyl | (R, S) 4-(N,N-diethylamino)phenyl | 6.1 | 570.1 |
| 67 | 2-F-benzyl | (R, S) 4-(N,N-diethylamino)phenyl | 5.6 | 510.3 |
| 68 | 3-F-benzyl | (R, S) 4-(N,N-diethylamino)phenyl | 5.7 | 510.3 |
| 69 | 2-NO$_2$-benzyl | (R, S) 4-(N,N-diethylamino)phenyl | 5.6 | 537.2 |
| 70 | 3-NO$_2$-benzyl | (R, S) 4-(N,N-diethylamino)phenyl | 5.7 | 537.2 |

-continued
FORMULA 56
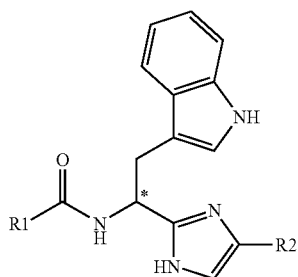
| | R1 | R2 | Analysis Tr (min) | [M + H]+ |
|---|---|---|---|---|
| 71 | 4-O₂N-C₆H₄-CH₂- | (R, S) 4-(Et₂N)-C₆H₄- | 5.7 | 537.3 |
| 72 | 2-CF₃-C₆H₄-CH₂- | (R, S) 4-(Et₂N)-C₆H₄- | 6.1 | 560.2 |
| 73 | 3-CF₃-C₆H₄-CH₂- | (R, S) 4-(Et₂N)-C₆H₄- | 6.2 | 560.2 |
| 74 | 4-CF₃-C₆H₄-CH₂- | (R, S) 4-(Et₂N)-C₆H₄- | 6.3 | 560.2 |
| 75 | 2-MeO-C₆H₄-CH₂- | (R, S) 4-(Et₂N)-C₆H₄- | 5.7 | 522.3 |
| 76 | 3-MeO-C₆H₄-CH₂- | (R, S) 4-(Et₂N)-C₆H₄- | 5.6 | 522.3 |
| 77 | 4-MeO-C₆H₄-CH₂- | (R, S) 4-(Et₂N)-C₆H₄- | 5.6 | 522.3 |

-continued
FORMULA 56
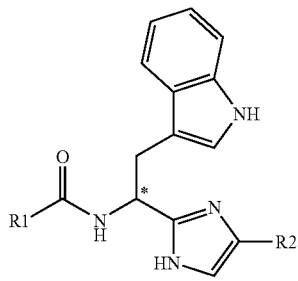
| | R1 | R2 | Tr (min) | [M + H]+ |
|---|---|---|---|---|
| 78 | benzyl | (R, S) 4-(diethylamino)phenyl | 5.6 | 492.3 |
| 79 | 4-(dimethylamino)benzyl | (R, S) 4-(diethylamino)phenyl | 4.7 | 535.3 |
FORMULA 57
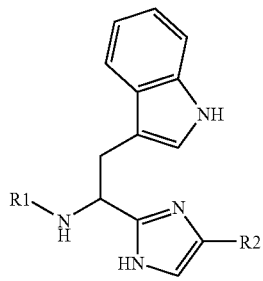
| | R1 | R2 | Tr (min) | [M + H]+ |
|---|---|---|---|---|
| 1 | cyclopentyl-NH-C(O)- | (R) phenyl | 14.4 | 414.2 |
| 2 | HO-(CH2)4-NH-C(O)- | (R) phenyl | 6.4 | 418.2 |
| 3 | Et2N-CH2CH2-NH-C(O)- | (R) phenyl | 11.1 | 445.3 |

-continued
FORMULA 57
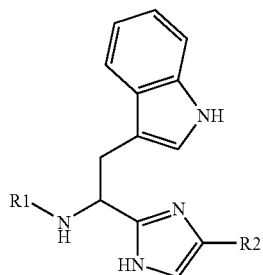
| | R1 | R2 | Tr (min) | [M + H]+ |
|---|---|---|---|---|
| 4 | N-methylpyrrolidin-2-yl-ethyl-NHC(O)- (R) | phenyl | 10.8 | 457.3 |
| 5 | (EtO)₂CHCH₂NHC(O)- (R) | phenyl | 14.3 | 462.2 |
| 6 | PhOCH₂CH₂NHC(O)- (R) | phenyl | 14.5 | 466.1 |
| 7 | indol-3-yl-ethyl-NHC(O)- (R) | phenyl | 14.5 | 489.2 |
| 8 | 1-benzylpiperidin-4-yl-NHC(O)- (R) | phenyl | 12.2 | 519.4 |
| 9 | 4-HO-C₆H₄-CH₂CH₂-NHC(O)- (R) | phenyl | 10.1 | 466.1 |
| 10 | naphth-1-yl-CH₂-NHC(O)- (R) | phenyl | 14.8 | 486.1 |
| 11 | morpholin-4-yl-ethyl-NHC(O)- (R) | phenyl | 12.1 | 459.3 |

-continued
FORMULA 57
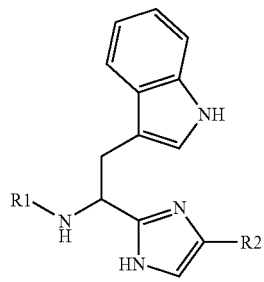
|    | R1 | R2 | Tr (min) | [M + H]+ |
|----|----|----|----------|----------|
| 12 | (piperonyl-CH2-NHC(O)-) (R) | phenyl | 14.4 | 480.1 |
| 13 | (1,2,3,4-tetrahydronaphthalen-1-yl-NHC(O)-) (R) | phenyl | 14.8 | 476.1 |
| 14 | (thiophen-2-yl-CH2-NHC(O)-) (R) | phenyl | 14.4 | 442.1 |
| 15 | (2-CF3-C6H4-CH2-NHC(O)-) (R) | phenyl | 14.8 | 504.1 |
| 16 | (4-Cl-C6H4-CH2-NHC(O)-) (R) | phenyl | 14.7 | 470.1 |
| 17 | (2-(2-hydroxymethylphenylthio)benzyl-NHC(O)-) (R) | phenyl | 14.7 | 574.1 |

-continued
FORMULA 57
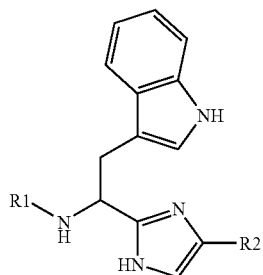
| | R1 | R2 | Tr (min) | [M + H]+ |
|---|---|---|---|---|
| 18 | (R) diphenylethyl-NH-C(O)- | phenyl | 15.0 | 526.2 |
| 19 | (R) imidazolyl-propyl-NH-C(O)- | phenyl | 12.0 | 454.3 |
| 20 | (R) 4-sulfamoylphenethyl-NH-C(O)- | phenyl | 8.0 | 529.1 |
| 21 | (S) cyclopentyl-NH-C(O)- | phenyl | 14.4 | 414.2 |
| 22 | (S) HO-(CH2)4-NH-C(O)- | phenyl | 6.3 | 418.2 |
| 23 | (S) Et2N-CH2CH2-NH-C(O)- | phenyl | 11.3 | 445.3 |
| 24 | (S) N-methylpyrrolidinyl-ethyl-NH-C(O)- | phenyl | 10.7 | 457.3 |
| 25 | (S) (EtO)2CH-CH2-NH-C(O)- | phenyl | 14.3 | 462.2 |

-continued
FORMULA 57
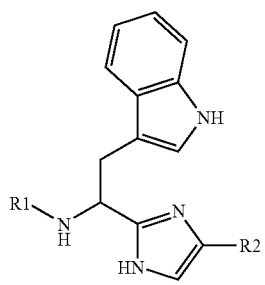
| | R1 | R2 | Analysis Tr (min) | [M + H]+ |
|---|---|---|---|---|
| 26 | PhO-CH2CH2-NH-C(=O)- (S) | Ph | 14.6 | 466.1 |
| 27 | (indol-3-yl)-CH2CH2-NH-C(=O)- (S) | Ph | 14.5 | 489.2 |
| 28 | 1-benzylpiperidin-4-yl-NH-C(=O)- (S) | Ph | 12.2 | 519.2 |
| 29 | 4-HO-C6H4-CH2CH2-NH-C(=O)- (S) | Ph | 11.7 | 466.1 |
| 30 | (naphth-1-yl)-CH2-NH-C(=O)- (S) | Ph | 14.8 | 486.1 |
| 31 | morpholino-CH2CH2-NH-C(=O)- (S) | Ph | 12.0 | 459.3 |
| 32 | (1,3-benzodioxol-5-yl)-CH2-NH-C(=O)- (S) | Ph | 14.4 | 480.1 |

-continued
FORMULA 57
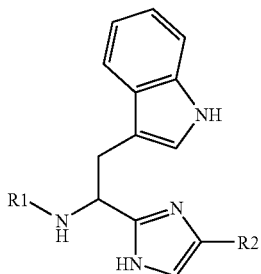
| | R1 | R2 | Tr (min) | [M + H]+ |
|---|---|---|---|---|
| 33 | (tetrahydronaphthalenyl-NHC(O)-) | (S) phenyl | 14.8 | 476.2 |
| 34 | (thiophen-2-ylmethyl-NHC(O)-) | (S) phenyl | 14.4 | 442.1 |
| 35 | (2-CF3-benzyl-NHC(O)-) | (S) phenyl | 14.7 | 504.1 |
| 36 | (4-Cl-benzyl-NHC(O)-) | (S) phenyl | 14.7 | 470.1 |
| 37 | (2-(2-hydroxymethylphenylthio)benzyl-NHC(O)-) | (S) phenyl | 14.7 | 574.1 |
| 38 | (2,2-diphenylethyl-NHC(O)-) | (S) phenyl | 14.9 | 526.2 |

-continued
FORMULA 57
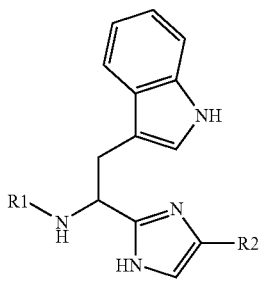
| | R1 | R2 | Analysis Tr (min) | [M + H]+ |
|---|---|---|---|---|
| 39 | imidazole-propyl-NHC(O)- (S) | phenyl | 11.8 | 454.3 |
| 40 | 4-sulfamoylphenyl-ethyl-NHC(O)- (S) | phenyl | 8.5 | 529.1 |
| 41 | cyclopentyl-NHC(O)- (R) | tBu | 14.3 | 394.2 |
| 42 | HO-(CH2)4-NHC(O)- (R) | tBu | 6.0 | 398.2 |
| 43 | (EtO)2CH-CH2-NHC(O)- (R) | tBu | 14.2 | 442.2 |
| 44 | PhO-CH2CH2-NHC(O)- (R) | tBu | 14.6 | 446.2 |
| 45 | indol-3-yl-ethyl-NHC(O)- (R) | tBu | 14.6 | 469.2 |
| 46 | 1-benzylpiperidin-4-yl-NHC(O)- (R) | tBu | 10.7 | 446.2 |

-continued
FORMULA 57
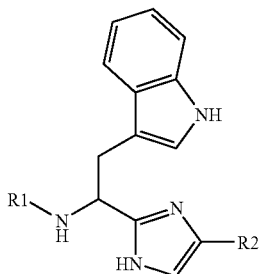
| | R1 | R2 | Tr (min) | [M + H]+ |
|---|---|---|---|---|
| 47 | naphthalen-1-ylmethyl-NHC(O)- | (R) tBu | 14.8 | 466.2 |
| 48 | morpholinoethyl-NHC(O)- | (R) tBu | 11.8 | 439.3 |
| 49 | benzo[1,3]dioxol-5-ylmethyl-NHC(O)- | (R) tBu | 14.4 | 460.1 |
| 50 | 1,2,3,4-tetrahydronaphthalen-1-yl-NHC(O)- | (R) tBu | 14.8 | 456.2 |
| 51 | thiophen-2-ylmethyl-NHC(O)- | (R) tBu | 14.4 | 422.1 |
| 52 | 2-(trifluoromethyl)benzyl-NHC(O)- | (R) tBu | 14.8 | 484.1 |
| 53 | 4-chlorobenzyl-NHC(O)- | (R) tBu | 14.7 | 450.1 |

-continued
FORMULA 57
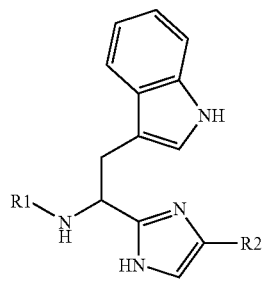
| | R1 | R2 | Analysis Tr (min) | [M + H]+ |
|---|---|---|---|---|
| 54 | (carbamoylmethyl-2-((2-(hydroxymethyl)phenyl)thio)benzyl) | (R) | 14.7 | 554.1 |
| 55 | 2,2-diphenylethylcarbamoyl | (R) | 15.0 | 506.2 |
| 56 | 3-(imidazol-1-yl)propylcarbamoyl | (R) | 11.6 | 434.3 |
| 57 | 4-sulfamoylphenethylcarbamoyl | (R) | 8.1 | 509.1 |
| 58 | cyclopentylcarbamoyl | (S) | 14.4 | 394.2 |
| 59 | 4-hydroxybutylcarbamoyl | (S) | 11.4 | 398.2 |
| 60 | 2,2-diethoxyethylcarbamoyl | (S) | 14.2 | 442.2 |

-continued
FORMULA 57
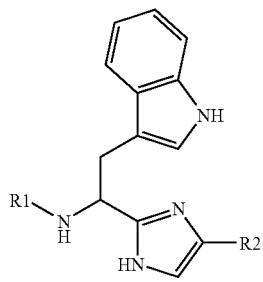
| | R1 | R2 | Tr (min) | [M + H]+ |
|---|---|---|---|---|
| 61 | phenoxyethyl-NH-C(O)- | (S) tBu | 14.6 | 446.2 |
| 62 | tryptamine-NH-C(O)- | (S) tBu | 14.6 | 469.2 |
| 63 | 4-hydroxyphenethyl-NH-C(O)- | (S) tBu | 11.0 | 446.2 |
| 64 | (1-naphthylmethyl)-NH-C(O)- | (S) tBu | 14.8 | 466.2 |
| 65 | (2-morpholinoethyl)-NH-C(O)- | (S) tBu | 11.8 | 439.3 |
| 66 | (benzo[d][1,3]dioxol-5-ylmethyl)-NH-C(O)- | (S) tBu | 14.4 | 460.2 |
| 67 | (1,2,3,4-tetrahydronaphthalen-1-yl)-NH-C(O)- | (S) tBu | 14.8 | 456.2 |

-continued
FORMULA 57
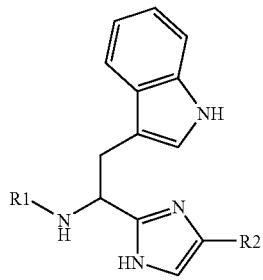
| | R1 | R2 | Tr (min) | [M + H]+ |
|---|---|---|---|---|
| 68 | thiophen-2-ylmethyl-NH-C(O)- (S) | tBu | 14.3 | 422.1 |
| 69 | 2-(trifluoromethyl)benzyl-NH-C(O)- (S) | tBu | 14.7 | 484.2 |
| 70 | 4-chlorobenzyl-NH-C(O)- (S) | tBu | 14.6 | 450.2 |
| 71 | 2-[(2-hydroxymethyl)phenylthio]benzyl-NH-C(O)- (S) | tBu | 14.7 | 554.1 |
| 72 | 2,2-diphenylethyl-NH-C(O)- (S) | tBu | 14.9 | 506.2 |
| 73 | 3-(imidazol-1-yl)propyl-NH-C(O)- (S) | tBu | 11.7 | 434.3 |

-continued
FORMULA 57
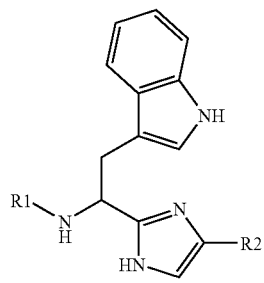
| | R1 | R2 | Analysis Tr (min) | [M + H]+ |
|---|---|---|---|---|
| 74 | 4-sulfamoylphenethyl-NH-C(O)- | (S) tBu | 8.4 | 509.2 |
FORMULA 58
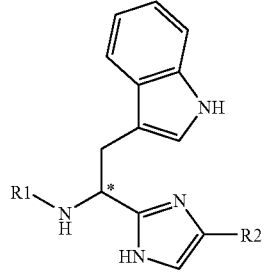
| | R1 | R2 | Analysis Tr (min) | [M + H]+ |
|---|---|---|---|---|
| 1 | PhNH-C(O)- | (R) Ph | 12.9 | 422.2 |
| 2 | 2-Cl-C6H4-NH-C(O)- | (R) Ph | 13.3 | 456.2 |
| 3 | BnNH-C(O)- | (R) Ph | 12.9 | 436.2 |

-continued
FORMULA 58
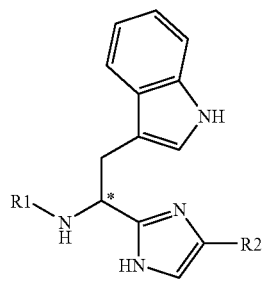
|   | R1 | R2 | Analysis Tr (min) | [M + H]+ |
|---|---|---|---|---|
| 4 | N-(naphthalen-1-yl)acetamide | (R)-phenyl | 13.6 | 472.3 |
| 5 | 4-phenoxyphenyl acetamide | (R)-phenyl | 14.5 | 514.2 |
| 6 | 2,6-diisopropylphenyl acetamide | (R)-phenyl | 14.6 | 506.3 |
| 7 | 3-(trifluoromethyl)phenyl acetamide | (R)-phenyl | 14.2 | 490.2 |
| 8 | ethyl 4-acetamidobenzoate | (R)-phenyl | 13.6 | 494.2 |
| 9 | 2,4-difluorophenyl acetamide | (R)-phenyl | 13.3 | 458.2 |

-continued
FORMULA 58
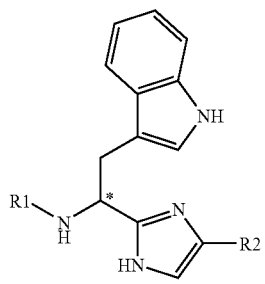
| | R1 | R2 | Analysis Tr (min) | [M + H]+ |
|---|---|---|---|---|
| 10 | 3-NO2-C6H4-NH-C(=O)- | (R) Ph | 13.3 | 467.2 |
| 11 | Ph-NH-C(=S)- | (R) Ph | 13.2 | 438.2 |
| 12 | Ph-C(=O)-NH-C(=S)- | (R) Ph | 13.8 | 466.2 |
| 13 | Ph-CH2-NH-C(=S)- | (R) Ph | 13.9 | 452.2 |
| 14 | 1-naphthyl-NH-C(=S)- | (R) Ph | 13.8 | 488.2 |
| 15 | 4-(PhCH2O)-C6H4-NH-C(=S)- | (R) Ph | 14.8 | 544.2 |
| 16 | 2-iPr-C6H4-NH-C(=S)- | (R) Ph | 14.3 | 480.2 |

-continued
FORMULA 58
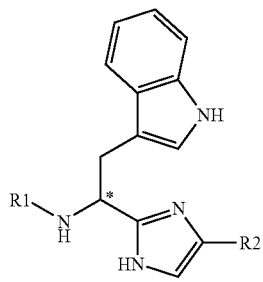
|  | R1 | R2 | Tr (min) | [M + H]+ |
|---|---|---|---|---|
| 17 | 3-chlorophenyl-NH-C(=S)- | phenyl (R) | 14.2 | 472.2 |
| 18 | pentyl-NH-C(=S)- | phenyl (R) | 14.7 | 446.3 |
| 19 | morpholino-ethyl-NH-C(=S)- | phenyl (R) | 10.4 | 475.2 |
| 20 | benzo[1,3]dioxol-5-ylmethyl-NH-C(=S)- | phenyl (R) | 13.8 | 496.2 |
| 21 | phenyl-NH-C(=O)- | phenyl (S) | 13.1 | 422.2 |
| 22 | 2-chlorophenyl-NH-C(=O)- | phenyl (S) | 13.4 | 456.2 |
| 23 | benzyl-NH-C(=O)- | phenyl (S) | 13.1 | 436.2 |

-continued
FORMULA 58
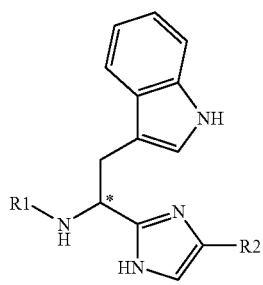
| | R1 | R2 | Analysis Tr (min) | [M + H]+ |
|---|---|---|---|---|
| 24 | N-(naphthalen-1-yl)acetamide group | (S) phenyl | 13.7 | 472.3 |
| 25 | 4-phenoxyphenyl acetamide group | (S) phenyl | 14.7 | 514.2 |
| 26 | 2,6-diisopropylphenyl acetamide group | (S) phenyl | 14.7 | 506.3 |
| 27 | 3-(trifluoromethyl)phenyl acetamide group | (S) phenyl | 14.3 | 490.2 |
| 28 | 4-(ethoxycarbonyl)phenyl acetamide group | (S) phenyl | 13.7 | 494.2 |
| 29 | 2,4-difluorophenyl acetamide group | (S) phenyl | 13.4 | 458.2 |

-continued
FORMULA 58
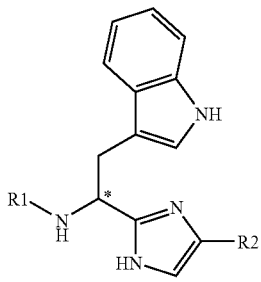
| | R1 | R2 | Analysis | |
|---|---|---|---|---|
| | | | Tr (min) | [M + H]+ |
| 30 | 3-nitrophenyl-NH-C(=O)- | (S)-phenyl | 13.6 | 467.2 |
| 31 | phenyl-NH-C(=S)- | (S)-phenyl | 13.3 | 438.2 |
| 32 | phenyl-C(=O)-NH-C(=S)- | (S)-phenyl | 13.9 | 466.2 |
| 33 | benzyl-NH-C(=S)- | (S)-phenyl | 13.9 | 452.2 |
| 34 | naphth-1-yl-NH-C(=S)- | (S)-phenyl | 14.0 | 488.2 |
| 35 | 4-(benzyloxy)phenyl-NH-C(=S)- | (S)-phenyl | 15.1 | 544.2 |
| 36 | 2-isopropylphenyl-NH-C(=S)- | (S)-phenyl | 14.5 | 480.2 |

-continued
FORMULA 58
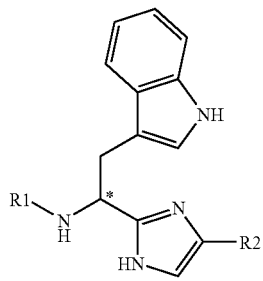
| | R1 | R2 | Tr (min) | [M + H]+ |
|---|---|---|---|---|
| | | | Analysis | |
| 37 | 3-Cl-C6H4-NH-C(=S)- | (S) Ph | 14.2 | 472.2 |
| 38 | 3,4-methylenedioxybenzyl-NH-C(=S)- | (S) Ph | 13.8 | 496.2 |
| 39 | Ph-NH-C(=O)- | (R) t-Bu | 13.1 | 402.2 |
| 40 | 2-Cl-C6H4-NH-C(=O)- | (R) t-Bu | 13.6 | 436.2 |
| 41 | 1-naphthyl-NH-C(=O)- | (R) t-Bu | 13.6 | 452.2 |
| 42 | 4-PhO-C6H4-NH-C(=O)- | (R) t-Bu | 14.8 | 494.2 |
| 43 | 2,6-diisopropyl-C6H3-NH-C(=O)- | (R) t-Bu | 14.9 | 486.3 |

-continued
FORMULA 58
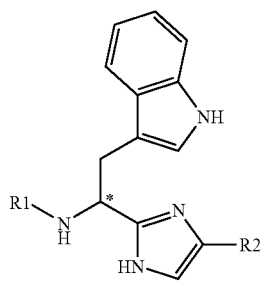
| | R1 | R2 | Tr (min) | [M + H]+ |
|---|---|---|---|---|
| 44 | 3-CF3-C6H4-NH-C(O)-CH2- | (R) tBu | 14.3 | 470.2 |
| 45 | 4-(EtO-C(O))-C6H4-NH-C(O)-CH2- | (R) tBu | 13.7 | 474.3 |
| 46 | 2,4-diF-C6H3-NH-C(O)-CH2- | (R) tBu | 13.4 | 438.2 |
| 47 | 3-NO2-C6H4-NH-C(O)-CH2- | (R) tBu | 13.2 | 418.2 |
| 48 | Ph-C(O)-NH-C(S)-CH2- | (R) tBu | 13.6 | 446.2 |
| 49 | Ph-CH2-NH-C(S)-CH2- | (R) tBu | 10.0 | 432.1 |
| 50 | 1-naphthyl-NH-C(S)-CH2- | (R) tBu | 10.1 | 468.1 |

-continued
FORMULA 58
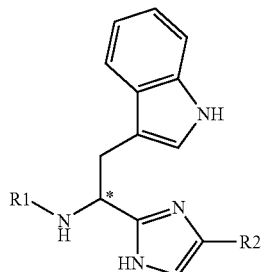
|  | R1 | R2 | Analysis Tr (min) | [M + H]+ |
|---|---|---|---|---|
| 51 | 2-isopropylphenyl-NHC(=S)- | (R) t-Bu | 14.2 | 460.2 |
| 52 | 3-chlorophenyl-NHC(=S)- | (R) t-Bu | 14.0 | 452.2 |
| 53 | hexyl-NHC(=S)- | (R) t-Bu | 14.8 | 426.3 |
| 54 | morpholinoethyl-NHC(=S)- | (R) t-Bu | 10.4 | 455.3 |
| 55 | (1,3-benzodioxol-5-yl)methyl-NHC(=S)- | (R) t-Bu | 13.9 | 476.2 |
| 56 | 2-chlorophenyl-NHC(=O)- | (S) t-Bu | 13.6 | 436.2 |
| 57 | 2,6-diisopropylphenyl-NHC(=O)- | (S) t-Bu | 14.9 | 486.3 |

-continued
FORMULA 58
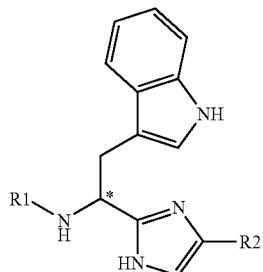
| | R1 | R2 | Tr (min) | [M + H]+ |
|---|---|---|---|---|
| 58 | 3-CF3-C6H4-NH-C(O)-CH2- | (S) tBu | 14.4 | 470.2 |
| 59 | 4-(EtO-C(O))-C6H4-NH-C(O)-CH2- | (S) tBu | 13.8 | 474.3 |
| 60 | 2,4-F2-C6H3-NH-C(O)-CH2- | (S) tBu | 13.4 | 438.2 |
| 61 | 3-NO2-C6H4-NH-C(O)-CH2- | (S) tBu | 13.3 | 447.2 |
| 62 | C6H5-NH-C(S)-CH2- | (S) tBu | 13.1 | 418.2 |
| 63 | C6H5-C(O)-NH-C(S)-CH2- | (S) tBu | 13.5 | 446.2 |
Analysis -continued
FORMULA 58
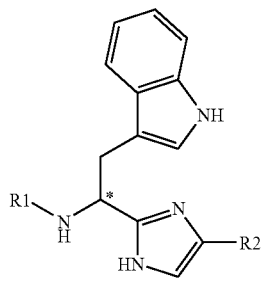
| | R1 | R2 | Tr (min) | [M + H]+ |
|---|---|---|---|---|
| 64 | N-benzyl thioamide | (S) isopropyl | 13.5 | 432.2 |
| 65 | N-(1-naphthyl) thioamide | (S) isopropyl | 13.7 | 468.2 |
| 66 | N-(4-benzyloxyphenyl) thioamide | (S) isopropyl | 14.7 | 524.2 |
| 67 | N-(2-isopropylphenyl) thioamide | (S) isopropyl | 14.3 | 460.2 |
| 68 | N-(3-chlorophenyl) thioamide | (S) isopropyl | 14.2 | 452.2 |
| 69 | N-(benzo[d][1,3]dioxol-5-ylmethyl) thioamide | (S) isopropyl | 13.8 | 476.2 |

What is claimed is:

1. A compound of the formula (I), (I)

the racemic-diastereomeric mixtures and optical isomers of said compound of formula (I) and pharmaceutically-acceptable salts thereof,
wherein
— represents an optional bond;
$R^1$ is H;
$R^2$ is H;
$R^3$ is —CH$_2$-indol-3-yl, —(CH$_2$)$_4$—NH—CO—O-t-Bu or —(CH$_2$)$_4$—NH$_2$;
$R^4$ is H or —(CH$_2$)$_m$—A$^1$;
 A$^1$ is —C(=Y)—N(X$^1$X$^2$), —C(=Y)—X$^2$, —C(=NH)—X$^2$ or X$^2$;
 Y is O or S;
 X$^1$ is H, (C$_1$-C$_{12}$)alkyl, —(CH$_2$)$_m$—NH—(C$_1$-C$_6$)alkyl, —(CH$_2$)$_m$—N-di-(C$_1$-C$_6$)alkyl or —(CH$_2$)$_m$-aryl;
 X$^2$ is —(CH$_2$)$_m$—Y$^1$—X$^3$ or optionally substituted (C$_1$-C$_{12}$)alkyl;
 Y$^1$ is O, S, NH, C=O, (C$_2$-C$_{12}$)alkenyl having one or more double bonds, —NH—CO—, —CO—NH—, —NH—CO—O—(CH$_2$)$_m$—, —C≡C—, SO$_2$ or a bond;
 X$^3$ is H, an optionally substituted moiety selected from the group consisting of (C$_1$-C$_{12}$)alkyl, (C$_3$-C$_8$)cycloalkyl, (C$_1$-C$_{12}$)alkoxy, aryloxy, (C$_1$-C$_{12}$)alkylamino, N,N-di-(C$_1$-C$_{12}$)alkylamino, —CH-di-(C$_1$-C$_{12}$)alkoxy, pyrrolidinyl, pyridinyl, thiophene, imidazolyl, piperidinyl, piperazinyl, benzothiazolyl, furanyl, indolyl, morpholino, benzo[b]furanyl, quinolinyl, isoquinolinyl, —(CH$_2$)$_m$-phenyl, naphthyl, fluorenyl, phthalamidyl, pyrimidinyl, or X$^1$ and X$^2$ are taken together with the nitrogen to which they are attached to form an optionally substituted moiety selected from the group consisting of thiazolyl Y$^2$ is CH—X$^4$, N—X$^4$, —C(X$^4$X$^4$), O or S;
X$^4$ for each occurrence is independently —(CH$_2$)$_m$—Y$^3$—X$^5$;
Y$^3$ is —C(O)—, —C(O)O— or a bond;
X$^5$ is hydroxy, (C$_1$-C$_{12}$)alkyl, amino, (C$_1$-C$_{12}$)alkylamino, N,N-di-(C$_1$-C$_{12}$)alkylamino, or an optionally substituted moiety selected from the group consisting of aryl, aryl(C$_1$-C$_4$)alkyl, furanyl, pyridinyl, indolyl, —CH(phenyl)$_2$, where m for each occurrence is independently 0 or an integer from 1 to 6:
$R^5$ is phenyl, o-methoxyphenyl, p-Br-phenyl, p-nitrophenyl or p-N,N-diethylamino-phenyl;
$R^6$ is H.

2. A compound according to claim 1 wherein $R^5$ is phenyl and $R^3$ is —(CH$_2$)-indol-3-yl and the stereochemistry at the carbon to which $R^3$ is attached is the R-configuration.

3. A pharmaceutical composition comprising a compound according to claim 1 or a pharmaceutically acceptable salt thereof and a pharmaceutically acceptable carrier.

4. A method of treating acromegaly, restenosis, Crohn's disease, systemic sclerosis, external and internal pancreatic pseudocysts and ascites, VIPoma, nesidoblastosis, hyperinsulinism, gastrinoma, Zollinger-Ellison Syndrome, diarrhea, AIDS related diarrhea, chemotherapy related diarrhea, scleroderma, Irritable Bowel Syndrome, pancreatitis, small bowel obstruction, gastroesophageal reflux, duodenogastric reflux, Cushing's Syndrome, hyperparathyroidism, Graves' Disease, diabetic neuropathy, Paget's disease, polycystic ovary disease, postprandial hypotension, hypotension, panic attacks, GH secreting adenomas or TSH secreting adenomas, in a subject in need thereof, which comprises administering a compound according to claim 1 or a pharmaceutically acceptable salt thereof to said subject.

5. A method of treating diabetes mellitus, hyperlipidemia, insulin insensitivity, Syndrome X, angiopathy, proliferative retinopathy, dawn phenomenon, peptic ulcers, enterocutaneous and pancreaticocutaneous fistula, Dumping syndrome, watery diarrhea syndrome, acute or chronic pancreatitis, gastrointestinal hormone secreting tumors, chronic allograft rejection, graft vessel bleeding or gastrointestinal bleeding in a subject in need thereof, which comprises administering a compound according to claim 1 or a pharmaceutically acceptable salt thereof to said subject.

* * * * *

UNITED STATES PATENT AND TRADEMARK OFFICE
CERTIFICATE OF CORRECTION

PATENT NO.         : 7,238,695 B2                                  Page 1 of 1
APPLICATION NO. : 10/771725
DATED              : July 3, 2007
INVENTOR(S)        : Christophe Alain Thurieau et al.

It is certified that error appears in the above-identified patent and that said Letters Patent is hereby corrected as shown below:

Column 599: claim 1, line 17 which reads "——represents an optional bond;" should read -- - - - - - represents an optional bond; --

Signed and Sealed this

Eleventh Day of March, 2008

JON W. DUDAS
*Director of the United States Patent and Trademark Office*